(12) United States Patent
Nakashima et al.

(10) Patent No.: US 7,709,624 B2
(45) Date of Patent: May 4, 2010

(54) **PROCESS FOR PRODUCING RECOMBINANT PROTEIN IN BACTERIUM BELONGING TO THE GENUS *RHODOCOCCUS***

(75) Inventors: Nobutaka Nakashima, Hokkaido (JP); Tomohiro Tamura, Hokkaido (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 581 days.

(21) Appl. No.: 10/553,979

(22) PCT Filed: Apr. 19, 2004

(86) PCT No.: PCT/JP2004/005585

§ 371 (c)(1),
(2), (4) Date: Oct. 20, 2005

(87) PCT Pub. No.: WO2004/094633

PCT Pub. Date: Nov. 4, 2004

(65) Prior Publication Data

US 2007/0004004 A1    Jan. 4, 2007

(30) Foreign Application Priority Data

Apr. 21, 2003   (JP) ............................. 2003-116280

(51) Int. Cl.
*C07H 21/04*     (2006.01)
*C12N 15/63*     (2006.01)
*C12N 1/21*      (2006.01)

(52) U.S. Cl. ................. 536/24.1; 435/320.1; 435/252.3
(58) Field of Classification Search .................... None
See application file for complete search history.

(56) References Cited

U.S. PATENT DOCUMENTS 5,164,305 A  * 11/1992  Wong .......................... 435/69.1
6,566,110 B1    5/2003  Pelzer et al.

FOREIGN PATENT DOCUMENTS

| EP | 1127943 | 8/2001 |
|---|---|---|
| JP | 10-248578 | 9/1998 |
| WO | WO 96/03521 | 2/1996 |
| WO | WO 01/48192 | 7/2001 |
| WO | WO 2004/016792 A1 | 2/2004 |

OTHER PUBLICATIONS

GenBank accession No. AB127601.*
Jaurin et al. Sequence elements determining ampC promoter strength in *E. coli*. EMBO 1(7): 875-881, 1982.*
Takano et al. Construction of thiostrepton-inducible, high-copy-number expression vectors for use in *Streptomyces* spp. Gene 166: 133-137, 1995.*

D.J. Holmes et al., "Autogenous transcriptional activation of a thiostrepton-induced gene in *Strep tomyces lividans*", EMBO J., 1993, vol. 12, No. 8, pp. 3183-3191.
M.S. Fenton et al., "Function of the bacterium TATAAT-10 element as single-stranded DNA during RNA polymerase isomerization," Proc. Natl. Acad. Sci. USA, 2001, vol. 98, No. 16, pp. 9020-9025.
J. Desomer et al., "The plasmid-encoded chloram phenicol-resistance protein of *Rhodococcus fascians* is homologous to the transmembrane tetracycline efflux proteins", Molecular Microbiology, 1992, vol. 6, No. 16, pp. 2377-2385.
R. DeMot. et al., "Structural analysis of the 6 kb cryptic plasmid pFAJ2600 from *Rhodococcus erythropolis* NI86/21 and construction of *Escherichia coli-Rhodococcus* shuttle vectors," Microbiology 1997, vol. 143, pp. 3137-1347.
Mary B. Slabaugh et al., "Vaccinia Virus Ribonucleotide Reductase Expression and Isolation of the Recombinant Large Subunit", The Journal of Biological Chemistry, vol. 268, No. 24, Issue of Aug. 25, 1993, pp. 17803-17810.
Anna Brandi et al., "Post-transcriptional regulation of CspA expression in *Escherichia coli*", Molecular Microbiology (1996), vol. 19, No. 2, pp. 231-240.
Maria Luisa Tutino et al., "A Novel replication element from an Antarctic plasmad as a tool for the expression of proteins at low temperature", Extremophiles (2001), 5:257-264.
Mujacic et al., Cold-inducible cloning vectors for low-temperature protein expression in *Escherichia coli*: application to the production of a toxic and proteolytically sensitive fusion protein., GENE, 1999, vol. 238, No. 2, pp. 325-332.
Enguita et al., An inducible expression system of histidine-tagged proteins in *Streptomyces lividans* for one-step purification by Ni2+ affinity chromatography., FEMS Microbiol. Lett., 1996, vol. 137, Nos. 2 to 3, pp. 135-140.
Lowell et al., Structure of the murine serum amyloid A gene family: Gene conversion., J. Biol. Chem., 1986, vol. 261, No. 18, pp. 8442-8452.
Kawai et al., Functional annotation of a full-length mouse cDNA collection., Nature, 2001, vol. 409, No. 6821, pp. 685-690.
Van Der Vliet et al., Apolipoprotein A-V: a novel apolipoprotein associated with an early phase of liver regeneration., J. Biol. Chem., 2001, vol. 276, No. 48, pp. 44512-44520.
Grusby et al., Molecular cloning of mouse cathepsin D., Nucleic Acids Res., 1990, vol. 18, No. 13, p. 4008.

(Continued)

*Primary Examiner*—Michele K. Joike
(74) *Attorney, Agent, or Firm*—Stephen A. Bent; Foley & Lardner LLP

(57) ABSTRACT

Provided is an expression vector capable of constitutive expression of a foreign gene in a bacterium belonging to the genus *Rhodococcus*. The vector is a constitutive expression vector for a bacterium belonging to the genus *Rhodococcus* comprising: DNA comprising a nucleotide sequence of a mutated TipA gene promoter where a mutation is incorporated into a –10 region sequence of a TipA gene promoter, the mutated TipA gene promoter being capable of thiostrepton-independent and constitutive expression of a gene located downstream thereof; a promoter sequence for the constitutive expression of a foreign gene; a ribosome-binding site sequence located downstream of the promoter sequence; and a multiple-cloning site sequence capable of incorporating a foreign gene therein, located downstream of the ribosome-binding site sequence.

7 Claims, 30 Drawing Sheets

OTHER PUBLICATIONS

Degen et al., Characterization of the cDNA coding for mouse prothrombin and localization of the gene on mouse chromosome 2., DNA Cell Biol., 1990, vol. 9, No. 7, pp. 487-498.

Evans et al., Mouse glandular kallikrein genes. Structure and partial sequence analysis of the kallikrein gene locus., J. Biol. Chem., 1987, vol. 262, No. 17, pp. 8027-8034.

Baron et al,. Cloning and characterization of an actin-resistant DNase I-like endonuclease secreted by macrophages., Gene, 1998, vol. 215, No. 2, pp. 291-301.

Shiokawa et al., DLAD, a novel mammalian divalent cation-independent endonuclease with homology to DNase II., Nucleic Acids Res., 1999, vol. 27, No. 20, pp. 4083-4089.

Ferrari et al., The mouse gene coding for highm obiilty group 1 protein (HMG1)., J. Biol. Chem., 1994, vol. 269, No. 46, pp. 28803-28808.

Tekki-Kessaris et al., "Characterization of the mouse Kid1 gene and identification of a highly erlated gene, Kid2," Gene, 1999, vol. 240, No. 1, pp. 13-22.

Oltvai et al., "Bcl-2 heterodimerizes in vivo with a conserved homolog, Bax, that accelerates programmed cell death," Cell, 1993, vol. 74, No. 4, pp. 609-619.

Postic et al., "Cloning and characterization of the mouse glucokinase gene locus and identification of distal liver-specific DNase I hypersensitive sites," Genomics, 1995, vol. 29, No. 3, pp. 740-750.

Holzl et al., "The regulatory complex of *Drosophila melanogaster* 26S proteasomes. Subunit composition and localization of a deubiquitylating enzyme," J. Cell. Biol., 2000, vol. 150, No. 1, pp. 119-130.

Rock et al., "Pantothenate kinase regulation of the intracellular concentration of coenzyme A," J. Biol. Chem., 2000, vol. 275, No. 2, pp. 1377-1383.

Wong et al., "Characterization of human and mouse peroxiredoxin IV: evidence for inhibition by Prx-IV of epidermal growth factor- and p53-induced reactive oxygen species," Antioxid. Redoxsignal, 2000, vol. 2, No. 3, pp. 507-518.

Whyte et al., Appl Environ Microbiol, 1998, 64:2578-2584.

Chiu et al., J. Biol. Chem. 1999,274:20578-20586.

Hashimoto et al., J. Gen Microbiol, 1992, 138:1003-1010.

Olins et al., Gene, 1988, 73:227-235.

\* cited by examiner

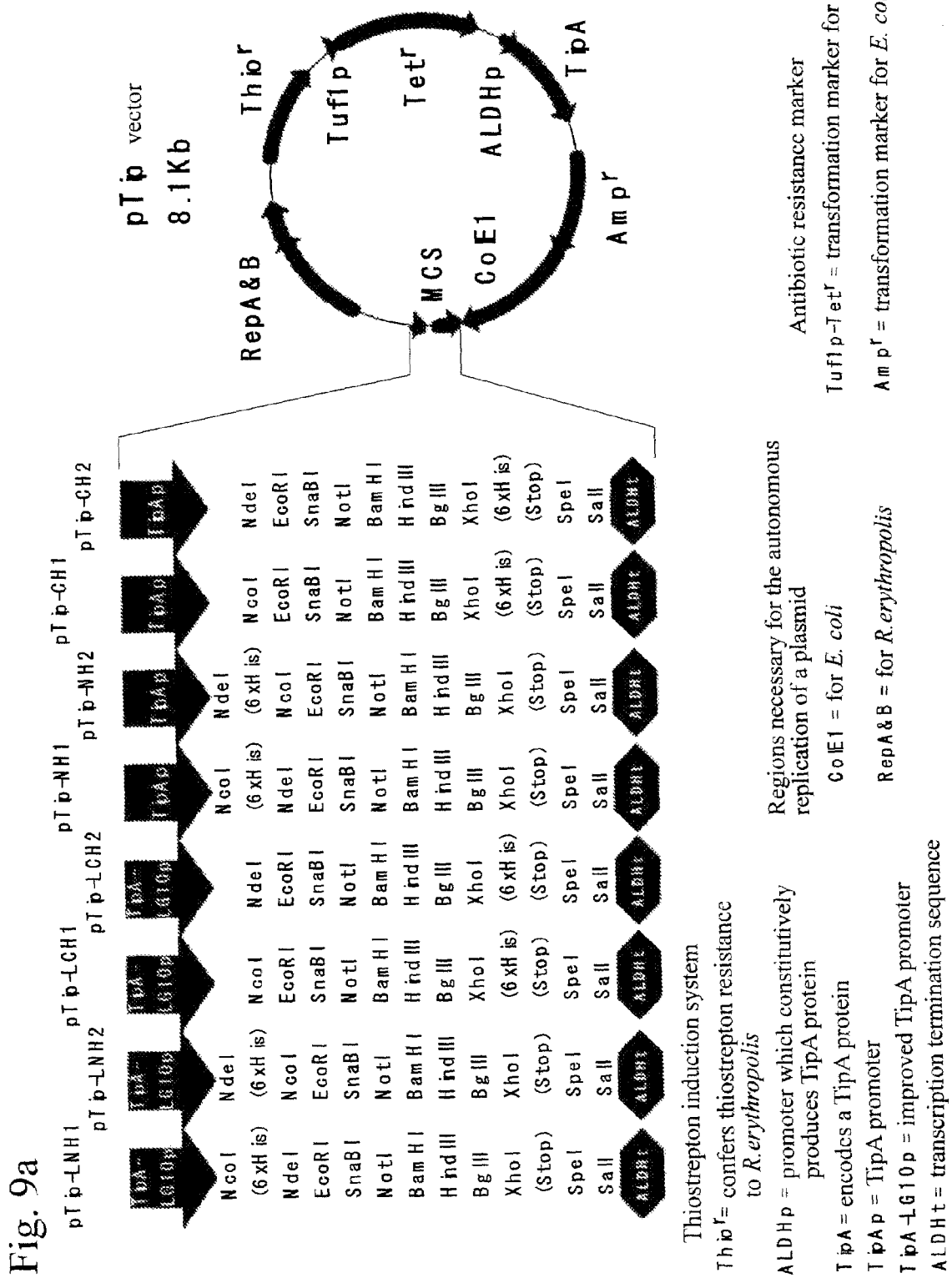

Fig. 15

|  | Motif IV | Motif I | Motif II | Motif III |
|---|---|---|---|---|
| Consensus | GLXXCGXXWCPXC | Xvt XTXRH | gXXgXXr a Xe Xt XgXXnGwHXHXhXl X | l a XYXXXKXqX |
| pRE8424 68 | GLRSCGKGW CPCC(126) | 26 MVTMTMRH(127) | 33 GCDGYVRAVEI THGK- NGWHVHVHALL(128) | 53 LAATLTKI AS (129) |
| pAP1 138 | GLHICGSVWACPVC(131) | 27 MLTLTQRH(132) | 33 GLVGYVRANEI THGK- HGWHVHSHVLI (133) | 67 I GNYVSKMQI (134) |
| pBL1 | | 76 MFVGTVRH(136) | 34 VEHTYSDYEVTDSWA- NGWHLHRNMLL (137) | 54 MATMLAKGVS (138) |
| pJV1 38 | GLVRCGRI WFCPEC(140) | 27 LVIFTARH(141) | 77 GYI GMVRAAEVTRSKKNGYHPHLNLLV(142) | 80 LI EMLTKNQD (143) |
| pIJ101 20 | GLMRCGRI WLCPVC(145) | 27 LVIFTARH(146) | 59 GYVGM RATEVTVGQI NGWPHI HAI V(147) | 69 LAEMI AKTQD(148) |
| pSN22 20 | GLMRCGRI WLCPVC(150) | 27 LVIFTARH(151) | 59 GYVGM RATEVTVGQI NGWPHI HAI V(152) | 69 LAEMI AKTQD(153) |
|  | ** ** .* .* .** * | .: : ** ** | . : .. : . : : . . .* * | .* : :* |

C-terminal motif

| Consensus | WXeyEXa XXgr Rai XWXr gl r |
|---|---|
| pRE8424 276 | WREFEFGSMGRRAI AWSRGLR(130) |
| pAP1 365 | WKEYEKASFGRRALTWSKGLR(135) |
| pBL1 250 | WREYEVGSKNLRS– SWSRGAK(139) |
| pJV1 352 | WAQYEEALAGRRAI EWTRGLR(144) |
| pIJ101 288 | WHEYERATRGRRAI EWTRYLR(149) |
| pSN22 288 | WHEYERATKGRRAI EWTRYLR(154) |
|  | * :: * . : : *** * |

Numbers in parentheses indicate SEQ ID NOs.

Fig. 16

```
pRE8424  5705  CGAGTCGAAGCC-GA-GCGCCT----AGCTGGGGGAG-  (SEQ ID NO: 155)
pAP1     2378  CAGTTATGC-G-GA-AAACTTT----AGCAACAA-     (SEQ ID NO: 156)
pBL1     1314  GAAATAGAA-CTGA-ACACTCTAAGCAACCGCA-      (SEQ ID NO: 157)
pJV1     3375  CTGTGAAAAAGGA--GCCT----AGCTAAAGGGTT     (SEQ ID NO: 158)
pIJ101   1346  GAGTGAAAA-CCGA-ACACTTT--GGGAAAGAAA-     (SEQ ID NO: 159)
pSN22    7805  GACCGAAAACCTGTCGGGCTT---CGGAAAGAAA-     (SEQ ID NO: 160)
                                          ‾‾‾
                                       Nicking site

DSO
``` ic replication in the bacterium belonging to the genus *Rhodococcus* were derived from a single endogenous plasmid. This is due to a phenomenon called plasmid incompatibility in which heterologous plasmids having the same autonomous replication origin can not coexist in a bacterium, and there has been a report on this phenomenon for many bacteria (Novick, Microbiol. Rev. 51 381-395 [1987]). If heterologous plasmids can be allowed to coexist in a single bacterial cell, several recombinant proteins can simultaneously be produced. For example, a protein complex called 20S proteasome is composed of two polypeptides, an α subunit and a β subunit. When functional 20S proteasome complex is produced as a recombinant, these two polypeptides must be coexpressed. The coexpression of two polypeptides in a single cell can also be achieved by introducing several foreign genes into a single expression vector. However, such an approach utilizes a large-sized vector and a complicated cloning step for restriction enzyme site reasons and as such, is inconvenient in most cases. An established coexpression system of recombinant proteins in a bacterium belonging to the genus *Rhodococcus* by the use of several expression vectors is described in WO02/055709.

PROCESS FOR PRODUCING RECOMBINANT PROTEIN IN BACTERIUM BELONGING TO THE GENUS *RHODOCOCCUS*

TECHNICAL FIELD

The present invention relates to an expression vector capable of expressing a foreign gene in a bacterium belonging to the genus *Rhodococcus*.

The present invention also relates to an inducible expression vector and a constitutive expression vector capable of expressing a recombinant protein in a host cell, and to a method of using any of the vectors to express a recombinant protein. The present invention further relates to a method of simultaneously expressing several genes encoded on different vectors in the cell of a bacterium belonging to the genus *Rhodococcus*.

BACKGROUND ART

Currently, an expression system using *Escherichia coli* as a host is widely used for preparing a large amount of a recombinant protein derived from a eukaryote. This is because the system is readily handled and its research progresses most (Weickert et al., Curr. Opin. Biotechnol. 7: 494-499 [1996]).

On the other hand, the present inventors have previously demonstrated that *Rhodococcus erythropolis* can also be used as a host for recombinant protein production (JP Patent Publication (Kokai) No. 2004-73032A and Japanese Patent Application No. 2002-235008). *R. erythropolis* is one of Actinobacteria capable of proliferation at temperatures ranging from 4° C. to 35° C. The biggest feature of an expression system that uses this bacterium as a host is in that a recombinant protein can be produced at temperatures not higher than 10° C. such as 4° C. In systems that employ other hosts including *Escherichia coli*, bacteria belonging to the genus *Bacillus*, yeasts, and Sf9 insect cells (Cereghino and Cregg, Curr. Opin. Biotechnol. 10 422-427 [1999]; and Miller, Curr. Opin. Genet. Dev. 3 97-101 [1993]), recombinant protein production at temperatures not higher than 10° C. is quite difficult. Recombinant protein production at temperatures not higher than 10° C. has allowed the production of proteins difficult to produce until then, for example, proteins inhibiting the proliferation of host cells, proteins getting insoluble at temperatures around 30° C., and proteins derived from organisms adapting to low temperatures.

The present inventors have constructed a group of expression vectors for a bacterium belonging to the genus *Rhodococcus* called pTip vectors and have used them in recombinant protein production (JP Patent Publication (Kokai) No. 2004-73032A and Japanese Patent Application No. 2002-235008). These vectors contain the promoter of a TipA gene whose expression is induced by antibiotic thiostrepton and also contain a multiple-cloning site (MCS) for cloning a foreign gene (gene to be expressed), located downstream of the promoter. Thus, the pTip vectors are thiostrepton-inducible expression vectors. In bacteria belonging to the genus *Rhodococcus* that are transformed with these expression vectors, foreign protein production is induced only when thiostrepton is added to a culture solution.

Non-Patent Document 1

Weickert et al., Curr. Opin. Biotechnol. 7: 494-499 [1996]

Non-Patent Document 2

Cereghino and Cregg, Curr. Opin. Biotechnol. 10 422-427 [1999]

Non-Patent Document 3

Miller, Curr. Opin. Genet. Dev. 3 97-101 [1993]

DISCLOSURE OF THE INVENTION

Although the present inventors, as described above, have constructed a group of expression vectors for a bacterium belonging to the genus *Rhodococcus* called pTip vectors and have used them in recombinant protein production, two things have been left for development.

First, several expression vectors containing the same autonomous replication origin but different foreign genes had difficulty in simultaneously and stably coexisting in a bacterium belonging to the genus *Rhodococcus*, because the DNA regions of all of the pTip vectors necessary for autonomous replication in the bacterium belonging to the genus *Rhodococcus* were derived from a single endogenous plasmid. This is due to a phenomenon called plasmid incompatibility in which heterologous plasmids having the same autonomous replication origin can not coexist in a bacterium, and there has been a report on this phenomenon for many bacteria (Novick, Microbiol. Rev. 51 381-395 [1987]). If heterologous plasmids can be allowed to coexist in a single bacterial cell, several recombinant proteins can simultaneously be produced. For example, a protein complex called 20S proteasome is composed of two polypeptides, an α subunit and a β subunit. When functional 20S proteasome complex is produced as a recombinant, these two polypeptides must be coexpressed. The coexpression of two polypeptides in a single cell can also be achieved by introducing several foreign genes into a single expression vector. However, such an approach utilizes a large-sized vector and a complicated cloning step for restriction enzyme site reasons and as such, is inconvenient in most cases. An established coexpression system of recombinant proteins in a bacterium belonging to the genus *Rhodococcus* by the use of several expression vectors is described in WO02/055709.

Second, in spite of the fact that a key tool in research for bacteria belonging to the genus *Rhodococcus* is not only inducible expression vectors but constitutive expression vector, the constitutive expression vector was undeveloped. Those using a mutated nitrile hydratase gene promoter (JP Patent Publication (Kokai) No. 9-28382A (1997) and JP Patent Publication (Kokai) No. 10-248578A (1998)) and using an rrn promoter are known as constitutive expression vectors in known bacteria belonging to the genus *Rhodococcus* (Matsui et al., Curr. Microbiol. 45 240-244 [2002]).

Among bacteria belonging to the genus *Rhodococcus*, many strains that decompose various persistent compounds such as PCB (polychlorinated biphenyl) and pesticides are known (bioremediation) (Bell et al., J. Appl. Microbiol. 85 195-210 [1998]), and a certain strain is known to accumulate useful compounds such as acrylamide in the bacterial cell and is already utilized in industrial production (bioprocess and bioreactor) (Yamada et al., Biosci. Biotech. Biochem. 60 1391-1400 [1996]). Thus, if the above-described two things to be improved were overcome, the availability of an expression vector for a bacterium belonging to the genus *Rhodococcus* would be increased not only in recombinant protein production but in research for bioremediation and bioprocess.

The solution to a problem of plasmid incompatibility requires newly separating and utilizing an equivalent sequence different from the sequences of the DNA regions used in the pTip vectors previously constructed by the present inventors, which are necessary for autonomous replication in a bacterium belonging to the genus *Rhodococcus*. The minimal RepAB gene-containing region (1.9 kilobase pairs; hereinafter, abbreviated to kb), necessary for autonomous replication, of an endogenous plasmid pRE2895 (5.4 kb) separated from a *R. erythropolis* strain JCM2895 has been used in all of the pTip vectors. Thus, the present inventors have decided to construct novel expression vectors by separating endogenous plasmids having different DNA sequences from other *R. erythropolis* strains. In the construction of the pTip vectors, only a tetracycline resistance gene has been developed as a selection marker for the transformant of a bacterium belonging to the genus *Rhodococcus*. However, the transformation of the bacterium belonging to the genus *Rhodococcus* with several plasmids requires other resistence genes. The present inventors have found that a *R. erythropolis* strain DSM313 is resistant to chloramphenicol and have decided to separate and utilize a gene that imparts resistance.

For developing a constitutive expression vector, the present inventors have further decided to introduce a mutation into the TipA gene promoter to produce a mutant that allows the constitutive expression, that is thiostrepton-independent expression of a foreign gene.

In this way, in addition to the pTip vectors having the region of the pRE2895 necessary for autonomous replication and the inducible TipA gene promoter, the present inventors have newly constructed: a vector having a different DNA region necessary for autonomous replication, which is a vector having the TipA gene promoter and allowing inducible expression; a vector having a different DNA region necessary for autonomous replication from those of the pTip vectors, which is a vector having a promoter where a mutation is introduced into the TipA gene promoter and allowing constitutive expression; and a vector having the same DNA region necessary for autonomous replication as those of the pTip vectors and a promoter where a mutation is introduced into the TipA gene promoter and allowing constitutive expression. Of these vectors, two types of vectors having different DNA regions necessary for autonomous replication and containing genes encoding foreign proteins different from each other can be used to cotransform one host. In addition, the different foreign proteins can simultaneously be coexpressed in the cotransformed host.

That is, the present invention is as follows:

[1] DNA comprising a nucleotide sequence of a mutated TipA gene promoter where a mutation is introduced into a −10 region sequence of a TipA gene promoter, the mutated TipA gene promoter capable of thiostrepton-independent and constitutive expression of a gene located downstream thereof;

[2] The DNA of [1], wherein the mutation in the −10 region sequence is a mutation of a CAGCGT sequence to a TATAAT sequence;

[3] The DNA of [2], having a nucleotide sequence represented by SEQ ID NO: 169 or SEQ ID NO: 170.

[4] A constitutive expression vector for a bacterium belonging to the genus *Rhodococcus* comprising: a promoter sequence for the constitutive expression of a foreign gene, the promoter sequence being a nucleotide sequence of DNA of any one of [1] to [3]; a ribosome-binding site sequence located downstream of the promoter sequence; and a multiple-cloning site sequence capable of incorporating a foreign gene therein, located downstream of the ribosome-binding site sequence;

[5] The constitutive expression vector for a bacterium belonging to the genus *Rhodococcus* of [4], wherein the vector is selected from the group consisting of pNit-RT1 having a nucleotide sequence represented by SEQ ID NO: 101, pNit-RT2 having a nucleotide sequence represented by SEQ ID NO: 102, pNit-RC1 having a nucleotide sequence represented by SEQ ID NO: 105, pNit-RC2 having a nucleotide sequence represented by SEQ ID NO: 106, pNit-QT1 having a nucleotide sequence represented by SEQ ID NO: 99, pNit-QT2 having a nucleotide sequence represented by SEQ ID NO: 100, pNit-QC1 having a nucleotide sequence represented by SEQ ID NO: 103, and pNit-QC2 having a nucleotide sequence represented by SEQ ID NO: 104;

[6] The expression vector of [4] or [5], wherein the bacterium belonging to the genus *Rhodococcus* is selected from the group consisting of *R. erythropolis*, *R. fascians*, and *R. opacus*;

[7] The expression vector of any one of [4] to [6], wherein the vector further comprises a DNA region necessary for the autonomous replication of a plasmid for *Escherichia coli*, and being capable of replication in *Escherichia coli*;

[8] A transformant comprising an expression vector of any one of [4] to [7]; and

[9] A method of producing a recombinant protein at the temperatures ranging from 4° C. to 35° C. by using an expression vector of any one of [4] to [7].

In addition, the present invention is as follows:

[10] A circular plasmid that replicates in the rolling-circle mode, isolated from a bacterium belonging to the genus *Rhodococcus*;

[11] The circular plasmid of [10] isolated from a bacterium belonging to the genus *Rhodococcus*, having a Rep gene, a double-stranded origin (DSO), and a single-stranded origin (SSO) essential for the rolling circle mode of replication;

[12] The circular plasmid of [11], wherein a nucleotide sequence of DNA essential for the rolling circle mode of replication is a nucleotide sequence at positions 3845 to 5849 in a nucleotide sequence represented by SEQ ID NO: 90;

[13] The plasmid of any one of [10] to [12], having DNA having a nucleotide sequence represented by SEQ ID NO: 90 or DNA that hybridizes under stringent conditions to DNA having a complementary sequence to the DNA whose nucleotide sequence is represented by SEQ ID NO: 90;

[14] A transformant comprising a circular plasmid of any one of [10] to [12];

[15] An expression vector that replicates in the rolling-circle mode, being capable of expression a foreign gene under a temperature ranging from 4° C. to 35° C. in a bacterium belonging to the genus *Rhodococcus*;

[16] The expression vector of [15] having a Rep gene, a double-stranded origin (DSO), and a single-stranded origin (SSO) essential for the rolling-circle mode of replication, which originates from an endogenous plasmid isolated from a bacterium belonging to the genus *Rhodococcus*;

[17] The expression vector of [16], wherein a nucleotide sequence of DNA essential for the rolling circle mode of replication is a nucleotide sequence at positions 3845 to 5849 in a nucleotide sequence represented by SEQ ID NO: 90;

[18] The expression vector of any one of [15] to [17], comprising an inducible promoter sequence for inducing a foreign gene expression, a ribosome-binding site sequence located downstream of the promoter sequence, and a multiple-cloning site sequence capable of incorporating a foreign gene therein, located downstream of the ribosome-binding site sequence;

[19] The expression vector of [18], wherein the inducible promoter for inducing expression is a TipA gene promoter and an inducer is thiostrepton;

[20] The expression vector of [4], wherein a nucleotide sequence of the promoter consists of a nucleotide sequence of DNA of any one of [1] to [3];

[21] The inducible expression vector for a bacterium belonging to the genus *Rhodococcus* of any one of [15] to [19], wherein the vector is selected from the group consisting of pTip-RT1 having a nucleotide sequence represented by SEQ ID NO: 93, pTip-RT2 having a nucleotide sequence represented by SEQ ID NO: 94, pTip-RC1 having a nucleotide sequence represented by SEQ ID NO: 97, and pTip-RC2 having a nucleotide sequence represented by SEQ ID NO: 98;

[22] An expression vector capable of expressing a foreign gence consititutively under temperature ranging from 4° C. to 35° C. in a bacterium belonging to the genus *Rhodococcus*, comprising a plasmid pRE2895-derived DNA sequence necessary for the autonomous replication of a plasmid in a bacterium belonging to the genus *Rhodococcus* and a promoter sequence DNA of any one of [1] to [3];

[23] The expression vector of [22], wherein the plasmid pRE2895-derived DNA sequence necessary for the autonomous replication of a plasmid in a bacterium belonging to the genus *Rhodococcus* is a DNA sequence of a 1.9-kb region containing RepA and RepB genes;

[24] The expression vector of [22] or [23], further comprising a ribosome-binding site sequence located downstream of the constitutive promoter sequence and a multiple-cloning site sequence capable of incorporating a foreign gene therein, located downstream of the ribosome-binding site sequence;

[25] The constitutive expression vector for a bacterium belonging to the genus *Rhodococcus* of any one of [22] to [24], wherein the vector is selected from the group consisting of pNit-QT1 having a nucleotide sequence represented by SEQ ID NO: 99, pNit-QT2 having a nucleotide sequence represented by SEQ ID NO: 100, pNit-QC1 having a nucleotide sequence represented by SEQ ID NO: 103, and pNit-QC2 having a nucleotide sequence represented by SEQ ID NO: 104;

[26] A bacterium belonging to the genus *Rhodococcus* having at least two types of plasmids:
(i) which are all derived from a bacterium belonging to the genus *Rhodococcus*,
(ii) which do not cause plasmid incompatibility with each other,
(iii) one of which has a DNA sequence involved in rolling-circle mode of replication and one of the other plasmids has DNA sequence derived from pRE2895 for autonomous replication;

[27] A bacterium belonging to the genus *Rhodococcus* having at least two types of expression plasmid vectors:
(i) which are all derived from a bacterium belonging to the genus *Rhodococcus*,
(ii) which do not cause plasmid incompatibility with each other,
(iii) which carry genes encoding foreign proteins to be coexpressed under a temperature ranging from 4° C. to 35° C.,
(iv) one of which has a DNA sequence involved in rolling-circle mode of replication and one of the other plasmids has DNA sequence derived from pRB2895 for autonomous replication;

[28] The bacterium belonging to the genus *Rhodococcus* of [27], wherein all of the two types of plasmid vectors respectively comprise a promoter sequence for foreign protein production, a ribosome-binding site sequence located downstream of the promoter sequence, and a multiple-cloning site sequence capable of incorporating a foreign gene therein, located downstream of the ribosome-binding site sequence;

[29] The bacterium belonging to the genus *Rhodococcus* of [27] or [28], wherein one of the at least two types of plasmid vectors is a vector of any one of [4], [5], [15] to [19], [20], and [21] and another is a vector of any one of [22] to [25] or a vector capable of inducible expression where a TipA gene promoter that serves as a inducible promoter is substituted for at least a promoter in the vector of any one of [22] to [25];

[30] The bacterium belonging to the genus *Rhodococcus* of any one [27] to [29], wherein one of the at least two types of plasmid vectors is a vector of any one of [4], [5], [15] to [19], [20], and [21] and another is a vector selected from the group consisting of pTip-NH1 having a nucleotide sequence represented by SEQ ID NO: 49, pTip-NH2 having a nucleotide sequence represented by SEQ ID NO: 50, pTip-CH1 having a nucleotide sequence represented by SEQ ID NO: 51, pTip-CH2 having a nucleotide sequence represented by SEQ ID NO: 52, pTip-LNH1 having a nucleotide sequence represented by SEQ ID NO: 53, pTip-LNH2 having a nucleotide sequence represented by SEQ ID NO: 54, pTip-LCH1 having a nucleotide sequence represented by SEQ ID NO: 55, pTip-LCH2 having a nucleotide sequence represented by SEQ ID NO: 56, pTip-QT1 having a nucleotide sequence represented by SEQ ID NO: 91, pTip-QT2 having a nucleotide sequence represented by SEQ ID NO: 92, pTip-QC1 having a nucleotide sequence represented by SEQ ID NO: 95, pTip-QC2 having a nucleotide sequence represented by SEQ ID NO: 96, pTip-CH1.1, pTip-CH2.1, pTip-LCH1.1, pTip-LCH2.1, a vector of any one of [22] to [25], or a vector capable of inducible expression where a TipA gene promoter that serves as a inducible promoter is substituted for at least a promoter in the vector of any one of [22] to [25];

[31] The bacterium belonging to the genus *Rhodococcus* of any one of [26] to [30], wherein the DNA sequence essential for the rolling circle mode of replication is a DNA sequence at positions 3845 to 5849 in a nucleotide sequence represented by SEQ ID NO: 90 and the DNA sequence necessary for the autonomous replication of a plasmid derived from pRE2895 is a DNA sequence of a 1.9-kb region containing RepA and RepB genes;

[32] A method of producing foreign proteins by transforming a bacterium belonging to the genus *Rhodococcus* with at least two types of expression plasmid vectors, culturing the bacterium, and coexpressing genes encoding foreign proteins that are respectively contained in the expression vectors under a temperature condition of 4° C. to 35° C., the bacterium belonging to the genus *Rhodococcus* comprising at least the two types of expression plasmid vectors derived from the bacterium belonging to the genus *Rhodococcus* that do not cause plasmid incompatibility with each other and comprise the genes encoding foreign protein, the at least two types of vectors each having a DNA sequence that is derived from the bacterium belonging to the genus *Rhodococcus* and has the rolling circle mode of replication and a DNA sequence necessary for the autonomous replication of a plasmid derived from pRE2895 as DNA sequences necessary for the autonomous replication of a plasmid;

[33] The method of [32], wherein all of the two types of plasmid vectors respectively comprise a promoter sequence for foreign protein production, a ribosome-binding site sequence located downstream of the promoter sequence, and a multiple-cloning site sequence capable of incorporating a foreign gene therein, located downstream of the ribosome-binding site sequence;

[34] The method of any one of [32] to [33], wherein one of the at least two types of plasmid vectors is a vector of any one of [4], [5], [15] to [19], [20], and [21] and another is a vector selected from the group consisting of pTip-NH1 having a nucleotide sequence represented by SEQ ID NO: 49, pTip-NH2 having a nucleotide sequence represented by SEQ ID NO: 50, pTip-CH1 having a nucleotide sequence represented by SEQ ID NO: 51, pTip-CH2 having a nucleotide sequence represented by SEQ ID NO: 52, pTip-LNH1 having a nucleotide sequence represented by SEQ ID NO: 53, pTip-LNH2 having a nucleotide sequence represented by SEQ ID NO: 54, pTip-LCH1 having a nucleotide sequence represented by SEQ ID NO: 55, pTip-LCH2 having a nucleotide sequence represented by SEQ ID NO: 56, pTip-QT1 having a nucleotide sequence represented by SEQ ID NO: 91, pTip-QT2 having a nucleotide sequence represented by SEQ ID NO: 92, pTip-QC1 having a nucleotide sequence represented by SEQ ID NO: 95, pTip-QC2 having a nucleotide sequence represented by SEQ ID NO: 96, pTip-CH1.1, pTip-CH2.1, pTip-LCH1.1, pTip-LCH2.1, a vector of any one of [22] to [25], or a vector capable of inducible expression where a TipA gene promoter that serves as a inducible promoter is substituted for at least a promoter in the vector of any one of [22] to [25]; and

[35] The method of any one of [32] to [34], wherein a nucleotide sequence of the DNA essential for the rolling circle mode of replication is a nucleotide sequence at positions 3845 to 5849 in a nucleotide sequence represented by SEQ ID NO: 90 and the DNA sequence necessary for the autonomous replication of a plasmid derived from pRE2895 is DNA composed of a 1.9-kb region containing RepA and RepB genes.

Hereinafter, the present invention will be described in detail.

The present invention encompasses a circular plasmid capable of replicating in the rolling-circle mode, isolated from a bacterium belonging to the genus *Rhodococcus*, and an expression vector constructed from the circular plasmid. The rolling circle mode of replication refers to a mode of replication of double-stranded circular DNA, in which a particular site on a particular DNA strand is nicked by the action of specific endonuclease and DNA synthesis starts from the 3'-OH end of the nicked site and takes a round of the circle with an unnicked circular DNA strand as a template. Such a mode of replication requires a DNA region necessary for the rolling circle mode of replication. Examples of the DNA region include a Rep gene. The rolling circle mode of replication further requires a double-stranded origin (DSO) and a single-stranded origin (SSO). Thus, the circular plasmid capable of replicating in the rolling-circle mode and the expression vector constructed from the circular plasmid of the present invention are a plasmid and an expression vector comprising a DNA region necessary for the rolling circle mode of replication, that is, a Rep gene, a double-stranded origin (DSO), and a single-stranded origin (SSO). Such a plasmid can be isolated from a bacterium belonging to the genus *Rhodococcus*. Examples of the plasmid include pRE8424 isolated from a *Rhodococcus erythropolis* strain DSM8424, and the full-length sequence of the pRE8424 is shown in SEQ ID NO: 90. In SEQ ID NO: 90, a region at positions 3845 to 5849 represents the DNA region necessary for the rolling circle mode of replication, that is, the DNA of the Rep gene, the double-stranded origin (DSO), and the single-stranded origin (SSO).

The present invention also encompasses a plasmid capable of replicating in the rolling-circle mode, which is composed of DNA that hybridizes under stringent conditions to DNA complementary to DNA constituting a plasmid represented by SEQ ID NO: 90. The stringent conditions used here refer to, for example, such conditions that a sodium concentration is 500 to 1000 mM, preferably 700 mM, and a temperature is 50 to 70° C., preferably 65° C. Such a plasmid is a plasmid whose full-length nucleotide sequence has 90% or more homology, preferably 95% or more homology, more preferably 98% or more homology to a nucleotide sequence represented by SEQ ID NO: 90 in calculation using BLAST or the like (e.g., using a default, i.e., a initialized parameter).

The present invention further encompasses an expression vector comprising a Rep gene, a double-stranded origin (DSO), and a single-stranded origin (SSO) as a DNA region necessary for the rolling circle mode of replication obtained from the plasmid and further comprising a promoter sequence, a ribosome-binding site sequence located downstream of the promoter sequence, and a multiple-cloning site sequence capable of incorporating a foreign gene therein, located downstream of the ribosome-binding site sequence. The expression vector may further contain a foreign gene and a transcription termination sequence. The DNA sequence having promoter activity, the foreign gene, and the transcription termination sequence constitute an expression cassette. The promoter sequence used here includes a promoter capable of inducer (such as a drug)-inducible expression of a foreign gene introduced downstream thereof and a promoter capable of inducer-independent and constitutive expression of a foreign gene. Examples of the former promoter capable of inducible expression of a foreign gene include a TipA gene promoter that inducibly expresses a foreign gene located downstream thereof in the presence of thiostrepton. The vector of the present invention may comprise a TipA gene encoding a TipA protein and an appropriate promoter inducing the expression of the TipA gene, such as a ThcA gene promoter. The TipA gene and the promoter for the expression of the TipA gene constitute an inducer cassette. When a host cell is a bacterium belonging to the genus *Rhodococcus*, a thiostrepton resistance gene or the like that imparts resistance to thiostrepton is incorporated into the vector because the bacterium is sensitive to thiostrepton. In addition, the TipA gene promoter may be any of those obtained by modifying the sequence of the TipA gene promoter, such as a TipA-LG10 promoter. The sequence of a mutant TipA gene promoter is shown as SEQ ID NO: 170 in FIG. 12.

Examples of the latter promoter capable of constitutive expression of a foreign gene include a modified promoter of the TipA gene promoter. Examples of such a modified TipA gene promoter include a promoter where a mutation is introduced into a −10 region sequence of the TipA gene promoter, and specifically include a promoter where the mutation in the −10 region sequence is a mutation of a CAGCGT sequence to a TATAAT sequence. Such a promoter can be exemplified by a promoter contained in a sequence shown in FIG. 19.

A polynucleotide consisting of DNA that hybridizes under stringent conditions to DNA complementary to DNA having a promoter sequence shown in FIG. 12 or DNA having a promoter sequence contained in a sequence shown in FIG. 19, and having activity equivalent to the activity of each of the promoter sequence can also be used as the promoter. The stringent conditions used here refer to, for example, such conditions that a sodium concentration is 500 to 1000 mM, preferably 700 mM, and a temperature is 50 to 70° C., preferably 65° C. Such a polynucleotide is a promoter whose full-length nucleotide sequence has 90% or more homology, preferably 95% or more homology, more preferably 98% or more homology to the nucleotide sequences of the above-described promoters in calculation using BLAST or the like (e.g., using a default, i.e., a initialized parameter).

The present invention further includes a vector composed of the above-described vector and further comprising a DNA region necessary for the autonomous replication of a plasmid for *Escherichia coli* and a selection marker for the transformant of *Escherichia coli*. Such a vector can be used as a shuttle vector between a bacterium belonging to the genus *Rhodococcus* and *Escherichia coli*. In this case, the vector can be used as a constitutive expression vector in *Escherichia coli*. Any of those known in the art such as ColE1 and ColE2 sequences can be used as the DNA region necessary for the autonomous replication of a plasmid for *Escherichia coli*, and any of those known in the art such as an ampicillin resistance gene can be used as the selection marker for the transformant of *Escherichia coli*. These can be obtained from a cloning vector for *Escherichia coli* known in the art.

An expression vector for *Rhodococcus* comprising a TipA gene promoter, and a DNA region necessary for the rolling circle mode of replication, that is, a double-stranded origin (DSO) and a single-stranded origin (SSO), and further comprising a ribosome-binding site sequence located downstream of the promoter sequence, a multiple-cloning site sequence capable of incorporating a foreign gene therein, located down stream of the ribosome-binding site sequence, and a DNA region necessary for the autonomous replication of a plasmid for *Escherichia coli* can be exemplified by pTip-RT1 having a nucleotide sequence represented by SEQ ID NO: 93, pTip-RT2 having a nucleotide sequence represented by SEQ ID NO: 94, pTip-RC1 having a nucleotide sequence represented by SEQ ID NO: 97, and pTip-RC2 having a nucleotide sequence represented by SEQ ID NO: 98. A vector having, instead of the TipA gene promoter, a promoter where a mutation in the −10 region sequence of the TipA gene promoter is a mutation of a CAGCGT sequence to a TATAAT sequence can be exemplified by pNit-RT1 having a nucleotide sequence represented by SEQ ID NO: 101, pNit-RT2 having a nucleotide sequence represented by SEQ ID NO: 102, pNit-RC1 having a nucleotide sequence represented by SEQ ID NO: 105, and pNit-RC2 having a nucleotide sequence represented by SEQ ID NO: 106. The present invention also encompasses a vector composed of DNA that hybridizes under stringent conditions to DNA complementary to DNA composed of any of the nucleotide sequences represented by these SEQ ID NOs and capable of expressing a foreign gene in a host microorganism. The stringent conditions used here refer to, for example, such conditions that a sodium concentration is 500 to 1000 mM, preferably 700 mM, and a temperature is 50 to 70° C., preferably 65° C. Such a vector is a vector whose full-length nucleotide sequence has 90% or more homology, preferably 95% or more homology, more preferably 98% or more homology to the nucleotide sequences represented by SEQ ID NOs of the above-described vectors in calculation using BLAST or the like (e.g., using a default, i.e., a initialized parameter). The same goes for vectors represented below by SEQ ID NOs.

The present invention also encompasses an expression vector comprising an alternative DNA region necessary for autonomous replication, other than the above-described DNA region (Rep gene, DSO, and SSO) necessary for the rolling circle mode of replication. Expression vectors having different DNA regions necessary for replication can be introduced simultaneously into a single host and maintained stably. Examples of the alternative DNA region necessary for autonomous replication include a RepA gene and a RepB gene. A DNA region containing the RepA gene and the RepB gene can be isolated from an endogenous plasmid pRE2895 separated from a bacterium belonging to the genus *Rhodococcus*, for example, a *R. erythropolis* strain JCM2895. A 1.9-kb region containing the RepA gene and the RepB gene is a region at positions 6233 to 8166 in SEQ ID NO: 49, of which RepA ORF is located at positions 6756 to 7652 and RepB ORF is located at positions 7652 to 7936. The DNA region containing the RepA gene and the RepB gene can be obtained by reference to the restriction map (FIG. 1) of a vector pHN129 described in Reference Example below. DNA that hybridizes under stringent conditions to DNA complementary to DNA consisting of a nucleotide sequence represented by positions 6233 to 8166 in SEQ ID NO: 49 and imparts autonomous replication ability to a vector can also be used as the 1.9-kb region containing the RepA gene and the RepB gene of the present invention. The stringent conditions used here refer to, for example, such conditions that a sodium concentration is 500 to 1000 mM, preferably 700 mM, and a temperature is 50 to 70° C., preferably 65° C. Such DNA is DNA whose full-length nucleotide sequence has 90% or more homology, preferably 95% or more homology, more preferably 98% or more homology to the nucleotide sequence represented by positions 6233 to 8166 in SEQ ID NO: 49 in calculation using BLAST or the like (e.g., using a default, i.e., a initialized parameter). An expression vector comprising this DNA region necessary for autonomous replication, a promoter having a −10 region sequence of a TipA gene promoter mutated from a CAGCGT sequence to a TATAAT sequence, a ribosome-binding site sequence located downstream of the promoter, and a multiple-cloning site sequence capable of incorporating a foreign gene therein, located downstream of the ribosome-binding site sequence allows the inducer-independent and constitutive expression of the foreign gene incorporated in the multiple-cloning site. Examples of such an expression vector include a constitutive expression vector for a bacterium belonging to the genus *Rhodococcus* selected from the group consisting of pNit-QT1 having a nucleotide sequence represented by SEQ ID NO: 99, pNit-QT2 having a nucleotide sequence represented by SEQ ID NO: 100, pNit-QC1 having a nucleotide sequence represented by SEQ ID NO: 103, and pNit-QC2 having a nucleotide sequence represented by SEQ ID NO: 104, and further include pTip-NH1 having a nucleotide sequence represented by SEQ ID NO: 49, pTip-NH2 having a nucleotide sequence represented by SEQ ID NO: 50, pTip-CH1 having a nucleotide sequence represented by SEQ ID NO: 51, pTip-CH2 having a nucleotide sequence represented by SEQ ID NO: 52, pTip-LNH1 having a nucleotide sequence represented by SEQ ID NO: 53, pTip-LNH2 having a nucleotide sequence represented by SEQ ID NO: 54, pTip-LCH1 having a nucleotide sequence represented by SEQ ID NO: 55, pTip-LCH2 having a nucleotide sequence represented by SEQ ID NO: 56, and a vector where the promoter having a −10 region sequence of the TipA gene promoter mutated from a CAGCGT sequence to a TATAAT sequence is substituted for the inducible promoter of pTip-CH1.1, pTip-CH2.1, pTip-LCH1.1, and pTip-LCH2.1, all of which allow the inducible expression of an introduced foreign gene in the presence of thiostrepton. It is noted that the inducible expression vector needs to further contain an inducer cassette containing a TipA gene or a mutant thereof and a promoter for the expression of the TipA gene as well as a thiostrepton resistance gene.

A foreign gene can be expressed by incorporating the foreign gene into the above-described expression vector of the present invention, introducing the expression vector into a host microorganism, and culturing the host microorganism. The incorporation of the foreign gene into the expression vector can be performed by a genetic engineering approach known in the art, and the introduction of the expression vector into the host microorganism can also be performed by an approach known in the art. In addition, the culture of the host microorganism may be performed under appropriate conditions using a medium suitable for each microorganism. Examples of a host organism into which the vector is incorporated include bacteria belonging to the genus *Rhodococcus* and *Escherichia coli*. The foreign gene used here refers to a gene encoding a target protein to be expressed using the vector of the present invention and encoding a protein derived from an organism other than a host cell. The protein to be expressed and produced using the vector of the present invention is not limited, and any protein can be the target protein. When a host organism into which the expression vector of the present invention is introduced is a microorganism capable of proliferation at low temperatures, for example, a bacterium belonging to the genus *Rhodococcus* such as *R. erythropolis*, *R. fascians*, and *R. opacus*, it is possible to express and produce a protein whose expression is difficult or impossible under a typical temperature condition suitable for the proliferation of a microorganism, that is, at moderate and high temperatures exceeding approximately 15° C. Examples of such a protein include: a protein that can not be expressed at temperatures falling within the optimum growth temperature range of a host cell but can be expressed at temperatures lower than temperatures falling within the preferred growth temperature range of the same or a different type of host microorganism cell; a protein that is lethal to a host microorganism cell when expressed at temperatures falling within the preferred growth temperature range of the host microorganism cell but is not lethal its host cell at temperatures lower than temperatures falling within the preferred growth temperature ranges of the same or the different type of host cell; a protein that inhibits the proliferation of a host cell when expressed at temperatures falling within the preferred growth temperature range of the host cell but does not inhibit the proliferation of its host cell at temperatures lower than temperatures falling within the preferred growth temperature ranges of the same or the different type of host cell; a protein that forms the agglutination of inactive proteins called an inclusion body when expressed at temperatures falling within the preferred growth temperature range of a host cell but becomes a soluble protein with activity when expressed in its host cell at temperatures lower than temperatures falling within the preferred growth temperature ranges of the same or the different type of host cell; and a protein derived from a psychrophile with a preferred growth temperature range not higher than 20° C., from a poikilotherm surviving under low temperature atmosphere, and from a plant surviving under low temperature atmosphere.

When a promoter contained in the expression vector is an inducible promoter, the expression and production of a foreign gene can be induced by adding an inducer to the culture medium of a host microorganism. Examples of the inducible promoter contained in the expression vector of the present invention include a TipA gene promoter. When the gene promoter is contained, the expression and production of a foreign gene is induced by the addition of thiostrepton. In this case, the thiostrepton may be added at a final concentration of 0.1 µg/ml or more, preferably 1 µg/ml or more. However, the addition of thiostrepton at a final concentration of 10 µg/ml or more deteriorates the growth of a host. When the expression vector of the present invention contains a constitutive promoter, a foreign gene is expressed and produced without the addition of an inducer.

Of the expression vectors of the present invention, the expression vectors having different DNA regions necessary for autonomous replication from each other can be cotransformed simultaneously into a single microorganism cell and thereby maintained stably in the cell to simultaneously express and produce foreign genes respectively contained in the vectors. In this case, the foreign genes respectively contained in the vectors may be those encoding the same or different proteins. For example, the subunits of a protein consisting of two subunits are respectively incorporated into separate expression vectors having different DNA regions necessary for autonomous replication from each other, and the expression vectors are introduced into an identical microorganism cell. As a result, the subunits are simultaneously expressed in the single cell and associated with each other to produce a complete protein. In this case, the expression vectors may be used in any combination of those capable of constitutive expression of a foreign gene and those capable of inducible expression of a foreign gene. Expression vectors capable of inducible expression of foreign genes are used as all of several expression vectors having different DNA regions necessary for autonomous replication, and the expression of the foreign genes is induced by an expression inducer, thereby allowing the simultaneous expression and production of two or more types of foreign proteins.

In addition, two types of proteins can also be expressed simultaneously in *Escherichia coli* by selecting different replications origins for *Escherichia coli* for the expression vectors of the present invention.

The present specification encompasses the contents described in the specification and/or drawings of Japanese Patent Application No. 2003-116280 that serves as a basis for the priority of the present application.

BRIEF DESCRIPTION OF THE DRAWINGS

FIG. 9a is a diagram showing the maps of the plasmids pTip-NH1, pTip-CH1, pTip-LNH1, pTip-LNH1, pTip-NH2, pTip-CH2, pTip-LNH2, and pTip-LCH2. The function of each region and the maps of the plasmids are shown; 6×His tags disclosed as SEQ ID NO: 168.

FIG. 15 is diagram showing the amino acid sequences of five motifs (Motif IV, Motif I, Motif II, Motif III, and C-terminal motif) that are conserved in Rep proteins among pRE8424 (SEQ ID NOS: 126-130), pAP1 (SEQ ID NOS: 131-135 ), pBL1 (SEQ ID NOS: 136-139), pJV1 (SEQ ID NOS: 140-144), pIJ101 (SEQ ID NO: 145-149), and pSN22 (SEQ ID NO: 150-154). A tyrosine residue allegedly important for the function of the Rep protein is boxed;

FIG. 16 is a diagram showing an especially conserved DNA sequence, of sequences likely to be the DSOs of the pRE8424 (SEQ ID NO: 155), the pAP1 (SEQ ID NO: 156), the pBL1 (SEQ ID NO: 157), the pJV1 (SEQ ID NO: 158), the pIJ101 (SEQ ID NO: 159), and the pSN22 (SEQ ID NO: 160);

FIG. 18-1 is a diagram showing the map of a pTip vector;

FIG. 18-2 is a diagram showing the map of a pNit vector;

BEST MODE FOR CARRYING OUT THE INVENTION

Figure 1:
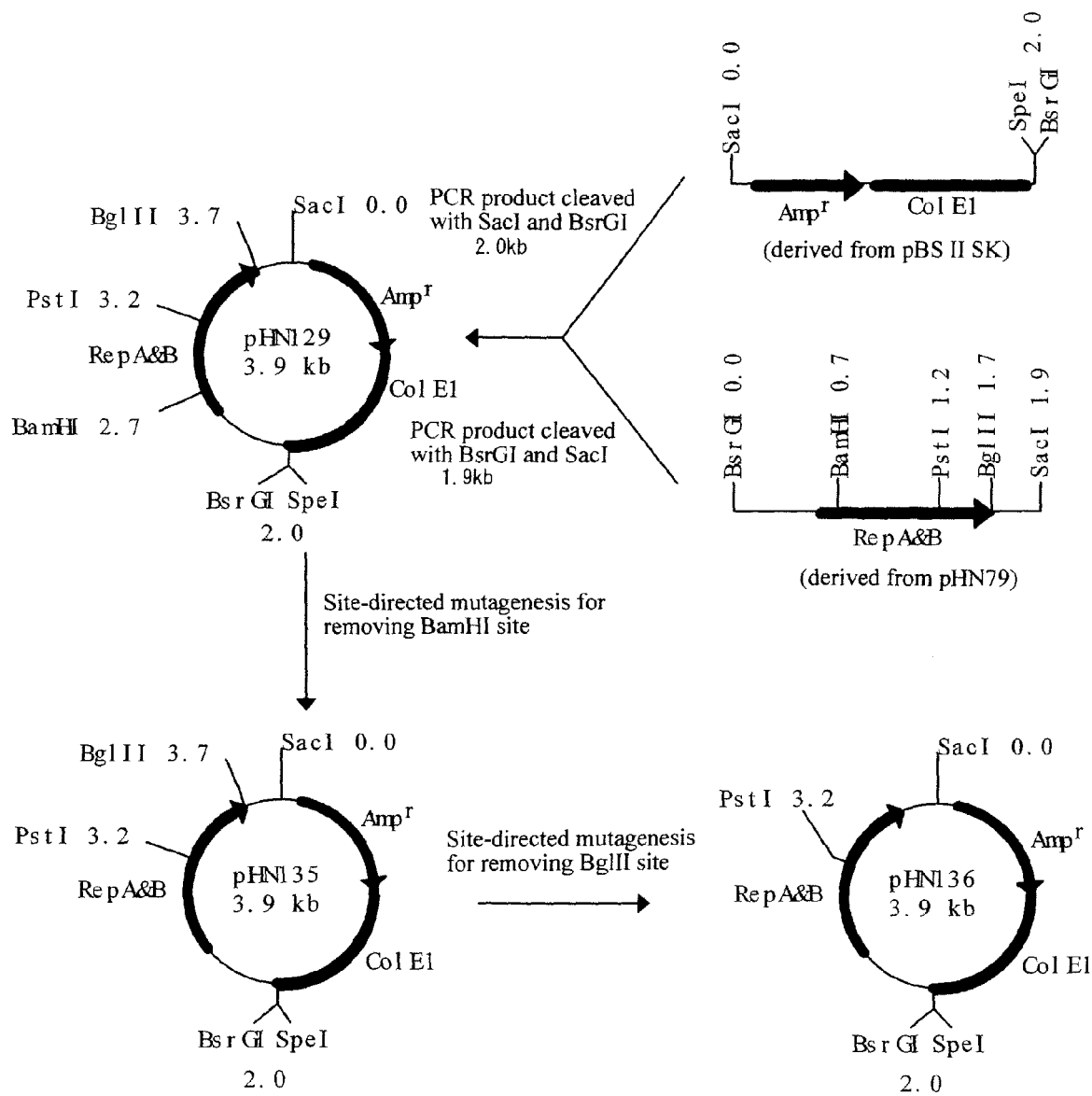
FIG. 1 is a diagram for illustrating the construction of a plasmid pHN136 that serves as the backbone of inducible expression vectors. In the drawing, the locations of restriction enzyme recognition sites and structural genes are shown. A numeric represents a base pair (kilobase pair: kb)

Hereinafter, the present invention will be described more fully with reference to Examples. However, the technical scope of the present invention is not intended to be limited to these Examples.

REFERENCE EXAMPLE 1

(1) Separation of a *Rhodococcus Erythropolis*-derived Plasmid Capable of Autonomous Replication in Bacterium Belonging to the Genus *Rhodococcus* and Determination of its Partial DNA Sequence For constructing a shuttle vector between *Rhodococcus erythropolis* and *Escherichia coli*, a small endogenous plasmid present in a bacterium belonging to the genus *Rhodococcus* was initially searched. As a result, its presence was confirmed in a *Rhodococcus erythropolis* strain JCM2895. This plasmid was designated as pRE2895. Hereinafter, the separation of the plasmid and the determination of its DNA sequence will specifically be described.

The QIAprep Spin Miniprep Kit (manufactured by QIAGEN) was used to purify pRE2895 from the cells of a *Rhodococcus erythropolis* strain JCM2895 cultured at 30° C. for 30 hours in 5 ml of a LB medium (1% Difco Bacto Tryptone, 0.5% Difco Yeast Extract, and 1.0% sodium chloride). These procedures were conducted according to the instruction except that the bacterial cells were supplemented with 5 µl of lysozyme (100 mg/ml) and incubated at 37° C. for 30 minutes before the addition of 250 µl of Buffer P2 following suspension in 250 µl of Buffer P1.

When the above-described DNA sample was treated with a restriction enzyme EcoRI and subjected to 1.0% agarose gel electrophoresis (100 V, 30 minutes), the presence of one DNA fragment of approximately 5.4 kb was confirmed.

This DNA fragment of approximately 5.4 kb was cut out of the gel and purified using the QIAquick Gel Extraction Kit (manufactured by QIAGEN) according to the instruction. The obtained EcoRI fragment was subcloned into the EcoRI site of a plasmid pBluescript II SK(+) (manufactured by STRATAGENE) according to an ordinary method (Sambrook et al., Molecular Cloning: a laboratory manual, 2nd edition [1989], Cold Spring Harbor Laboratory Press, Cold Spring Harbor, N.Y.). This plasmid was designated as pHN79.

The nucleotide sequence of the pHN79 was determined by approximately 400 bases at a time using both reverse and M13-20 primers (both manufactured by STRATAGENE) and using a DNA sequencer ABI PRISM(R) 3100 Genetic Analyzer (manufactured by ABI) according to the instruction. As a result of homology search, 99.8% of the sequence of the *Rhodococcus erythropolis* strain JCM2895-derived DNA region subcloned into the pHN79 matched to that of pN30, a circular DNA having 5403 base pairs registered as Accession No. AF312210 in the GenBank.

The full nucleotide sequence of the separated pRE2895 was not determined. However, because the pRE2895 has high homology to the pN30 and its restriction enzyme cleavage map also matched to that predicted from the sequence of the pN30, this homology between the pRE2895 and the pN30 was estimated to extend throughout the plasmids. Moreover, the pN30 has high homology to an endogenous plasmid pAL5000 (Rauzer et al., Gene 71 315-321 [1988]; and Stolt and Stoker, Microbiology 142 2795-2802 [1996]) separated from a *Mycobacterium fortuitum* strain 002 and pFAJ2600 (De Mot et al., Microbiology 143 3137-3147 [1997]) separated from a *Rhodococcus erythropolis* strain NI86/21, and they were considered to autonomously replicate in similar mechanisms. Because only a region containing a putative RepA gene, a putative RepB gene, and a putative replication origin is sufficient for the autonomous replication of the pAL5000 in each bacterium, the incorporation of only a similar region into an expression vector was also considered to be sufficient for the autonomous replication of the pRE2895 separated by the present inventors in a bacterium belonging to the genus *Rhodococcus*.

(2) Construction of a Vector Plasmid pHN136

To construct shuttle vector between *Escherichia coli* and *Rhodococcus erythropolis*, the following procedures were performed (FIG. 1).

Synthetic oligodeoxyribonucleotide primers (hereinafter, abbreviated to primers) represented by SEQ ID NOs: 1 and 2 in the sequence listing were used to perform DNA amplification by a polymerase chain reaction method (hereinafter, abbreviated to PCR; Saiki et al., Science, 239 487-491 [1988]) with a plasmid pBluescript II SK(−) (manufactured by STRATAGENE) as a template. An enzyme used for PCR is the Pfu turbo (manufactured by STRATAGENE). As a result, a 2.0-kb amplified DNA containing an ampicillin resistance gene (indicated by Amp$^r$ in the drawings) and a ColE1 sequence region necessary for autonomous replication in *Escherichia coli* was obtained. This DNA fragment was doubly digested with restriction enzymes SacI and BsrGI and subjected to 1.0% agarose gel electrophoresis (100 V, 30 minutes). The DNA fragment was cut out of the gel and purified using the QIAquick Gel Extraction Kit according to the instruction.

On the other hand, primers that amplify a region likely to be necessary for autonomous replication in a bacterium belonging to the genus *Rhodococcus* were designed on the basis of the sequence of the pN30 (the above (1)). The sequences of the primers are shown in SEQ ID NOs: 3 and 4 in the sequence listing. Both of the primers were used to perform amplification by PCR with the plasmid pHN79 as a template to yield a 1.9-kb amplified DNA. This DNA fragment was doubly digested with restriction enzymes BsrGI and SacI and subjected to 1.0% agarose gel electrophoresis (100 V, 30 minutes). The DNA fragment was cut out of the gel and purified in the same way as above.

These two purified DNA fragments were ligated to a plasmid using the DNA Ligation Kit Ver. 2 (manufactured by Takara Shuzo) according to the instruction. The resulting plasmid was designated as pHN129.

For eliminating restriction enzyme recognition sites BamHI and SalI present in the pHN129, the following procedures were performed. At first, primers represented by SEQ ID NOs: 5 and 6 in the sequence listing were used to perform amplification by PCR with the pHN129 as a template. A 0.5-kb DNA fragment obtained by doubly digesting this PCR fragment with BglII and PstI was subcloned into the BamHI and PstI sites of the pHN129. Consequently, although the portion of the ligation between BglII and BamHI was situated within the open reading frame (hereinafter, abbreviated to ORF) of the putative RepA gene, the BamHI recognition site was eliminated without any substitution in encoded amino acids. The SalI recognition site had been located in close proximity to the BamHI recognition site and however, was also eliminated simultaneously with the elimination of the BamHI recognition site because the primer represented by SEQ ID NO: 5 was designed so that the SalI recognition site was eliminated without any substitution in encoded amino acids. This plasmid was designated as pHN135.

Next, for eliminating a restriction enzyme recognition site BglII present in the pHN135, the following procedures were performed. At first, primers represented by SEQ ID NOs: 5 and 6 in the sequence listing were used to perform amplification by PCR with the plasmid pHN135 as a template. A 0.5-kb DNA fragment obtained by doubly digesting this PCR fragment with PstI and BamHI was subcloned into the PstI and BglII sites of the pHN135. Consequently, although the portion of the ligation between BamHI and BglII was the ORF portion of the putative RepB gene, the BglII recognition site was eliminated without any substitution in encoded amino acids. The resulting plasmid was designated as pHN136.

(3) Construction of a Vector Plasmid pHN143

Figure 2:
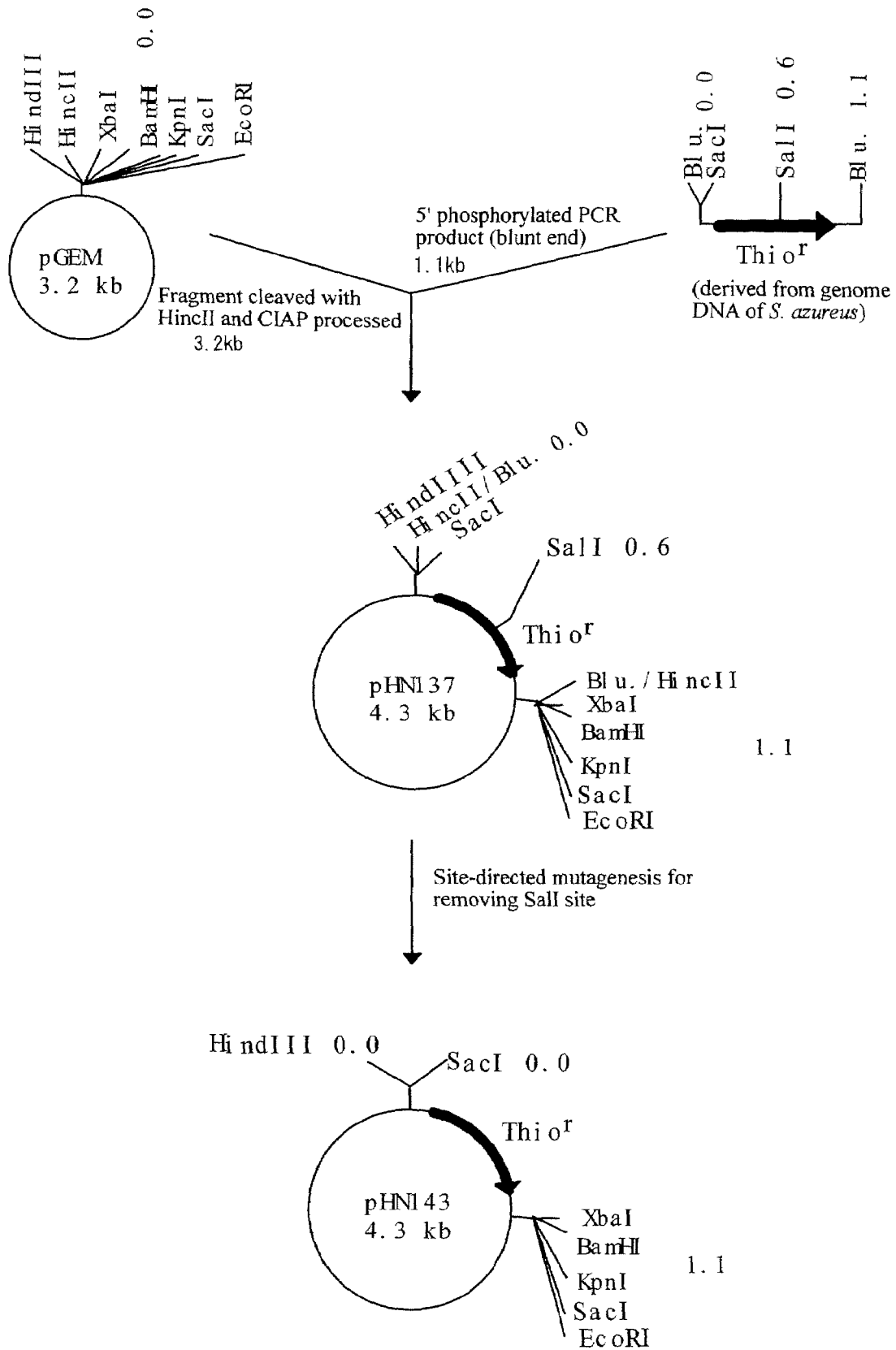
FIG. 2 is a diagram for illustrating the construction of a plasmid pHN143 having a thiostrepton resistance gene. In the drawing, the locations of restriction enzyme recognition sites and structural genes are shown. A numeric represents a base pair (kilobase pair: kb). CIAP means calf intestine alkaline phosphatase, and Blu. means a blunt end.

Although an antibiotic thiostrepton is used for inducing protein expression, *Rhodococcus erythropolis* is sensitive to the antibiotic. Therefore, thiostrepton resistance must be imparted to *Rhodococcus erythropolis*. Thus, it has been decided that a thiostrepton resistance gene, a tsr gene, of *Streptomyces azureus* (Bibb et al., Mol. Gen. Genet. 199 26-36 [1985]; indicated by Thio$^r$ in the drawings) is incorporated into the shuttle vector. It has been already reported that this gene functions in *Rhodococcus erythropolis* and imparts thiostrepton resistance (Shao and Behki, Lett. Appl. Microbiol. 21 261-266 [1995]). Hereinafter, the separation of the gene will specifically be described (FIG. 2).

The genomic DNA of a *Streptomyces azureus* strain JCM4217 used as a PCR template was prepared as follows. The strain cultured at 30° C. in 5 ml of a SB medium (1% Difco Bacto Tryptone, 0.5% Difco Yeast Extract, 0.5% sodium chloride, 0.1% glucose, 5 mM magnesium chloride, and 0.5% glycine) was suspended in 500 µl of a SET buffer (75 mM sodium chloride, 25 mM EDTA [pH 8.0], and 20 mM Tris-HCl [pH 7.5]). To this suspension, 5 µl of a lysozyme solution (100 mg/ml) was added and incubated at 37° C. for 30 minutes. The resulting mixture solution was then supplemented with 14 µl of a protease K solution (20 mg/ml) and 60 µl of a sodium dodecyl sulfate solution (10%) and sufficiently mixed, followed by incubation at 55° C. for 2 hours. The resulting mixture solution was then supplemented with 200 µl of a sodium chloride solution (5 M) and 500 µl of chloroform and stirred by rotation at room temperature for 20 minutes. Following centrifugation, 700 µl of a supernatant was obtained. After this supernatant was subjected to isopropanol precipitation, the resulting DNA pellet was dried and dissolved in 50 µl of a TE solution (10 mM Tris-HCl [pH 8.0] and 1 mM EDTA [pH 8.0]).

Primers represented by SEQ ID NOs: 7 and 8 in the sequence listing were used to perform amplification by PCR using the genomic DNA of the *Streptomyces azureus* strain JCM4217 purified as described above as a template. As a result, a 1.1-kb amplified DNA containing the thiostrepton resistance gene was obtained. The ends of this DNA fragment were blunt ends because the Platinum Pfx DNA Polymerase (manufactured by Gibco BRL) was used in the PCR. This DNA fragment was purified, and its 5' ends were phosphorylated with T4 polynucleotide kinase according to an ordinary method (Sambrook et al., Molecular Cloning: a laboratory manual, 2nd edition [1989], Cold Spring Harbor Laboratory Press, Cold Spring Harbor, N.Y.). Then, the DNA fragment was subcloned into the HincII site of a plasmid pGEM-3Zf(+) (manufactured by Promega) (subcloned in the orientation of HindIII recognition site-tsr gene ORF-EcoRI recognition site in the 5' to 3' direction of the DNA). This plasmid was designated as pHN137.

Next, for eliminating a restriction enzyme recognition site SalI present in the pHN137, the following procedures were performed. At first, primers represented by SEQ ID NOs: 9 and 10 in the sequence listing were used to perform amplification by PCR with the plasmid pHN137 as a template. The Platinum Pfx DNA Polymerase was used in this PCR. A 0.6-kb DNA fragment obtained by digesting the ends on one side of this PCR fragment with HindIII was purified, and its 5' end on the blunt end side was phosphorylated with T4 polynucleotide kinase according to an ordinary method. On the other hand, primers represented by SEQ ID NOs: 11 and 12 in the sequence listing were used to perform amplification by PCR with the plasmid pHN137 as a template. The Platinum Pfx DNA Polymerase was used in this PCR. A 0.5-kb DNA fragment obtained by digesting the ends on one side of this PCR fragment with EcoRI was purified, and its 5' end on the blunt end side was phosphorylated with T4 polynucleotide kinase according to an ordinary method. These two PCR fragments were simultaneously subcloned into the HindIII and EcoRI sites of a plasmid pGEM-3Zf(+). Consequently, although the portion of the ligation between blunt ends was the ORF portion of the tsr gene, the SalI recognition site was eliminated without any substitution in the encoded amino acids. This plasmid was designated as pHN143.

(4) Construction of a Vector Plasmid pHN62

Figure 3:
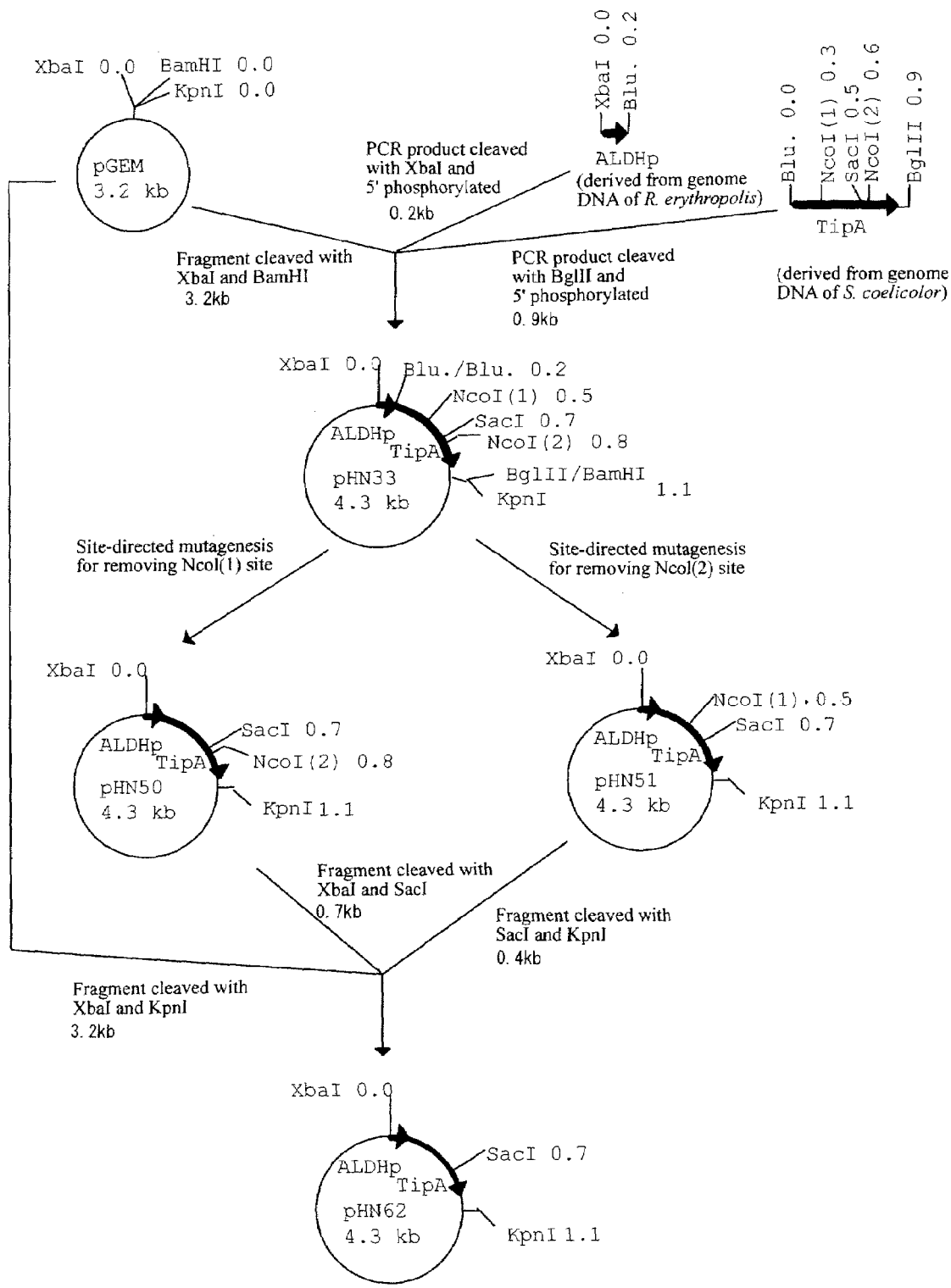
FIG. 3 is a diagram for illustrating the construction of a plasmid pHN62 having an inducer cassette. In the drawing, the locations of restriction enzyme recognition sites and structural genes are shown. A numeric represents a base pair (kilobase pair: kb). Blu. means a blunt end.

For thiostrepton-inducible expression, a TipA protein must be present in a bacterium belonging to the genus *Rhodococcus*. Therefore, a constitutive promoter was separated from *Rhodococcus erythropolis*, and a structural gene encoding the TipA protein was ligated downstream of the promoter (FIG. 3). The promoter sequence of a ThcA gene (Nagy et al., J. Bacteriol. 177 676-687 [1995]) encoding the aldehyde dehydrogenase-like protein of *Rhodococcus erythropolis* was used as the constitutively functioning promoter.

The genomic DNA of a *Streptomyces coelicolor* strain A3(2) used as a template was prepared and purified in the same procedures as those for the preparation of the genomic DNA from *Streptomyces azureus*. In addition, the genomic DNA of a *Rhodococcus erythropolis* strain JCM3201 was prepared and purified in the same procedures as those for the preparation of the genomic DNA from *Streptomyces azureus* except that the strain JCM3201 was cultured in 5 ml of a LB medium.

Primers represented by SEQ ID NOs: 13 and 14 in the sequence listing were used to perform amplification by PCR using the genomic DNA of the *Streptomyces coelicolor* strain A3(2) purified as described above as a template. The Platinum Pfx DNA Polymerase was used in this PCR. As a result, DNA (indicated by TipA in the drawings) containing the ORF of the TipA gene and a transcription termination sequence located downstream thereof was obtained.

A 0.9-kb DNA fragment obtained by digesting the ends on one side of this PCR fragment with BglII was purified, and its 5' end on the blunt end side was phosphorylated with T4 polynucleotide kinase according to an ordinary method. On the other hand, primers represented by SEQ ID NOs: 15 and 16 in the sequence listing were used to perform amplification by PCR using the genomic DNA of the *Rhodococcus erythropolis* strain JCM3201 purified as described above as a template. As a result, DNA containing the promoter sequence (indicated by ALDHp in the drawings) of the ThcA gene (Nagy et al., J. Bacteriol. 177 676-687 [1995]) encoding the aldehyde dehydrogenase-like protein was obtained. The Platinum Pfx DNA Polymerase was used in this PCR. A 0.2-kb DNA fragment obtained by digesting the ends on one side of this PCR fragment with XbaI was purified, and its 5' end on the blunt end side was phosphorylated with T4 polynucleotide kinase according to an ordinary method. These two PCR fragments were simultaneously subcloned into the XbaI and BamHI sites of a plasmid pGEM-3Zf(+). Consequently, a plasmid containing the ORF of the TipA gene and the transcription termination sequence located immediately downstream of the promoter sequence of the ThcA gene was constructed and designated as pHN33.

Next, for eliminating two NcoI restriction enzyme recognition sites (hereinafter, indicated by NcoI(1) and NcoI(2)) present in the pHN33, the following procedures were performed.

At first, primers represented by SEQ ID NOs: 9 and 17 in the sequence listing were used to perform amplification by PCR with the plasmid pHN33 as a template. The Platinum Pfx DNA Polymerase was used in this PCR. A 0.5-kb DNA fragment obtained by digesting the ends on one side of this PCR fragment with XbaI was purified, and its 5' end on the blunt end side was phosphorylated with T4 polynucleotide kinase according to an ordinary method. On the other hand, primers represented by SEQ ID NOs: 18 and 12 in the sequence listing were used to perform amplification by PCR with the plasmid pHN33 as a template. The Platinum Pfx DNA Polymerase was used in this PCR. A 0.6-kb DNA fragment obtained by digesting the ends on one side of this PCR fragment with KpnI was purified, and its 5' end on the blunt end side was phosphorylated with T4 polynucleotide kinase according to an ordinary method. These two PCR fragments were simultaneously subcloned into the XbaI and KpnI sites of a plasmid pGEM-3Zf(+). Consequently, although the portion of the ligation between blunt ends was the ORF portion of the TipA gene, the NcoI(1) recognition site was eliminated without any substitution in encoded amino acids. This plasmid was designated as pHN50.

Next, for eliminating the restriction enzyme recognition site NcoI(2) present in the pHN33, the following procedures were performed. At first, primers represented by SEQ ID NOs: 9 and 19 in the sequence listing were used to perform amplification by PCR with the plasmid pHN33 as a template. The Platinum Pfx DNA Polymerase was used in this PCR. A 0.8-kb DNA fragment obtained by digesting the ends on one side of this PCR fragment with XbaI was purified, and its 5' end on the blunt end side was phosphorylated with T4 polynucleotide kinase according to an ordinary method. On the other hand, primers represented by SEQ ID NOs: 20 and 12 in the sequence listing were used to perform amplification by PCR with the plasmid pHN33 as a template. The Platinum Pfx DNA Polymerase was used in this PCR. A 0.3-kb DNA fragment obtained by digesting the ends on one side of this PCR fragment with KpnI was purified, and its 5' end on the blunt end side was phosphorylated with T4 polynucleotide kinase according to an ordinary method. These two PCR fragments were simultaneously subcloned into the XbaI and KpnI sites of a plasmid pGEM-3Zf(+). Consequently, although the portion of the ligation between blunt ends was the ORF portion of the TipA gene, the NcoI(2) recognition site was eliminated without any substitution in encoded amino acids. This plasmid was designated as pHN51.

In the last place, the following procedures were performed. A 0.7-kb DNA fragment obtained by doubly digesting the pHN50 with XbaI and SacI and a 0.4-kb fragment obtained by doubly digesting the pHN51 with SacI and KpnI were simultaneously subcloned into the XbaI and KpnI sites of a plasmid pGEM-3Zf(+). Consequently, a plasmid having the TipA gene but lacking both NcoI(1) and NcoI(2) restriction sites was obtained and designated as pHN62.

(5) Construction of a Vector Plasmid pHN153

Figure 4:
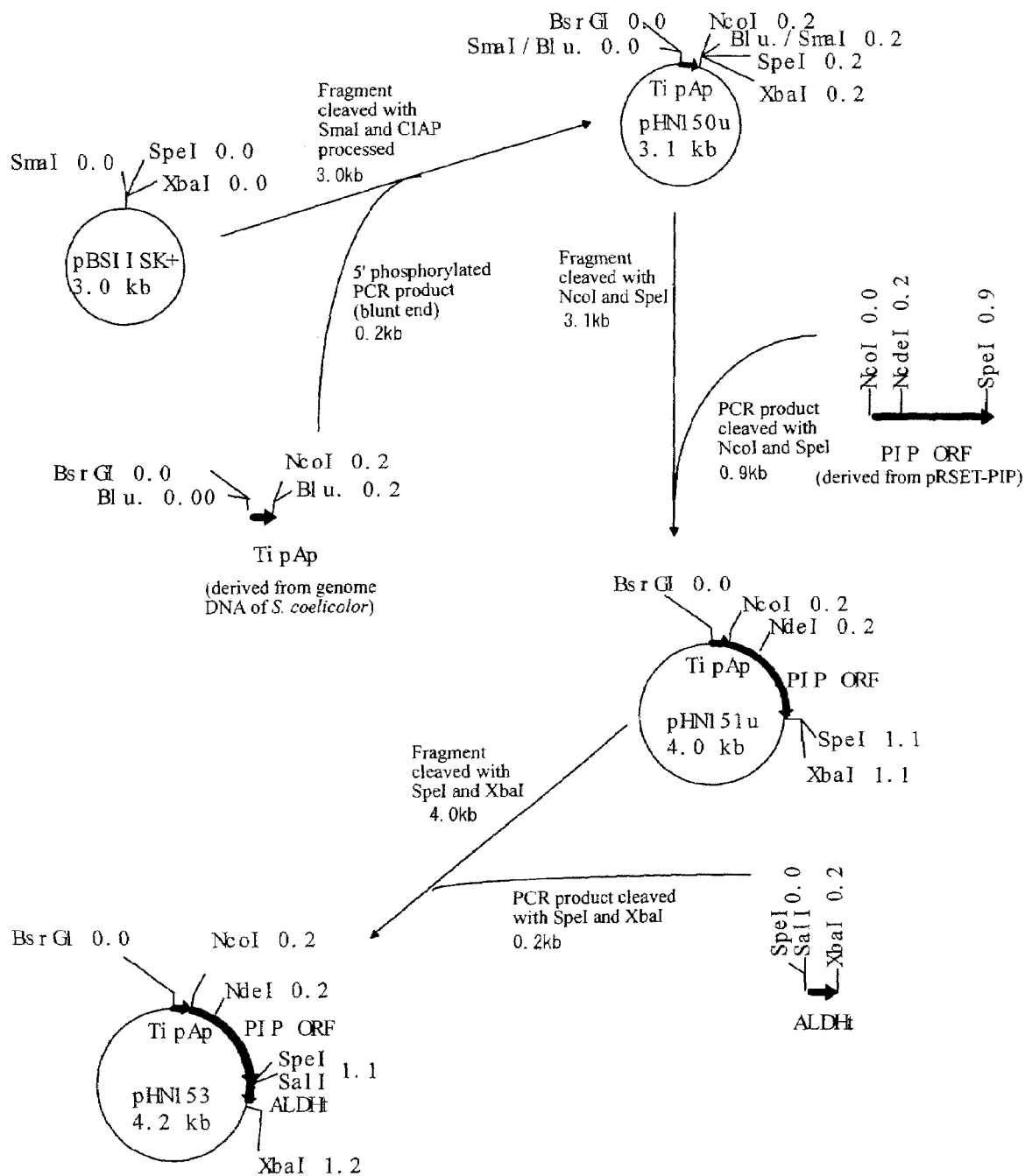
FIG. 4 is a diagram for illustrating the construction of a plasmid pHN153 having an expression cassette. In the drawing, the locations of restriction enzyme recognition sites and structural genes are shown. A numeric represents a base pair (kilobase pair: kb). CIAP means calf intestine alkaline phosphatase, and Blu. means a blunt end.

For confirming whether a protein of interest can be inducibly expressed, the ORF (indicated by PIP ORF in the drawings) of a gene encoding *Thermoplasma acidophilum*-derived proline iminopeptidase (Tamura et al., FEBS Lett. 398 101-105 [1996]; hereinafter, abbreviated to PIP) was ligated, as a reporter gene, downstream of the TipA gene promoter, and a transcription termination sequence was further ligated downstream of the ORF for suppressing transcriptional readthrough. Hereinafter, the procedures will specifically be described (FIG. 4).

Primers represented by SEQ ID NOs: 21 and 22 in the sequence listing were used to perform amplification by PCR using the genomic DNA of the *Streptomyces coelicolor* strain A3(2) purified in the above (4) as a template. As a result, a 0.2-kb amplified DNA containing the TipA gene promoter sequence (indicated by TipAp in the drawings) was obtained. The Platinum Pfx DNA Polymerase was used in this PCR. This DNA fragment was purified, and its 5' ends were phosphorylated with T4 polynucleotide kinase according to an ordinary method. Then, the DNA fragment was subcloned into the SmaI site of a plasmid pBluescript II SK(+) (subcloned in the orientation of KpnI recognition site-TipA gene promoter sequence-SacI recognition site in the 5' to 3' direction of the DNA). This plasmid was designated as pHN150u.

Next, primers represented by SEQ ID NOs: 23 and 24 in the sequence listing were used to perform amplification by PCR with a plasmid pRSET-PIP (Tamura et al., FEBS Lett. 398 101-105 [1996]; hereinafter, abbreviated to PIP) as a template. The primer represented by SEQ ID NO: 24 in the sequence listing is designed so that 6×His tag (SEQ ID NO: 168) is attached to the C terminus of a PIP protein in order to eliminate the termination codon of the PIP gene and facilitate protein purification. The 6×His tag (SEQ ID NO: 168) is a consecutive sequence consisting of six consecutive histidine residues, and a protein fused with this tag exhibits high affinity for a nickel ion or the like. Thus, the protein is readily purified by metal chelate chromatography that employs the nickel ion or the like (Crowe et al., Methods Mol. Biol. 31 371-387 [1994]). This 0.9-kb DNA fragment containing the PIP gene was doubly digested with restriction enzymes NcoI and SpeI and subcloned into the NcoI and SpeI sites of the pHN150u. Consequently, a plasmid containing the ORF of the PIP gene located immediately downstream of the TipA gene promoter sequence was constructed and designated as pHN151u.

Next, primers represented by SEQ ID NOs: 25 and 26 in the sequence listing were used to perform amplification by PCR using the genomic DNA of the *Rhodococcus erythropolis* strain JCM3201 purified in the above (4) as a template. As a result, DNA containing the transcription termination sequence (Nagy et al., J. Bacteriol. 177 676-687 [1995], indicated by ALDHt in the drawings) of the ThcA gene was obtained. This 0.2-kb DNA fragment was doubly digested with restriction enzymes SpeI and XbaI and subcloned into the SpeI and XbaI sites of the pHN151u. Consequently, a plasmid containing the ORF of the PIP gene located immediately downstream of the TipA gene promoter sequence and the transcription termination sequence of the ThcA gene located immediately downstream of the ORF was constructed and designated as pHN153.

(6) Construction of a Vector Plasmid pHN169

Figure 5:
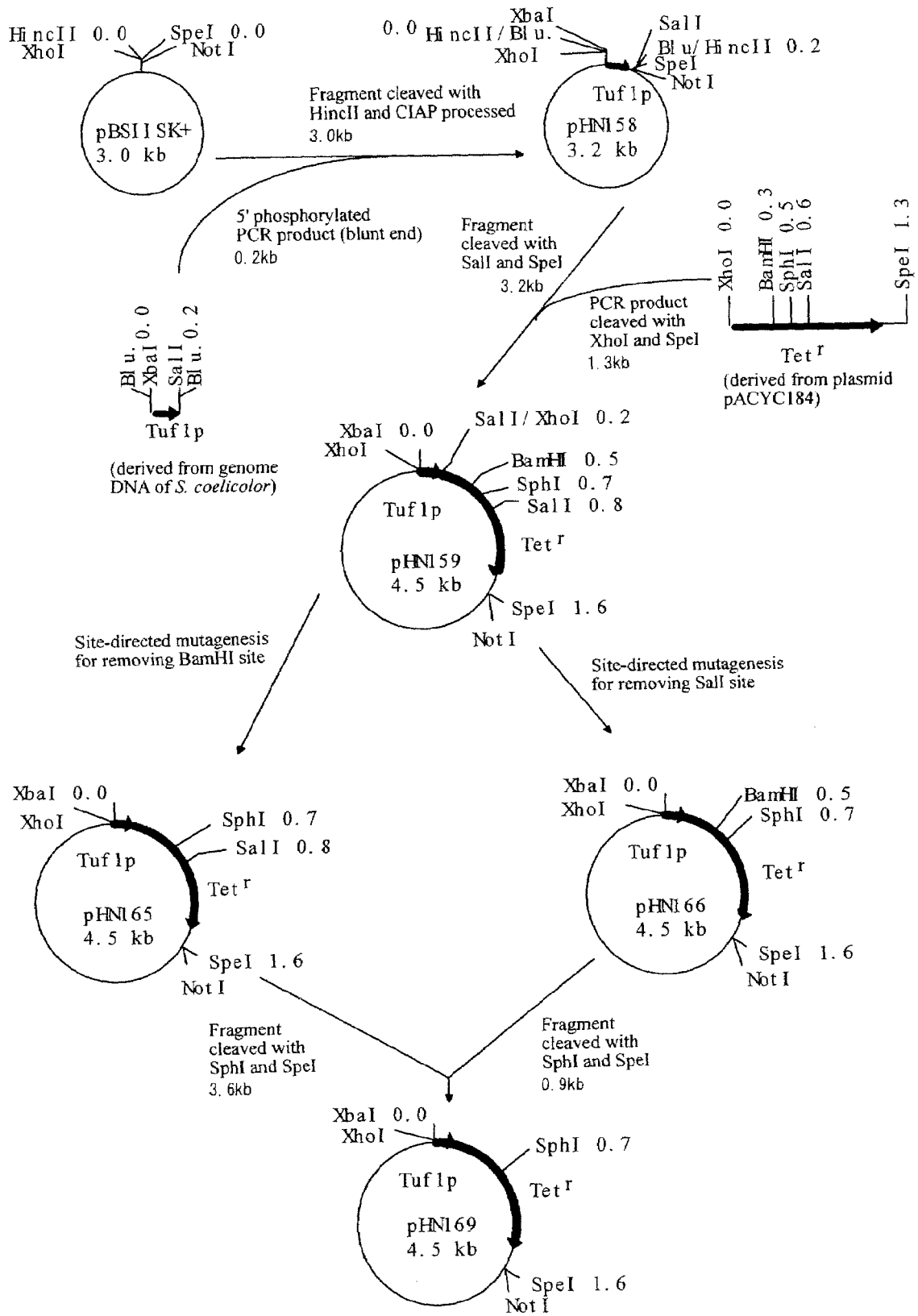
FIG. 5 is a diagram for illustrating the construction of a plasmid pHN169 having a tetracycline resistance gene. In the drawing, the locations of restriction enzyme recognition sites and structural genes are shown. A numeric represents a base pair (kilobase pair: kb). CIAP means calf intestine alkaline phosphatase, and Blu. means a blunt end.

The transformation of *Rhodococcus erythropolis* with a plasmid requires an appropriate transformation marker. Thus, it has been decided to use a drug resistance gene ligated downstream of a strong promoter that functions in a bacterium belonging to the genus *Rhodococcus*. It has been decided to use, as the promoter, the promoter of a *Streptomyces* bacterium-derived Tuf1 gene encoding an elongation factor Tu. This is because this promoter has been reported to strongly direct the transcription of a gene located downstream thereof (Wezel et al., Biochim. Biophys. Acta 1219 543-547 [1994]). Besides, a tetracycline resistance gene easily available was used as the drug resistance gene. Hereinafter, the procedures will specifically be described (FIG. 5).

Primers represented by SEQ ID NOs: 27 and 28 in the sequence listing were used to perform amplification by PCR using the genomic DNA of the *Streptomyces coelicolor* strain A3(2) purified in the above (4) as a template. As a result, a 0.2-kb amplified DNA containing the Tuf1 gene promoter sequence (indicated by Tuf1p in the drawings) was obtained. The Platinum Pfx DNA Polymerase was used in this PCR. This DNA fragment was purified, and its 5' ends were phosphorylated with T4 polynucleotide kinase according to an ordinary method. Then, the DNA fragment was subcloned into the HincII site of a plasmid pBluescript II SK(+) (subcloned in the orientation of KpnI recognition site-Tuf1 gene promoter sequence-EcoRI recognition site in the 5' to 3' direction of the DNA). This plasmid was designated as pHN158.

Next, primers represented by SEQ ID NOs: 29 and 30 in the sequence listing were used to perform amplification by PCR with a plasmid pACYC184 (Rose, Nucleic Acids Res. 16 355 [1988]) as a template. As a result, DNA containing the tetracycline resistance gene (indicated by Tet$^r$ in the drawings)

was obtained. This 1.3-kb DNA fragment was doubly digested with restriction enzymes XhoI and SpeI and subcloned into the SalI and SpeI sites of the pHN158. Consequently, a plasmid containing the tetracycline resistance gene located immediately downstream of the Tuf1 gene promoter sequence was constructed and designated as pHN159.

Next, for eliminating a restriction enzyme recognition site BamHI present in the pHN159, the following procedures were performed. At first, primers represented by SEQ ID NOs: 31 and 32 in the sequence listing were used to perform amplification by PCR with the plasmid pHN159 as a template. This DNA fragment had blunt ends because the Pfu turbo DNA Polymerase was used in the PCR. A 0.5-kb DNA fragment obtained by digesting the ends on one side of this PCR fragment with XhoI was purified, and its 5' end on the blunt end side was phosphorylated with T4 polynucleotide kinase according to an ordinary method. On the other hand, primers represented by SEQ ID NOs: 33 and 34 in the sequence listing were used to perform amplification by PCR with the plasmid pHN159 as a template. The Pfu turbo DNA Polymerase was used in this PCR. A 1.1-kb DNA fragment obtained by digesting the ends on one side of this PCR fragment with NotI was purified, and its 5' end on the blunt end side was phosphorylated with T4 polynucleotide kinase according to an ordinary method. These two PCR fragments were simultaneously subcloned into the XhoI and NotI sites of a plasmid pBluescript II SK(+). Consequently, although the portion of the ligation between blunt ends was the ORF portion of the tetracycline resistance gene, the BamHI recognition site was eliminated without any substitution in encoded amino acids. This plasmid was designated as pHN165.

Next, for eliminating a restriction enzyme recognition site SalI present in the pHN159, the following procedures were performed. At first, primers represented by SEQ ID NOs: 31 and 35 in the sequence listing were used to perform amplification by PCR with the plasmid pHN159 as a template. The Pfu turbo DNA Polymerase was used in this PCR. A 0.8-kb DNA fragment obtained by digesting the ends on one side of this PCR fragment with XhoI was purified, and its 5' end on the blunt end side was phosphorylated with T4 polynucleotide kinase according to an ordinary method. On the other hand, primers represented by SEQ ID NOs: 36 and 34 in the sequence listing were used to perform amplification by PCR with the plasmid pHN159 as a template. The Pfu turbo DNA Polymerase was used in this PCR. A 0.8-kb DNA fragment obtained by digesting the ends on one side of this PCR fragment with NotI was purified, and its 5' end on the blunt end side was phosphorylated with T4 polynucleotide kinase according to an ordinary method. These two PCR fragments were simultaneously subcloned into the XhoI and NotI sites of a plasmid pBluescript II SK(+). Consequently, although the portion of the ligation between blunt ends was the ORF portion of the tetracycline resistance gene, the SalI recognition site was eliminated without any substitution in encoded amino acids. This plasmid was designated as pHN166.

In the last place, the following procedures were performed. A 0.9-kb DNA fragment obtained by doubly digesting the pHN166 with SphI and SpeI was subcloned into the SphI and SpeI sites of the pHN165. Consequently, a tetracycline resistance gene clone lacking both restriction enzyme recognition sites BamHI and SalI was obtained, and this plasmid was designated as pHN169.

(7) Construction of Vector Plasmids pHN170 and pHN171

Figure 6:
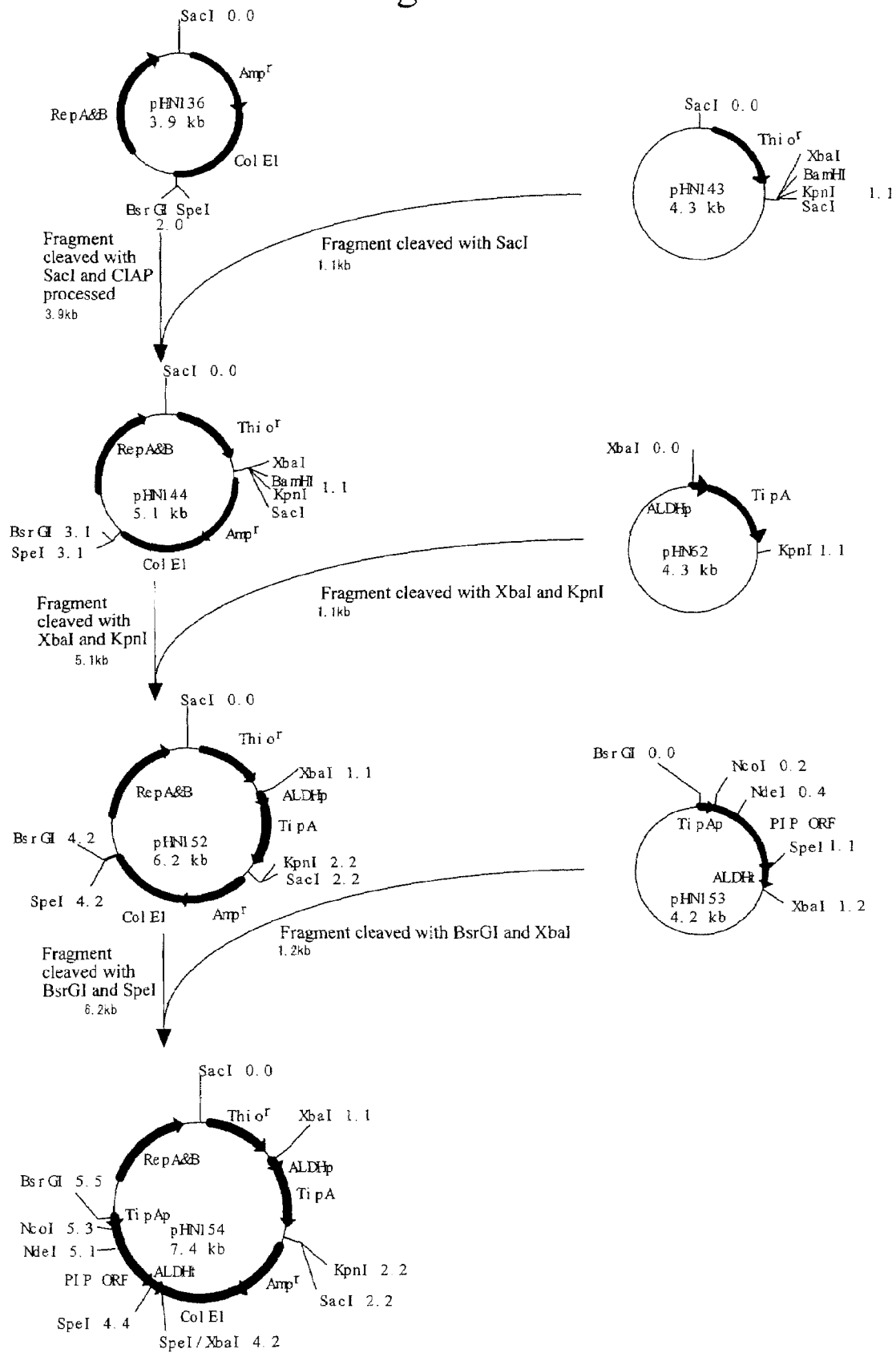
FIG. 6 is a diagram for illustrating the construction of inducible expression vector plasmids pHN170 and pHN171 having a PIP gene as a reporter gene. In the drawing, the locations of restriction enzyme recognition sites and structural genes are shown. A numeric represents a base pair (kilobase pair: kb). CIAP means calf intestine alkaline phosphatase.
Figure 6:
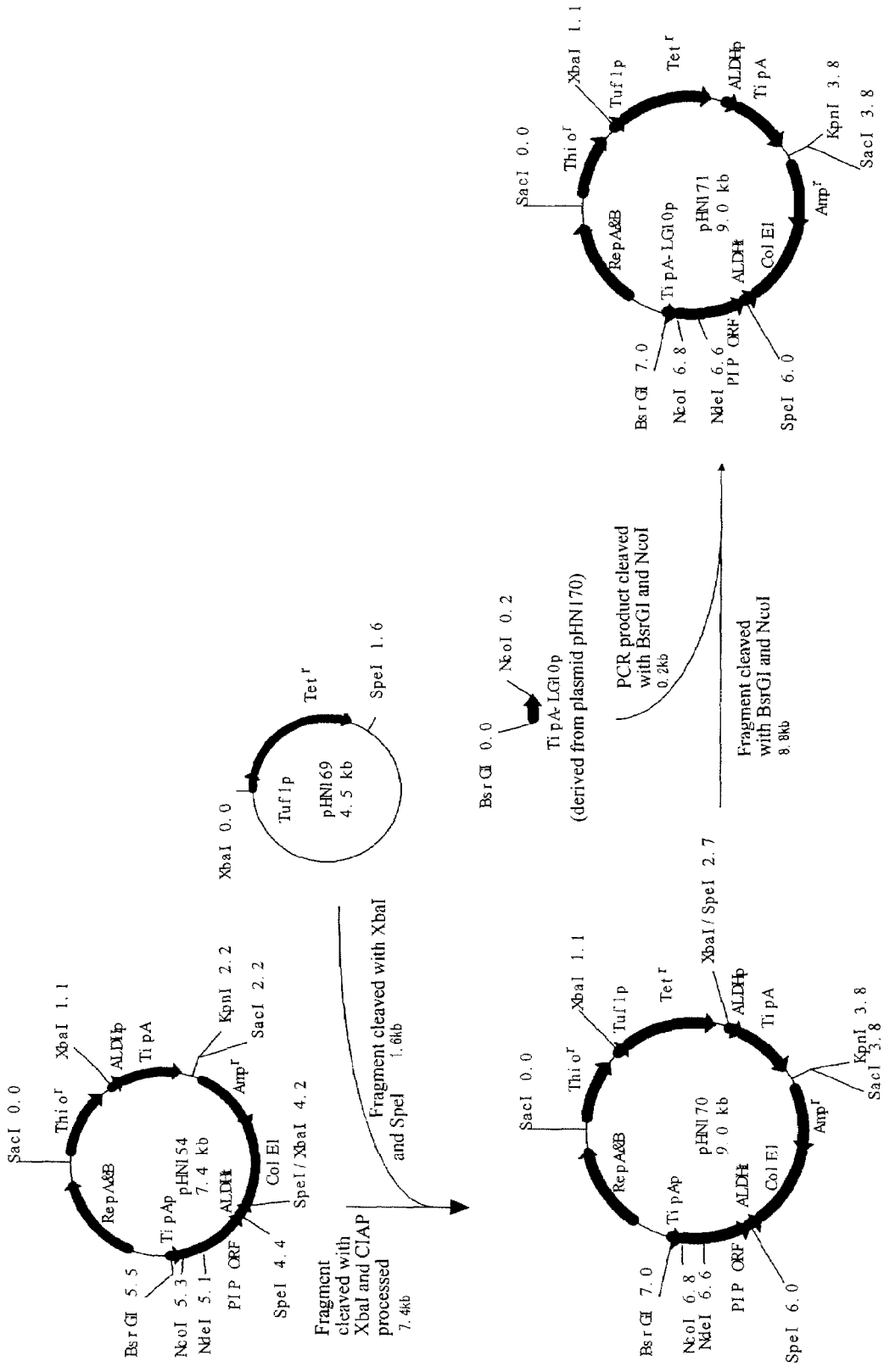

For ligating the genes separated in the above (2) to (6) to construct an expression vector inducible in a bacterium belonging to the genus *Rhodococcus*, the following procedures were performed (FIG. 6).

A 1.1-kb DNA fragment obtained by digesting the pHN143 with SacI was subcloned into the SacI site of the pHN136 (subcloned in the orientation of putative RepB gene ORF-tsr gene ORF-ampicillin resistance gene ORF in the 5' to 3' direction of the DNA). The resulting plasmid was designated as pHN144.

Next, a 1.1-kb DNA fragment obtained by doubly digesting the pHN62 with XbaI and KpnI was subcloned into the XbaI and KpnI sites of the pHN144. The resulting plasmid was designated as pHN152.

Subsequently, a 1.2-kb DNA fragment obtained by doubly digesting the pHN153 with BsrGI and XbaI was subcloned into the BsrGI and SpeI sites of the pHN152. The resulting plasmid was designated as pHN154.

Thereafter, a 1.6-kb DNA fragment obtained by doubly digesting the pHN169 with XbaI and SpeI was subcloned into the XbaI site of the pHN154 (subcloned in the orientation of tsr gene ORF-tetracycline resistance gene ORF-ThcA gene promoter sequence in the 5' to 3' direction of the DNA). Consequently, a plasmid containing the PIP gene placed under the control of the TipA gene promoter was constructed and designated as pHN170.

For the high-level expression of a recombinant protein, a ribosome-binding site located downstream of the TipA gene promoter was altered into a lambda phage gene 10-derived sequence (Gold and Stormo, Methods Enzymol. 185 89-93 [1990]) allegedly having good translation efficiency (FIG. 6). Hereinafter, the procedures will specifically be described.

Figure 12:
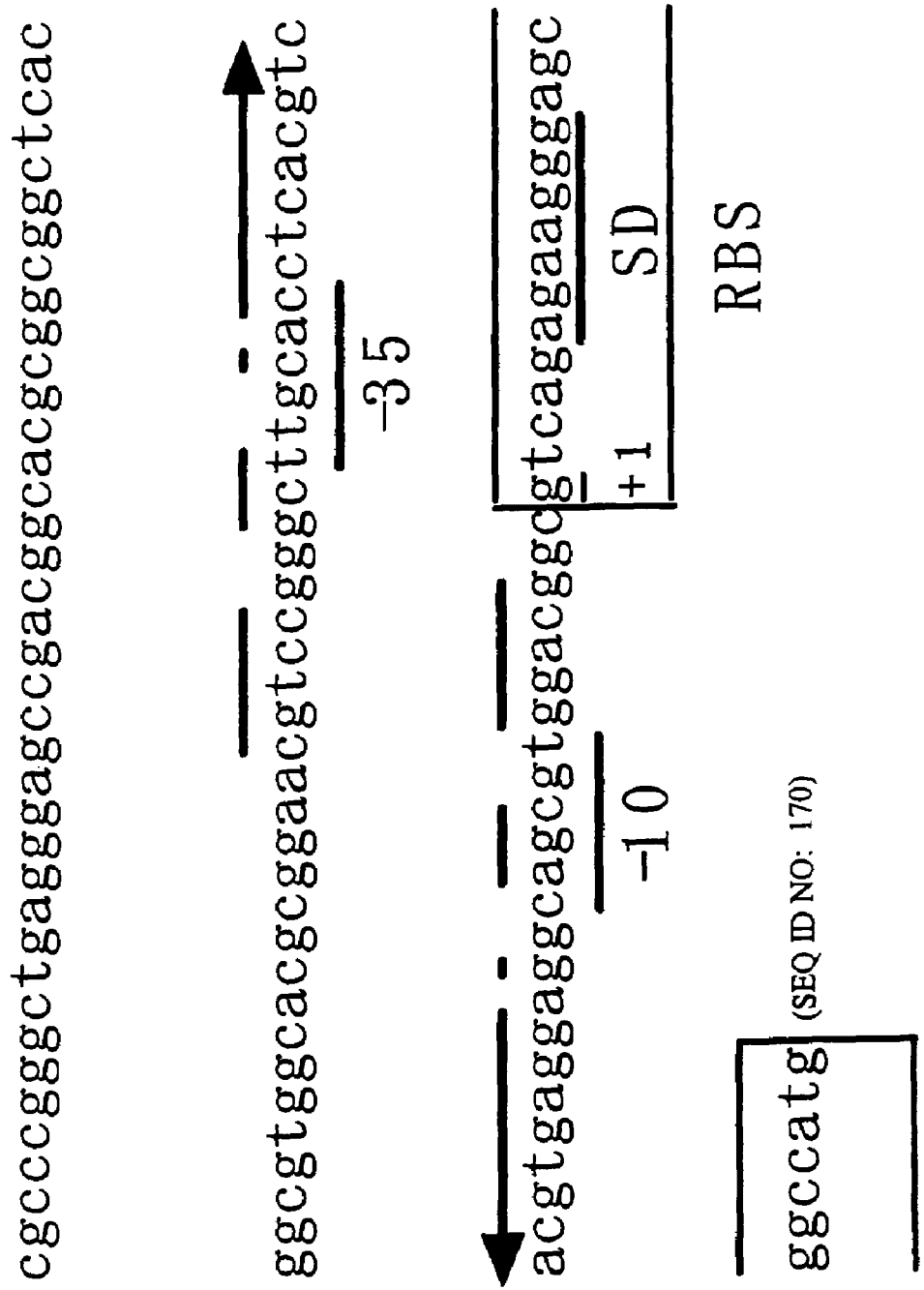
FIG. 12 is a diagram showing a mutant TipA gene promoter sequence (SEQ ID NO: 170)
Figure 13:
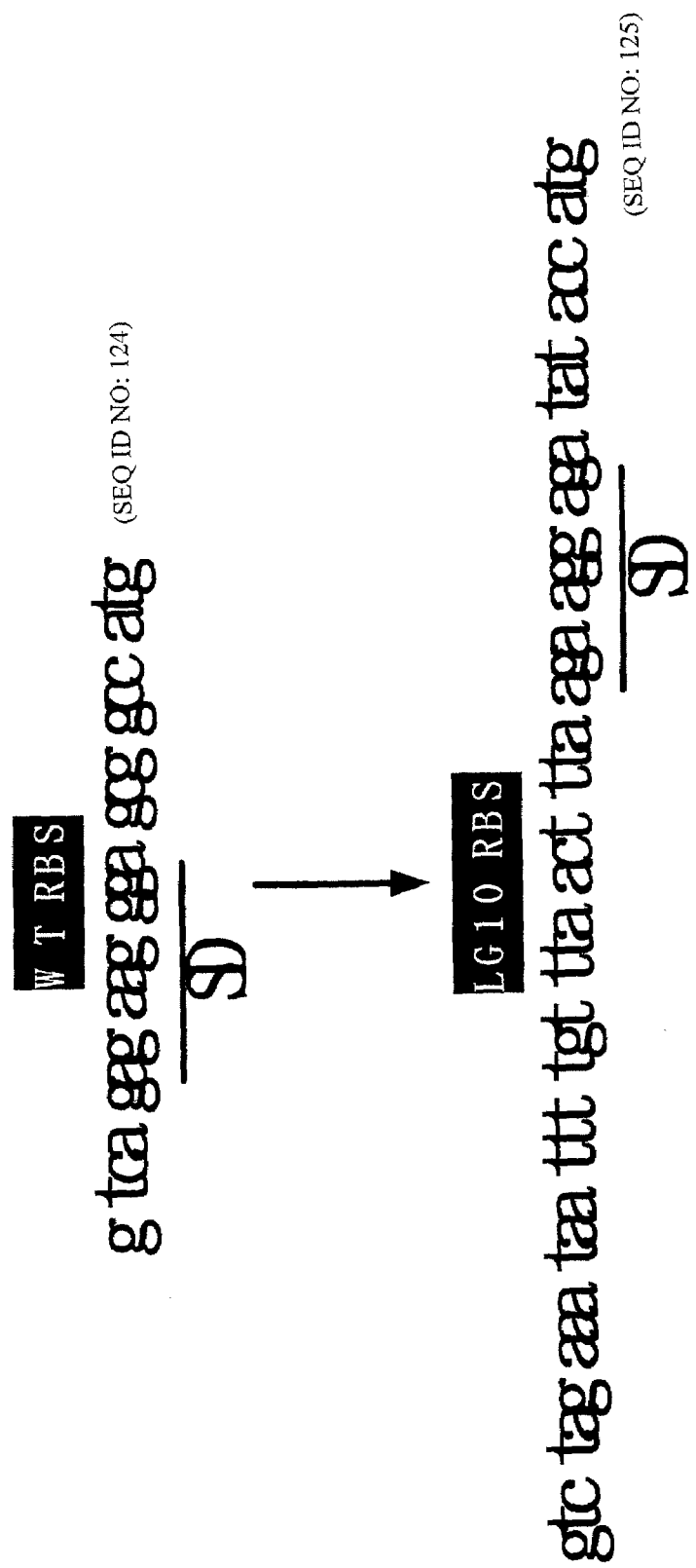
FIG. 13 is a diagram showing the modification of a TipA gene promoter (SEQ ID NO: 124) to a TipA-LG10 promoter (SEQ ID NO: 125)

Primers represented by SEQ ID NOs: 21 and 37 in the sequence listing were used to perform amplification by PCR with the plasmid pHN170 as a template. As a result, a hybrid promoter (hereinafter, indicated by a TipA-LG10 promoter; indicated by TipA-LG10p in the drawings) consisting of the TipA gene promoter and the ribosome-binding site derived from the lambda phage gene 10 was obtained. This 0.2-kb DNA fragment was doubly digested with restriction enzymes BsrGI and NcoI and subcloned into the BsrGI and NcoI sites of the pHN170. Consequently, a plasmid containing the PIP gene placed under the control of the TipA-LG10 promoter was constructed and designated as pHN171. FIG. 12 shows a mutant TipA promoter sequence (SEQ ID NO: 170), and FIG. 13 shows the modification of the ribosome-binding site (RBS) sequence for altering the mutant TipA promoter (SEQ ID NO: 170) into the TipA-LG10 promoter (SEQ ID NO: 169).

(8) Construction of Vector Plasmids pTip-NH1, pTip-CH1, pTip-LNH1, and pTip-LCH1

Figure 7:
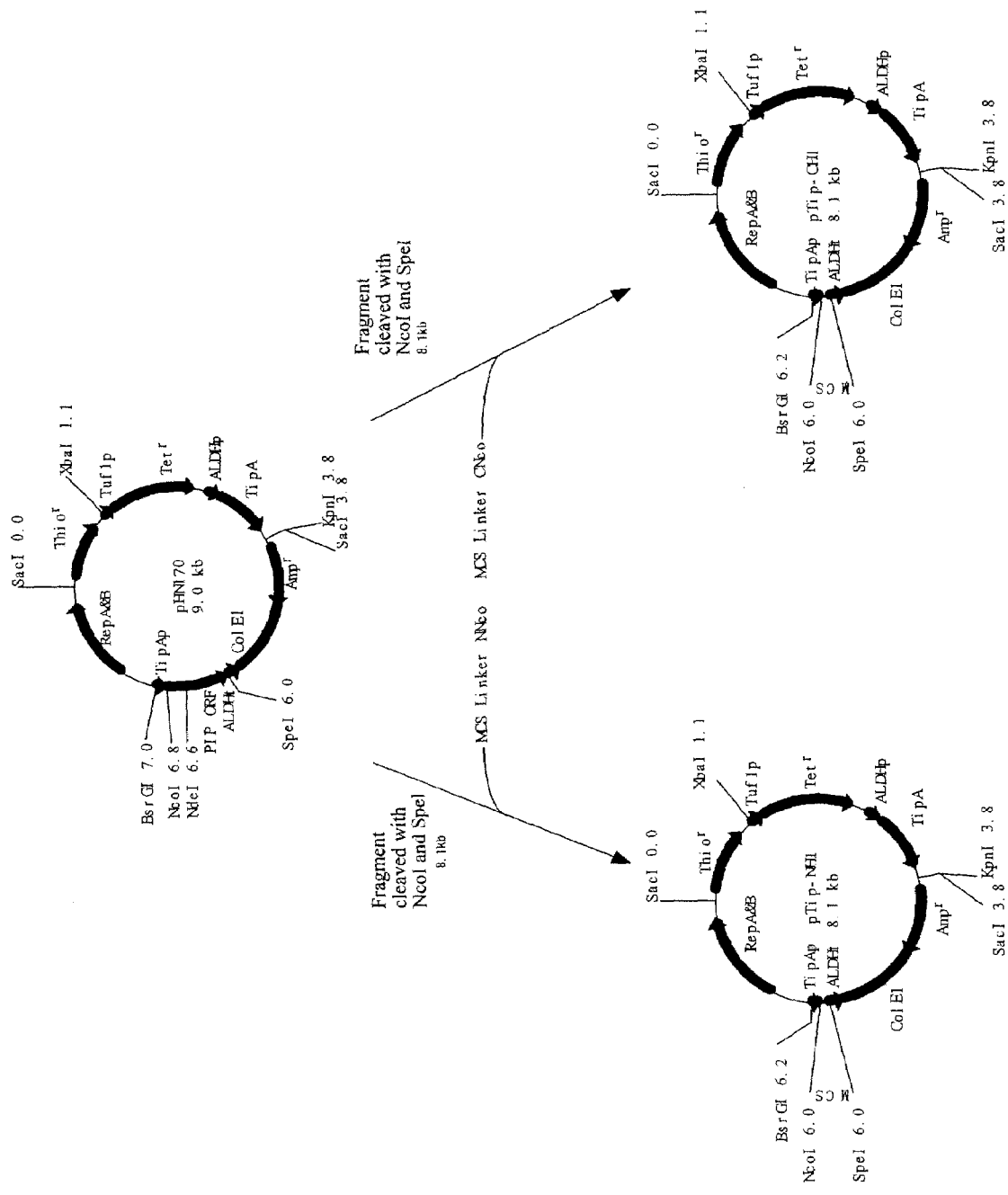
FIG. 7 is a diagram for illustrating the construction of inducible expression vector plasmids pTip-NH1, pTip-CH1, pTip-LNH1, and pTip-LCH1 having a multiple-cloning site. In the drawing, the locations of restriction enzyme recognition sites and structural genes are shown. A numeric represents a base pair (kilobase pair: kb)
Figure 7:
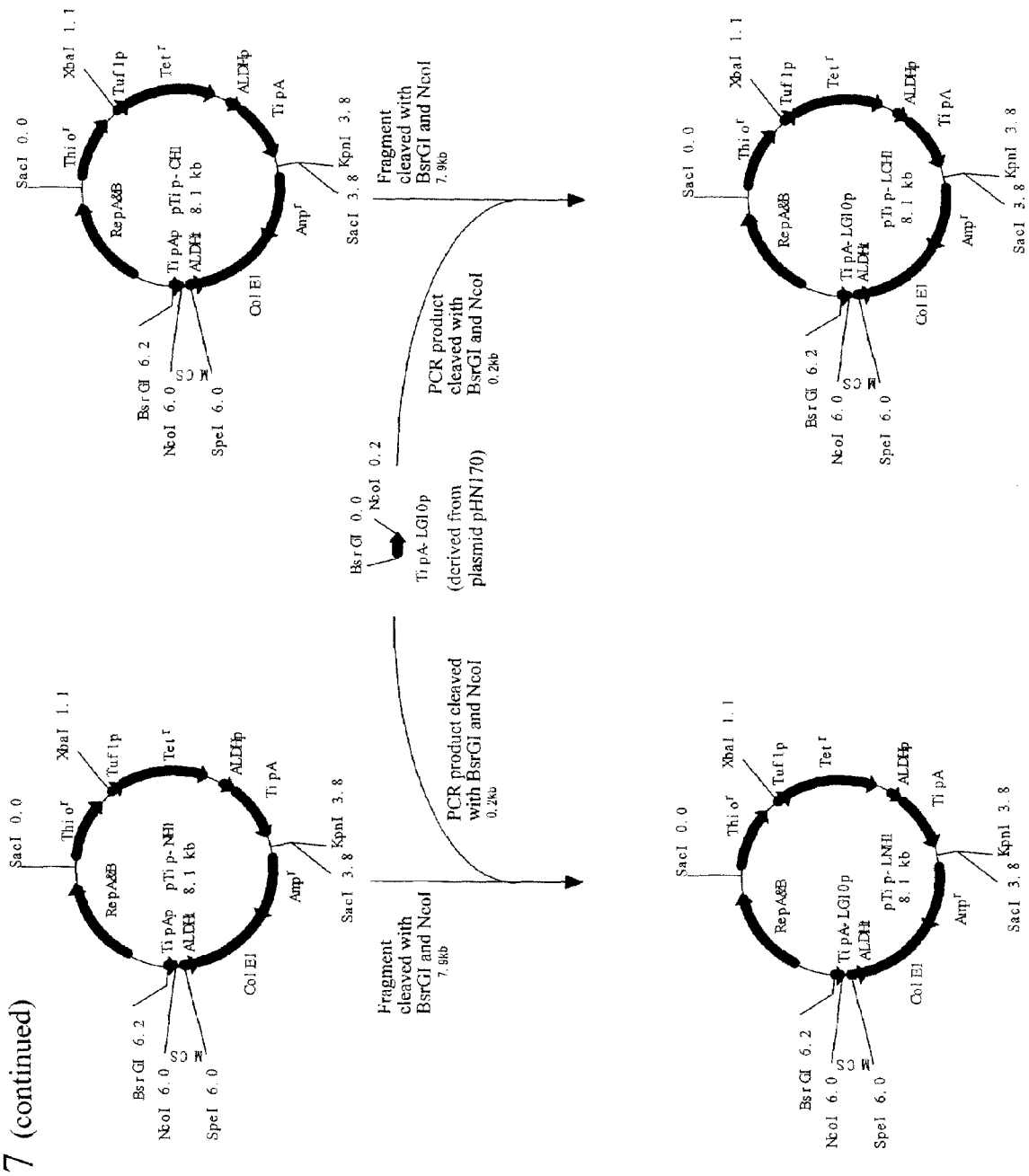

For eliminating the PIP gene as a reporter gene from the plasmid described in the above (7) and introducing a multiple-cloning site, the following procedures were performed (FIG. 7).

Synthetic oligodeoxyribonucleotides represented by SEQ ID NOs: 38 and 39 in the sequence listing contain a sequence that serves as a multiple-cloning site and have sequences complementary to each other. These two oligodeoxyribonucleotides were mixed in equimolar amounts and treated at 70° C. for 10 minutes. The oligodeoxyribonucleotides were cooled to room temperature over 20 minutes and converted into a double strand. As a result, its ends became capable of ligation with a vector doubly digested with NcoI and SpeI. This synthetic double-stranded DNA (indicated by MCS Linker NNco in the drawings) was subcloned into the NcoI and SpeI sites of the pHN170. The resulting plasmid was designated as pTip-NH1. Synthetic DNA (indicated by MCS Linker CNco in the drawings) where synthetic oligodeoxyribonucleotides (containing a sequence that serves as a multiple-cloning site and having sequences complementary to each other) represented by SEQ ID NOs: 40 and 41 in the sequence listing were converted into a double strand in the same way was subcloned into the NcoI and SpeI sites of the pHN170. The resulting plasmid was designated as pTip-CH1.

The hybrid DNA consisting of the TipA gene promoter sequence and the ribosome-binding site derived from the lambda phage gene 10, which was described in the above (7), was doubly digested with restriction enzymes BsrGI and NcoI and subcloned into the BsrGI and NcoI sites of the pTip-NH1 and pTip-CH1, respectively. The resulting plasmids were designated as pTip-LNH1 and pTip-LCH1, respectively.

(9) Construction of Vector Plasmids pTip-NH2, pTip-CH2, pTip-LNH2, and pTip-LCH2

Figure 8:
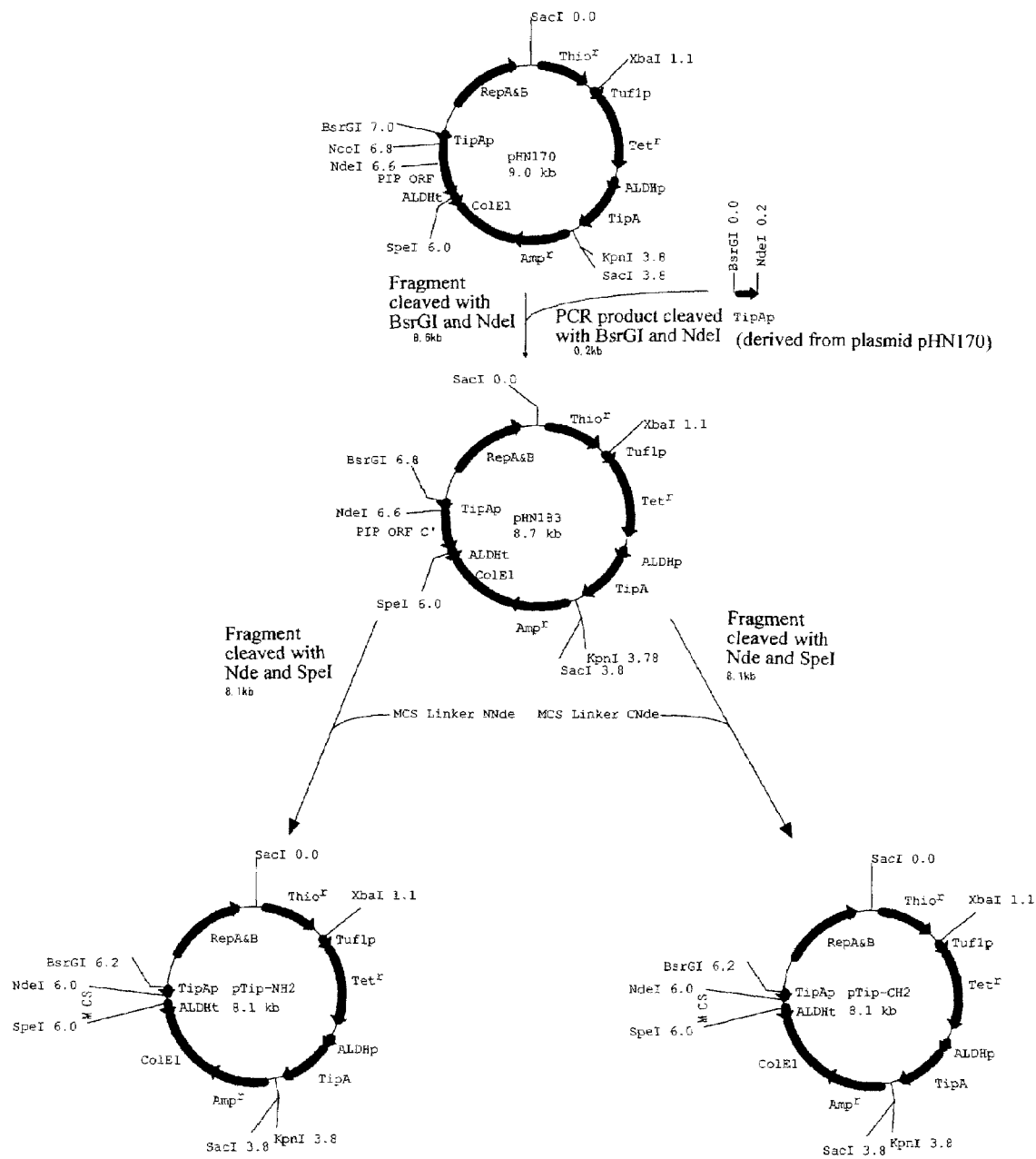
FIG. 8 is a diagram for illustrating the construction of inducible expression vector plasmids pTip-NH2, pTip-CH2, pTip-LNH2, and pTip-LCH2 having a multiple-cloning site. In the drawing, the locations of restriction enzyme recognition sites and structural genes are shown. A numeric represents a base pair (kilobase pair: kb)
Figure 8:
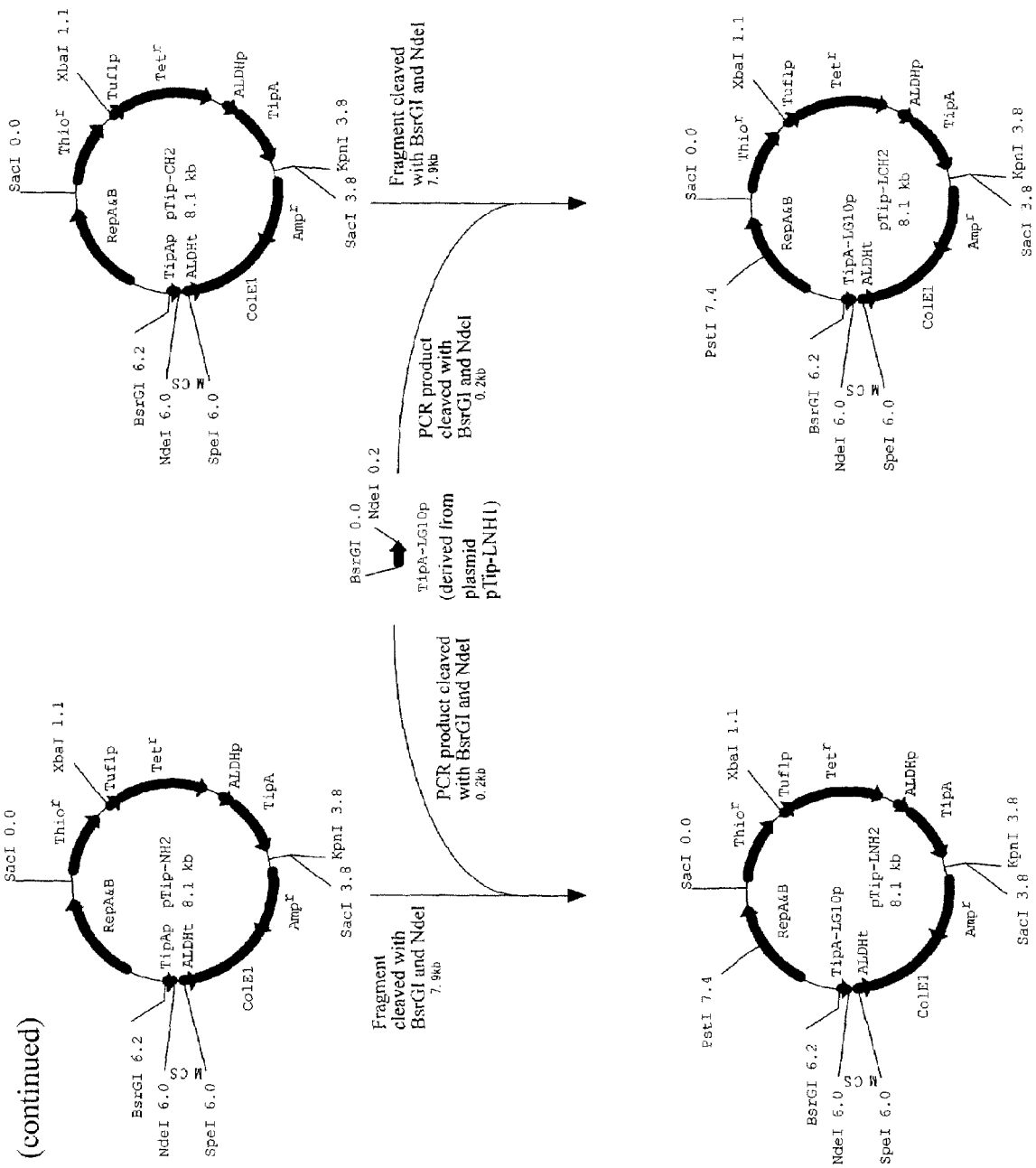
Figure 9B:
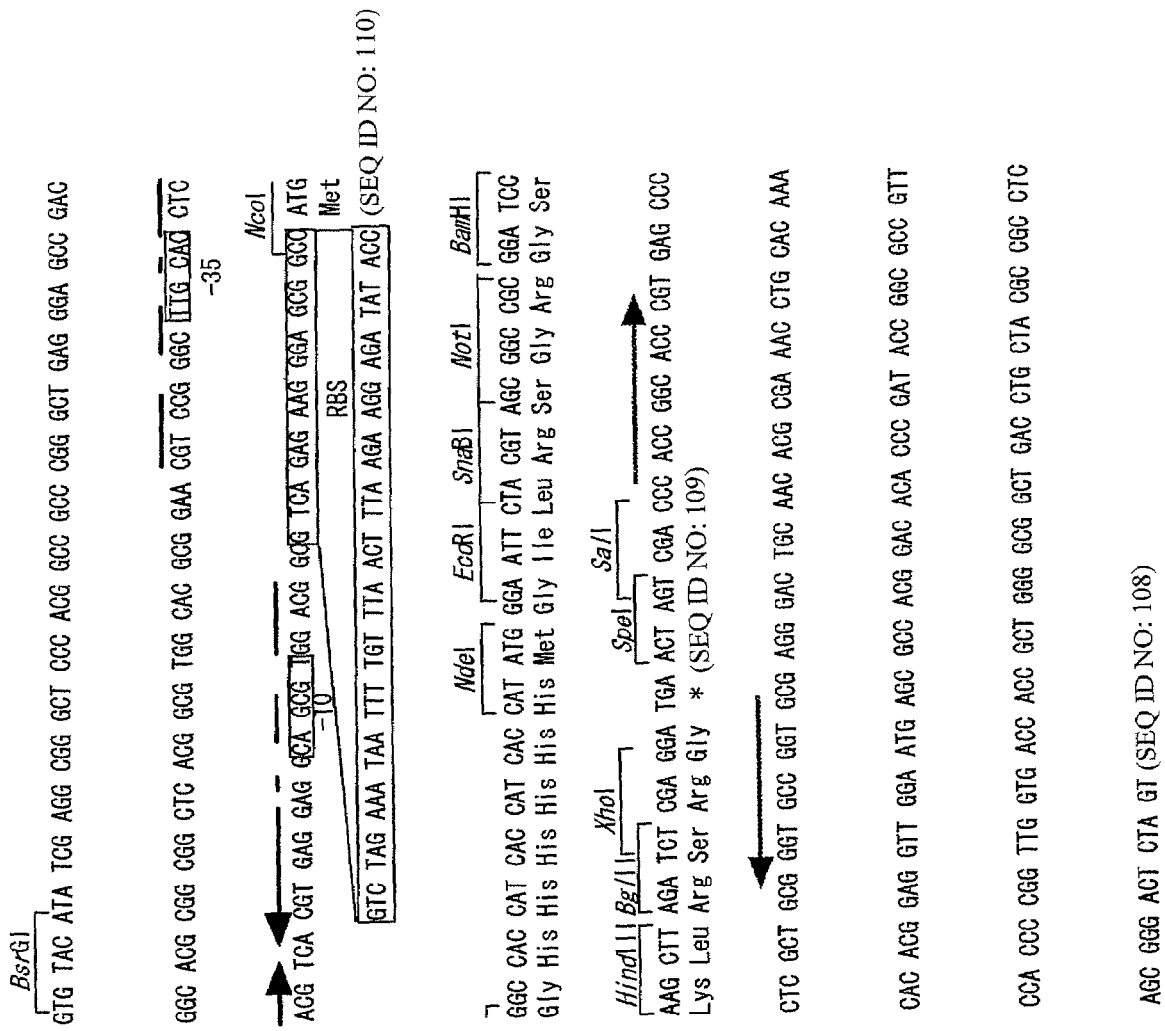
FIG. 9b shows the DNA sequence of the pTip-NH 1 or the pTip-LNH 1 from a TipA gene promoter sequence or a TipA-LG10 promoter sequence via a multiple-cloning site to a ThcA gene transcription termination sequence; Figure discloses SEQ ID NO: 108 coding SEQ ID NO: 109; short DNA sequence is SEQ ID NO: 110.
Figure 9C:
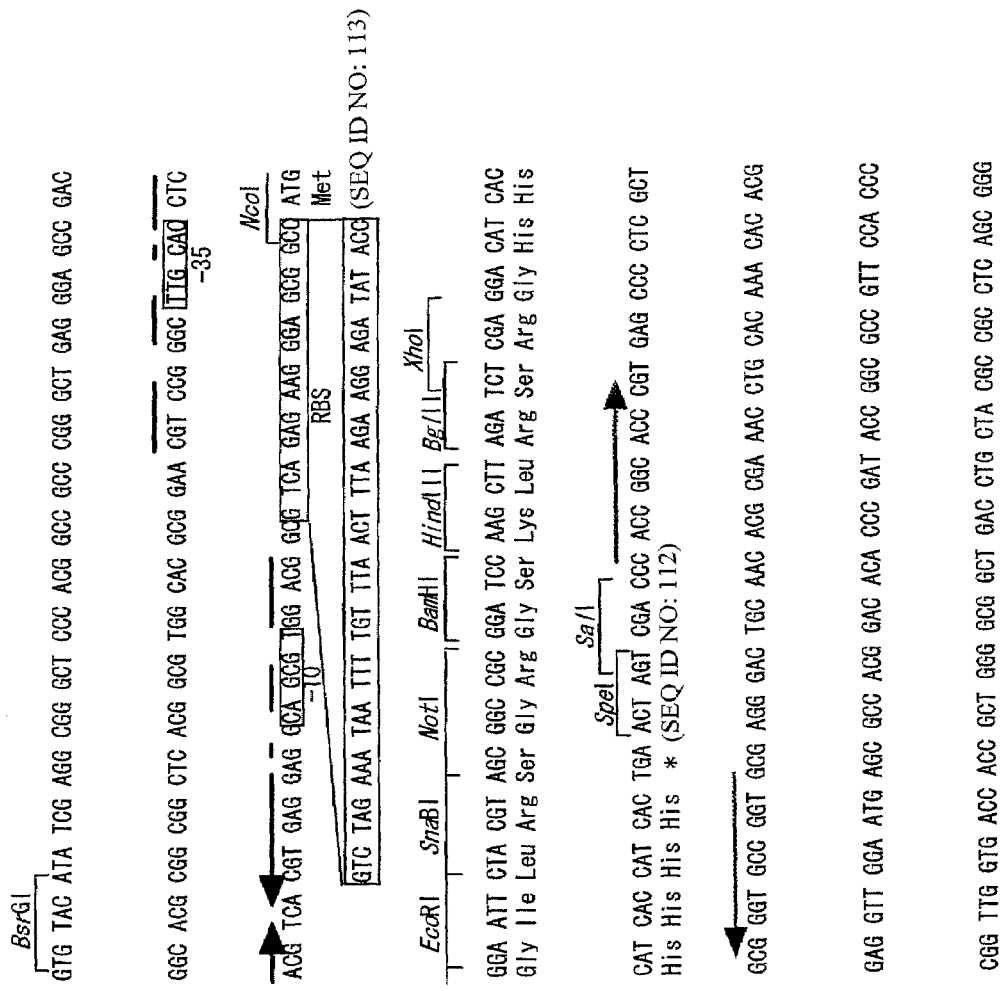
FIG. 9c shows the DNA sequence of the pTip-CH1 or the pTip-LCH1 from a TipA gene promoter sequence or a TipA-LG10 promoter sequence via a multiple-cloning site to a ThcA gene transcription termination sequence; Figure discloses SEQ ID NO: 111 coding SEQ ID NO: 112; short DNA sequence is SEQ ID NO: 113.
Figure 9D:
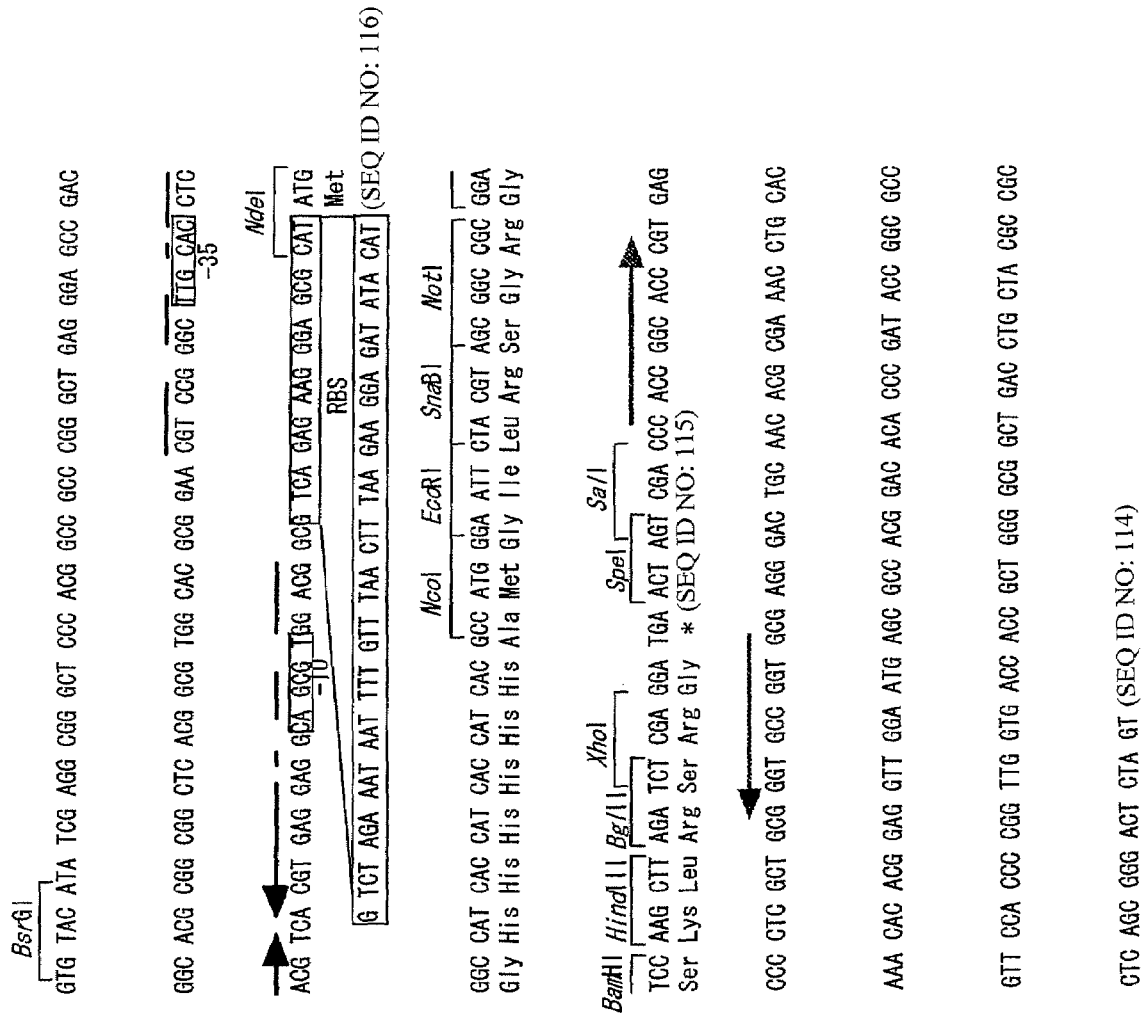
FIG. 9d shows the DNA sequence of the pTip-NH2 or the pTip-LNH2 from a TipA gene promoter sequence or a TipA-LG10 promoter sequence via a multiple-cloning site to a ThcA gene transcription termination sequence; Figure discloses SEQ ID NO: 114 coding SEQ ID NO: 115: short DNA sequence is SEQ ID NO: 116.
Figure 9E:
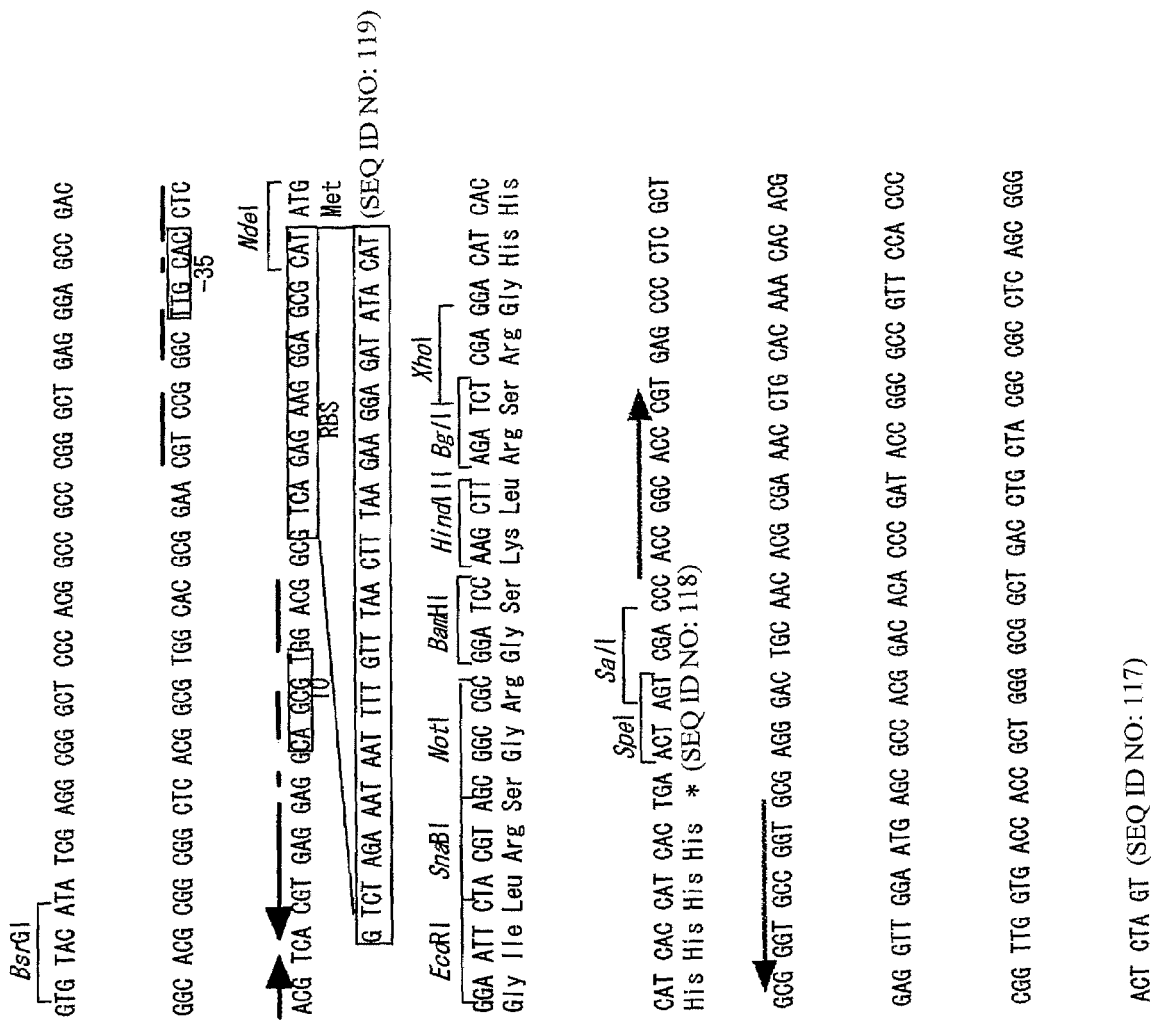
FIG. 9e shows the DNA sequence of the pTip-CH2 or the pTip-LCH2 from a TipA gene promoter sequence or a TipA-LG10 promoter sequence via a multiple-cloning site to a ThcA gene transcription termination sequence; Figure discloses SEQ ID NO: 117 coding SEQ ID NO: 118; short DNA sequence is SEQ ID NO: 119.

For altering, into a NdeI site, the NcoI site, the most upstream site in the multiple-cloning site, in the plasmids pTip-NH1, pTip-CH1, pTip-LNH1, and pTip-LCH1 described in the above (8), the following procedures were performed (FIG. 8).

Primers represented by SEQ ID NOs: 21 and 42 in the sequence listing were used to perform amplification by PCR with the plasmid pHN170 as a template. As a result, DNA containing the TipA gene promoter was obtained. This 0.2-kb DNA fragment was doubly digested with restriction enzymes BsrGI and NdeI and subcloned into the BsrGI and NdeI sites of the pHN170. The resulting plasmid was designated as pHN183.

Synthetic oligodeoxyribonucleotides represented by SEQ ID NOs: 43 and 44 in the sequence listing contain a sequence that serves as a multiple-cloning site and have sequences complementary to each other. These two oligodeoxyribonucleotides were mixed in equimolar amounts and treated at 70° C. for 10 minutes. The oligodeoxyribonucleotides were cooled to room temperature over 20 minutes and converted into a double strand. As a result, its ends became capable of ligation with a vector doubly digested with NdeI and SpeI. This synthetic double-stranded DNA (indicated by MCS Linker NNde in the drawings) was subcloned into the NdeI and SpeI sites of the pHN183. The resulting plasmid was designated as pTip-NH2. Synthetic DNA (indicated by MCS Linker CNde in the drawings) where synthetic oligodeoxyribonucleotides (containing a sequence that serves as a multiple-cloning site and having sequences complementary to each other) represented by SEQ ID NOs: 45 and 46 in the sequence listing were converted into a double strand in the same way was subcloned in the NdeI and SpeI sites of the pHN183. The resulting plasmid was designated as pTip-CH2.

Primers represented by SEQ ID NOs: 21 and 47 in the sequence listing were used to perform amplification by PCR with the plasmid pTip-LNH1 as a template. As a result, hybrid DNA consisting of the TipA gene promoter and the ribosome-binding site derived from lambda phage gene 10 was obtained. This 0.2-kb DNA fragment was doubly digested with restriction enzymes BsrGI and NdeI and subcloned into the BsrGI and NdeI sites of the pTip-NH2 and the pTip-CH2, respectively. The resulting plasmids were designated as pTip-LNH2 and pTip-LCH2, respectively.

FIG. 9 collectively shows the maps of the plasmids constructed in the above (8) and (9) and the peripheral sequences of the multiple-cloning sites. In the drawing, a solid line with an arrow head denotes an inverted repeat sequence present in the TipA gene promoter; and a dashed line with an arrow head denotes an inverted repeat sequence present in the ThcA gene transcription termination sequence. In addition, a −10 region, a −35 region, and RBS generally present in the promoter regions of prokaryotes and important for gene transcription are boxed. The most important SD sequence (Shine and Dalgarno, Eur. J. Biochem. 57 221-230 [1975]) in RBS is underlined.

(10) Construction of Vector Plasmids pTip-CH1.1, pTip-CH2.1, pTip-LCH1.1, and pTip-LCH2.1

Figure 10:
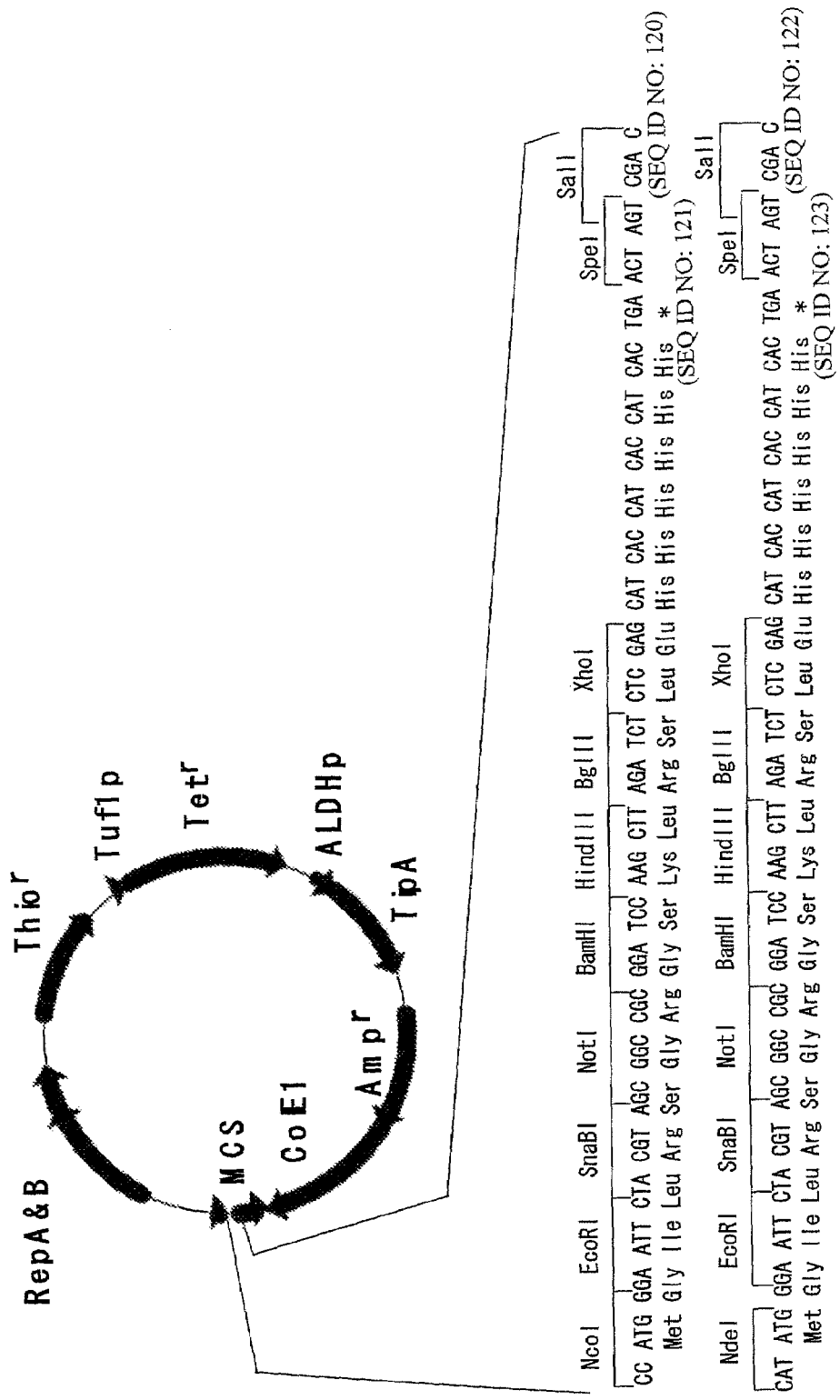
FIG. 10 is a diagram showing the maps of pTip-CH1.1 (SEQ ID NO: 120), pTip-LCH1.1 (SEQ ID NO: 121), pTip-CH2.1 (SEQ ID NO: 122), and pTip-LCH2.1 (SEQ ID NO: 123)

For bringing a reading frame following the XhoI site in the multiple-cloning site in the plasmids pTip-CH1, pTip-CH2, pTip-LCH1, and pTip-LCH2 described in the above (8) and (9) into agreement with the reading frame of a commercially-available pET vector (Novagen), the following procedures were performed (FIG. 10).

Primers represented by SEQ ID NOs: 21 and 48 in the sequence listing were used to perform amplification by PCR with the plasmid pTip-CH1 as a template. As a result, DNA containing the TipA gene promoter and the multiple-cloning site was obtained. This 0.3-kb DNA fragment was doubly digested with restriction enzymes BsrGI and SpeI and subcloned into the BsrGI and SpeI sites of the pTip-CH1. The resulting plasmid was designated as pTip-CH1.1.

Primers represented by SEQ ID NOs: 21 and 48 in the sequence listing were used to perform amplification by PCR with the plasmid pTip-CH2 as a template. As a result, DNA containing the TipA gene promoter and the multiple-cloning site was obtained. This 0.3-kb DNA fragment was doubly digested with restriction enzymes BsrGI and SpeI and subcloned into the BsrGI and SpeI sites of the pTip-CH1. The resulting plasmid was designated as pTip-CH2.1.

Primers represented by SEQ ID NOs: 21 and 48 in the sequence listing were used to perform amplification by PCR with the plasmid pTip-LCH1 as a template. As a result, DNA containing the TipA-LG10 gene promoter and the multiple-cloning site was obtained. This 0.3-kb DNA fragment was doubly digested with restriction enzymes BsrGI and SpeI and subcloned into the BsrGI and SpeI sites of the pTip-CH1. The resulting plasmid was designated as pTip-LCH1.1.

Primers represented by SEQ ID NOs: 21 and 48 in the sequence listing were used to perform amplification by PCR with the plasmid pTip-LCH2 as a template. As a result, DNA containing the TipA-LG10 gene promoter and the multiple-cloning site was obtained. This 0.3-kb DNA fragment was doubly digested with restriction enzymes BsrGI and SpeI and subcloned into the BsrGI and SpeI sites of the pTip-CH1. The resulting plasmid was designated as pTip-LCH2.1.

(11) Construction of Vector Plasmids pHN172 and pHN173

Figure 11:
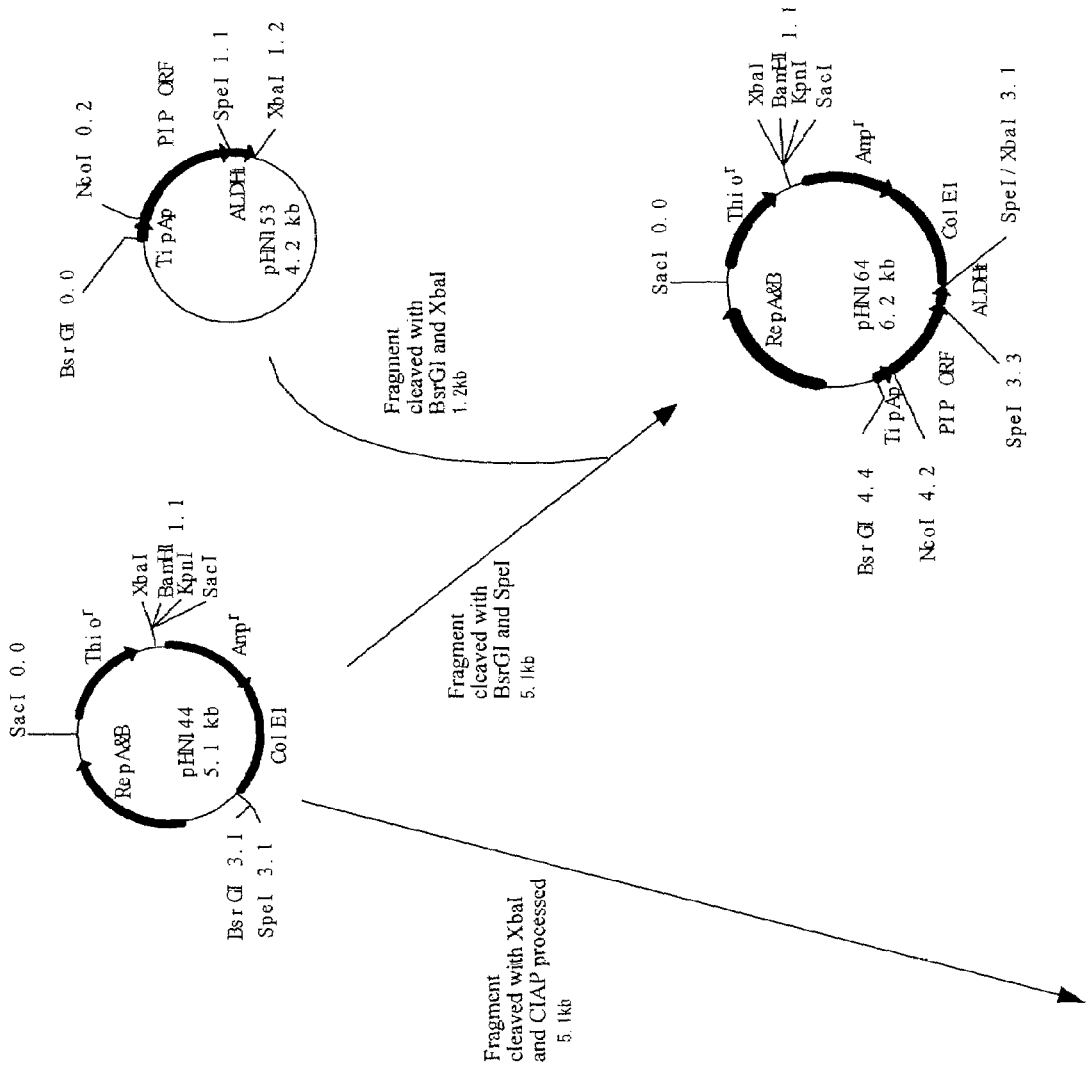
FIG. 11 is a diagram for illustrating the construction of control plasmids pHN172 and pHN173 for the activity measurement of PIP. In the drawing, the locations of restriction enzyme recognition sites and structural genes are shown. A numeric represents a base pair (kilobase pair: kb). CIAP means calf intestine alkaline phosphatase. The pHN170 has both of an "expression cassette" and an "inducer cassette", while the pHN173 has only the "expression cassette" and the pHN172 lacks both cassettes.
Figure 11:
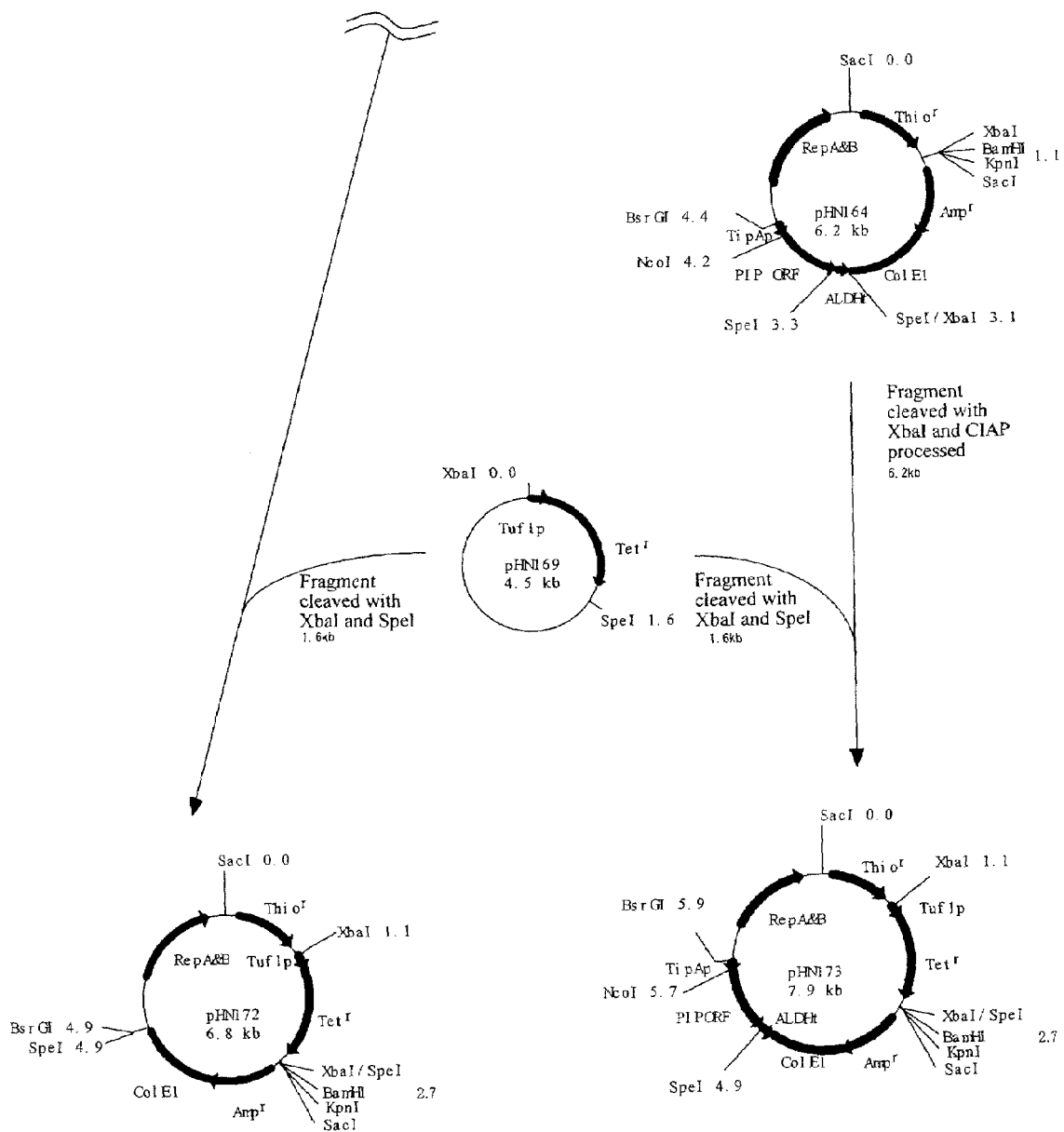

For investigating whether the induction of expression was strictly regulated, a plasmid for a control experiment as described below was constructed (FIG. 11).

A 1.6-kb DNA fragment obtained by doubly digesting the pHN169 with XbaI and SpeI was subcloned into the XbaI site of the pHN144 (subcloned in the orientation of tsr gene ORF-tetracycline resistance gene ORF-ampicillin resistance gene ORF in the 5' to 3' direction of the DNA). The resulting plasmid was designated as pHN172.

Next, a 1.2-kb DNA fragment obtained by doubly digesting the pHN153 with BsrGI and XbaI was subcloned into the BsrGI and SpeI sites of the pHN144. The resulting plasmid was designated as pHN164. Subsequently, a 1.6-kb DNA fragment obtained by doubly digesting the pHN169 with XbaI and SpeI was subcloned into the XbaI site of the pHN164 (subcloned in the orientation of tsr gene ORF-tetracycline resistance gene ORF-ampicillin resistance gene ORF in the 5' to 3' direction of the DNA). The resulting plasmid was designated as pHN173.

The pHN170 carries a gene cassette where three elements, the TipA gene promoter, the PIP ORF located downstream of the promoter, and the ThcA gene transcription termination sequence located downstream of the PIP ORF, are connected (hereinafter, indicated by an expression cassette) as well as a gene cassette where two elements, the ThcA gene promoter and the TipA gene located downstream of the promoter, are connected (hereinafter, indicated by an inducer cassette). The pHN173 has only the expression cassette, and the pHN 172 lacks both cassettes.

(12) Transformation of Bacterium Belonging to Genus Rhodococcus

A *Rhodococcus erythropolis* strain JCM3201 was subjected to shaking culture at 30° C. in 100 ml of a LB medium until reaching the logarithmic growth phase. The resulting culture solution was cooled on ice for 30 minutes and centrifuged to recover the bacterial cells. These bacterial cells were supplemented with 100 ml of ice-cold sterile water, then sufficiently stirred, and centrifuged again to recover the bacterial cells. These bacterial cells were supplemented with 100 ml of ice-cold 10% glycerol solution, then sufficiently stirred, and centrifuged to recover the bacterial cells. After this washing with ice-cold 10% glycerol solution was repeated again, the resulting bacterial cells were suspended in 5 ml of ice-cold 10% glycerol solution. A 400-μl aliquot thereof was dispensed and momentarily frozen with liquid nitrogen. The bacterial cells were stored at −80° C. until use. The bacterial cells stored at −80° C. were thawed on ice and supplemented with 3 μl of the plasmid pHN170 or pHN172 or pHN173 (each approximately 300 ng). This mixture solutions of the bacterial cell and the DNA were transferred to electroporation cuvettes (manufactured by Bio-Rad; 0.2-cm-gap cuvettes), to which electric pulses were respectively applied with a gene transfer apparatus Gene Pulser II (also manufactured by Bio-Rad) at electric field strength of 12.5 kV/cm, with the pulse controller set to capacitance of 25 μF and external resistance of 400Ω. The mixture solutions of the bacterial cell and the DNA treated with electric pulses were mixed with 1 ml of a LB medium and cultured at 30° C. for 4 hours to recover the bacterial cells. The bacterial cells were spread onto LB agar media (agar concentration: 1.8%) containing 20 μg/ml tetracycline and cultured at 30° C. for 3 days to yield the respective transformants.

EXAMPLE 1

Experimental Method

At first, approaches used in experiments described in Examples 2 to 12 below are enumerated.

All plasmids were constructed according to an ordinary method (Sambrook et al., Molecular Cloning: a laboratory manual, 2nd edition [1989], Cold Spring Harbor Laboratory Press, Cold Spring Harbor, N.Y.). All polymerase chain reaction methods (hereinafter, abbreviated to PCR; Saiki et al., Science 239 487-491 [1988]) employed the Pfu turbo (manufactured by STRATAGENE). DNA fragments excised from the plasmids were subjected to 1.0% agarose gel electrophoresis, and DNA fragments of interest were excised from the gels and purified using the QIA quick Gel Extraction Kit (manufactured by QIAGEN) according to the instruction. Procedures for separating the genomic DNAs of a *Streptomyces coelicolor* strain A3(2) and a *R. erythropolis* strain DSM313 and for purifying plasmid DNA from a bacterium belonging to the genus *Rhodococcus* were performed in the same way as described in Reference Example 1. The genomic DNA of an *Escherichia coli* strain ER2508 (manufactured by New England Biolabs) was purified using the QIAGEN RNA/DNA Mini Kit (manufactured by QIAGEN) according to the instruction. When the 5' ends of the DNA fragments need to be phosphorylated, T4 polynucleotide kinase (manufactured by Toyobo) was used. A DNA sequencer ABI PRISM(R) 3100 Genetic Analyzer (manufactured by ABI) was used in the determination of nucleotide sequences. T4 DNA ligase (manufactured by New England Biolabs) was employed in ligase reaction.

Main plasmids and strains used are shown in Tables 1 and 2. A bacterium belonging to the genus *Rhodococcus*, a *Streptomyces coelicolor* strain A3(2), and *Escherichia coli* were cultured in Luria Broth (LB; 1% Bacto trypton, 0.5% Bacto yeast extract, and 1% sodium chloride). Although procedures for constructing the competent cell of a bacterium belonging to the genus *Rhodococcus* and for its transformation were described in Reference Example 1, the construction of the competent cell of a bacterium belonging to the genus *Rhodococcus* that was transformed with a plasmid in advance was performed from bacterial cells cultured in a LB medium containing an appropriate antibiotic. For selecting a transformant, tetracycline (at concentrations of 8 μg/ml in a liquid medium and 20 μg/ml in a solid medium), chloramphenicol (34 μg/ml), and ampicillin (50 μg/ml) were used.

When proline iminopeptidase (hereinafter, PIP) or green fluorescent protein (hereinafter, GFP) was expressed in a bacterium belonging to the genus *Rhodococcus* with an inducible vector, the transformant of the bacterium belonging to the genus *Rhodococcus* was cultured at 30° C. in a LB medium containing an appropriate antibiotic, and supplemented with thiostrepton (solvent: dimethylsulfoxide) at the final concentration of 1 μg/ml at the point in time when an optical density measured at a wavelength of 600 nm (O.D. 600) reached 0.6, followed by additional 16-hour culture. When PIP or GFP was expressed with a constitutive vector, the transformant of the bacterium belonging to the genus *Rhodococcus* was cultured at 30° C. in a LB medium containing an appropriate antibiotic to an O.D. 600 of 2.0.

Hereinafter, procedures for measuring peptidase activity of PIP will be described in detail. The culture solution of the bacterium belonging to the genus *Rhodococcus* where the PIP was expressed as described above was brought up to 200 μl with a LB medium containing an appropriate antibiotic (8 μg/ml) and heated at 60° C. for 1 minute. To the solution, 2 μl of H-Pro-βNA (100 mM; solvent: dimethylsulfoxide) was added as a substrate for the PIP and incubated at 60° C. for 20 minutes (optimum temperature for PIP: 60° C.). For monitoring βNA liberated from the H-Pro-βNA by PIP hydrolysis, 134 μl of a Fast Garnet GBC Salt solution (manufactured by Wako Pure Chemical Industries; concentration: 0.5 mg/ml; solvent: 1M sodium acetate buffer (pH 4.2) and 10% Triton X-100) was added as a coloring agent. The above-described mixture solution turns yellow without the expression of PIP or turns red with the expression of PIP. The absorbance at 550 nm (A550) of the developed red color was measured with an absorption spectrophotometer to quantify PIP activity. The measurement was performed after the mixture solution supplemented with Fast Garnet GBC Salt was diluted with 666 μl of sterile water.

In the measurement at 550 nm, the optical density of the cell was also measured. Accordingly, the optical density of the cell at 550 nm (O.D. 550) was separately measured. A value corrected by subtracting a value corresponding to O.D. 550 used at the time of measurement from a value of A550 is used as Ac550, that is, calculated by Ac550=A550−O.D. 550× Amount (ml) of culture solution used in activity measurement of PIP. A unit value is meant to a "value of Ac550 per ml of the culture solution for O.D. 600=1 obtained in 20-minute measurement" and calculated by "AC550÷Amount (ml) of culture solution used in activity measurement of PIP÷O.D. 600."

EXAMPLE 2

Separation of Novel Endogenous Plasmid pRE8424 Present in R. Erythropolis

The present inventors searched for a novel endogenous plasmid present in R. erythropolis and found small circular plasmids from four strains, R. erythropolis JCM2893, R. erythropolis JCM2894, R. erythropolis DSM43200, and R. erythropolis DSM8424. These plasmids were designated as pRE2893, pRE2894, pRE43200, and pRE8424, respectively. Of these plasmids, the DNA sequences of the plasmids pRE2893, pRE2894, and pRE43200 were partially determined. As a result, they had a sequence nearly identical to that of the pRE2895 (see Reference Example 1), which had been separated previously by the present inventors from an R. erythropolis strain JCM2895. The pRE2895 has, as RepAB operon, genes encoding RepA and RepB proteins, which are involved in the replication of plasmids. These proteins are highly similar to RepA and RepB proteins encoded by a plasmid pAL5000 separated from Mycobacterium fortuitum, and it has been suggested that the pRE2895 and the pAL5000 autonomously replicate in a similar mode (Stolt and Stoker, Microbiology 142 2795-2802 [1996]; Reference Example 1). Although the modes of replication of the pRE2895 and the pAL5000 have not been elucidated, it has been considered that the RepA proteins of both plasmids have homology to the Rep protein of a plasmid ColE2, so that they have the "θ type" mode of autonomous replication as with the plasmid ColE2 (Hiraga et al., J. Bacteriol. 176 7233-7243 [1994]).

On the other hand, the pRE8424 had a DNA sequence completely different from that of the pRE2895 (SEQ ID NO: 90 in the sequence listing; FIG. 1). This plasmid carries six open reading frames (ORFs; ORF1 to ORF6). Of these ORFs, the ORF6 encoded a protein (FIG. 14) with high homology to proteins encoded by the Rep genes of a group of plasmids that autonomously replicate in the rolling circle mode (Khan, Microiol. Mol. Biol. Rev. 61 442-455 [1997]). The pRE8424 had especially high homology to pAP1 derived from Arcanobacterium pyrogenes (Billington et al., J. Bacteriol. 180 3233-3236 [1998]), pIJ101 derived from Streptomyces lividans (Kendall et al., J. Bacteriol. 170 4634-4651 [1988]), pJV1 derived from Streptomyces phaeochromogenes (Servin-Gonzalez et al., Microbiology 141 2499-2510 [1995]), pBL1 derived from Brevibacterium lactofermentum (Fernandez-Gonzalez et al., J. Bacteriol. 176 3154-3161 [1994]), and pSN22 derived from Streptomyces nigrifaciens (Kataoka et al., Plasmid 32 55-69 [1994]) (FIG. 15). All of these plasmids belong to the pIJ101/pJV1 family among rolling-circle-replication plasmids (Khan, Microiol. Mol. Biol. Rev. 61 442-455 [1997]). This has suggested the possibility that the pRE8424 is also a rolling-circle-replication plasmid belonging to this family. Hereinafter, ORF6 is referred to as Rep.

Figure 14:
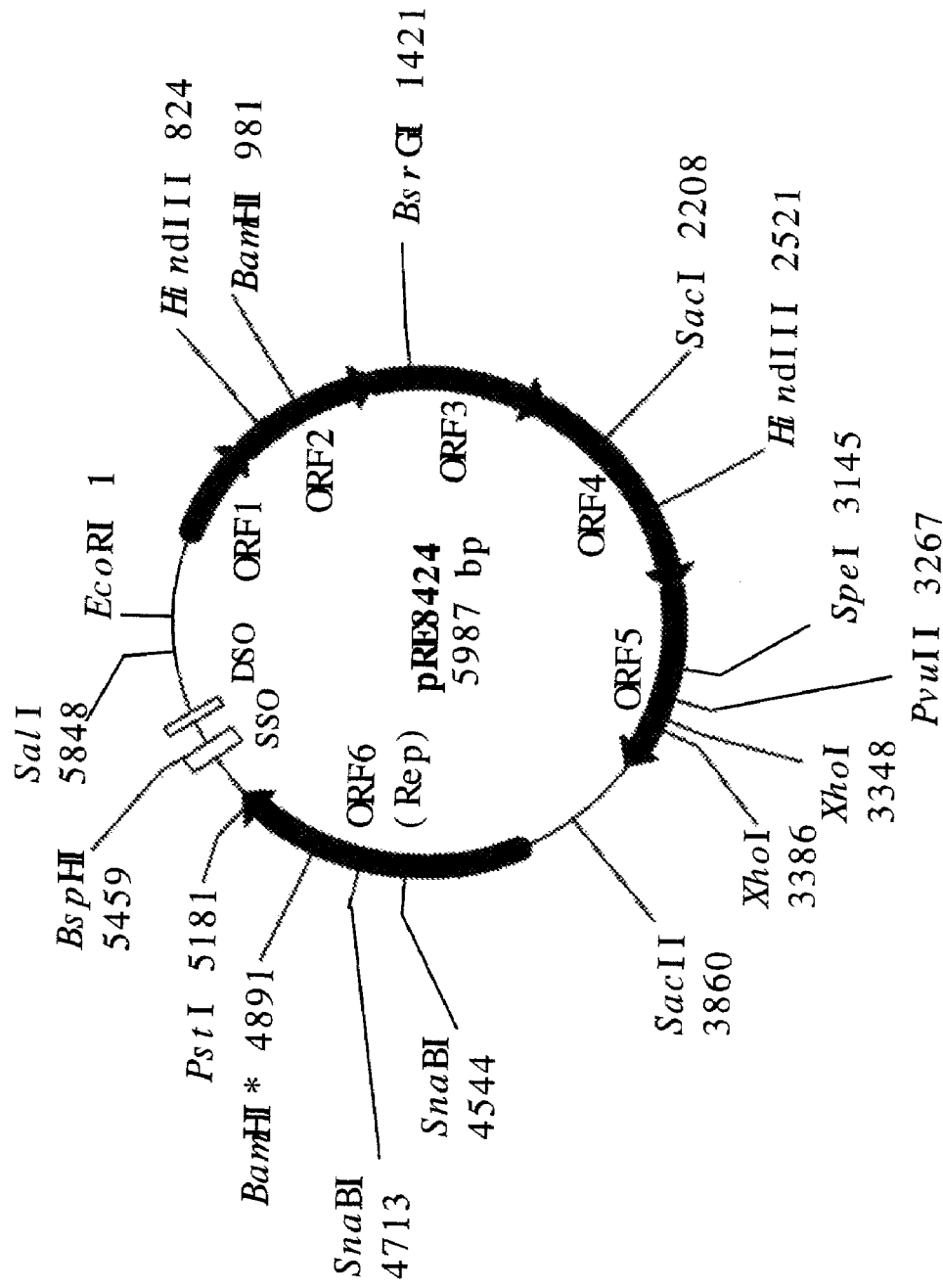
FIG. 14 is a diagram showing the map of pRE8424. In the drawing, main restriction enzyme recognition sites are shown, and an open reading frame (ORF) is indicated by an arrow. The locations of DSO and SSO are indicated by a box.
Figure 17:
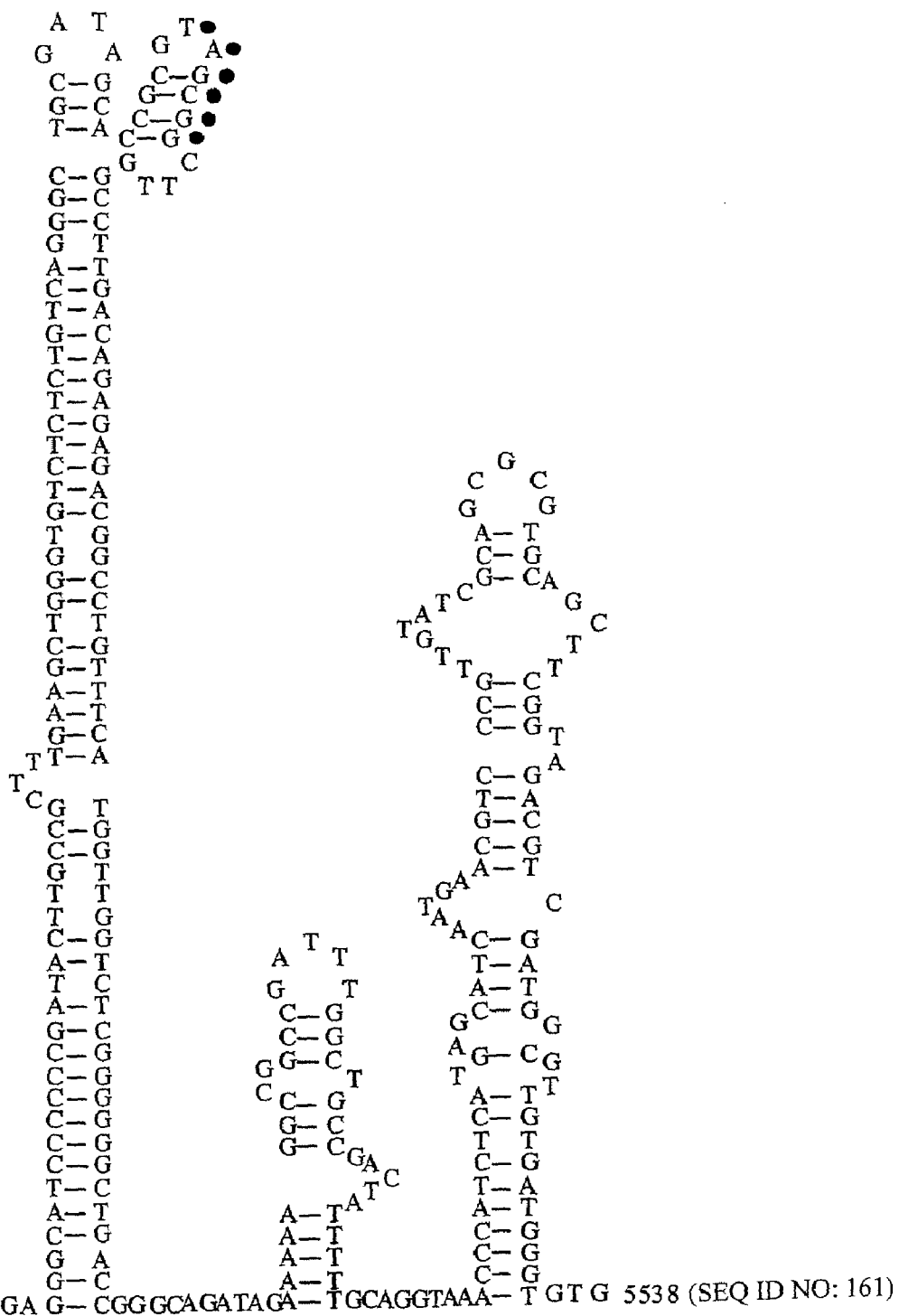
FIG. 17 is a diagram showing the SSO of the pRE8424 (SEQ ID NO: 161), that is, a sequence of nucleotide Nos. 5268 to 5538 in SEQ ID NO: 90 in the sequence listing, and a possible secondary structure.

In general, the autonomous replication of the rolling-circle-replication plasmid in a host cell requires DNA sequences that serve as a double-stranded origin (hereinafter, DSO) and a single-stranded origin (hereinafter, SSO), in addition to the foregoing Rep. The present inventors have constructed a variety of pRE8424 mutants with which R. erythropolis was then transformed, and have conducted various analyses to identify the localization of DSO and SSO sequences (FIG. 14). Although the DSO has been considered to be located within nucleotide Nos. 5514 to 5970 in SEQ ID NO: 90 in the sequence listing, comparison with the DSO sequences of other rolling-circle-replication plasmids has indicated that a sequence of nucleotide Nos. 5705 to 5734 in SEQ ID NO: 90 in the sequence listing is most important for the function of the DSO (FIG. 16). The identified SSO sequence is shown in FIG. 17. SSO sequences generally have a high secondary structure such as the stem-loop structure. Plasmids in the pIJ101/pJV1 family often have a consensus sequence consisting of, for example, TAGCGT, in the loop region of the stem-loop structure. The SSO of the pRE8424 also has a high secondary structure and has a TAGCGG sequence in the loop region (FIG. 17).

The present inventors have found that the derived plasmids of pRE8424 having a mutation in the above-described TAGCGG sequence are accumulated as single-stranded DNAs in large amounts in the cells of R. erythropolis. The accumulation of single-stranded DNA is a hallmark of rolling-circle-replication plasmids (Khan, Microiol. Moi. Biol. Rev. 61 442-455 [1997]) and as such, the pRE8424 has been shown to autonomously replicate in the rolling circle mode.

A 2.0-kb region containing Rep, DSO, and SSO, that is, a region of nucleotide Nos. 3845 to 5849 in SEQ ID NO: 90 in the sequence listing, was sufficient for the autonomous replication of the derived plasmids of pRE8424 in R. erythropolis used as a host cell (see Example 3 below).

FIG. 14 shows the map of the pRE8424. In FIG. 14, main restriction enzyme recognition sites are shown, and six ORFs are indicated by arrows. The locations of DSO and SSO are indicated by boxes.

FIG. 15 shows the amino acid sequences of five motifs (Motif IV, Motif I, Motif II, Motif III, and C-terminal motif; see Billington et al., J. Bacteriol. 180 3233-3236 [1998]) that are conserved in Rep proteins from the pRE8424, the pAP1, the pBL1, the pJV1, the PIJ101, and the pSN22. A numeric denotes the number of an amino acid residue located between the motifs, that is, the number of an amino acid residue in a gap. A perfectly conserved amino acid residue, a highly conserved region, and a relatively conserved region are indicated by an asterisk (*), two dots (:), and one dot (.), respectively. A tyrosine residue allegedly important for the function of the Rep protein is boxed.

FIG. 16 shows an especially conserved DNA region in sequences likely to be the DSOs of the pRE8424, the pAP1, the pBL1, the pJV1, the pIJ101, and the pSN22. In addition, a GG dinucleotide particularly important for the function of the DSO is underlined (see Billington et al., J. Bacteriol. 180 3233-3236 [1998]).

FIG. 17 shows the SSO of the pRE8424, that is, a sequence of nucleotide Nos. 5268 to 5538 in SEQ ID NO: 90 in the sequence listing, and a possible secondary structure. The prediction of the secondary structure was performed by the mfold program, version 3.0 (Michael Zuker, Washington University, St. Louis, Mo.; http://www.bioinfo.rpi.edu/applications/mfold/old/dna/form1.cgi). The above-described TAGCGG sequence is indicated by a filled-in circle.

EXAMPLE 3

Construction of pHN372

For eliminating an unnecessary restriction enzyme recognition site BamHI present in the 2.0-kb region essential for the autonomous replication of the pRE8424, the following procedures were performed.

Synthetic oligodeoxyribonucleotide primers (hereinafter, abbreviated to primers) represented by SEQ ID NOs: 57

(sHN389) and 58 (sHN390) in the sequence listing were used to perform DNA amplification by PCR with the pRE8424 as a template. The obtained 1.0-kb fragment contains the 5' end portion of the Rep. The 5' ends of this fragment were phosphorylated, and the fragment was introduced into the HincII site of pBluescript II SK(+) (manufactured by STRATAGENE) to yield a plasmid, which was designated as pHN371. Primers represented by SEQ ID NOs: 59 (sHN391) and 60 (sHN321) in the sequence listing were used to perform DNA amplification by PCR with the pRE8424 as a template. The obtained 1.0-kb fragment contains the 3' end portion of the Rep. This fragment was digested with BamHI, and its 5' ends were phosphorylated. The fragment was introduced into the EcoRV/BglII sites of the pHN371. The resulting plasmid was designated as pHN372. The pHN372 has the 2.0-kb region essential for the autonomous replication of the pRE8424 and lacks the BamHI site present in the pRE8424. The elimination of the BamHI site did not affect the function of the autonomous replication of the pRE8424.

EXAMPLE 4

Construction of pHN346

In the construction of the vectors shown in Reference Example, only a tetracycline resistance gene was developed as a selection marker for the transformant of a bacterium belonging to the genus *Rhodococcus*. However, the transformation of the bacterium belonging to the genus *Rhodococcus* with several plasmids requires newly developing resistance genes to other antibiotics. The present inventors have found that a *R. erythropolis* strain DSM313 is resistant to chloramphenicol and have decided to separate a gene that imparts resistance. Two chloramphenicol resistance genes have already been separated from bacteria belonging to the genus *Rhodococcus* (cmrA gene and cmr gene), and these genes have high homology to each other (De Mot et al., Microbiology 143 3137-3147 [1997]; and Desomer et al., Mol. Microbiol. 6 2377-2385 [1992]).

Because the chloramphenicol resistance gene of the *R. erythropolis* strain DSM313 was expected to be homologous to these genes, primers represented by SEQ ID NOs: 61 (sHN335) and 62 (sHN336) in the sequence listing were used to perform DNA amplification by PCR with the genomic DNA of the *R. erythropolis* strain DSM313 as a template. The primers were designed on the basis of sequences having the highest homology in the cmrA gene and the cmr gene. As a result, a 0.7-kb amplified band was confirmed. When the DNA sequence of this PCR product was determined, the sequence had considerably high homology to that of the cmrA gene. Primers represented by SEQ ID NOs: 63 (sHN349) and 64 (sHN351) in the sequence listing were designed based on the determined sequence, and the full-length chloramphenicol resistance gene of the *R. erythropolis* strain DSM313 was separated by inverse PCR (Ochman et al., Genetics 120 621-623 [1988]). DNA used as a template was obtained by cleaving 0.1 µg of the genomic DNA of the *R. erythropolis* strain DSM313 with SalI and circularizing the cleaved genomic DNA by self-ligation with ligase. The obtained PCR product was 2.3 kb, and the full DNA sequence of this fragment was determined. One ORF was present in this fragment, and this gene was designated as ChlA (indicated by Chl$^r$ in the drawings).

Primers represented by SEQ ID NOs: 65 (sHN361) and 66 (sHN362) in the sequence listing were used to perform DNA amplification by PCR with the genomic DNA of the *R. erythropolis* strain DSM313 as a template. The obtained 0.5-kb fragment contains the 5' end portion of the chloramphenicol resistance gene. This fragment was digested with SacI, and its 5' ends were phosphorylated. On the other hand, primers represented by SEQ ID NOs: 67 (sHN363) and 68 (sHN364) in the sequence listing were used to perform DNA amplification by PCR with the genomic DNA of the *R. erythropolis* strain DSM313 as a template. The obtained 1.3-kb fragment contains the 3' end portion of the chloramphenicol resistance gene. This fragment was digested with SpeI, and its 5' ends were phosphorylated. These two DNA fragments were simultaneously introduced into the SacI/SpeI sites of pBluescript II SK(+) to yield a plasmid, which was designated as pHN346. The pHN346 has the full-length chloramphenicol resistance gene but lacks the EcoRI site originally present in the ORF (without any change in the amino acid sequences of encoded proteins).

EXAMPLE 5

Construction of Inducible Expression Vectors Having Proline Iminopeptidase (PIP) Gene as a Reporter Gene; Construction of pHN171, pHN379, pHN348, and pHN380

A 1.8-kb fragment containing the chloramphenicol resistance gene was excised from the pHN346 (Example 4) with XbaI and SpeI and introduced into the XbaI site of pHN154 (Japanese Patent Application No. 2002-235008). The resulting plasmid was designated as pHN347. A 1.1-kb fragment was excised from the pHN171 (see Reference Example) with BsrGI and SpeI and introduced into the BsrGI/SpeI sites of the pHN347. The resulting plasmid was designated as pHN348.

Although both of the pHN171 and the pHN348 were expression vectors where a PIP gene, a reporter gene, was introduced into the MCS of the pTip vector (see Reference Example), the difference between them is only in a transformation marker: a tetracycline resistance gene for the pHN171 and a chloramphenicol resistance gene for the pHN348. In any of the plasmids, a ribosome-binding site sequence originally located downstream of the TipA gene promoter (TipA-RBS) is altered into a bacteriophage gene 10-derived ribosome-binding site sequence having good translation efficiency (TipA-LG10 promoter; see Reference Example). A 6×His tag (SEQ ID NO: 168) is adapted to be attached to the C terminus of PIP in order to facilitate protein purification. The 6×His tag (SEQ ID NO: 168) is a consecutive sequence consisting of six consecutive histidine residues, and a protein fused with this tag exhibits high affinity for a nickel ion or the like. Thus, the protein is readily purified by metal chelate chromatography that employs the nickel ion or the like (Crowe et al., Methods Mol. Biol. 31 371-387 [1994]).

For altering a 1.9-kb region essential for the autonomous replication of plasmids derived from pRE2895 in the DNA sequences of the above-described pHN171 and pHN348 into a 2.0-kb region essential for the autonomous replication of plasmids derived from pRE8424, the following procedures were performed.

Primers represented by SEQ ID NOs: 69 (sHN368) and 70 (sHN373) in the sequence listing were used to perform DNA amplification by PCR with the pHN171 as a template. The obtained 0.2-kb fragment contains the 5' end portion of the thiostrepton resistance gene (tsr gene; indicated by Thio$^r$ in the drawings) (Bibb et al., Mol. Gen. Genet. 199 26-36 [1985]). This fragment was digested with BsrGI and ClaI and introduced into the BsrGI/ClaI sites of the pHN171 and the pHN348, respectively. The resulting plasmids were designated as pHN357 and pHN358, respectively. A 2.0-kb fragment containing a region essential for the autonomous replication of plasmids derived from pRE8424 was excised from the pHN372 (Example 3) with BsrGI and HpaI and introduced into the BsrGI/HpaI sites of the pHN357 and the pHN358, respectively. The resulting plasmids were designated as pHN379 and pHN380, respectively.

EXAMPLE 6

Construction of pTip Vectors

The process of constructing eight pTip vectors by introducing MCS instead of the PIP gene of the plasmids pHN171, pHN348, pHN379, and pHN380 (Example 5) will be illustrated. Four (pTip-RT1, pTip-RT2, pTip-RC1, and pTip-RC2, which will be described below) of the pTip vectors constructed this time are different in a DNA region necessary for the autonomous replication of a plasmid in a bacterium belonging to the genus Rhodococcus from the pTip vectors described in Reference Example 1, and do not cause incompatibility with all of the pTip vectors described in Reference Example 1 in a bacterium belonging to the genus Rhodococcus (described below). Alternatively, the remaining four (pTip-QT1, pTip-QT2, pTip-QC1, and pTip-QC2, which will be described below) are different in a part of a MCS sequence from the pTip vectors described in Reference Example 1.

Synthetic oligodeoxyribonucleotides represented by SEQ ID NOs: 71 and 72 in the sequence listing contain a sequence that serves as a MCS site and have sequences complementary to each other. These two oligodeoxyribonucleotides were mixed in equimolar amounts and treated at 70° C. for 10 minutes. The oligodeoxyribonucleotides were cooled to room temperature over 20 minutes and converted into a double strand (MCS type 1). As a result, its ends became capable of ligation with a vector doubly digested with NcoI and SpeI. This synthetic double-stranded DNA was subcloned into the NcoI/SpeI sites of the pHN379 and the pHN380, respectively. The resulting plasmids were designated as pTip-RT1 and pTip-RC1, respectively. Synthetic oligodeoxyribonucleotides represented by SEQ ID NOs: 73 and 74 in the sequence listing were converted into a double strand (MCS type 2) in the same way. On the other hand, a 0.2-kb fragment containing the TipA gene promoter and LG10-RBS was excised from the pTip-LNH2 (see Reference Example 1) with BsrGI and NdeI. These two DNA fragments were simultaneously introduced into the BsrGI/SpeI sites of the pHN379 and the pHN380, respectively. The resulting plasmids were designated as pTip-RT2 and pTip-RC2, respectively. A 0.3-kb fragment containing the TipA gene promoter, the LG10-RBS, and the MCS type 1 was excised from the pTip-RT1 with BsrGI and SpeI and introduced into the BsrGI/SpeI sites of the pHN171 and the pHN348, respectively. The resulting plasmids were designated as pTip-QT1 and pTip-QC1, respectively. A 0.3-kb fragment containing the TipA gene promoter, the LG10-RBS, and the MCS type 2 was excised from the pTip-RT2 with BsrGI and SpeI and introduced into the BsrGI/SpeI sites of the pHN171 and the pHN348, respectively. The resulting plasmids were designated as pTip-QT2 and pTip-QC2, respectively.

Figures 1, 18:
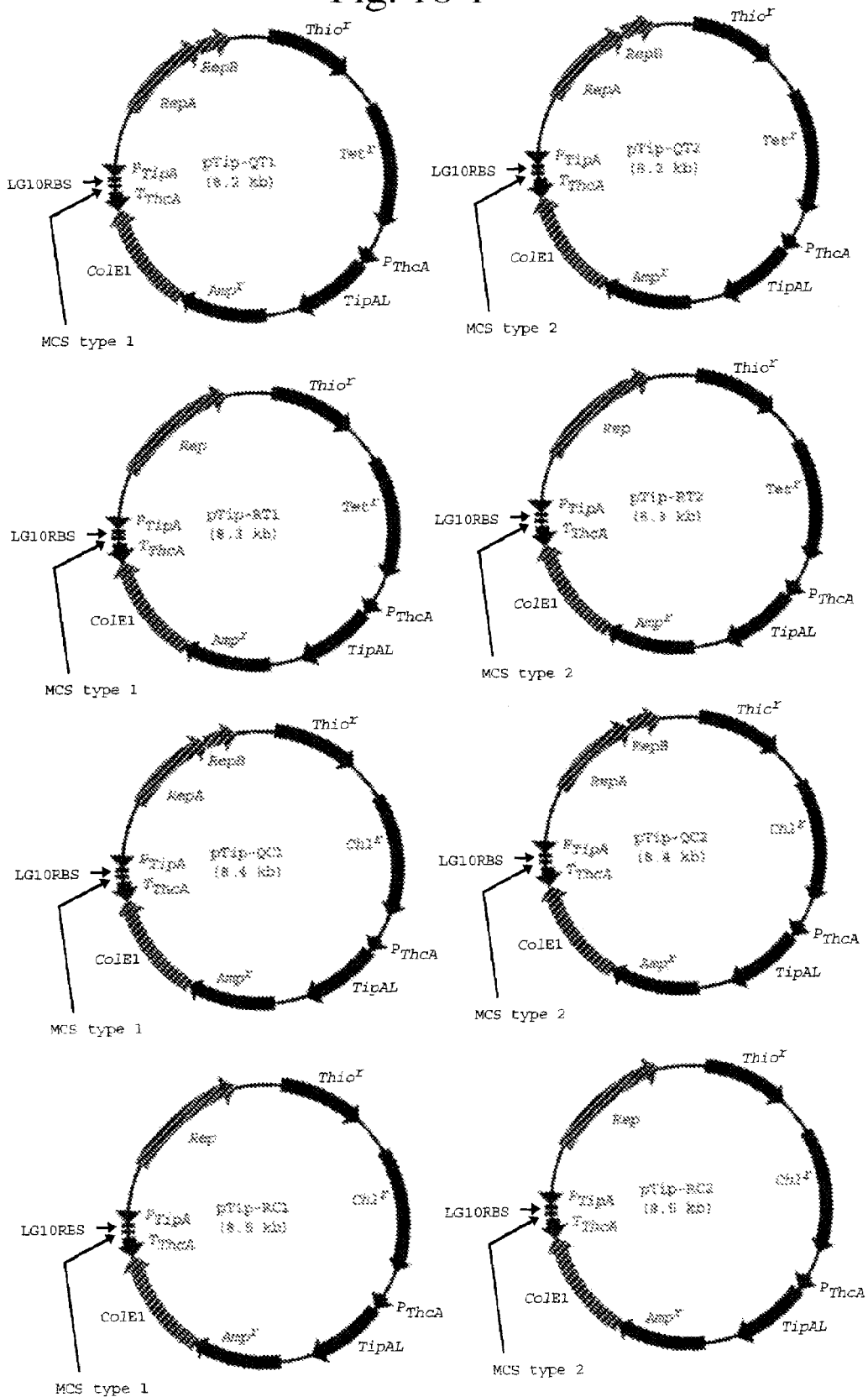
Figures 2, 18:
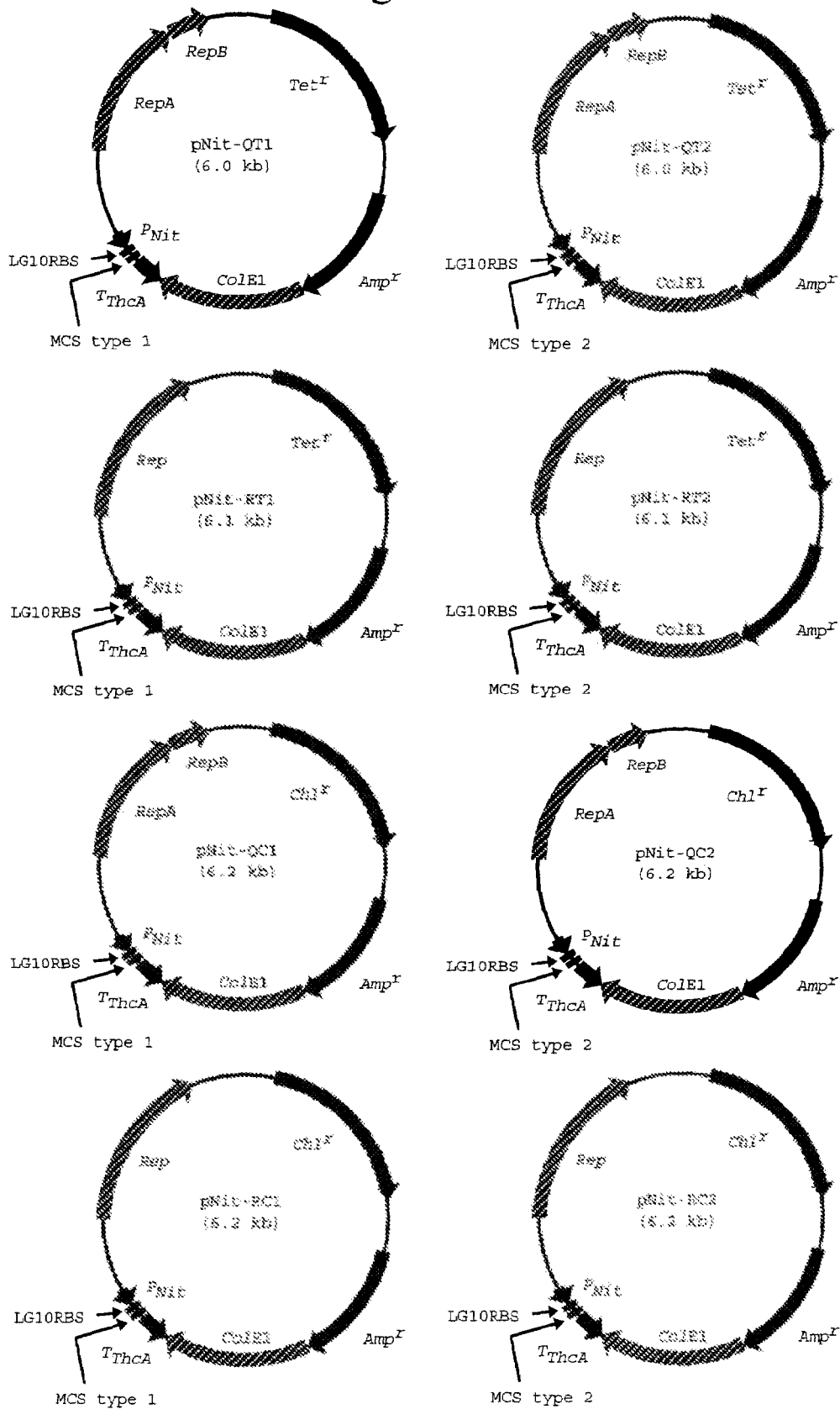

FIG. 18-1 shows the maps of the pTip vectors (pTip-QT1, pTip-QT2, pTip-RT1, pTip-RT2, pTip-QC1, pTip-QC2, pTip-RC1, and pTip-RC2). In the drawing, Thio$^r$ denotes a thiostrepton resistance gene; Tuflp denotes a Tuf1 gene promoter; Tet$^r$ denotes a tetracycline resistance gene; Chl$^r$ denotes a chloramphenicol resistance gene (each pTip vector has any one of Tuflp-Tet$^r$ or Chl$^r$); ALDHp denotes a ThcA promoter that allows the transcription of the TipA gene (TipA); Amp$^r$ denotes an ampicillin resistance gene; ColE1 denotes the replication origin of *Escherichia coli*; ALDHt denotes a ThcA gene transcription termination sequence; MCS denotes a multiple-cloning site (each pTip vector has any one of MCS type 1 or MCS type 2); TipAp denotes a TipA gene promoter; TipA-LG10p denotes a TipA-LG10 promoter; RepA&B denotes a region essential for the autonomous replication of plasmids derived from pRE2895 in *R. erythropolis*; and Rep denotes a region essential for the autonomous replication of plasmids derived from pRE8424 in *R. erythropolis* (each pTip vector has any one of RepA&B or Rep). Incidentally, a diagram for pNit vectors (described below) described in Example 9 is indicated in a right half in the drawing, and the same symbols are used to designate the same components.

Figure 20:
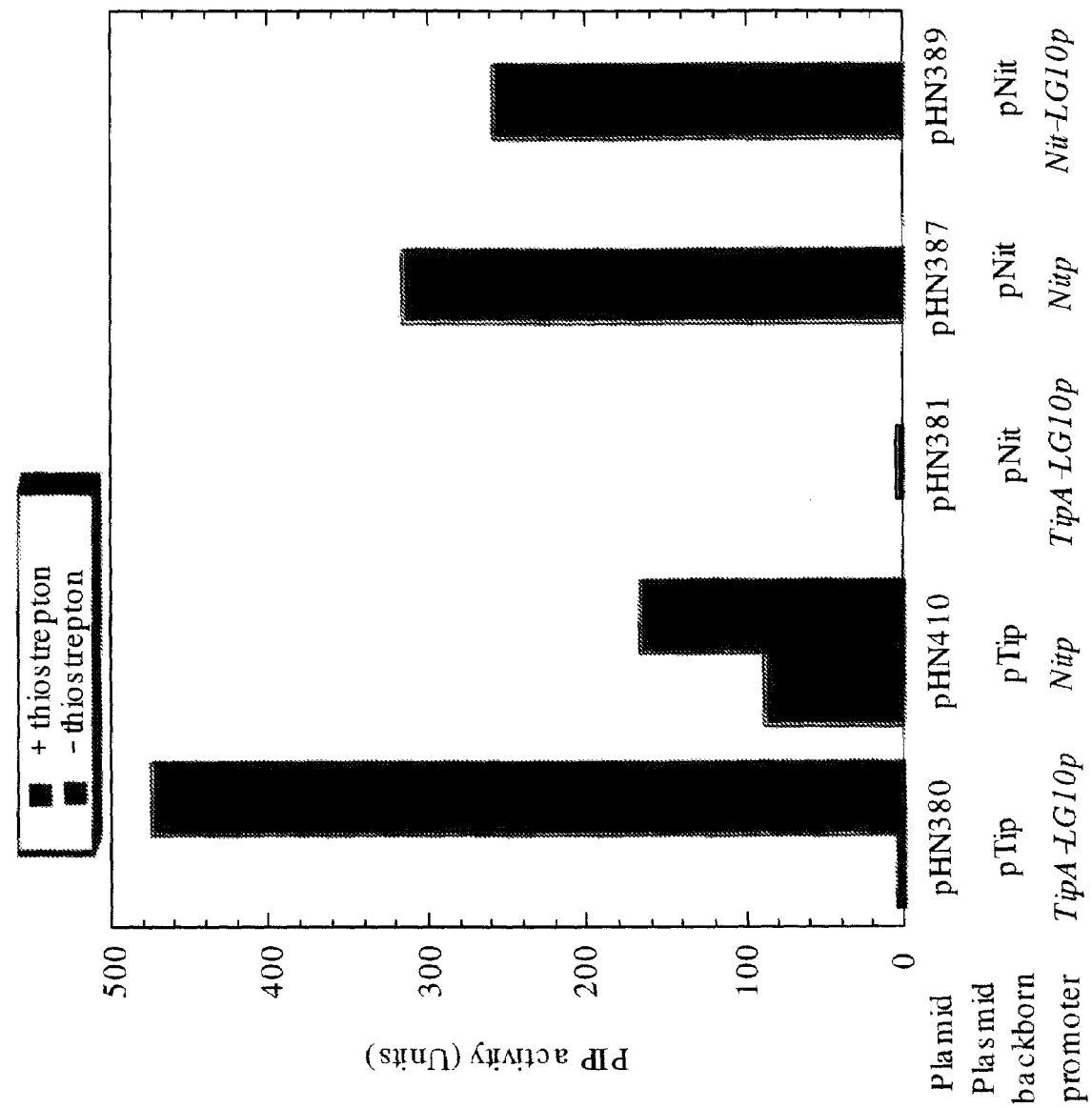
FIG. 20 is a diagram showing a result of measuring PIP for peptidase activity, after the transformation of a *R. erythropolis* strain JCM3201 with pHN380, pHN410, pHN381, pHN387, and pHN389.

FIG. 20 shows the DNA sequence of TipA-LG10 promoter-MCS-ThcA gene terminator. In the drawing, a solid line with an arrow head denotes an inverted repeat sequence present in the TipA gene promoter; and a dashed line with an arrow head denotes an inverted repeat sequence present in the ThcA gene transcription termination sequence. In addition, a −10 region and a −35 region generally present in the promoter regions of prokaryotes and important for gene transcription are boxed. A TATAAT sequence that is boxed shows an introduced mutation in the construction of a Nit promoter from the TipA gene promoter (described in detail in Example 7).

EXAMPLE 7

Construction of pHN231

Figure 19:
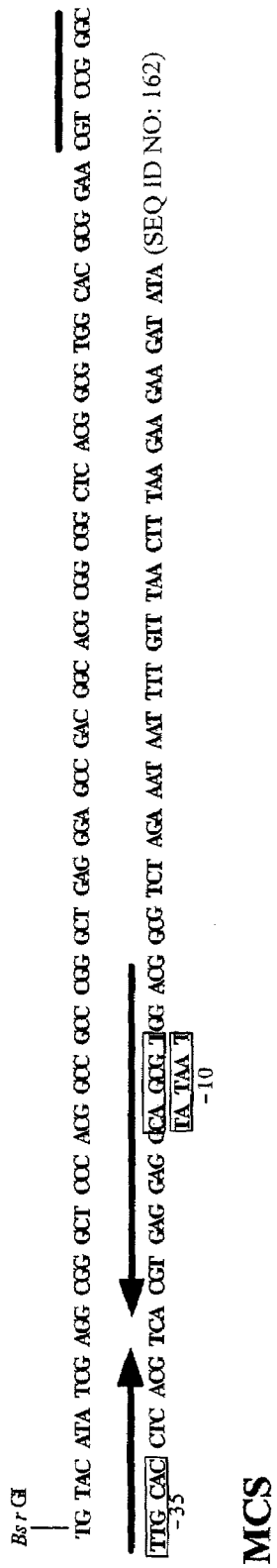
FIG. 19 is a diagram showing the DNA sequence of TipA-LG10p-MCS-ALDHt or Nit-LG10-MCS-ALDHt. A wild-type −10 region sequence of a TipA gene promoter is CAGCGT, and a −10 region sequence of a Nit promoter is TATAAT. These sequences are boxed, respectively; Figure discloses SEQ ID NOS: 162-167, respectively, in order of appearance.

At first, the present inventors have decided that a mutation is introduced into the TipA gene promoter to alter the inducible promoter to a constitutive promoter. It has long been known that a thiostrepton-TipA protein complex binds to the "inverted repeat" region in the TipA gene promoter sequence to promote the transcription of its own gene (Holmes et al., EMBO J. 12 3183-3191 [1993]). Thus, the present inventors have speculated that the mutations in the inverted repeat sequence would bring about some change in the transcription activity of the TipA gene promoter, and have therefore constructed a variety of TipA gene promoter mutants. Of these mutants, in a mutant where a mutation was introduced into the so-called −10 region of the TipA gene promoter (Fenton and Gralla. Proc. Natl. Acad. Sci. USA 98 9020-9025 [2001]) (FIG. 19; mutation from CAGCGT to TATAAT), the expression of the reporter gene was observed even in the absence of thiostrepton (FIG. 20; described in detail in Example 10). This DNA sequence consisting of TATAAT is a sequence frequently found in a −10 region in a DNA sequence that functions as a considerably strong promoter in *Escherichia coli*. The conclusion drawn from the above view is that this mutated TipA gene promoter is a constitutive promoter. This constitutive promoter was designated as a Nit (non-inducible TipA; indicated by Nitp in the drawings) promoter.

The process of constructing the Nit promoter will be illustrated below. Primers represented by SEQ ID NOs: 75 (sHN217) and 76 (sHN218) in the sequence listing were used to perform DNA amplification by inverse PCR with the pHN150u (see Reference Example 1) as a template. The pHN150u is a plasmid obtained by cloning a wild-type TipA gene promoter into the MCS of pBluescript II SK(+). The 5' ends of the above-described two primers were respectively phosphorylated. This inverse PCR fragment was circularized by self-ligation through ligase reaction. The resulting plasmid was designated as pHN231. The pHN231 assumes the form where the Nit promoter was cloned into the MCS of the pBluescript II SK(+).

EXAMPLE 8

Construction of Inducible Expression Vectors Having Proline Iminopeptidase (PIP) Gene as a Reporter Gene; Construction of pHN407, pHN385, pHN409, and pHN389

Primers represented by SEQ ID NOs: 77 (sHN395) and 78 (sHN396) in the sequence listing were used to perform DNA amplification by PCR with the pTip-NH1 (see Reference Example 1) as a template. The obtained 1.6-kb fragment contains the tetracycline resistance gene. This fragment was digested with HpaI and KpnI and introduced into the HpaI/KpnI sites of the pHN379 (Example 5). The resulting plasmid was designated as pHN381. Primers represented by SEQ ID NOs: 79 (sHN397) and 80 (sHN398) in the sequence listing were used to perform DNA amplification by PCR with the pHN346 (Example 4) as a template. The obtained 1.8-kb fragment contains the chloramphenicol resistance gene. This fragment was digested with HpaI and KpnI and introduced into the HpaI/KpnI sites of the pHN380 (Example 5). The resulting plasmid was designated as pHN382. A 0.2-kb fragment containing the Nit promoter was excised from the pHN231 (Example 7) with BsrGI and NcoI and introduced into the BsrGI/NcoI sites of the pHN381 and the pHN382, respectively. The resulting plasmids were designated as pHN383 and pHN387, respectively. Primers represented by SEQ ID NOs: 81 (sHN147) and 82 (sHN376) in the sequence listing were used to perform DNA amplification by PCR with the pHN231 (Example 7) as a template. The obtained 0.2-kb fragment lacks the RBS portion of the Nit promoter. This fragment was digested with BsrGI and XbaI and introduced into the BsrGI/XbaI sites of the pHN381 and the pHN382, respectively. The resulting plasmids were designated as pHN385 and pHN389, respectively. The hybrid DNA between this Nit promoter (except for the RBS portion) and LG10RBS was designated as a Nit-LG10 promoter. Primers represented by SEQ ID NOs: 83 (sHN388) and 84 (sHN120) in the sequence listing were used to perform DNA amplification by PCR with the pHN171 as a template. The obtained 1.9-kb fragment contains the RepAB operon derived from the pRE2895. This fragment was digested with BsrGI and HpaI and introduced into the BsrGI/HpaI sites of the pHN387 and the pHN389, respectively. The resulting plasmids were designated as pHN407 and pHN409, respectively.

In addition, for constructing a plasmid for a control experiment, a 0.2-kb Nit promoter was excised from the pHN387 with BsrGI and NcoI. This DNA fragment was introduced into the BsrGI/NcoI sites of the pHN380 (Example 5). The resulting plasmid was designated as pHN410.

EXAMPLE 9

Construction of pNit Vectors

The process of constructing eight pNit vectors by introducing MCS instead of the PIP gene of the plasmids pHN407, pHN385, pHN409, and pHN389 (Example 8) will be illustrated.

A 2.2-kb fragment was excised from the pTip-RT1 (Example 6) with NcoI and KpnI and introduced into the NcoI/KpnI sites of the pHN407, the pHN385, the pHN409, and the pHN389, respectively. The resulting plasmids were designated as pNit-QT1, pNit-RT1, pNit-QC1, and pNit-RC1, respectively. Primers represented by SEQ ID NOs: 81 (sHN147) and 85 (sHN160) in the sequence listing were used to perform DNA amplification by PCR with the pHN385 (Example 8) as a template. The obtained 0.2-kb fragment contains the Nit-LG10 promoter. This fragment was digested with BsrGI and NdeI. On the other hand, a 2.0-kb fragment containing the MCS type 2, the ampicillin resistance gene, and the ColE1 was excised from the pTip-RT2 (Example 6) with NdeI and KpnI. These two DNA fragments were simultaneously introduced into the BsrGI/KpnI sites of the pHN407, the pHN385, the pHN409, and the pHN389 (Example 8), respectively. The resulting plasmids were designated as pNit-QT2, pNit-RT2, pNit-QC2, and pNit-RC2, respectively.

FIG. 18-2 shows the maps of the pNit vectors (pNit-QT1, pNit-QT2, pNit-RT1, pNit-RT2, pNit-QC1, pNit-QC2, pNit-RC1, and pNit-RC2). Symbols and so on are as described in Example 6.

EXAMPLE 10

Expression of PIP Gene from TipA Gene Promoter and Nit Promoter

Using the plasmids pHN380, pHN410, pHN381, pHN387, and pHN389, the mode of gene expression from the pTip and pNit vectors was observed. Hereinafter, its process and result will be illustrated.

At first, a *R. erythropolis* strain JCM3201 was transformed with the pHN380, the pHN410, the pHN381, the pHN387, and the pHN389. These transformants were used to measure the peptidase activity of PIP. The result is shown in FIG. 20.

In FIG. 20, the designations and simple features of the plasmids used in transformation were shown. A filled-in bar and a shaded bar denote the peptidase activity of PIP with the treatment of the transformant with thiostrepton and without the treatment of the transformant with thiostrepton, respectively. Thiostrepton-controlled gene expression works in the transformant obtained with the pHN380 (having, in the pTip vector skeleton, the gene cassette consisting of TipA-LG10 promoter-PIP), whereas thiostrepton-controlled gene expression does not work in the transformant obtained with the pHN410 (having, in the pTip vector skeleton, the gene cassette consisting of Nit promoter-PIP). Alternatively, the pHN387 is a plasmid assuming the form where the thiostrepton resistance gene and the gene cassette consisting of ThcA gene promoter-TipA gene have been removed from the pHN410. The PIP gene was also expressed in the transformant obtained with this plasmid even in the absence of thiostrepton. This means that gene expression from the Nit promoter occurs even in the absence of the TipA protein. Results of using the transformants obtained with the pHN387 and the pHN389 have suggested that a RBS sequence is not involved in thiostrepton-controlled gene expression. The pHN381 was a plasmid obtained by substituting a TipA-LG10 promoter for the Nit-LG10 promoter of the pHN389. The expression of the PIP gene is not constitutive in the transformant obtained with the pHN381. The above view has revealed that the Nit promoter and the Nit-LG10 promoter are constitutive promoters under which the expression of a PIP gene does not require a TipA protein.

It was confirmed that the PIP can also be expressed from the pTip and pNit vectors at 4° C. in addition to at 30° C.

EXAMPLE 11

Comparison of Regions Essential for Autonomous Replication of Plasmids Derived from pRE2895 and pRE8424

Using the pTip and pNit vectors, the features of regions essential for the autonomous replication of plasmids derived from pRE2895 and pRE8424 was investigated.

At first, the transformation efficiency of the pNit-QC2 and the pNit-RC2 for *R. erythropolis* JCM 3201, *R. fascians* JCM10002, *R. opacus* DSM44193, *R. ruber* JCM3205, and *R. rhodochrous* JCM3202 was investigated. The result is shown in Table 3. Table 3 shows the number of colonies appearing on a solid medium containing chloramphenicol in the case that 1 µg each of the plasmid DNA was used in transformation. This result has demonstrated that *R. erythropolis* JCM 3201, *R. fascians* JCM10002, and *R. opacus* DSM44193 can be transformed with both of the pNit-QC2 and the pNit-RC2, though with a difference in efficiency. Neither *R. ruber* JCM3205 nor *R. rhodochrous* JCM3202 produced a transformant.

Next, *R. erythropolis* JCM3201, *R. fascians* JCM10002, and *R. opacus* DSM44193 were transformed with the pHN409 and the pHN389 (Example 9). The difference between the pHN409 and the pHN389 is only in that a region essential for autonomous replication is derived from pRE2895 or pRE8424. When the peptidase activity of PIP was compared between the cells of the *R. erythropolis* JCM3201 transformed with the pHN409 and the cells of the *R. erythropolis* JCM3201 transformed with the pHN389, there was almost no difference or otherwise, slightly higher activity in the cells transformed with the pHN409. Almost the same results were obtained when the *R. fascians* JCM10002 and the *R. opacus* DSM44193 were used as hosts. For all of the plasmids used, the peptidase activity of PIP in the *R. fascians* JCM10002 and the *R. opacus* DSM44193 was lower than the peptidase activity of PIP in the *R. erythropolis* JCM3201.

Next, the copy numbers of plasmids of the pNit-QC2 and the pNit-RC2 in the cell of *R. erythropolis* JCM3201 were investigated. The experimental approach conformed to the method by Projan et al. (Projan et al., Plasmid 9 182-190 [1983]). This method requires knowing the genome size of the *R. erythropolis* JCM3201 in order to calculate the copy numbers of plasmids. According to van der Geize et al., the genome size of a *R. erythropolis* strain RG1, a strain derived from a *R. erythropolis* strain ATCC4277, is 6 megabase pairs (Mbp), and the *R. erythropolis* strain ATCC4277 and the *R. erythropolis* strain JCM3201 are nearly equivalent strains. Therefore, calculation was conducted with the genome size of the *R. erythropolis* strain JCM3201 as 6 Mbp. The results of the copy numbers were 47±5 for the pNit-QC2 and 64±5 for the pNit-RC2.

EXAMPLE 12

Plasmid Incompatibility

In most cases, heterologous plasmids having the same replication origin generally can not coexist in the cell of a bacterium. This is due to a phenomenon called plasmid incompatibility (Novick, Microbiol. Rev. 51 381-395 [1987]), and there has been a report on plasmid incompatibility for *Mycobacterium*, the related genus of *Rhodococcus* (Stolt and Stoker, Microbiology 142 2795-2802 [1996]). The present inventors have separated two endogenous plasmids (pRE2895 and pRE8424) having different sequences from *R. erythropolis*, and have therefore considered that several plasmids can be utilized in recombinant protein production by allowing them to coexist in a single cell. Thus, the plasmid incompatibility of the pTip and pNit vectors was initially investigated.

A first transformation of *R. erythropolis* JCM3201 was carried out with the pNit-QC2 or the pNit-RC2, and a second transformation of these transformant cells was conducted with the pNit-QT2 or the pNit-RT2. After the second transformation, each transformant was selected on a LB solid medium containing only tetracycline. The result is shown in Table 4. In Table 4, the second column from the right represents the number of colonies appearing on the solid medium containing tetracycline in the case that 1 µg each of the plasmid DNA was used in the second transformation. The rightmost column indicates the percentage (%) of the colony where the plasmid used in the first transformation remains after the second transformation, that is, the incidence of colonies resistant to tetracycline after the second transformation. In this case, the number of colonies investigated is 20 colonies each (n=20). As shown in Table 4, the use of two plasmids having the same replication origin resulted in extreme reduction in the efficiency of the second transformation and frequent loss of the plasmid used in the first transformation after the second transformation and as such, can be said to cause incompatibility. By contrast, two plasmids having different replication origins did not reduce the efficiency of the second transformation and allowed the plasmids used in the first transformation to stably exist even after the second transformation. Thus, it has been suggested that the plasmids having different replication origins do not cause incompatibility. This means plasmids derived from pRE2895 and plasmids derived from pRE8424 are fully "compatible."

EXAMPLE 13

Coexpression of Recombinant Proteins in Single Cell

As described in Example 12, the plasmids derived from pRE2895 and the plasmids derived from pRE8424 were fully compatible and could coexist in the single cell of *R. erythropolis*. From this point of view, the present inventors have attempted the coexpression of PIP and GFP in a single cell.

At first, primers represented by SEQ ID NO: 86 (sHN337) and 87 (sHN338) in the sequence listing were used to perform DNA amplification by PCR with the pHN187 (see Reference Example 1) as a template. The obtained 0.2-kb fragment contains the 5' end portion of the GFP gene. This fragment was digested with NcoI, and its 5' ends were phosphorylated. On the other hand, primers represented by SEQ ID NO: 88 (sHN339) and 89 (sHN340) in the sequence listing were used to perform DNA amplification by PCR with the pHN187 as a template. The obtained 0.5-kb fragment contains the 3' end portion of the GFP gene. This fragment was digested with BglI, and its 5' ends were phosphorylated. These two DNA fragments were simultaneously introduced into the NcoI/BglI sites of the pNit-QT1 and the pNit-RT1, respectively. The resulting plasmids were designated as pHN425 and pHN426, respectively. The pHN425 and the pHN426 contain the full-length GFP gene and are fused with a sequence for attaching a 6×His tag (SEQ ID NO: 168) to the C terminus of GFP. Although the NcoI site present within the GFP gene is eliminated during the above-described procedures, the function of the GFP is not changed.

*R. erythropolis* JCM3201 was cotransformed with the pHN425 and the pHN389, and a cotransformant was selected on a medium containing both tetracycline and chioramphenicol. Alternatively, *R. eythropolis* JCM3201 was cotransformed with the pHN426 and the pHN409, a cotransformant was selected on a medium containing both tetracycline and chloramphenicol. As a control experiment, *R. erythropolis* JCM3201 was separately transformed with the pHN425, the pHN426, the pHN389, and the pHN409. These six types of transformants were allowed to express PIP and GFP as described in Example 1, which were in turn purified by metal chelate chromatography that employs a nickel ion. SDS polyacrylamide electrophoresis for the purification of the recombinant proteins and for the samples before and after purification was conducted by the following procedures. The 6×His tag (SEQ ID NO: 168) was attached to the C terminus of the PIP, and purification was performed using the Ni-NTA Superflow (manufactured by QIAGEN) according to the instruction.

Hereinafter, a specific purification method will be illustrated. Procedures for the purification were performed at 4° C. The bacterial cells (in 20 ml culture solution) where the protein was expressed were recovered and suspended in 1 ml of the NT-Buffer (50 mM Tris-HCI (pH 8.0), 100 mM sodium chloride, and 1 mM dithiothreitol), to which 1 g of glass beads (with a diameter of 0.105 to 0.125 mm) was then added. These beads were put into a reciprocating shaking motion at a speed of 6 in/sec for 20 seconds in the Fast-prep FP120 (manufactured by SAVANT) to destroy the cells. Following centrifugation at 20,000×g, 700 µl of the resulting supernatant was supplemented with the Ni-NTA Superflow equilibrated in advance with the NT-Buffer to bring the bed volume to 40 µl. While this was stirred by rotation for 1 hour, the Ni-NTA Super flow beads were bound to the protein attached to the 6×His tag (SEQ ID NO: 168). These beads were washed four times with the NT-Buffer and then suspended three times in 120 µl of the NTE-Buffer (50 mM Tris-HCI (pH 7.0), 100 mM sodium chloride, 1 mM dithiothreitol, and 400 mM imidazole), thereby eluting the protein attached to the 6×His tag (SEQ ID NO: 168) from the beads. A 1-µl aliquot of the sample was subjected to 12% SDS polyacrylamide electrophoresis according to an ordinary method. A result of staining the gel with Coomassie Brilliant Green G-250 after analysis by SDS polyacrylamide electrophoresis is shown in FIG. 21.

Figure 21:
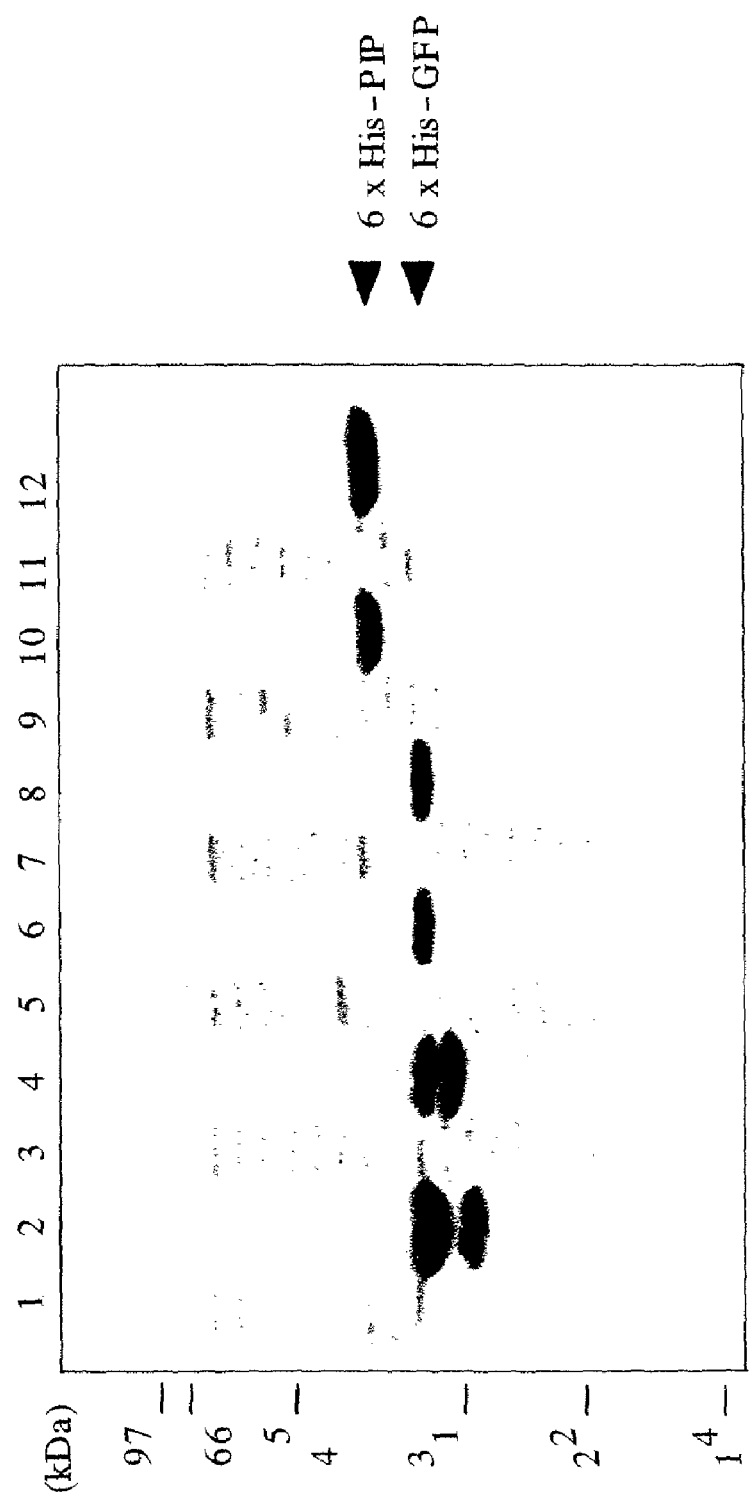
FIG. 21 is a photograph showing a result obtained by the following procedures: PIP and GFP genes are incorporated into two vectors that do not cause incompatibility with each other, PIP and GFP expressed in a single *R. eythropolls* strain JCM3201 cell are purified and analyzed by SDS polyacrylamide electrophoresis, followed by the staining of the gels with Coomassie Brilliant Green G-250. 6×His tags disclosed as SEQ ID NO: 168.

In FIG. 21, an odd-numbered lane indicates the crude extract of the cell (i.e., sample before purification), and an even-numbered lane indicates the sample purified by metal chelate chromatography. In addition, the drawing shows the samples from the R. erythropolis JCM3201 cotransformed with the pHN425 and the pHN389 (lanes 1 and 2) and with the pHN426 and the pHN409 (lanes 3 and 4) as well as the samples from the R. erythropolis JCM3201 transformed with the pHN425 (lanes 5 and 6), with the pHN426 (lanes 7 and 8), with the pHN389 (lanes 9 and 10), and with the pHN409 (lanes 11 and 12).

Two bands are seen in each of the lanes 2 and 4 in FIG. 21. This has indicated that the PIP and the GFP were coexpressed in the single cell and purified. No significant difference was observed in the expression levels of the PIP and the GFP between coexpression (lanes 2 and 4) and independent expression (lanes 6, 8, 10, and 12).

Table 1 shows a list of plasmids used in Examples. Table 2 shows a list of strains used in Examples. Table 3 shows the transformation efficiency of the pNit-QC2 and the pNit-RC2 for R. erythropolis JCM3201, R. fascians JCM10002, and R. opacus DSM44193. Table 4 shows a result of the cotransformation of R. erythropolis JCM 3201 with the pNit-QC2, the pNit-RC2, the pNit-QT2, and the pNit-RT2.

TABLE 1

Table 1 Main plasmids used in the present invention
(6xHis tags disclosed as SEQ ID NO:168)

| Classification | Designation of plasmid | Remarks | Source |
|---|---|---|---|
| Cryptic plasmids of R. erythropolis | pRE2895 | Source of RepAB (cryptic plasmid isolated from R. erythropolis JCM2895) | Japanese Patent Application No. 2002-235008 |
| | pRE8424 | Source of Rep (cryptic plasmid isolated from R. erythropolis DSM8424) | This study |
| | PRE2893 | Cryptic plasmid isolated from R. erythropolis JCM2893 | This study |
| | PRE2894 | Cryptic plasmid isolated from R. erythropolis JCM2694 | This study |
| | PRE43200 | Cryptic plasmid isolated from R. erythropolis DSM43200 | This study |
| For identification of DSO and SSO of pRE8424 | pHN267 | Kan$^r$ on pGEM 3Zf(+) | This study |
| | pHN317 | Rep, DSO, IR I, IR II (SSO) on pHN267 | This study |
| | pHN345 | Rep, DSO, mutated IR I, IR II (SSO) on pHN267 | This study |
| | pHN362 | Rep, DSO, IR I, mutated IR II on pHN267 | This study |
| | pHN363 | Rep, DSO, mutated IR I, mutated IR II on pHN267 | This study |
| | pHN322 | Rep, DSO, IR I, IR II (SSO) on pHN267 | This study |
| | pHN343 | Rep, DSO, IR II (SSO) an pHN267 | This study |
| | pHN344 | Rep, DSO, IR I, IR II (SSO) on pHN267 | This study |
| | pHN324 | Rep, IR I, IR II (SSO) on pHN267 | This Study |
| Source of Rep region for pTip- and pNit-vectors | pHN372 | 2.0-kb region originating from pRE8424 on pBluescript SK (+), BamHI site is eliminated | This study |
| pTip-vectors | pTip-QT1 | $P_{TipA}$, Tet$^r$, RepAB (pRE2895), MCS type 1 | This study |
| | pTip-QT2 | $P_{TipA}$, Tet$^r$, RepAB (pRE2895), MCS type 2 | This study |
| | pTip-RT1 | $P_{TipA}$, Tet$^r$, Rep (pRE8424), MCS type 1 | This study |
| | pTip-RT2 | $P_{TipA}$, Tet$^r$, Rep (pRE8424), MCS type 2 | This study |
| | pTip-QC1 | $P_{TipA}$, Chl$^r$, RepAB (pRE2895), MCS type 1 | This study |
| | pTip-QC2 | $P_{TipA}$, Chl$^r$, RepAB (pRE2895), MCS type 2 | This study |
| | pTip-RC1 | $P_{TipA}$, Chl$^r$, Rep (pRE8424), MCS type 1 | This study |
| | pTip-RC2 | $P_{TipA}$, Chl$^r$, Rep (pRE8424), MCS type 2 | This study |
| pNit-vectors | pNit-QT1 | $P_{Nit}$, Tet$^r$, RepAB (pRF2895), MCS type 1 | This study |
| | pNit-QT2 | $P_{Nit}$, Tet$^r$, RepAB (pRE2895), MCS type 2 | This study |
| | pNit-RT1 | $P_{Nit}$, Tet$^r$, Rep (pRE8424), MCS type 1 | This study |
| | pNit-RT2 | $P_{Nit}$, Tet$^r$, Rep (pRE8424), MCS type 2 | This study |
| | pnit-QC1 | $P_{Nit}$, Chl$^r$, RepAB (pRE2895), MCS type 1 | This study |
| | pNit-QC2 | $P_{Nit}$, Chl$^r$, RepAB (pRE2895), MCS type 2 | This study |
| | pNit-RC1 | $P_{Nit}$, Chl$^r$, Rep (pRE8424), MCS type 1 | This study |
| | pNit-RC2 | $P_{Nit}$, Chl$^r$, Rep (pRE8424), MCS Type 2 | This study |

TABLE 1-continued

Table 1 Main plasmids used in the present invention
(6xHis tags disclosed as SEQ ID NO:168)

| Classification | Designation of plasmid | Remarks | Source |
|---|---|---|---|
| PIP expression vectors | pHN771 | 6xHis-PIP in MCS of pTip-LCH1 | Japanese Patent Application No. 2002-235008 |
| | pHN379 | 6xHis-PIP in MCS of pTip-RT1 | This study |
| | pHN348 | 6xHis-PIP in MCS of pTip-QC1 | This study |
| | pHN380 | 6xHis-PIP in MCS of pTip-RC1 | This study |
| | pHN407 | 6xHis-PIP in MCS of pNit-QT1 | This study |
| | pHN885 | 6xHis-PIP in MCS of pNit-RT1 | This study |
| | pHN409 | 6xHis-PIP in MCS of pNit-QC1 | This study |
| | pHN389 | 6xHis-PIP in MCS of pNit-RC1 | This study |
| | pHN410 | $P_{TipA}$ and LG10-RBS of pHN380 were substituted into $P_{Nit}$ and wild-type TipA-RBS, respectively | This study |
| | pHN387 | LG10-RBS of pHN389 was substituted into wild-type RBS of TipA-RBS | This study |
| | pHN381 | $P_{Nit}$ of pHN389 was substituted into $P_{TipA}$ | This study |
| GFP expression vectors | pHN425 | 6xHis-GFP in MCS of pTip-QT1 | This study |
| | pHN426 | 6xHis-GFP in MCS of pTip-RT1 | This study |

TABLE 2

Main strains used in the present invention

| Genus/Species | Strain | Source | Application |
|---|---|---|---|
| Rhodococcus erythropolis | JCM2895 | Japan Collection of Microorganisms | Source of pRE2895 |
| Rhodococcus erythropolis | DSM8424 | German Collection of Microorganisms end Cell Cultures | Source of pRE8424 |
| Rhodococcus erythropolis | JCM2893 | Japan Collection of Microorganisms | Source of pRE2893 |
| Rhodococcus erythropolis | JCM2894 | Japan Collection of Microorganisms | Source of pRE2894 |
| Rhodococcus erythropolis | DSM43200 | German Collection of Microorganisms and Cell Cultures | Source of pRE43200 |
| Rhodococcus erythropolis | JCM3201 | Japan Collection of Microorganisms | Host strain to express recombinant proteins |
| Rhodococcus fascians | JCM10002 | Japan Collection of Microorganisms | Host strain to express recombinant proteins |
| Rhodococcus opacus | DSM44193 | German Collection of Microorganisms and Cell Cultures | Host strain to express recombinant proteins |
| Rhodococcus ruber | JCM3205 | Japan Collection of Microorganisms | Host strain to express recombinant proteins |
| Rhodococcus rhodochrous | JCM3202 | Japan Collection of Microorganisms | Host strain to express recombinant Proteins |
| Streptomyces coelicolor | JCM4979 | Japan Collection of Microorganisms | Source of dnak transcription terminator |
| Escherichia coli | DH5α | | General cloning |
| Escherichia coli | ER2508 | New England Biolabs | Source of Kan$^r$ |

TABLE 3

Transformation efficiency of pNit-QC2 and pNit-RC2

| | Host cell | | |
|---|---|---|---|
| Plasmid | R. erythropolis | R. fascians | R. opacus |
| pNit-QC2 | $3.8 \times 10^5$ | $8.2 \times 10^2$ | $1.6 \times 10^4$ |
| pNit-RC2 | $2.8 \times 10^5$ | $4.0 \times 10^2$ | $5.2 \times 10^2$ |

TABLE 4

Plasmid incompatibility for *R. erythropolis* strain JCM3201

| Plasmid used in first transformation | Plasmid used in second transformation | Efficiency of second transformation | Percentage of colony where plasmid used in first transformation remains (%; n = 20) |
|---|---|---|---|
| not used | pNit-QT2 | $3.2 \times 10^5$ | — |
| pNit-QC2 | pNit-QT2 | $2.0 \times 10^3$ | 50 |
| pNit-RC2 | pNit-QT2 | $1.3 \times 10^5$ | 100 |
| not used | pNit-RT2 | $4.4 \times 10^4$ | — |
| pNit-QC2 | pNit-RT2 | $3.3 \times 10^4$ | 100 |
| pNit-RC2 | pNit-RT2 | $2.4 \times 10^2$ | 65 |

All publications, patents, and patent applications cited herein are incorporated herein by reference in their entirety.

INDUSTRIAL APPLICABILITY

By using novel vectors of the present invention capable of replication in the rolling circle mode of replication, which are an expression vector capable of inducer-inducible expression of a foreign gene under a temperature condition of 4° C. to 35° C. in a bacterium belonging to the genus *Rhodococcus* and a vector capable of inducer-independent and constitutive expression of a foreign gene in a bacterium belonging to the genus *Rhodococcus*, a foreign protein can efficiently be produced in a bacterium belonging to the genus *Rhodococcus*. Especially the use of a microorganism capable of proliferation even at low temperatures as a host microorganism makes it possible to express and produce a protein whose expression is difficult or impossible under a typical temperature condition suitable for the proliferation of a microorganism, that is, at moderate and high temperatures exceeding approximately 15° C. In addition, there is a remarkable feature in the expression plasmid vectors presented here. Stable co-transformants with at least two vectors can be obtained without causing plasmid incompatibility. For the co-transformation, one vector should carry a DNA region involved in rolling-circle mode of replication, and another one should carry a DNA sequence that originates from pRE2895 and is involved in autonomous replication of a plasmid. Furthermore, such co-transformation makes it possible to co-express foreign proteins in an identical microorganism, if the genes for co-expression are respectively integrated into different vectors.

Sequence Listing Free Text
SEQ ID NOs: 1 to 48: primer and linker sequences
SEQ ID NOs: 49 to 56: vector sequences
SEQ ID NOs: 57 to 89: primer and linker sequences
SEQ ID NO: 90: endogenous plasmid pRE8424 sequence
SEQ ID NOs: 91 to 106: vector sequences
SEQ ID NO: 107: modified TipA gene promoter sequence

The invention claimed is:

1. A DNA comprising a nucleotide sequence of a mutated TipA gene promoter where a mutation of a CAGCGT sequence to a TATAAT sequence is introduced into a −10 region sequence of a TipA gene promoter, wherein (a) the mutated TipA gene promoter is capable of thiostrepton-independent and constitutive expression of a gene located downstream thereof, and (b) said nucleotide sequence is SEQ ID NO: 169.

2. A constitutive expression vector for a bacterium belonging to the genus *Rhodococcus* comprising: a promoter sequence for the constitutive expression of a foreign gene, the promoter sequence being the nucleotide sequence according to claim 1; a ribosome-binding site sequence located downstream of the promoter sequence; and a multiple-cloning site sequence capable of incorporating a foreign gene therein, located downstream of the ribosome-binding site sequence.

3. The constitutive expression vector for a bacterium belonging to the genus *Rhodococcus* according to claim 2, wherein the vector is selected from the group consisting of pNit-RT1 by of SEQ ID NO: 101, pNit-RC1 of SEQ ID NO: 105, pNit-QT1 of SEQ ID NO: 99, and pNit-QC1 of SEQ ID NO: 103.

4. The expression vector according to claim 2, wherein the bacterium belonging to the genus *Rhodococcus* is selected from the group consisting of *R. erythropolis*, *R. fascians*, and *R. opacus*.

5. The expression vector according to claim 3, wherein the vector further comprises a DNA region necessary for the autonomous replication of a plasmid for *Escherichia coli*, and is capable of replication in *Escherichia coli*.

6. A transformant comprising an expression vector according to claim 3.

7. A method of producing a recombinant protein at a temperature ranging from 4° C. to 35° C. by using an expression vector according to claim 3.

* * * * *

```
                        SEQUENCE LISTING

<160> NUMBER OF SEQ ID NOS: 170

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer sHN1

<400> SEQUENCE: 1
cagagctcgt caggtggcac ttttc                                           25

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer sHN2

<400> SEQUENCE: 2
gttgtacaac tagtcgtgcc agctgcatta                                      30

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer sHN120

<400> SEQUENCE: 3
gctgtacacc cgagaagctc ccagcg                                          26
```

```
<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      primer sHN121

<400> SEQUENCE: 4
cggagctctt gaacgagagt tggccgttg                                29

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      primer sHN122

<400> SEQUENCE: 5
tcagatctat cgtcatcgac tgcgatcacg ttgacgccg                     39

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: Synthetic
      primer sHN123

<400> SEQUENCE: 6
acggatcctc cgctgaaatc tcgccgtgcc t                             31

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer sHN130

<400> SEQUENCE: 7
cttcatatgc ggagctcgac cgcgcggg                                 28

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer sHN131

<400> SEQUENCE: 8
atcgagtcgt tcaagggcgt cggc                                     24

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer NEB1233

<400> SEQUENCE: 9
agcggataac aatttcacac agg                                      23

<210> SEQ ID NO 10
```

-continued

```
<211> LENGTH: 19
<212> TYPE: DNA
<213> ORGANISM: Artificial Sequence
<220> FEATURE:
<223> OTHER INFORMATION: Description of Artificial Sequence: Synthetic
      primer sHN10

<400> SEQUENCE: 10
caccaggatg atccccgac                                                      19

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer sHN11

<400> SEQUENCE: 11
gacagtgaca tcaccagc                                                       18

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer NEB1224

<400> SEQUENCE: 12
cgccagggtt ttcccagtca cgac                                                24

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer sHN40

<400> SEQUENCE: 13
atgagctact ccgtgggaca ggtg                                                24

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
      primer sHN41

<400> SEQUENCE: 14
tgcagatctt ccgtttcgac gtgacggag                                           29

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer sHN42

<400> SEQUENCE: 15
cagtctagaa ttgatctcct cgaccg                                              26

<210> SEQ ID NO 16
<211> LENGTH: 20
```

-continued

```
<212> TYPE: DNA
<213> ORGANISM: Artificial Sequence
<220> FEATURE:
<223> OTHER INFORMATION: Description of Artificial Sequence: Synthetic
      primer sHN43

<400> SEQUENCE: 16
tgcaagctcc tatgtaaacg                                                   20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      primer sHN55

<400> SEQUENCE: 17
cgcctgctcc acggccgcc                                                    19

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer sHN56

<400> SEQUENCE: 18
atggaggcac gcagcatg                                                     18

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer sHN57

<400> SEQUENCE: 19
cgccccctcg gagtcggcg                                                    19

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer sHN58

<400> SEQUENCE: 20
atggacgccg ccgaggac                                                     18

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      primer sHN147

<400> SEQUENCE: 21
cgtgtacata tcgaggcggg ctccca                                            26

<210> SEQ ID NO 22
<211> LENGTH: 31
<212> TYPE: DNA
```

```
<213> ORGANISM: Artificial Sequence
<220> FEATURE:
<223> OTHER INFORMATION: Description of Artificial Sequence: Synthetic
      primer sHN39

<400> SEQUENCE: 22
atccatggcc gctcccttct ctgacgccgt c                              31

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer sHN36

<400> SEQUENCE: 23
accatggatc aggaatgcat ag                                        22

<210> SEQ ID NO 24
<211> LENGTH: 59
<212> TYPE: DNA
<213> ORGANISM: Artificial Sequence
<220> FEATURE:
<223> OTHER INFORMATION: Description of Artificial Sequence: Synthetic
      primer sHN37

<400> SEQUENCE: 24
ttactagttt attaatgatg atgatgatga tgcaggtgtt tcaggatgaa atccgaaag    59

<210> SEQ ID NO 25
<211> LENGTH: 29
<212> TYPE: DNA
<213> ORGANISM: Artificial Sequence
<220> FEATURE:
<223> OTHER INFORMATION: Description of Artificial Sequence: Synthetic
      primer sHN6

<400> SEQUENCE: 25
cgtctagagt cccgctgagg cggcgtagc                                 29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      primer sHN9

<400> SEQUENCE: 26
ctactagtcg acccaccggc acccgtgag                                 29

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
      primer sHN141

<400> SEQUENCE: 27
aatctagagt aacgggctac tccgtttaac                                30

<210> SEQ ID NO 28
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer sHN142

<400> SEQUENCE: 28
gggtcgacgg tcctcctgtg gagtggttct                                           30

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer sHN145

<400> SEQUENCE: 29
gcactcgaga tgaaatctaa caatgcgctc atc                                       33

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      primer sHN152

<400> SEQUENCE: 30
agactagtcc tcaacgacag gagcacgatc                                           30

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer T7

<400> SEQUENCE: 31
gtaatacgac tcactatagg gc                                                   22

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer sHN153

<400> SEQUENCE: 32
aatccacagg acgggtgtgg                                                      20

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer sHN154

<400> SEQUENCE: 33
ctctacgccg gacgcatcg                                                       19

<210> SEQ ID NO 34
<211> LENGTH: 22
<212> TYPE: DNA
<213> ORGANISM: Artificial Sequence
<220> FEATURE:
```

<223> OTHER INFORMATION: Description of Artificial Sequence: Synthetic
      primer T3

<400> SEQUENCE: 34
gcaattaacc ctcactaaag gg                                          22

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer sHN155

<400> SEQUENCE: 35
acgacgctct cccttatgcg                                             20

<210> SEQ ID NO 36
<211> LENGTH: 19
<212> TYPE: DNA
<213> ORGANISM: Artificial Sequence
<220> FEATURE:
<223> OTHER INFORMATION: Description of Artificial Sequence: Synthetic
      primer sHN156

<400> SEQUENCE: 36
ccgatgccct tgagagcct                                              19

<210> SEQ ID NO 37
<211> LENGTH: 67
<212> TYPE: DNA
<213> ORGANISM: Artificial Sequence
<220> FEATURE:
<223> OTHER INFORMATION: Description of Artificial Sequence: Synthetic
      primer sHN110

<400> SEQUENCE: 37
aaccatggta tatctccttc ttaaagttaa acaaaattat ttctagacgc cgtccacgct    60
gcctcct                                                           67

<210> SEQ ID NO 38
<211> LENGTH: 77
<212> TYPE: DNA
<213> ORGANISM: Artificial Sequence
<220> FEATURE:
<223> OTHER INFORMATION: Description of Artificial Sequence: Synthetic
      primer NNco1

<400> SEQUENCE: 38
catgggccac catcaccatc accatatggg aattctacgt agcggccgcg gatccaagct    60
tagatctcga ggatgaa                                                77

<210> SEQ ID NO 39
<211> LENGTH: 77
<212> TYPE: DNA
<213> ORGANISM: Artificial Sequence
<220> FEATURE:
<223> OTHER INFORMATION: Description of Artificial Sequence: Synthetic
      primer NNco2

<400> SEQUENCE: 39
ctagttcatc ctcgagatct aagcttggat ccgcggccgc tacgtagaat cccatatgg    60 tgatggtgat ggtggcc                                                77

```
<210> SEQ ID NO 40
<211> LENGTH: 71
<212> TYPE: DNA
<213> ORGANISM: Artificial Sequence
<220> FEATURE:
<223> OTHER INFORMATION: Description of Artificial Sequence: Synthetic
      primer CNco1

<400> SEQUENCE: 40
catgggaatt ctacgtagcg gccgcggatc caagcttaga tctcgaggac atcaccatca      60
ccatcactga a                                                          71

<210> SEQ ID NO 41
<211> LENGTH: 71
<212> TYPE: DNA
<213> ORGANISM: Artificial Sequence
<220> FEATURE:
<223> OTHER INFORMATION: Description of Artificial Sequence: Synthetic
      primer CNco2

<400> SEQUENCE: 41
ctagttcagt gatggtgatg gtgatgtcct cgagatctaa gcttggatcc gcggccgcta      60
cgtagaattc c                                                          71

<210> SEQ ID NO 42
<211> LENGTH: 29
<212> TYPE: DNA
<213> ORGANISM: Artificial Sequence
<220> FEATURE:
<223> OTHER INFORMATION: Description of Artificial Sequence: Synthetic
      primer sHN159

<400> SEQUENCE: 42
tccatatgcg ctcccttctc tgacgccgt                                       29

<210> SEQ ID NO 43
<211> LENGTH: 80
<212> TYPE: DNA
<213> ORGANISM: Artificial Sequence
<220> FEATURE:
<223> OTHER INFORMATION: Description of Artificial Sequence: Synthetic
      primer NNde1

<400> SEQUENCE: 43
tatgggccat caccatcacc atcacgccat gggaattcta cgtagcggcc gcggatccaa      60
gcttagatct cgaggatgaa                                                 80

<210> SEQ ID NO 44
<211> LENGTH: 82
<212> TYPE: DNA
<213> ORGANISM: Artificial Sequence
<220> FEATURE:
<223> OTHER INFORMATION: Description of Artificial Sequence: Synthetic
      primer NNde2

<400> SEQUENCE: 44
ctagttcatc ctcgagatct aagcttggat ccgcggccgc tacgtagaat tcccatggcg      60
tgatggtgat ggtgatggcc ca                                              82

<210> SEQ ID NO 45
<211> LENGTH: 71
<212> TYPE: DNA
<213> ORGANISM: Artificial Sequence
<220> FEATURE:
<223> OTHER INFORMATION: Description of Artificial Sequence: Synthetic
```

-continued primer CNde1

<400> SEQUENCE: 45
tatgggaatt ctacgtagcg gccgcggatc caagcttaga tctcgaggac atcaccatca    60
ccatcactga a    71

<210> SEQ ID NO 46
<211> LENGTH: 73
<212> TYPE: DNA
<213> ORGANISM: Artificial Sequence
<220> FEATURE:
<223> OTHER INFORMATION: Description of Artificial Sequence: Synthetic
      primer CNde2

<400> SEQUENCE: 46
ctagttcagt gatggtgatg gtgatgtcct cgagatctaa gcttggatcc gcggccgcta    60
cgtagaattc cca    73

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
      primer sHN160

<400> SEQUENCE: 47
aacatatgta tatctccttc ttaaagttaa ac    32

<210> SEQ ID NO 48
<211> LENGTH: 41
<212> TYPE: DNA
<213> ORGANISM: Artificial Sequence
<220> FEATURE:
<223> OTHER INFORMATION: Description of Artificial Sequence: Synthetic
      primer sHN343

<400> SEQUENCE: 48
aaactagttc agtgatggtg atggtgatgc tcgagagatc t    41

<210> SEQ ID NO 49
<211> LENGTH: 8166
<212> TYPE: DNA
<213> ORGANISM: Artificial Sequence
<220> FEATURE:
<223> OTHER INFORMATION: Description of Artificial Sequence: Synthetic
      vector pTip-NH1 sequence

<400> SEQUENCE: 49
gagctcgacc gcgcgggtcc cggacgggga agagcgggga gctttgccag agagcgacga    60
cttccccttg cgttggtgat tgccggtcag ggcagccatc cgccatcgtc gcgtagggtg   120
tcacacccca ggaatcgcgt cactgaacac agcagcggt aggacgacca tgactgagtt   180
ggacaccatc gcaaatccgt ccgatcccgc ggtgcagcgg atcatcgatg tcaccaagcc   240
gtcacgatcc aacataaaga caacgttgat cgaggacgtc gagcccctca tgcacagcat   300
cgcggccggg gtggagttca tcgaggtcta cggcagcgac agcagtcctt ttccatctga   360
gttgctggat ctgtgcgggc ggcagaacat accggtccgc ctcatcgact cctcgatcgt   420
caaccagttg ttcaagggggg agcggaaggc caagacattc ggcatcgccc gcgtccctcg   480
cccggccagg ttcggcgata tcgcgagccg cgtgtgggac gtcgtcgttc tcgacggggt   540
gaagatcgtc gggaacatcg gcgcgatagt acgcacgtcg ctcgcgctcg gagcgtcggg   600

```
gatcatcctg gtggacagtg acatcaccag catcgcggac cggcgtctcc aaagggccag    660
ccgaggttac gtcttctccc ttcccgtcgt tctctccggt cgcgaggagg ccatcgcctt    720
cattcgggac agcggtatgc agctgatgac gctcaaggcg gatggcgaca tttccgtgaa    780
ggaactcggg gacaatccgg atcggctggc cttgctgttc ggcagcgaaa agggtgggcc    840
ttccgacctg ttcgaggagg cgtcttccgc ctcggtttcc atcccatga tgagccagac    900 cgagtctctc aacgtttccg tttccctcgg aatcgcgctg cacgagagga tcgacaggaa    960
tctcgcggcc aaccgataag cgcctctgtt cctcggacgc tcggttcctc gacctcgatt   1020
cgtcagtgat gatcacctca cacggcagcg atcaccactg acatatcgag gtcaacggtc   1080
gtggtccggg cggcactcc tcgaaggcgc ggccgacgcc cttgaacgac tcgatgactc    1140
tagagtaacg ggctactccg tttaacggac cccgttctca cgctttaggc ttgaccccgg   1200
agcctgcatg gggcattccg ccgtgaaccc ggtggaatgc cccggcacc cgggctttcc    1260 agcaaagatc acctggcgcc gatgagtaag gcgtacagaa ccactccaca ggaggaccgt   1320
cgagatgaaa tctaacaatg cgctcatcgt catcctcggc accgtcaccc tggatgctgt   1380
aggcataggc ttggttatgc cggtactgcc gggcctcttg cgggatatcg tccattccga   1440
cagcatcgcc agtcactatg gcgtgctgct agcgctatat gcgttgatgc aatttctatg   1500
cgcacccgtt ctcggagcac tgtccgaccg ctttggccgc cgcccagtcc tgctcgcttc   1560
gctacttgga gccactatcg actacgcgat catggcgacc acacccgtcc tgtggattct   1620
ctacgccgga cgcatcgtgg ccggcatcac cggcgccaca ggtgcggttg ctggcgccta   1680
tatcgccgac atcaccgatg gggaagatcg ggctcgccac ttcgggctca tgagcgcttg   1740
tttcggcgtg ggtatggtgg caggcccccgt ggccggggga ctgttgggcg ccatctcctt   1800
gcatgcacca ttccttgcgg cggcggtgct caacggcctc aacctactac tgggctgctt   1860
cctaatgcag gagtcgcata agggagagcg tcgtccgatg cccttgagag ccttcaaccc   1920
agtcagctcc ttccggtggg cgcggggcat gactatcgtc gccgcactta tgactgtctt   1980
ctttatcatg caactcgtag gacaggtgcc ggcagcgctc tgggtcattt tcggcgagga   2040
ccgctttcgc tggagcgcga cgatgatcgg cctgtcgctt gcggtattcg gaatcttgca   2100
cgccctcgct caagccttcg tcactggtcc cgccaccaaa cgtttcggcg agaagcaggc   2160
cattatcgcc ggcatggcgg ccgacgcgct gggctacgtc ttgctggcgt tcgcgacgcg   2220
aggctggatg gccttcccca ttatgattct tctcgcttcc ggcggcatcg ggatgcccgc   2280
gttgcaggcc atgctgtcca ggcaggtaga tgacgaccat cagggacagc ttcaaggatc   2340
gctcgcggct cttaccagcc taacttcgat cattggaccg ctgatcgtca cggcgattta   2400
tgccgcctcg gcgagcacat ggaacgggtt ggcatggatt gtaggcgccg ccctataccct   2460 tgtctgcctc cccgcgttgc gtcgcggtgc atggagccgg ccacctcga cctgaatgga    2520 agccggcggc acctcgctaa cggattcacc actccaagaa ttggagccaa tcaattcttg   2580
cggagaactg tgaatgcgca aaccaaccct tggcagaaca tatccatcgc gtccgccatc   2640
tccagcagcc gcacgcggcg catctcgggc agcgttgggt cctggccacg ggtgcgcatg   2700
atcgtgctcc tgtcgttgag gactagaatt gatctcctcg accgccaatt gggcatctga   2760
gaatcatctg cgtttctcgc acgcaacgta cttgcaacgt tgcaactcct agtgttgtga   2820
atcacacccc accggggggt gggattgcag tcaccgattt ggtgggtgcg cccaggaaga   2880
tcacgtttac ataggagctt gcaatgagct actccgtggg acaggtggcc ggcttcgccg   2940
```

```
gagtgacggt gcgcacgctg caccactacg acgacatcgg cctgctcgta ccgagcgagc    3000
gcagccacgc gggccaccgg cgctacagcg acgccgacct cgaccggctg cagcagatcc    3060
tgttctaccg ggagctgggc ttcccgctcg acgaggtcgc cgccctgctc gacgacccgg    3120
ccgcggaccc gcgcgcgcac ctgcgccgcc agcacgagct gctgtccgcc cggatcggga    3180
aactgcagaa gatggcggcg gccgtggagc aggcgatgga ggcacgcagc atgggaatca    3240
acctcacccc ggaggagaag ttcgaggtct tcggcgactt cgaccccgac cagtacgagg    3300
aggaggtccg ggaacgctgg gggaacaccg acgcctaccg ccagtccaag gagaagaccg    3360
cctcgtacac caaggaggac tggcagcgca tccaggacga ggccgacgag ctcacccggc    3420
gcttcgtcgc cctgatggac gcgggtgagc ccgccgactc cgaggggggcg atggacgccg    3480 ccgaggacca ccgcagggc atcgcccgca accactacga ctgcgggtac gagatgcaca    3540
cctgcctggg cgagatgtac gtgtccgacg aacgtttcac gcgaaacatc gacgccgcca    3600
agccgggcct cgccgcctac atgcgcgacg cgatcctcgc caacgccgtc cggcacaccc    3660
cctgagcggt ggtcgtggcc cgggtctccc gcccggtctc accccacggc tcactcccgg    3720
gccacgacca ccgccgtccc gtacgcgcac acctcggtgc ccacgtccgc cgcctccgtc    3780
acgtcgaaac ggaagatccc cgggtaccga gctcgtcagg tggcactttt cggggaaatg    3840
tgcgcggaac ccctatttgt ttattttcct aaatacattc aaatatgtat ccgctcatga    3900
gacaataacc ctgataaatg cttcaataat attgaaaaag gaagagtatg agtattcaac    3960
atttccgtgt cgcccttatt cccttttttg cggcattttg ccttcctgtt tttgctcacc    4020
cagaaacgct ggtgaaagta aaagatgctg aagatcagtt gggtgcacga gtgggttaca    4080
tcgaactgga tctcaacagc ggtaagatcc ttgagagttt tcgccccgaa gaacgttttc    4140
caatgatgag cacttttaaa gttctgctat gtggcgcggt attatcccgt attgacgccg    4200
ggcaagagca actcggtcgc cgcatacact attctcagaa tgacttggtt gagtactcac    4260
cagtcacaga aaagcatctt acggatggca tgacagtaag agaattatgc agtgctgcca    4320
taaccatgag tgataacact gcggccaact tacttctgac aacgatcgga ggaccgaagg    4380
agctaaccgc ttttttgcac aacatggggg atcatgtaac tcgccttgat cgttgggaac    4440
cggagctgaa tgaagccata ccaaacgacg agcgtgacac cacgatgcct gtagcaatgg    4500
caacaacgtt gcgcaaacta ttaactggcg aactacttac tctagcttcc cggcaacaat    4560
taatagactg gatggaggcg gataaagttg caggaccact tctgcgctcg gcccttccgg    4620
ctggctggtt tattgctgat aaatctggag ccggtgagcg tgggtctcgc ggtatcattg    4680
cagcactggg gccagatggt aagccctccc gtatcgtagt tatctacacg acggggagtc    4740
aggcaactat ggatgaacga aatagacaga tcgctgagat aggtgcctca ctgattaagc    4800
attggtaact gtcagaccaa gtttactcat atatacttta gattgattta aaacttcatt    4860
tttaatttaa aaggatctag gtgaagatcc ttttttgataa tctcatgacc aaaatccctt    4920
aacgtgagtt ttcgttccac tgagcgtcag accccgtaga aagatcaaa ggatcttctt    4980 gagatccttt ttttctgcgc gtaatctgct gcttgcaaac aaaaaaacca ccgctaccag    5040
cggtggtttg tttgccggat caagagctac caactctttt tccgaaggta actggcttca    5100
gcagagcgca gataccaaat actgttcttc tagtgtagcc gtagttaggc caccacttca    5160
agaactctgt agcaccgcct acatacctcg ctctgctaat cctgttacca gtggctgctg    5220
ccagtggcga taagtcgtgt cttaccgggt tggactcaag acgatagtta ccggataagg    5280
cgcagcggtc gggctgaacg gggggttcgt gcacacagcc cagcttggag cgaacgacct    5340
```

-continued

```
acaccgaact gagataccta cagcgtgagc tatgagaaag cgccacgctt cccgaaggga    5400
gaaaggcgga caggtatccg gtaagcggca gggtcggaac aggagagcgc acgagggagc    5460
ttccaggggg aaacgcctgg tatctttata gtcctgtcgg gtttcgccac ctctgacttg    5520
agcgtcgatt tttgtgatgc tcgtcagggg ggcggagcct atggaaaaac gccagcaacg    5580 cggcctttt  acgttcctg  gccttttgct ggccttttgc tcacatgttc tttcctgcgt    5640
tatcccctga ttctgtggat aaccgtatta ccgcctttga gtgagctgat accgctcgcc    5700
gcagccgaac gaccgagcgc agcgagtcag tgagcgagga agcggaagag cgcccaatac    5760
gcaaaccgcc tctccccgcg cgttggccga ttcattaatg cagctggcac gactagagtc    5820 ccgctgagc  ggcgtagcag gtcagccgcc ccagcgtgg  tcaccaaccg gggtggaacg    5880
gcgccggtat cgggtgtgtc cgtggcgctc attccaacct ccgtgtgttt gtgcaggttt    5940
cgcgtgttgc agtccctcgc accggcaccc gcagcgaggg gctcacgggt gccggtgggt    6000
cgactagttc atcctcgaga tctaagcttg gatccgcggc cgctacgtag aattcccata    6060
tggtgatggt gatggtggcc catggccgct cccttctctg acgccgtcca cgctgcctcc    6120
tcacgtgacg tgaggtgcaa gcccggacgt tccgcgtgcc acgccgtgag ccgccgcgtg    6180
ccgtcggctc cctcagcccg ggcggccgtg ggagcccgcc tcgatatgta cacccgagaa    6240
gctcccagcg tcctcctggg ccgcgatact cgaccaccac gcacgcacac cgcactaacg    6300
attcggccgg cgctcgattc ggccggcgct cgattcggcc ggcgtcgat  tcggccggcg    6360 ctcgattcgg ccggcgctcg attcggccga gcagaagagt gaacaaccac cgaccacgct    6420
tccgctctgc gcgccgtacc cgacctacct cccgcagctc gaagcagctc ccgggagtac    6480
cgccgtactc acccgcctgt gctcaccatc caccgacgca aagcccaacc cgagcacacc    6540
tcttgcacca aggtgccgac cgtggctttc cgctcgcagg gttccagaag aaatcgaacg    6600
atccagcgcg gcaaggttca aaaagcaggg gttggtgggg aggaggtttt gggggtgtc    6660 gccgggatac ctgatatggc tttgttttgc gtagtcgaat aattttccat atagcctcgg    6720
cgcgtcggac tcgaatagtt gatgtgggcg ggcacagttg ccccatgaaa tccgcaacgg    6780
ggggcgtgct gagcgatcgg caatgggcgg atgcggtgtt gcttccgcac cggccgttcg    6840
cgacgaacaa cctccaacga ggtcagtacc ggatgagccg cgacgacgca ttggcaatgc    6900
ggtacgtcga gcattcaccg cacgcgttgc tcggatctat cgtcatcgac tgcgatcacg    6960
ttgacgccgc gatgcgcgca ttcgagcaac catccgacca tccggcgccg aactgggtcg    7020
cacaatcgcc gtccggccgc gcacacatcg gatggtggct cggccccaac cacgtgtgcc    7080
gcaccgacag cgcccgactg acgccactgc gctacgccca ccgcatcgaa ccggcctca    7140 agatcagcgt cggcggcgat ttcgcgtatg gcgggcaact gaccaaaaac ccgattcacc    7200
ccgattggga gacgatctac ggcccggcca ccccgtacac attgcggcag ctggccacca    7260
tccacacacc ccggcagatg ccgcgtcggc ccgatcgggc cgtgggcctg gccgcaacg    7320 tcaccatgtt cgacgccacc cggcgatggg cataccgca  gtggtggcaa caccgaaacg    7380
gaaccggccg cgactgggac catctcgtcc tgcagcactg ccacgccgtc aacaccgagt    7440
tcacgacacc actgccgttc accgaagtac gcgccaccgc gcaatccatc tccaaatgga    7500
tctggcgcaa tttcaccgaa gaacagtacc gagcccgaca agcgcatctc ggtcaaaaag    7560
gcggcaaggc aacgcacactc gccaaacaag aagccgtccg aaacaatgca agaaagtacg    7620
acgaacatac gatgcgagag gcgattatct gatgggcgga gccaaaaatc cggtgcgccg    7680
```

```
aaagatgacg gcagcagcag cagccgaaaa attcggtgcc tccactcgca caatccaacg    7740
cttgtttgct gagccgcgtg acgattacct cggccgtgcg aaagctcgcc gtgacaaagc    7800
tgtcgagctg cggaagcagg ggttgaagta ccgggaaatc gccgaagcga tggaactctc    7860
gaccgggatc gtcggccgat tactgcacga cgcccgcagg cacggcgaga tttcagcgga    7920
ggatctgtcg gcgtaaccaa gtcagcgggt tgtcgggttc cggccggcgc tcggcactcg    7980
gaccggccgg cggatggtgt tctgcctctg gcgcagcgtc agctaccgcc gaaggcctgt    8040
catcgaccgg cttcgactga agtatgagca acgtcacagc ctgtgattgg atgatccgct    8100
cacgctcgac cgctacctgt tcagctgccg cccgctgggc atgagcaacg gccaactctc    8160
gttcaa                                                               8166
```

<210> SEQ ID NO 50
<211> LENGTH: 8169
<212> TYPE: DNA
<213> ORGANISM: Artificial Sequence
<220> FEATURE:
<223> OTHER INFORMATION: Description of Artificial Sequence: Synthetic vector pTip-NH2 sequence

<400> SEQUENCE: 50

```
gagctcgacc gcgcgggtcc cggacgggga agagcgggga gctttgccag agagcgacga     60
cttccccttg cgttggtgat tgccggtcag ggcagccatc cgccatcgtc gcgtagggtg    120
tcacacccca ggaatcgcgt cactgaacac agcagccggt aggacgacca tgactgagtt    180
ggacaccatc gcaaatccgt ccgatcccgc ggtgcagcgg atcatcgatg tcaccaagcc    240
gtcacgatcc aacataaaga caacgttgat cgaggacgtc gagcccctca tgcacagcat    300
cgcggccggg gtggagttca tcgaggtcta cggcagcgac agcagtcctt ttccatctga    360
gttgctggat ctgtgcgggc ggcagaacat accggtccgc ctcatcgact cctcgatcgt    420
caaccagttg ttcaaggggg agcggaaggc caagacattc ggcatcgccc gcgtccctcg    480
cccggccagg ttcggcgata tcgcgagccg gcgtggggac gtcgtcgttc tcgacggggt    540
gaagatcgtc gggaacatcg gcgcgatagt acgcacgtcg ctcgcgctcg gagcgtcggg    600
gatcatcctg gtggacagtg acatcaccag catcgcggac cggcgtctcc aaagggccag    660
ccgaggttac gtcttctccc ttcccgtcgt tctctccggt cgcgaggagg ccatcgcctt    720
cattcgggac agcggtatgc agctgatgac gctcaaggcg gatggcgaca tttccgtgaa    780
ggaactcggg gacaatccgg atcggctggc cttgctgttc ggcagcgaaa agggtggggcc    840 ttccgacctg ttcgaggagg cgtcttccgc ctcggtttcc atccccatga tgagccagac    900
cgagtctctc aacgttttcg tttccctcgg aatcgcgctg cacgagagga tcgacaggaa    960
tctcgcggcc aaccgataag cgcctctgtt cctcggacgc tcggttcctc gacctcgatt   1020
cgtcagtgat gatcacctca cacggcagcg atcaccactg acatatcgag gtcaacggtc   1080
gtggtccggg cggcactcc tcgaaggcgc ggccgacgcc cttaacgac tcgatgactc    1140 tagagtaacg ggctactccg tttaacggac cccgttctca cgctttaggc ttgaccccgg   1200
agcctgcatg gggcattccg ccgtgaaccc ggtggaatgc ccccggcacc cgggcttcc    1260 agcaaagatc acctggcgcc gatgagtaag gcgtacagaa ccactccaca ggaggaccgt    1320
cgagatgaaa tctaacaatg cgctcatcgt catcctcggc accgtcaccc tggatgctgt    1380
aggcataggc ttggttatgc cggtactgcc gggcctcttg cgggatatcg tccattccga    1440
cagcatcgcc agtcactatg gcgtgctgct agcgctatat gcgttgatgc aatttctatg    1500
```

```
cgcacccgtt ctcggagcac tgtccgaccg cttttggccgc cgcccagtcc tgctcgcttc   1560
gctacttgga gccactatcg actacgcgat catggcgacc acacccgtcc tgtggattct   1620
ctacgccgga cgcatcgtgg ccggcatcac cggcgccaca ggtgcggttg ctggcgccta   1680
tatcgccgac atcaccgatg gggaagatcg ggctcgccac ttcgggctca tgagcgcttg   1740
tttcggcgtg gtatggtgg caggccccgt ggccggggga ctgttgggcg ccatctcctt   1800
gcatgcacca ttccttgcgg cggcggtgct caacggcctc aacctactac tgggctgctt   1860
cctaatgcag gagtcgcata agggagagcg tcgtccgatg cccttgagag ccttcaaccc   1920
agtcagctcc ttccggtggg cgcggggcat gactatcgtc gccgcactta tgactgtctt   1980
ctttatcatg caactcgtag acaggtgcc ggcagcgctc tgggtcattt tcggcgagga   2040
ccgctttcgc tggagcgcga cgatgatcgg cctgtcgctt gcggtattcg gaatcttgca   2100
cgccctcgct caagccttcg tcactggtcc cgccaccaaa cgtttcggcg agaagcaggc   2160
cattatcgcc ggcatggcgg ccgacgcgct gggctacgtc ttgctggcgt tcgcgacgcg   2220
aggctggatg gccttcccca ttatgattct tctcgcttcc ggcggcatcg ggatgcccgc   2280
gttgcaggcc atgctgtcca ggcaggtaga tgacgaccat cagggacagc ttcaaggatc   2340
gctcgcggct cttaccagcc taacttcgat cattggaccg ctgatcgtca cggcgattta   2400
tgccgcctcg gcgagcacat ggaacgggtt ggcatggatt gtaggcgccg ccctatacct   2460
tgtctgcctc ccgcgttgc gtcgcggtgc atggagccgg ccacctcga cctgaatgga   2520 agccggcgga acctcgctaa cggattcacc actccaagaa ttggagccaa tcaattcttg   2580
cggagaactg tgaatgcgca aaccaaccct tggcagaaca tatccatcgc gtccgccatc   2640
tccagcagcc gcacgcggcg catctcgggc agcgttgggt cctggccacg ggtgcgcatg   2700
atcgtgctcc tgtcgttgag gactagaatt gatctcctcg accgccaatt gggcatctga   2760
gaatcatctg cgtttctcgc acgcaacgta cttgcaacgt tgcaactcct agtgttgtga   2820
atcacacccc accgggggt gggattgcag tcaccgattt ggtgggtgcg cccaggaaga   2880
tcacgtttac ataggagctt gcaatgagct actccgtggg acaggtggcc ggcttcgccg   2940
gagtgacggt gcgcacgctg caccactacg acgacatcgg cctgctcgta ccgagcgagc   3000
gcagccacgc gggccaccgg cgctacagcg acgccgacct cgaccggctg cagcagatcc   3060
tgttctaccg ggagctgggc ttcccgctcg acgaggtcgc cgccctgctc gacgacccgg   3120
ccgcggaccc gcgcgcgcac ctgcgccgcc agcacgagct gctgtccgcc cggatcggga   3180
aactgcagaa gatggcggcg ccgtggagc aggcgatgga ggcacgcagc atgggaatca   3240
acctcacccc ggaggagaag ttcgaggtct tcggcgactt cgaccccgac cagtacgagg   3300
aggaggtccg ggaacgctgg gggaacaccg acgcctaccg ccagtccaag gagaagaccg   3360
cctcgtacac caaggaggac tggcagcgca tccaggacga ggccgacgag ctcacccggc   3420
gcttcgtcgc cctgatggac gcgggtgagc ccgccgactc cgaggggcg atggacgccg   3480 ccgaggacca ccggcagggc atcgcccgca accactacga ctgcgggtac gagatgcaca   3540
cctgcctggg cgagatgtac gtgtccgacg aacgtttcac gcgaaacatc gacgccgcca   3600 gccgggcct cgccgcctac atgcgcgacg cgatcctcgc caacgccgtc cggcacaccc   3660
cctgagcggt ggtcgtggcc cgggtctccc gcccggtctc accccacggc tcactcccgg   3720
gccacgacca ccgccgtccc gtacgcgcac acctcggtgc ccacgtccgc cgcctccgtc   3780
acgtcgaaac ggaagatccc cgggtaccga gctcgtcagg tggcactttt cggggaaatg   3840
tgcgcggaac ccctatttgt ttatttttct aaatacattc aaatatgtat ccgctcatga   3900
```

-continued

```
gacaataacc ctgataaatg cttcaataat attgaaaaag gaagagtatg agtattcaac   3960
atttccgtgt cgcccttatt cccttttttg cggcattttg ccttcctgtt tttgctcacc   4020
cagaaacgct ggtgaaagta aaagatgctg aagatcagtt gggtgcacga gtgggttaca   4080
tcgaactgga tctcaacagc ggtaagatcc ttgagagttt cgccccgaa gaacgttttc    4140
caatgatgag cacttttaaa gttctgctat gtggcgcggt attatcccgt attgacgccg   4200
ggcaagagca actcggtcgc cgcatacact attctcagaa tgacttggtt gagtactcac   4260
cagtcacaga aaagcatctt acggatggca tgacagtaag agaattatgc agtgctgcca   4320
taaccatgag tgataacact gcggccaact tacttctgac aacgatcgga ggaccgaagg   4380
agctaaccgc ttttttgcac aacatggggg atcatgtaac tcgccttgat cgttgggaac   4440
cggagctgaa tgaagccata ccaaacgacg agcgtgacac cacgatgcct gtagcaatgg   4500
caacaacgtt gcgcaaacta ttaactggcg aactacttac tctagcttcc cggcaacaat   4560
taatagactg gatggaggcg gataaagttg caggaccact tctgcgctcg gcccttccgg   4620
ctggctggtt tattgctgat aaatctggag ccggtgagcg tgggtctcgc ggtatcattg   4680
cagcactggg gccagatggt aagccctccc gtatcgtagt tatctacacg acggggagtc   4740
aggcaactat ggatgaacga atagacaga tcgctgagat aggtgcctca ctgattaagc    4800
attggtaact gtcagaccaa gtttactcat atatacttta gattgattta aaacttcatt   4860
tttaatttaa aaggatctag gtgaagatcc tttttgataa tctcatgacc aaaatccctt   4920
aacgtgagtt ttcgttccac tgagcgtcag accccgtaga aaagatcaaa ggatcttctt   4980
gagatccttt ttttctgcgc gtaatctgct gcttgcaaac aaaaaaacca ccgctaccag   5040
cggtggtttg tttgccggat caagagctac caactctttt tccgaaggta actggcttca   5100
gcagagcgca gataccaaat actgttcttc tagtgtagcc gtagttaggc caccacttca   5160
agaactctgt agcaccgcct acatacctcg ctctgctaat cctgttacca gtggctgctg   5220
ccagtggcga taagtcgtgt cttaccgggt tggactcaag acgatagtta ccggataagg   5280
cgcagcggtc gggctgaacg gggggttcgt gcacacagcc cagcttggag cgaacgacct   5340
acaccgaact gagataccta cagcgtgagc tatgagaaag cgccacgctt cccgaaggga   5400
gaaaggcgga caggtatccg gtaagcggca gggtcggaac aggagagcgc acgagggagc   5460
ttccagggg aaacgcctgg tatctttata gtcctgtcgg gtttcgccac ctctgacttg    5520
agcgtcgatt tttgtgatgc tcgtcagggg ggcggagcct atggaaaaac gccagcaacg   5580
cggccttttt acggttcctg gccttttgct ggccttttgc tcacatgttc tttcctgcgt   5640
tatcccctga ttctgtggat aaccgtatta ccgcctttga gtgagctgat accgctcgcc   5700
gcagccgaac gaccgagcgc agcgagtcag tgagcgagga agcggaagag cgcccaatac   5760
gcaaaccgcc tctccccgcg cgttggccga ttcattaatg cagctggcac gactagagtc   5820
ccgctgaggc ggcgtagcag gtcagccgcc ccagcggtgg tcaccaaccg ggtggaacg    5880
gcgccggtat cgggtgtgtc cgtggcgctc attccaacct ccgtgtgttt gtgcaggttt   5940
cgcgtgttgc agtccctcgc accggcaccc gcagcgaggg gctcacgggt gccggtgggt   6000
cgactagttc atcctcgaga tctaagcttg gatccgcggc cgctacgtag aattcccatg   6060
gcgtgatggt gatggtgatg gcccatatgc gctcccttct ctgacgccgt ccacgctgcc   6120
tcctcacgtg acgtgaggtg caagcccgga cgttccgcgt gccacgccgt gagccgccgc   6180
gtgccgtcgg ctccctcagc ccgggcggcc gtgggagccc gcctcgatat gtacacccga   6240
```

```
gaagctccca gcgtcctcct gggccgcgat actcgaccac cacgcacgca caccgcacta   6300
acgattcggc cggcgctcga ttcggccggc gctcgattcg gccggcgctc gattcggccg   6360
gcgctcgatt cggccggcgc tcgattcggc cgagcagaag agtgaacaac caccgaccac   6420
gcttccgctc tgcgcgccgt acccgaccta cctcccgcag ctcgaagcag ctcccgggag   6480
taccgccgta ctcacccgcc tgtgctcacc atccaccgac gcaaagccca acccgagcac   6540
acctcttgca ccaaggtgcc gaccgtggct ttccgctcgc agggttccag aagaaatcga   6600
acgatccagc gcggcaaggt tcaaaaagca ggggttggtg gggaggaggt tttgggggt    6660 gtcgccggga tacctgatat ggctttgttt tgcgtagtcg aataatttc catatagcct    6720 cggcgcgtcg gactcgaata gttgatgtgg gcgggcacag ttgccccatg aaatccgcaa   6780 cgggggggcgt gctgagcgat cggcaatggg cggatgcgt gttgcttccg caccggccgt    6840
tcgcgacgaa caacctccaa cgaggtcagt accggatgag ccgcgacgac gcattggcaa   6900
tgcggtacgt cgagcattca ccgcacgcgt tgctcggatc tatcgtcatc gactgcgatc   6960
acgttgacgc cgcgatgcgc gcattcgagc aaccatccga ccatccggcg ccgaactggg   7020
tcgcacaatc gccgtccggc cgcgcacaca tcggatggtg gctcggcccc aaccacgtgt   7080
gccgcaccga cagcgcccga ctgacgccac tgcgctacgc ccaccgcatc gaaaccggcc   7140
tcaagatcag cgtcggcggc gatttcgcgt atggcgggca actgaccaaa aacccgattc   7200
accccgattg ggagacgatc tacggcccgg ccaccccgta cacattgcgg cagctggcca   7260
ccatccacac accccggcag atgccgcgtc ggcccgatcg ggccgtgggc ctgggccgca   7320
acgtcaccat gttcgacgcc acccggcgat gggcataccc gcagtggtgg caacaccgaa   7380
acggaaccgg ccgcgactgg gaccatctcg tcctgcagca ctgccacgcc gtcaacaccg   7440
agttcacgac accactgccg ttcaccgaag tacgcgccac cgcgcaatcc atctccaaat   7500
ggatctggcg caatttcacc gaagaacagt accgagcccg acaagcgcat ctcggtcaaa   7560
aaggcggcaa ggcaacgaca ctcgccaaac aagaagccgt ccgaaacaat gcaagaaagt   7620
acgacgaaca tacgatgcga gaggcgatta tctgatgggc ggagccaaaa atccggtgcg   7680
ccgaaagatg acggcagcag cagcagccga aaaattcggt gcctccactc gcacaatcca   7740
acgcttgttt gctgagccgc gtgacgatta cctcggccgt gcgaaagctc gccgtgacaa   7800
agctgtcgag ctgcggaagc aggggttgaa gtaccgggaa atcgccgaag cgatggaact   7860
ctcgaccggg atcgtcggcc gattactgca cgacgcccgc aggcacggcg agatttcagc   7920
ggaggatctg tcggcgtaac caagtcagcg ggttgtcggg ttccggccgg cgctcggcac   7980
tcggaccggc cggcgatgg tgttctgcct ctggcgcagc gtcagctacc gccgaaggcc    8040
tgtcatcgac cggcttcgac tgaagtatga gcaacgtcac agcctgtgat tggatgatcc   8100
gctcacgctc gaccgctacc tgttcagctg ccgcccgctg gcatgagca acggccaact    8160 ctcgttcaa                                                            8169
```

<210> SEQ ID NO 51
<211> LENGTH: 8160
<212> TYPE: DNA
<213> ORGANISM: Artificial Sequence
<220> FEATURE:
<223> OTHER INFORMATION: Description of Artificial Sequence: Synthetic
      vector pTip-CH1 sequence

<400> SEQUENCE: 51

```
gagctcgacc gcgcgggtcc cggacgggga agagcgggga gctttgccag agagcgacga    60
```

```
cttcccttg cgttggtgat tgccggtcag ggcagccatc cgccatcgtc gcgtagggtg    120
tcacacccca ggaatcgcgt cactgaacac agcagccggt aggacgacca tgactgagtt    180
ggacaccatc gcaaatccgt ccgatcccgc ggtgcagcgg atcatcgatg tcaccaagcc    240
gtcacgatcc aacataaaga caacgttgat cgaggacgtc gagcccctca tgcacagcat    300
cgcggccggg gtggagttca tcgaggtcta cggcagcgac agcagtcctt ttccatctga    360
gttgctggat ctgtgcgggc ggcagaacat accggtccgc ctcatcgact cctcgatcgt    420
caaccagttg ttcaaggggg agcggaaggc caagacattc ggcatcgccc gcgtccctcg    480
cccggccagg ttcggcgata tcgcgagccg gcgtggggac gtcgtcgttc tcgacggggt    540
gaagatcgtc gggaacatcg gcgcgatagt acgcacgtcg ctcgcgctcg agcgtcggg    600 gatcatcctg gtggacagtg acatcaccag catcgcggac cggcgtctcc aaagggccag    660
ccgaggttac gtcttctccc ttcccgtcgt tctctccggt cgcgaggagg ccatcgcctt    720
cattcgggac agcggtatgc agctgatgac gctcaaggcg gatggcgaca tttccgtgaa    780
ggaactcggg gacaatccgg atcggctggc cttgctgttc ggcagcgaaa agggtgggcc    840
ttccgacctg ttcgaggagg cgtcttccgc ctcggtttcc atcccatga tgagccagac    900 cgagtctctc aacgtttccg tttccctcgg aatcgcgctg cacgagagga tcgacaggaa    960
tctcgcggcc aaccgataag cgcctctgtt cctcggacgc tcggttcctc gacctcgatt   1020
cgtcagtgat gatcacctca cacggcagcg atcaccactg acatatcgag gtcaacggtc   1080
gtggtccggg cggcactcc tcgaaggcgc ggccgacgcc cttgaacgac tcgatgactc   1140
tagagtaacg ggctactccg tttaacggac cccgttctca cgctttaggc ttgaccccgg   1200
agcctgcatg gggcattccg ccgtgaaccc ggtggaatgc ccccggcacc cgggctttcc   1260
agcaaagatc acctggcgcc gatgagtaag gcgtacagaa ccactccaca ggaggaccgt   1320
cgagatgaaa tctaacaatg cgctcatcgt catcctcggc accgtcaccc tggatgctgt   1380
aggcataggc ttggttatgc cggtactgcc gggcctcttg cgggatatcg tccattccga   1440
cagcatcgcc agtcactatg gcgtgctgct agcgctatat gcgttgatgc aatttctatg   1500
cgcacccgtt ctcggagcac tgtccgaccg cttggccgc cgcccagtcc tgctcgcttc   1560
gctacttgga gccactatcg actacgcgat catggcgacc acaccgtcc tgtggattct   1620 ctacgccgga cgcatcgtgg ccggcatcac cggcgccaca ggtgcggttg ctggcgccta   1680
tatcgccgac atcaccgatg gggaagatcg ggctcgccac ttcgggctca tgagcgcttg   1740
tttcggcgtg ggtatggtgg caggccccgt ggccggggga ctgttgggcg ccatctcctt   1800
gcatgcacca ttccttgcgg cggcggtgct caacggcctc aacctactac tgggctgctt   1860
cctaatgcag gagtcgcata agggagagcg tcgtccgatg cccttgagag ccttcaaccc   1920
agtcagctcc ttccggtggg cgcggggcat gactatcgtc gccgcactta tgactgtctt   1980
ctttatcatg caactcgtag acaggtgcc ggcagcgctc tgggtcattt tcggcgagga   2040
ccgctttcgc tggagcgcga cgatgatcgg cctgtcgctt gcggtattcg gaatcttgca   2100
cgccctcgct caagccttcg tcactggtcc cgccaccaaa cgtttcggcg agaagcaggc   2160
cattatcgcc ggcatggcgg ccgacgcgct gggctacgtc ttgctggcgt tcgcgacgcg   2220
aggctggatg gccttcccca ttatgattct tctcgcttcc ggcggcatcg gatgcccgc    2280 gttgcaggcc atgctgtcca ggcaggtaga tgacgaccat cagggacagc ttcaaggatc   2340
gctcgcggct cttaccagcc taacttcgat cattggaccg ctgatcgtca cggcgattta   2400
tgccgcctcg gcgagcacat ggaacgggtt ggcatggatt gtaggcgccg ccctatacct   2460
```

```
tgtctgcctc cccgcgttgc gtcgcggtgc atggagccgg gccacctcga cctgaatgga    2520
agccggcggc acctcgctaa cggattcacc actccaagaa ttggagccaa tcaattcttg    2580
cggagaactg tgaatgcgca aaccaaccct tggcagaaca tatccatcgc gtccgccatc    2640
tccagcagcc gcacgcggcg catctcgggc agcgttgggt cctggccacg ggtgcgcatg    2700
atcgtgctcc tgtcgttgag gactagaatt gatctcctcg accgccaatt gggcatctga    2760
gaatcatctg cgtttctcgc acgcaacgta cttgcaacgt tgcaactcct agtgttgtga    2820
atcacacccc accgggggt gggattgcag tcaccgattt ggtgggtgcg cccaggaaga    2880
tcacgtttac ataggagctt gcaatgagct actccgtggg acaggtggcc ggcttcgccg    2940
gagtgacggt gcgcacgctg caccactacg acgacatcgg cctgctcgta ccgagcgagc    3000
gcagccacgc gggccaccgg cgctacagcg acgccgacct cgaccggctg cagcagatcc    3060
tgttctaccg ggagctgggc ttcccgctcg acgaggtcgc cgccctgctc gacgacccgg    3120
ccgcggaccc gcgcgcgcac ctgcgccgcc agcacgagct gctgtccgcc cggatcggga    3180
aactgcagaa gatggcggcg ccgtggagc aggcgatgga ggcacgcagc atgggaatca    3240
acctcacccc ggaggagaag ttcgaggtct tcggcgactt cgaccccgac cagtacgagg    3300
aggaggtccg ggaacgctgg gggaacaccg acgcctaccg ccagtccaag gagaagaccg    3360
cctcgtacac caaggaggac tggcagcgca tccaggacga ggccgacgag ctcacccggc    3420
gcttcgtcgc cctgatggac gcgggtgagc ccgccgactc cgagggggcg atggacgccg    3480
ccgaggacca ccggcagggc atcgcccgca accactacga ctgcgggtac gagatgcaca    3540
cctgcctggg cgagatgtac gtgtccgacg aacgtttcac gcgaaacatc gacgccgcca    3600
agccgggcct cgccgcctac atgcgcgacg cgatcctcgc caacgccgtc cggcacaccc    3660
cctgagcggt ggtcgtggcc cgggtctccc gcccggtctc accccacggc tcactcccgg    3720
gccacgacca ccgccgtccc gtacgcgcac acctcggtgc ccacgtccgc cgcctccgtc    3780
acgtcgaaac ggaagatccc cgggtaccga gctcgtcagg tggcactttt cggggaaatg    3840
tgcgcggaac ccctatttgt ttattttct aaatacattc aaatatgtat ccgctcatga    3900
gacaataacc ctgataaatg cttcaataat attgaaaaag gaagagtatg agtattcaac    3960
atttccgtgt cgcccttatt cccttttttg cggcattttg ccttcctgtt tttgctcacc    4020
cagaaacgct ggtgaaagta aaagatgctg aagatcagtt gggtgcacga gtgggttaca    4080
tcgaactgga tctcaacagc ggtaagatcc ttgagagttt tcgccccgaa gaacgttttc    4140
caatgatgag cacttttaaa gttctgctat gtggcgcggt attatcccgt attgacgccg    4200
ggcaagagca actcggtcgc cgcatacact attctcagaa tgacttggtt gagtactcac    4260
cagtcacaga aaagcatctt acggatggca tgacagtaag agaattatgc agtgctgcca    4320
taaccatgag tgataacact gcggccaact tacttctgac aacgatcgga ggaccgaagg    4380
agctaaccgc ttttttgcac aacatggggg atcatgtaac tcgccttgat cgttgggaac    4440
cggagctgaa tgaagccata ccaaacgacg agcgtgacac cacgatgcct gtagcaatgg    4500
caacaacgtt gcgcaaacta ttaactggcg aactacttac tctagcttcc cggcaacaat    4560
taatagactg gatggaggcg gataaagttg caggaccact tctgcgctcg gcccttccgg    4620
ctggctggtt tattgctgat aaatctggag ccggtgagcg tgggtctcgc ggtatcattg    4680
cagcactggg gccagatggt aagccctccc gtatcgtagt tatctacacg acggggagtc    4740
aggcaactat ggatgaacga aatagacaga tcgctgagat aggtgcctca ctgattaagc    4800
```

```
attggtaact gtcagaccaa gtttactcat atatacttta gattgattta aaacttcatt    4860
tttaatttaa aaggatctag gtgaagatcc tttttgataa tctcatgacc aaaatccctt    4920
aacgtgagtt ttcgttccac tgagcgtcag accccgtaga aaagatcaaa ggatcttctt    4980
gagatccttt ttttctgcgc gtaatctgct gcttgcaaac aaaaaaacca ccgctaccag    5040
cggtggtttg tttgccggat caagagctac caactctttt tccgaaggta actggcttca    5100
gcagagcgca gataccaaat actgttcttc tagtgtagcc gtagttaggc caccacttca    5160
agaactctgt agcaccgcct acatacctcg ctctgctaat cctgttacca gtggctgctg    5220
ccagtggcga taagtcgtgt cttaccgggt tggactcaag acgatagtta ccggataagg    5280
cgcagcggtc gggctgaacg gggggttcgt gcacacagcc cagcttggag cgaacgacct    5340
acaccgaact gagataccta cagcgtgagc tatgagaaag cgccacgctt cccgaaggga    5400
gaaaggcgga caggtatccg gtaagcggca gggtcggaac aggagagcgc acgagggagc    5460
ttccaggggg aaacgcctgg tatctttata gtcctgtcgg gtttcgccac ctctgacttg    5520
agcgtcgatt tttgtgatgc tcgtcagggg gcggagcct atggaaaaac gccagcaacg    5580
cggccttttt acgttcctg gccttttgct ggccttttgc tcacatgttc tttcctgcgt    5640
tatcccctga ttctgtggat aaccgtatta ccgcctttga gtgagctgat accgctcgcc    5700
gcagccgaac gaccgagcgc agcgagtcag tgagcgagga agcggaagag cgcccaatac    5760
gcaaaccgcc tctccccgcg cgttggccga ttcattaatg cagctggcac gactagagtc    5820
ccgctgaggc ggcgtagcag gtcagccgcc ccagcgtgg tcaccaaccg gggtggaacg    5880
gcgccggtat cgggtgtgtc cgtggcgctc attccaacct ccgtgtgttt gtgcaggttt    5940
cgcgtgttgc agtccctcgc accggcaccc gcagcgaggg gctcacgggt gccggtgggt    6000
cgactagttc agtgatggtg atggtgatgt cctcgagatc taagcttgga tccgcggccg    6060
ctacgtagaa ttcccatggc cgctcccttc tctgacgccg tccacgctgc ctcctcacgt    6120
gacgtgaggt gcaagcccgg acgttccgcg tgccacgccg tgagccgccg cgtgccgtcg    6180
gctccctcag cccgggcggc cgtgggagcc cgcctcgata tgtacacccg agaagctccc    6240
agcgtcctcc tgggccgcga tactcgacca ccacgcacgc acaccgcact aacgattcgg    6300
ccggcgctcg attcggccgg cgctcgattc ggcggcgct cgattcggcc ggcgctcgat    6360
tcggccggcg ctcgattcgg ccgagcagaa gagtgaacaa ccaccgacca cgcttccgct    6420
ctgcgcgccg tacccgacct acctcccgca gctcgaagca gctcccggga gtaccgccgt    6480
actcacccgc ctgtgctcac catccaccga cgcaaagccc aacccgagca cacctcttgc    6540
accaaggtgc cgaccgtggc tttccgctcg cagggttcca gaagaaatcg aacgatccag    6600
cgcggcaagg ttcaaaaagc aggggttggt ggggaggagg ttttgggggg tgtcgccggg    6660
atacctgata tggctttgtt ttgcgtagtc gaataatttt ccatatagcc tcggcgcgtc    6720
ggactcgaat agttgatgtg ggcgggcaca gttgccccat gaaatccgca acggggggcg    6780
tgctgagcga tcggcaatgg gcggatgcgg tgttgcttcc gcaccggccg ttcgcgacga    6840
acaacctcca acgaggtcag taccggatga gccgcgacga cgcattggca atgcggtacg    6900
tcgagcattc accgcacgcg ttgctcggat ctatcgtcat cgactgcgat cacgttgacg    6960
ccgcgatgcg cgcattcgag caaccatccg accatccggc gccgaactgg gtcgcacaat    7020
cgccgtccgg ccgcgcacac atcggatggt ggctcggccc caaccacgtg tgccgcaccg    7080
acagcgcccg actgacgcca ctgcgctacg cccaccgcat cgaaaccggc ctcaagatca    7140
gcgtcggcgg cgatttcgcg tatggcgggc aactgaccaa aaacccgatt caccccgatt    7200
```

```
gggagacgat ctacggcccg gccacccgt acacattgcg gcagctggcc accatccaca     7260
caccccggca gatgccgcgt cggcccgatc gggccgtggg cctgggccgc aacgtcacca     7320
tgttcgacgc cacccggcga tgggcatacc cgcagtggtg gcaacaccga aacggaaccg     7380
gccgcgactg ggaccatctc gtcctgcagc actgccacgc cgtcaacacc gagttcacga     7440
caccactgcc gttcaccgaa gtacgcgcca ccgcgcaatc catctccaaa tggatctggc     7500
gcaatttcac cgaagaacag taccgagccc gacaagcgca tctcggtcaa aaaggcggca     7560
aggcaacgac actcgccaaa caagaagccg tccgaaacaa tgcaagaaag tacgacgaac     7620
atacgatgcg agaggcgatt atctgatggg cggagccaaa aatccggtgc gccgaaagat     7680
gacggcagca gcagcagccg aaaaattcgg tgcctccact cgcacaatcc aacgcttgtt     7740
tgctgagccg cgtgacgatt acctcggccg tgcgaaagct cgccgtgaca agctgtcga      7800 gctgcggaag caggggttga agtaccggga atcgccgaa gcgatggaac tctcgaccgg      7860
gatcgtcggc cgattactgc acgacgcccg caggcacggc gagatttcag cggaggatct     7920
gtcggcgtaa ccaagtcagc gggttgtcgg gttccggccg cgctcggca ctcggaccgg      7980 ccggcggatg gtgttctgcc tctggcgcag cgtcagctac cgccgaaggc ctgtcatcga     8040
ccggcttcga ctgaagtatg agcaacgtca cagcctgtga ttggatgatc cgctcacgct     8100
cgaccgctac ctgttcagct gccgcccgct gggcatgagc aacggccaac tctcgttcaa     8160
```

<210> SEQ ID NO 52
<211> LENGTH: 8160
<212> TYPE: DNA
<213> ORGANISM: Artificial Sequence
<220> FEATURE:
<223> OTHER INFORMATION: Description of Artificial Sequence: Synthetic
      vector pTip-CH2 sequence

<400> SEQUENCE: 52

```
gagctcgacc gcgcgggtcc cggacgggga agagcgggga gctttgccag agagcgacga       60 cttcccttg cgttggtgat tgccggtcag ggcagccatc cgccatcgtc gcgtagggtg      120
tcacacccca ggaatcgcgt cactgaacac agcagccggt aggacgacca tgactgagtt     180
ggacaccatc gcaaatccgt ccgatcccgc ggtgcagcgg atcatcgatg tcaccaagcc     240
gtcacgatcc aacataaaga caacgttgat cgaggacgtc gagcccctca tgcacagcat     300
cgcggccggg gtggagttca tcgaggtcta cggcagcgac agcagtcctt ttccatctga     360
gttgctggat ctgtgcgggc ggcagaacat accggtccgc ctcatcgact cctcgatcgt     420
caaccagttg ttcaagggg agcggaaggc caagacattc ggcatcgccc gcgtccctcg      480
cccggccagg ttcggcgata tcgcgagccg gcgtggggac gtcgtcgttc tcgacggggt     540
gaagatcgtc gggaacatcg gcgcgatagt acgcacgtcg ctcgcgctcg gagcgtcggg    600
gatcatcctg gtggacagtg acatcaccag catcgcggac cggcgtctcc aaagggccag     660
ccgaggttac gtcttctccc ttcccgtcgt tctctccggt cgcgaggagg ccatcgcctt     720
cattcgggac agcggtatgc agctgatgac gctcaaggcg gatggcgaca tttccgtgaa    780
ggaactcggg gacaatccgg atcggctggc cttgctgttc ggcagcgaaa agggtgggcc     840
ttccgacctg ttcgaggagg cgtcttccgc ctcggttttcc atccccatga tgagccagac     900
cgagtctctc aacgtttccg tttccctcgg aatcgcgctg cacgagagga tcgacaggaa    960
tctcgcggcc aaccgataag cgcctctgtt cctcggacgc tcggttcctc gacctcgatt    1020
cgtcagtgat gatcaccctca cacggcagcg atcaccactg acatatcgag gtcaacggtc    1080
```

```
gtggtccggg cgggcactcc tcgaaggcgc ggccgacgcc cttgaacgac tcgatgactc    1140
tagagtaacg ggctactccg tttaacggac cccgttctca cgctttaggc ttgaccccgg    1200
agcctgcatg gggcattccg ccgtgaaccc ggtggaatgc ccccggcacc cgggctttcc    1260
agcaaagatc acctggcgcc gatgagtaag gcgtacagaa ccactccaca ggaggaccgt    1320
cgagatgaaa tctaacaatg cgctcatcgt catcctcggc accgtcaccc tggatgctgt    1380
aggcataggc ttggttatgc cggtactgcc gggcctcttg cgggatatcg tccattccga    1440
cagcatcgcc agtcactatg gcgtgctgct agcgctatat gcgttgatgc aatttctatg    1500
cgcacccgtt ctcggagcac tgtccgaccg cttggccgc cgcccagtcc tgctcgcttc    1560
gctacttgga gccactatcg actacgcgat catggcgacc acacccgtcc tgtggattct    1620
ctacgccgga cgcatcgtgg ccggcatcac cggcgccaca ggtgcggttg ctggcgccta    1680
tatcgccgac atcaccgatg gggaagatcg ggctcgccac ttcgggctca tgagcgcttg    1740
tttcggcgtg ggtatggtgg caggccccgt ggccggggga ctgttgggcg ccatctcctt    1800
gcatgcacca ttccttgcgg cggcggtgct caacggcctc aacctactac tgggctgctt    1860
cctaatgcag gagtcgcata agggagagcg tcgtccgatg cccttgagag ccttcaaccc    1920
agtcagctcc ttccggtggg cgcggggcat gactatcgtc gccgcactta tgactgtctt    1980
ctttatcatg caactcgtag acaggtgcc ggcagcgctc tgggtcattt tcggcgagga    2040
ccgctttcgc tggagcgcga cgatgatcgg cctgtcgctt gcggtattcg gaatcttgca    2100
cgccctcgct caagccttcg tcactggtcc cgccaccaaa cgtttcggcg agaagcaggc    2160
cattatcgcc ggcatggcgg ccgacgcgct gggctacgtc ttgctggcgt tcgcgacgcg    2220
aggctggatg gccttcccca ttatgattct tctcgcttcc ggcggcatcg ggatgcccgc    2280
gttgcaggcc atgctgtcca ggcaggtaga tgacgaccat cagggacagc ttcaaggatc    2340
gctcgcggct cttaccagcc taacttcgat cattggaccg ctgatcgtca cggcgattta    2400
tgccgcctcg gcgagcacat ggaacggggtt ggcatggatt gtaggcgccg ccctatacct    2460
tgtctgcctc cccgcgttgc gtcgcggtgc atggagccgg ccacctcga cctgaatgga    2520 agccggcggc acctcgctaa cggattcacc actccaagaa ttggagccaa tcaattcttg    2580
cggagaactg tgaatgcgca aaccaaccct tggcagaaca tatccatcgc gtccgccatc    2640
tccagcagcc gcacgcggcg catctcgggc agcgttgggt cctggccacg ggtgcgcatg    2700
atcgtgctcc tgtcgttgag gactagaatt gatctcctcg accgccaatt gggcatctga    2760
gaatcatctg cgtttctcgc acgcaacgta cttgcaacgt tgcaactcct agtgttgtga    2820
atcacacccc accgggggt gggattgcag tcaccgattt ggtgggtgcg cccaggaaga    2880
tcacgtttac ataggagctt gcaatgagct actccgtggg acaggtggcc ggcttcgccg    2940
gagtgacggt gcgcacgctg caccactacg acgacatcgg cctgctcgta ccgagcgagc    3000
gcagccacgc gggccaccgg cgctacagcg acgccgacct cgaccggctg cagcagatcc    3060
tgttctaccg ggagctgggc ttcccgctcg acgaggtcgc cgccctgctc gacgacccgg    3120
ccgcggaccc gcgcgcgcac ctgcgccgcc agcacgagct gctgtccgcc cggatcggga    3180
aactgcagaa gatggcggcg gccgtggagc aggcgatgga ggcacgcagc atgggaatca    3240
acctcacccc ggaggagaag ttcgaggtct tcggcgactt cgaccccgac cagtacgagg    3300
aggaggtccg ggaacgctgg gggaacaccg acgcctaccg ccagtccaag gagaagaccg    3360
cctcgtacac caaggaggac tggcagcgca tccaggacga ggccgacgag ctcacccggc    3420
```

| | |
|---|---|
| gcttcgtcgc cctgatggac gcgggtgagc ccgccgactc cgagggggcg atggacgccg | 3480 |
| ccgaggacca ccggcagggc atcgcccgca accactacga ctgcgggtac gagatgcaca | 3540 |
| cctgcctggg cgagatgtac gtgtccgacg aacgtttcac gcgaaacatc gacgccgcca | 3600 |
| agccgggcct cgccgcctac atgcgcgacg cgatcctcgc caacgccgtc cggcacaccc | 3660 |
| cctgagcggt ggtcgtggcc cgggtctccc gcccggtctc accccacggc tcactcccgg | 3720 |
| gccacgacca ccgccgtccc gtacgcgcac acctcggtgc ccacgtccgc cgcctccgtc | 3780 |
| acgtcgaaac ggaagatccc cgggtaccga gctcgtcagg tggcactttt cggggaaatg | 3840 |
| tgcgcggaac ccctatttgt ttattttttct aaatacattc aaatatgtat ccgctcatga | 3900 |
| gacaataacc ctgataaatg cttcaataat attgaaaaag gaagagtatg agtattcaac | 3960 |
| atttccgtgt cgcccttatt ccttttttg cggcattttg ccttcctgtt tttgctcacc | 4020 |
| cagaaacgct ggtgaaagta aaagatgctg aagatcagtt gggtgcacga gtgggttaca | 4080 |
| tcgaactgga tctcaacagc ggtaagatcc ttgagagttt cgccccgaa gaacgttttc | 4140 |
| caatgatgag cacttttaaa gttctgctat gtggcgcggt attatcccgt attgacgccg | 4200 |
| ggcaagagca actcggtcgc cgcatacact attctcagaa tgacttggtt gagtactcac | 4260 |
| cagtcacaga aaagcatctt acggatggca tgacagtaag agaattatgc agtgctgcca | 4320 |
| taaccatgag tgataacact gcggccaact tacttctgac aacgatcgga ggaccgaagg | 4380 |
| agctaaccgc ttttttgcac aacatggggg atcatgtaac tcgccttgat cgttgggaac | 4440 |
| cggagctgaa tgaagccata ccaaacgacg agcgtgacac cacgatgcct gtagcaatgg | 4500 |
| caacaacgtt gcgcaaacta ttaactggcg aactacttac tctagcttcc cggcaacaat | 4560 |
| taatagactg gatggaggcg gataaagttg caggaccact tctgcgctcg gcccttccgg | 4620 |
| ctggctggtt tattgctgat aaatctggag ccggtgagcg tgggtctcgc ggtatcattg | 4680 |
| cagcactggg gccagatggt aagccctccc gtatcgtagt tatctacacg acggggagtc | 4740 |
| aggcaactat ggatgaacga atagacaga tcgctgagat aggtgcctca ctgattaagc | 4800 |
| attggtaact gtcagaccaa gtttactcat atatacttta gattgattta aaacttcatt | 4860 |
| tttaatttaa aaggatctag gtgaagatcc ttttttgataa tctcatgacc aaaatccctt | 4920 |
| aacgtgagtt ttcgttccac tgagcgtcag accccgtaga aaagatcaaa ggatcttctt | 4980 |
| gagatccttt ttttctgcgc gtaatctgct gcttgcaaac aaaaaaacca ccgctaccag | 5040 |
| cggtggtttg tttgccggat caagagctac caactctttt tccgaaggta actggcttca | 5100 |
| gcagagcgca gataccaaat actgttcttc tagtgtagcc gtagttaggc caccacttca | 5160 |
| agaactctgt agcaccgcct acatacctcg ctctgctaat cctgttacca gtggctgctg | 5220 |
| ccagtggcga taagtcgtgt cttaccgggt tggactcaag acgatagtta ccggataagg | 5280 |
| cgcagcggtc gggctgaacg gggggttcgt gcacacagcc cagcttggag cgaacgacct | 5340 |
| acaccgaact gagataccta cagcgtgagc tatgagaaag cgccacgctt cccgaaggga | 5400 |
| gaaaggcgga caggtatccg gtaagcggca gggtcggaac aggagagcgc acgagggagc | 5460 |
| ttccaggggg aaacgcctgg tatctttata gtcctgtcgg gtttcgccac ctctgacttg | 5520 |
| agcgtcgatt tttgtgatgc tcgtcagggg gcggagcct atggaaaaac gccagcaacg | 5580 |
| cggccttttt acgttcctg gccttttgct ggccttttgc tcacatgttc tttcctgcgt | 5640 |
| tatcccctga ttctgtggat aaccgtatta ccgcctttga gtgagctgat accgctcgcc | 5700 |
| gcagccgaac gaccgagcgc agcgagtcag tgagcgagga agcggaagag cgcccaatac | 5760 |
| gcaaaccgcc tctccccgcg cgttggccga ttcattaatg cagctggcac gactagagtc | 5820 |

```
ccgctgaggc ggcgtagcag gtcagccgcc ccagcggtgg tcaccaaccg gggtggaacg    5880
gcgccggtat cgggtgtgtc cgtggcgctc attccaacct ccgtgtgttt gtgcaggttt    5940
cgcgtgttgc agtccctcgc accggcaccc gcagcgaggg gctcacgggt gccggtgggt    6000
cgactagttc agtgatggtg atggtgatgt cctcgagatc taagcttgga tccgcggccg    6060
ctacgtagaa ttcccatatg cgctcccttc tctgacgccg tccacgctgc ctcctcacgt    6120
gacgtgaggt gcaagcccgg acgttccgcg tgccacgccg tgagccgccg cgtgccgtcg    6180
gctccctcag cccgggcggc cgtgggagcc cgcctcgata tgtacacccg agaagctccc    6240
agcgtcctcc tgggccgcga tactcgacca ccacgcacgc acaccgcact aacgattcgg    6300
ccggcgctcg attcggccgg cgctcgattc ggcggcgct cgattcggcc ggcgctcgat    6360
tcggccggcg ctcgattcgg ccgagcagaa gagtgaacaa ccaccgacca cgcttccgct    6420
ctgcgcgccg tacccgacct acctcccgca gctcgaagca gctcccggga gtaccgccgt    6480
actcacccgc ctgtgctcac catccaccga cgcaaagccc aacccgagca cacctcttgc    6540
accaaggtgc cgaccgtggc tttccgctcg cagggttcca gaagaaatcg aacgatccag    6600
cgcggcaagg ttcaaaaagc aggggttggt ggggaggagg ttttgggggg tgtcgccggg    6660
atacctgata tggctttgtt ttgcgtagtc gaataatttt ccatatagcc tcggcgcgtc    6720
ggactcgaat agttgatgtg ggcgggcaca gttgccccat gaaatccgca acgggggcg    6780 tgctgagcga tcggcaatgg gcggatgcgg tgttgcttcc gcaccggccg ttcgcgacga    6840
acaacctcca acgaggtcag taccggatga gccgcgacga cgcattggca atgcggtacg    6900
tcgagcattc accgcacgcg ttgctcggat ctatcgtcat cgactgcgat cacgttgacg    6960
ccgcgatgcg cgcattcgag caaccatccg accatccggc gccgaactgg gtcgcacaat    7020
cgccgtccgg ccgcgcacac atcggatggt ggctcggccc caaccacgtg tgccgcaccg    7080
acagcgccca actgacgcca ctgcgctacg cccaccgcat cgaaaccggc ctcaagatca    7140
gcgtcggcgg cgatttcgcg tatggcgggc aactgaccaa aaacccgatt caccccgatt    7200
gggagacgat ctacggcccg gccacccccgt acacattgcg gcagctggcc accatccaca    7260 cacccccggca gatgccgcgt cggcccgatc gggccgtggg cctgggccgc aacgtcacca    7320
tgttcgacgc caccccggcga tgggcatacc cgcagtggtg gcaacaccga aacggaaccg    7380
gccgcgactg ggaccatctc gtcctgcagc actgccacgc cgtcaacacc gagttcacga    7440
caccactgcc gttcaccgaa gtacgcgcca ccgcgcaatc catctccaaa tggatctggc    7500
gcaatttcac cgaagaacag taccgagccc gacaagcgca tctcggtcaa aaaggcggca    7560
aggcaacgac actcgccaaa caagaagccg tccgaaacaa tgcaagaaag tacgacgaac    7620
atacgatgcg agaggcgatt atctgatggg cggagccaaa aatccggtgc gccgaaagat    7680
gacggcagca gcagcagccg aaaaattcgg tgcctccact cgcacaatcc aacgcttgtt    7740
tgctgagccg cgtgacgatt acctcggccg tgcgaaagct cgccgtgaca agctgtcga    7800 gctgcggaag caggggttga agtaccggga aatcgccgaa gcgatggaac tctcgaccgg    7860
gatcgtcggc cgattactgc acgacgcccg caggcacggc gagatttcag cggaggatct    7920
gtcggcgtaa ccaagtcagc gggttgtcgg gttccggccg gcgctcggca ctcggaccgg    7980
ccggcggatg gtgttctgcc tctggcgcag cgtcagctac cgccgaaggc ctgtcatcga    8040
ccggcttcga ctgaagtatg agcaacgtca cagcctgtga ttggatgatc cgctcacgct    8100
cgaccgctac ctgttcagct gccgcccgct gggcatgagc aacggccaac tctcgttcaa    8160
```

<210> SEQ ID NO 53
<211> LENGTH: 8189
<212> TYPE: DNA
<213> ORGANISM: Artificial Sequence
<220> FEATURE:
<223> OTHER INFORMATION: Description of Artificial Sequence: Synthetic
vector pTip-LNH1 sequence

<400> SEQUENCE: 53

```
gagctcgacc gcgcgggtcc cggacgggga agagcgggga gctttgccag agagcgacga      60
cttccccttg cgttggtgat tgccggtcag ggcagccatc cgccatcgtc gcgtagggtg     120
tcacacccca ggaatcgcgt cactgaacac agcagccggt aggacgacca tgactgagtt     180
ggacaccatc gcaaatccgt ccgatcccgc ggtgcagcgg atcatcgatg tcaccaagcc     240
gtcacgatcc aacataaaga caacgttgat cgaggacgtc gagcccctca tgcacagcat     300
cgcggccggg gtggagttca tcgaggtcta cggcagcgac agcagtcctt ttccatctga     360
gttgctggat ctgtgcgggc ggcagaacat accggtccgc ctcatcgact cctcgatcgt     420
caaccagttg ttcaaggggg agcggaaggc caagacattc ggcatcgccc gcgtccctcg     480
cccggccagg ttcggcgata tcgcgagccg gcgtgggggac gtcgtcgttc tcgacggggt     540
gaagatcgtc gggaacatcg gcgcgatagt acgcacgtcg ctcgcgctcg gagcgtcggg     600
gatcatcctg gtggacagtg acatcaccag catcgcggac cggcgtctcc aaagggccag     660
ccgaggttac gtcttctccc ttcccgtcgt tctctccggt cgcgaggagg ccatcgcctt     720
cattcgggac agcggtatgc agctgatgac gctcaaggcg gatggcgaca tttccgtgaa     780
ggaactcggg gacaatccgg atcggctggc cttgctgttc ggcagcgaaa agggtgggcc     840
ttccgacctg ttcgaggagg cgtcttccgc ctcggtttcc atcccatga tgagccagac     900
cgagtctctc aacgtttccg tttccctcgg aatcgcgctg cacgagagga tcgacaggaa     960
tctcgcggcc aaccgataag cgcctctgtt cctcggacgc tcggttcctc gacctcgatt    1020
cgtcagtgat gatcacctca cacggcagcg atcaccactg acatatcgag gtcaacggtc    1080
gtggtccggg cgggcactcc tcgaaggcgc ggccgacgcc cttgaacgac tcgatgactc    1140
tagagtaacg ggctactccg tttaacggac cccgttctca cgctttaggc ttgaccccgg    1200
agcctgcatg gggcattccg ccgtgaaccc ggtggaatgc ccccggcacc cgggcttttcc    1260
agcaaagatc acctggcgcc gatgagtaag gcgtacagaa ccactccaca ggaggaccgt    1320
cgagatgaaa tctaacaatg cgctcatcgt catcctcggc accgtcaccc tggatgctgt    1380
aggcataggc ttggttatgc cggtactgcc gggcctcttg cgggatatcg tccattccga    1440
cagcatcgcc agtcactatg gcgtgctgct agcgctatat gcgttgatgc aatttctatg    1500
cgcacccgtt ctcggagcac tgtccgaccg ctttggccgc cgcccagtcc tgctcgcttc    1560
gctacttgga gccactatcg actacgcgat catggcgacc acacccgtcc tgtggattct    1620
ctacgccgga cgcatcgtgg ccggcatcac cggcgccaca ggtgcggttg ctggcgccta    1680
tatcgccgac atcaccgatg gggaagatcg ggctcgccac ttcgggctca tgagcgcttg    1740
tttcggcgtg ggtatggtgg caggccccgt ggccggggga ctgttgggcg ccatctcctt    1800
gcatgcacca ttccttgcgg cggcggtgct caacggcctc aacctactac tgggctgctt    1860
cctaatgcag gagtcgcata agggagagcg tcgtccgatg cccttgagag ccttcaaccc    1920
agtcagctcc ttccggtggg cgcggggcat gactatcgtc gccgcactta tgactgtctt    1980
ctttatcatg caactcgtag gacaggtgcc ggcagcgctc tgggtcattt tcggcgagga    2040
```

```
ccgctttcgc tggagcgcga cgatgatcgg cctgtcgctt gcggtattcg gaatcttgca    2100
cgccctcgct caagccttcg tcactggtcc cgccaccaaa cgtttcggcg agaagcaggc    2160
cattatcgcc ggcatggcgg ccgacgcgct gggctacgtc ttgctggcgt tcgcgacgcg    2220
aggctggatg gccttcccca ttatgattct tctcgcttcc ggcggcatcg ggatgcccgc    2280
gttgcaggcc atgctgtcca ggcaggtaga tgacgaccat cagggacagc ttcaaggatc    2340
gctcgcggct cttaccagcc taacttcgat cattggaccg ctgatcgtca cggcgattta    2400
tgccgcctcg gcgagcacat ggaacggggtt ggcatggatt gtaggcgccg ccctatacct    2460
tgtctgcctc cccgcgttgc gtcgcggtgc atggagccgg gccacctcga cctgaatgga    2520
agccggcggc acctcgctaa cggattcacc actccaagaa ttggagccaa tcaattcttg    2580
cggagaactg tgaatgcgca aaccaaccct tggcagaaca tatccatcgc gtccgccatc    2640
tccagcagcc gcacgcggcg catctcgggc agcgttgggt cctggccacg ggtgcgcatg    2700
atcgtgctcc tgtcgttgag gactagaatt gatctcctcg accgccaatt gggcatctga    2760
gaatcatctg cgtttctcgc acgcaacgta cttgcaacgt gcaactcct agtgttgtga    2820 atcacacccc accgggggt gggattgcag tcaccgattt ggtgggtgcg cccaggaaga    2880
tcacgtttac ataggagctt gcaatgagct actccgtggg acaggtggcc ggcttcgccg    2940
gagtgacggt gcgcacgctg caccactacg acgacatcgg cctgctcgta ccgagcgagc    3000
gcagccacgc gggccaccgg cgctacagcg acgccgacct cgaccggctg cagcagatcc    3060
tgttctaccg ggagctgggc ttcccgctcg acgaggtcgc cgccctgctc gacgacccgg    3120
ccgcggaccc gcgcgcgcac ctgcgccgcc agcacgagct gctgtccgcc cggatcggga    3180
aactgcagaa gatggcggcg gccgtggagc aggcgatgga ggcacgcagc atgggaatca    3240 acctcaccccc ggaggagaag ttcgaggtct tcggcgactt cgaccccgac cagtacgagg    3300
aggaggtccg ggaacgctgg gggaacaccg acgcctaccg ccagtccaag agaagaccg    3360 cctcgtacac caaggaggac tggcagcgca tccaggacga ggccgacgag ctcacccggc    3420
gcttcgtcgc cctgatggac gcgggtgagc ccgccgactc cgaggggcg atggacgccg    3480 ccgaggacca ccggcagggc atcgcccgca accactacga ctgcgggtac gagatgcaca    3540
cctgcctggg cgagatgtac gtgtccgacg aacgtttcac gcgaaacatc gacgccgcca    3600 agcccgggcct cgccgcctac atgcgcgacg cgatcctcgc caacgccgtc cggcacaccc    3660
cctgagcggt ggtcgtggcc cgggtctccc gcccggtctc accccacggc tcactcccgg    3720
gccacgacca ccgccgtccc gtacgcgcac acctcggtgc ccacgtccgc cgcctccgtc    3780
acgtcgaaac ggaagatccc cgggtaccga gctcgtcagg tggcactttt cggggaaatg    3840
tgcgcggaac ccctatttgt ttattttct aaatacattc aaatatgtat ccgctcatga    3900
gacaataacc ctgataaatg cttcaataat attgaaaaag gaagagtatg agtattcaac    3960
atttccgtgt cgcccttatt ccctttttg cggcattttg ccttcctgtt tttgctcacc    4020
cagaaacgct ggtgaaagta aaagatgctg aagatcagtt gggtgcacga gtgggttaca    4080
tcgaactgga tctcaacagc ggtaagatcc ttgagagttt cgcccccgaa gaacgttttc    4140
caatgatgag cacttttaaa gttctgctat gtggcgcggt attatcccgt attgacgccg    4200
ggcaagagca actcggtcgc cgcatacact attctcagaa tgacttggtt gagtactcac    4260
cagtcacaga aaagcatctt acggatggca tgacagtaag agaattatgc agtgctgcca    4320
taaccatgag tgataacact gcggccaact tacttctgac aacgatcgga ggaccgaagg    4380
agctaaccgc ttttttgcac aacatggggg atcatgtaac tcgccttgat cgttgggaac    4440
```

```
cggagctgaa tgaagccata ccaaacgacg agcgtgacac cacgatgcct gtagcaatgg    4500
caacaacgtt gcgcaaacta ttaactggcg aactacttac tctagcttcc cggcaacaat    4560
taatagactg gatggaggcg gataaagttg caggaccact tctgcgctcg gcccttccgg    4620
ctggctggtt tattgctgat aaatctggag ccggtgagcg tgggtctcgc ggtatcattg    4680
cagcactggg gccagatggt aagccctccc gtatcgtagt tatctacacg acggggagtc    4740
aggcaactat ggatgaacga atagacaga tcgctgagat aggtgcctca ctgattaagc     4800
attggtaact gtcagaccaa gtttactcat atatacttta gattgattta aaacttcatt    4860
tttaatttaa aaggatctag gtgaagatcc tttttgataa tctcatgacc aaaatccctt    4920
aacgtgagtt ttcgttccac tgagcgtcag accccgtaga aaagatcaaa ggatcttctt    4980
gagatccttt ttttctgcgc gtaatctgct gcttgcaaac aaaaaaacca ccgctaccag    5040
cggtggtttg tttgccggat caagagctac caactctttt tccgaaggta actggcttca    5100
gcagagcgca gataccaaat actgttcttc tagtgtagcc gtagttaggc caccacttca    5160
agaactctgt agcaccgcct acatacctcg ctctgctaat cctgttacca gtggctgctg    5220
ccagtggcga taagtcgtgt cttaccgggt tggactcaag acgatagtta ccggataagg    5280
cgcagcggtc gggctgaacg gggggttcgt gcacacagcc cagcttggag cgaacgacct    5340
acaccgaact gagataccta cagcgtgagc tatgagaaag cgccacgctt cccgaaggga    5400
gaaaggcgga caggtatccg gtaagcggca gggtcggaac aggagagcgc acagggagc     5460 ttccaggggg aaacgcctgg tatctttata gtcctgtcgg gtttcgccac ctctgacttg    5520
agcgtcgatt tttgtgatgc tcgtcagggg gcggagcct atggaaaaac gccagcaacg     5580 cggcctttt acgttcctg gccttttgct ggccttttgc tcacatgttc tttcctgcgt      5640
tatcccctga ttctgtggat aaccgtatta ccgcctttga gtgagctgat accgctcgcc    5700
gcagccgaac gaccgagcgc agcgagtcag tgagcgagga agcggaagag cgcccaatac    5760
gcaaaccgcc tctccccgcg cgttggccga ttcattaatg cagctggcac gactagagtc    5820
ccgctgaggc ggcgtagcag gtcagccgcc ccagcgtgg tcaccaaccg gggtggaacg    5880
gcgccggtat cgggtgtgtc cgtggcgctc attccaacct ccgtgtgttt gtgcaggttt    5940
cgcgtgttgc agtccctcgc accggcaccc gcagcgaggg gctcacgggt gccggtgggt    6000
cgactagttc atcctcgaga tctaagcttg gatccgcggc cgctacgtag aattcccata    6060
tggtgatggt gatggtggcc catggtatat ctccttctta agttaaaca aaattatttc     6120 tagacgccgt ccacgctgcc tcctcacgtg acgtgaggtg caagcccgga cgttccgcgt    6180
gccacgccgt gagccgccgc gtgccgtcgg ctccctcagc ccgggcggcc gtgggagccc    6240
gcctcgatat gtacacccga gaagctccca gcgtcctcct gggccgcgat actcgaccac    6300
cacgcacgca caccgcacta acgattcggc cggcgctcga ttcggccggc gctcgattcg    6360
gccggcgctc gattcggccg gcgctcgatt cggccggcgc tcgattcggc cgagcagaag    6420
agtgaacaac caccgaccac gcttccgctc tgcgcgccgt acccgaccta cctcccgcag    6480
ctcgaagcag ctcccgggag taccgccgta ctcacccgcc tgtgctcacc atccaccgac    6540
gcaaagccca acccgagcac acctcttgca ccaaggtgcc gaccgtggct ttccgctcgc    6600
agggttccag aagaaatcga acgatccagc gcggcaaggt tcaaaagca ggggttggtg     6660 gggaggaggt tttgggggt gtcgccggga tacctgatat ggctttgttt tgcgtagtcg     6720
aataattttc catatagcct cggcgcgtcg gactcgaata gttgatgtgg gcgggcacag    6780
```

```
ttgccccatg aaatccgcaa cgggggcgt gctgagcgat cggcaatggg cggatgcgt      6840 gttgcttccg caccggccgt tcgcgacgaa caacctccaa cgaggtcagt accggatgag    6900
ccgcgacgac gcattggcaa tgcggtacgt cgagcattca ccgcacgcgt tgctcggatc    6960
tatcgtcatc gactgcgatc acgttgacgc cgcgatgcgc gcattcgagc aaccatccga    7020
ccatccggcg ccgaactggg tcgcacaatc gccgtccggc cgcgcacaca tcggatggtg    7080
gctcggcccc aaccacgtgt gccgcaccga cagcgcccga ctgacgccac tgcgctacgc    7140
ccaccgcatc gaaaccggcc tcaagatcag cgtcggcggc gatttcgcgt atggcgggca    7200
actgaccaaa aacccgattc accccgattg ggagacgatc tacggcccgg ccaccccgta    7260
cacattgcgg cagctggcca ccatccacac accccggcag atgccgcgtc ggcccgatcg    7320
ggccgtgggc ctgggccgca acgtcaccat gttcgacgcc accggcgat gggcataccc     7380 gcagtggtgg caacaccgaa acggaaccgg ccgcgactgg gaccatctcg tcctgcagca    7440
ctgccacgcc gtcaacaccg agttcacgac accactgccg ttcaccgaag tacgcgccac    7500
cgcgcaatcc atctccaaat ggatctggcg caatttcacc gaagaacagt accgagcccg    7560
acaagcgcat ctcggtcaaa aaggcggcaa ggcaacgaca ctcgccaaac aagaagccgt    7620
ccgaaacaat gcaagaaagt acgacgaaca tacgatgcga gaggcgatta tctgatgggc    7680
ggagccaaaa atccggtgcg ccgaaagatg acggcagcag cagcagccga aaaattcggt    7740
gcctccactc gcacaatcca acgcttgttt gctgagccgc gtgacgatta cctcggccgt    7800
gcgaaagctc gccgtgacaa agctgtcgag ctgcggaagc aggggttgaa gtaccgggaa    7860
atcgccgaag cgatggaact ctcgaccggg atcgtcggcc gattactgca cgacgcccgc    7920
aggcacggcg agatttcagc ggaggatctg tcggcgtaac caagtcagcg ggttgtcggg    7980
ttccggccgg cgctcggcac tcggaccggc cggcggatgg tgttctgcct ctggcgcagc    8040
gtcagctacc gccgaaggcc tgtcatcgac cggcttcgac tgaagtatga gcaacgtcac    8100
agcctgtgat tggatgatcc gctcacgctc gaccgctacc tgttcagctg ccgcccgctg    8160
ggcatgagca acggccaact ctcgttcaa                                       8189
```

<210> SEQ ID NO 54
<211> LENGTH: 8183
<212> TYPE: DNA
<213> ORGANISM: Artificial Sequence
<220> FEATURE:
<223> OTHER INFORMATION: Description of Artificial Sequence: Synthetic
      vector pTip-LNH2 sequence

<400> SEQUENCE: 54

```
gagctcgacc gcgcgggtcc cggacgggga agagcgggga gctttgccag agagcgacga      60 cttcccttg cgttggtgat tgccggtcag ggcagccatc cgccatcgtc gcgtagggtg      120
tcacacccca ggaatcgcgt cactgaacac agcagccggt aggacgacca tgactgagtt     180
ggacaccatc gcaaatccgt ccgatcccgc ggtgcagcgg atcatcgatg tcaccaagcc     240
gtcacgatcc aacataaaga caacgttgat cgaggacgtc gagcccctca tgcacagcat     300
cgcggccggg gtggagttca tcgaggtcta cggcagcgac agcagtcctt ttccatctga     360
gttgctggat ctgtgcgggc ggcagaacat accggtccgc ctcatcgact cctcgatcgt     420
caaccagttg ttcaaggggg agcggaaggc caagacattc ggcatcgccc gcgtccctcg     480
cccggccagg ttcggcgata tcgcgagccg cgtgggggac gtcgtcgttc tcgacggggt     540
gaagatcgtc gggaacatcg gcgcgatagt acgcacgtcg ctcgcgctcg gagcgtcggg     600
```

```
gatcatcctg gtggacagtg acatcaccag catcgcggac cggcgtctcc aaagggccag      660
ccgaggttac gtcttctccc ttcccgtcgt tctctccggt cgcgaggagg ccatcgcctt      720
cattcgggac agcggtatgc agctgatgac gctcaaggcg gatggcgaca tttccgtgaa      780
ggaactcggg gacaatccgg atcggctggc cttgctgttc ggcagcgaaa agggtgggcc      840
ttccgacctg ttcgaggagg cgtcttccgc ctcggtttcc atccccatga tgagccagac      900
cgagtctctc aacgtttccg tttccctcgg aatcgcgctg cacgagagga tcgacaggaa      960
tctcgcggcc aaccgataag cgcctctgtt cctcggacgc tcggttcctc gacctcgatt     1020
cgtcagtgat gatcacctca cacggcagcg atcaccactg acatatcgag gtcaacggtc     1080
gtggtccggg cggcactcc tcgaaggcgc ggccgacgcc cttgaacgac tcgatgactc      1140
tagagtaacg ggctactccg tttaacggac cccgttctca cgctttaggc ttgacccccgg    1200 agcctgcatg gggcattccg ccgtgaaccc ggtggaatgc ccccggcacc cgggctttcc     1260
agcaaagatc acctggcgcc gatgagtaag gcgtacagaa ccactccaca ggaggaccgt     1320
cgagatgaaa tctaacaatg cgctcatcgt catcctcggc accgtcaccc tggatgctgt     1380
aggcataggc ttggttatgc cggtactgcc gggcctcttg cgggatatcg tccattccga     1440
cagcatcgcc agtcactatg gcgtgctgct agcgctatat gcgttgatgc aatttctatg     1500
cgcacccgtt ctcggagcac tgtccgaccg ctttggccgc cgcccagtcc tgctcgcttc     1560
gctacttgga gccactatcg actacgcgat catggcgacc acacccgtcc tgtggattct     1620
ctacgccgga cgcatcgtgg ccggcatcac cggcgccaca ggtgcggttg ctggcgccta     1680
tatcgccgac atcaccgatg gggaagatcg ggctcgccac ttcgggctca tgagcgcttg     1740
tttcggcgtg gtatggtgg caggcccccgt ggccggggga ctgttgggcg ccatctcctt     1800
gcatgcacca ttccttgcgg cggcggtgct caacggcctc aacctactac tgggctgctt     1860
cctaatgcag gagtcgcata agggagagcg tcgtccgatg cccttgagag ccttcaaccc     1920
agtcagctcc ttccggtggg cgcggggcat gactatcgtc gccgcactta tgactgtctt     1980
ctttatcatg caactcgtag gacaggtgcc ggcagcgctc tgggtcattt tcggcgagga     2040
ccgctttcgc tggagcgcga cgatgatcgg cctgtcgctt gcggtattcg gaatcttgca     2100
cgccctcgct caagccttcg tcactggtcc cgccaccaaa cgtttcggcg agaagcaggc     2160
cattatcgcc ggcatggcgg ccgacgcgct gggctacgtc ttgctggcgt tcgcgacgcg     2220
aggctggatg gccttcccca ttatgattct tctcgcttcc ggcggcatcg ggatgcccgc     2280
gttgcaggcc atgctgtcca ggcaggtaga tgacgaccat cagggacagc ttcaaggatc     2340
gctcgcggct cttaccagcc taacttcgat cattggaccg ctgatcgtca cggcgattta     2400
tgccgcctcg gcgagcacat ggaacgggtt ggcatggatt gtaggcgccg ccctataccct    2460 tgtctgcctc cccgcgttgc gtcgcggtgc atggagccgg ccacctcga cctgaatgga     2520 agccggcggc acctcgctaa cggattcacc actccaagaa ttggagccaa tcaattcttg     2580
cggagaactg tgaatgcgca aaccaaccct tggcagaaca tatccatcgc gtccgccatc     2640
tccagcagcc gcacgcggcg catctcgggc agcgttgggt cctggccacg ggtgcgcatg     2700
atcgtgctcc tgtcgttgag gactagaatt gatctcctcg accgccaatt gggcatctga     2760
gaatcatctg cgtttctcgc acgcaacgta cttgcaacgt tgcaactcct agtgttgtga     2820
atcacacccc accggggggt gggattgcag tcaccgattt ggtgggtgcg cccaggaaga     2880
tcacgtttac ataggagctt gcaatagagct actccgtggg acaggtggcc ggcttcgccg     2940
gagtgacggt gcgcacgctg caccactacg acgacatcgg cctgctcgta ccgagcgagc     3000
```

```
gcagccacgc gggccaccgg cgctacagcg acgccgacct cgaccggctg cagcagatcc    3060
tgttctaccg ggagctgggc ttcccgctcg acgaggtcgc cgccctgctc gacgacccgg    3120
ccgcggaccc gcgcgcgcac ctgcgccgcc agcacgagct gctgtccgcc cggatcggga    3180
aactgcagaa gatggcggcg gccgtggagc aggcgatgga ggcacgcagc atgggaatca    3240
acctcacccc ggaggagaag ttcgaggtct tcggcgactt cgaccccgac cagtacgagg    3300
aggaggtccg ggaacgctgg gggaacaccg acgcctaccg ccagtccaag gagaagaccg    3360
cctcgtacac caaggaggac tggcagcgca tccaggacga ggccgacgag ctcacccggc    3420
gcttcgtcgc cctgatggac gcgggtgagc ccgccgactc cgaggggcg atggacgccg     3480
ccgaggacca ccggcagggc atcgcccgca accactacga ctgcgggtac agatgcaca    3540
cctgcctggg cgagatgtac gtgtccgacg aacgtttcac gcgaaacatc gacgccgcca    3600
agccgggcct cgccgcctac atgcgcgacg cgatcctcgc caacgccgtc cggcacaccc    3660
cctgagcggt ggtcgtggcc cgggtctccc gcccggtctc accccacggc tcactcccgg    3720
gccacgacca ccgccgtccc gtacgcgcac acctcggtgc ccacgtccgc cgcctccgtc    3780
acgtcgaaac ggaagatccc cgggtaccga gctcgtcagg tggcactttt cggggaaatg    3840
tgcgcggaac ccctatttgt ttattttct aaatacattc aaatatgtat ccgctcatga    3900
gacaataacc ctgataaatg cttcaataat attgaaaaag gaagagtatg agtattcaac    3960
atttccgtgt cgcccttatt cccttttttg cggcattttg ccttcctgtt tttgctcacc    4020
cagaaacgct ggtgaaagta aaagatgctg aagatcagtt gggtgcacga gtgggttaca    4080
tcgaactgga tctcaacagc ggtaagatcc ttgagagttt tcgccccgaa gaacgttttc    4140
caatgatgag cacttttaaa gttctgctat gtggcgcggt attatcccgt attgacgccg    4200
ggcaagagca actcggtcgc cgcatacact attctcagaa tgacttggtt gagtactcac    4260
cagtcacaga aaagcatctt acggatggca tgacagtaag agaattatgc agtgctgcca    4320
taaccatgag tgataacact gcggccaact tacttctgac aacgatcgga ggaccgaagg    4380
agctaaccgc ttttttgcac aacatggggg atcatgtaac tcgccttgat cgttgggaac    4440
cggagctgaa tgaagccata ccaaacgacg agcgtgacac cacgatgcct gtagcaatgg    4500
caacaacgtt gcgcaaacta ttaactggcg aactacttac tctagcttcc cggcaacaat    4560
taatagactg gatggaggcg gataaagttg caggaccact tctgcgctcg gcccttccgg    4620
ctggctggtt tattgctgat aaatctggag ccggtgagcg tgggtctcgc ggtatcattg    4680
cagcactggg gccagatggt aagccctccc gtatcgtagt tatctacacg acggggagtc    4740
aggcaactat ggatgaacga aatagacaga tcgctgagat aggtgcctca ctgattaagc    4800
attggtaact gtcagaccaa gtttactcat atatacttta gattgattta aaacttcatt    4860
tttaatttaa aaggatctag gtgaagatcc ttttttgataa tctcatgacc aaaatccctt    4920
aacgtgagtt ttcgttccac tgagcgtcag accccgtaga aaagatcaaa ggatcttctt    4980
gagatccttt ttttctgcgc gtaatctgct gcttgcaaac aaaaaaacca ccgctaccag    5040
cggtggtttg tttgccggat caagagctac caactctttt tccgaaggta actggcttca    5100
gcagagcgca gataccaaat actgttcttc tagtgtagcc gtagttaggc caccacttca    5160
agaactctgt agcaccgcct acatacctcg ctctgctaat cctgttacca gtggctgctg    5220
ccagtggcga taagtcgtgt cttaccgggt tggactcaag acgatagtta ccggataagg    5280
cgcagcggtc gggctgaacg gggggttcgt gcacacagcc cagcttggag cgaacgacct    5340
```

```
acaccgaact gagataccta cagcgtgagc tatgagaaag cgccacgctt cccgaaggga    5400
gaaaggcgga caggtatccg gtaagcggca gggtcggaac aggagagcgc acgagggagc    5460
ttccagggggg aaacgcctgg tatctttata gtcctgtcgg gtttcgccac ctctgacttg    5520
agcgtcgatt tttgtgatgc tcgtcagggg ggcggagcct atggaaaaac gccagcaacg    5580
cggccttttt acggttcctg gccttttgct ggccttttgc tcacatgttc tttcctgcgt    5640
tatcccctga ttctgtggat aaccgtatta ccgcctttga gtgagctgat accgctcgcc    5700
gcagccgaac gaccgagcgc agcgagtcag tgagcgagga agcggaagag cgcccaatac    5760
gcaaaccgcc tctccccgcg cgttggccga ttcattaatg cagctggcac gactagagtc    5820
ccgctgaggc ggcgtagcag gtcagccgcc ccagcggtgg tcaccaaccg gggtggaacg    5880
gcgccggtat cgggtgtgtc cgtggcgctc attccaacct ccgtgtgttt gtgcaggttt    5940
cgcgtgttgc agtccctcgc accggcaccc gcagcgaggg gctcacgggt gccggtgggt    6000
cgactagttc agtgatggtg atggtgatgt cctcgagatc taagcttgga tccgcggccg    6060
ctacgtagaa ttcccatggt atatctcctt cttaaagtta aacaaaatta tttctagacg    6120
ccgtccacgc tgcctcctca cgtgacgtga ggtgcaagcc cggacgttcc gcgtgccacg    6180
ccgtgagccg ccgcgtgccg tcggctccct cagcccgggc ggccgtggga cccgcctcg    6240
atatgtacac ccgagaagct cccagcgtcc tcctgggccg cgatactcga ccaccacgca    6300
cgcacaccgc actaacgatt cggccggcgc tcgattcggc cggcgctcga ttcggccggc    6360
gctcgattcg gccggcgctc gattcggccg gcgctcgatt cggccgagca aaagagtgaa    6420
caaccaccga ccacgcttcc gctctgcgcg ccgtacccga cctacctccc gcagctcgaa    6480
gcagctcccg ggagtaccgc cgtactcacc cgcctgtgct caccatccac cgacgcaaag    6540
cccaacccga gcacacctct tgcaccaagg tgccgaccgt ggctttccgc tcgcagggtt    6600
ccagaagaaa tcgaacgatc cagcgcggca aggttcaaaa agcaggggtt ggtgggagg    6660
aggttttggg gggtgtcgcc gggataccatg atatggcttt gttttgcgta gtcgaataat    6720
tttccatata gcctcggcgc gtcggactcg aatagttgat gtgggcgggc acagttgccc    6780
catgaaatcc gcaacggggg gcgtgctgag cgatcggcaa tgggcggatg cggtgttgct    6840
tccgcaccgg ccgttcgcga cgaacaacct ccaacgaggt cagtaccgga tgagccgcga    6900
cgacgcattg gcaatgcggt acgtcgagca ttcaccgcac gcgttgctcg gatctatcgt    6960
catcgactgc gatcacgttg acgccgcgat gcgcgcattc gagcaaccat ccgaccatcc    7020
ggcgccgaac tgggtcgcac aatcgccgtc cggccgcgca cacatcggat ggtggctcgg    7080
ccccaaccac gtgtgccgca ccgacagcgc ccgactgacg ccactgcgct acgcccaccg    7140
catcgaaacc ggcctcaaga tcagcgtcgg cggcgatttc gcgtatggcg ggcaactgac    7200
caaaaacccg attcaccccg attgggagac gatctacggc ccggccaccc cgtacacatt    7260
gcggcagctg gccaccatcc acacacccg gcagatgccg cgtcggcccg atcgggccgt    7320
gggcctgggc cgcaacgtca ccatgttcga cgccacccgg cgatgggcat acccgcagtg    7380
gtggcaacac cgaaacggaa ccggccgcga ctgggaccat ctcgtcctgc agcactgcca    7440
cgccgtcaac accgagttca cgacaccact gccgttcacc gaagtacgcg ccaccgcgca    7500
atccatctcc aaatggatct ggcgcaattt caccgaagaa cagtaccgag cccgacaagc    7560
gcatctcggt caaaaaggcg gcaaggcaac gacactcgcc aaacaagaag ccgtccgaaa    7620
caatgcaaga aagtacgacg aacatacgat gcgagaggcg attatctgat gggcggagcc    7680
aaaaatccgg tgcgccgaaa gatgacggca gcagcagcag ccgaaaaatt cggtgcctcc    7740
```

-continued

| | |
|---|---|
| actcgcacaa tccaacgctt gtttgctgag ccgcgtgacg attacctcgg ccgtgcgaaa | 7800 |
| gctcgccgtg acaaagctgt cgagctgcgg aagcaggggt tgaagtaccg ggaaatcgcc | 7860 |
| gaagcgatgg aactctcgac cgggatcgtc ggccgattac tgcacgacgc ccgcaggcac | 7920 |
| ggcgagattt cagcggagga tctgtcggcg taaccaagtc agcgggttgt cgggttccgg | 7980 |
| ccggcgctcg gcactcggac cggcggcgg atggtgttct gcctctggcg cagcgtcagc | 8040 |
| taccgccgaa ggcctgtcat cgaccggctt cgactgaagt atgagcaacg tcacagcctg | 8100 |
| tgattggatg atccgctcac gctcgaccgc tacctgttca gctgccgccc gctgggcatg | 8160 |
| agcaacggcc aactctcgtt caa | 8183 |

<210> SEQ ID NO 55
<211> LENGTH: 8123
<212> TYPE: DNA
<213> ORGANISM: Artificial Sequence
<220> FEATURE:
<223> OTHER INFORMATION: Description of Artificial Sequence: Synthetic
  vector pTip-LCH1 sequence

<400> SEQUENCE: 55

| | |
|---|---|
| gagctcgacc gcgcgggtcc cggacgggga agagcgggga gctttgccag agagcgacga | 60 |
| cttccccttg cgttggtgat tgccggtcag ggcagccatc cgccatcgtc gcgtagggtg | 120 |
| tcacacccca ggaatcgcgt cactgaacac agcagccggt aggacgacca tgactgagtt | 180 |
| ggacaccatc gcaaatccgt ccgatcccgc ggtgcagcgg atcatcgatg tcaccaagcc | 240 |
| gtcacgatcc aacataaaga caacgttgat cgaggacgtc gagcccctca tgcacagcat | 300 |
| cgcggccggg gtggagttca tcgaggtcta cggcagcgac agcagtcctt ttccatctga | 360 |
| gttgctggat ctgtgcgggc ggcagaacat accggtccgc ctcatcgact cctcgatcgt | 420 |
| cccggccagg ttcggcgata tcgcgagccg cgtgggggac gtcgtcgttc tcgacggggt | 480 |
| gaagatcgtc gggaacatcg gcgcgatagt acgcacgtcg ctcgcgctcg gagcgtcggg | 540 |
| gatcatcctg gtggacagtg acatcaccag catcgcggac cggcgtctcc aaagggccag | 600 |
| ccgaggttac gtcttctccc ttcccgtcgt tctctccggt cgcgaggagg ccatcgcctt | 660 |
| cattcgggac agcggtatgc agctgatgac gctcaaggcg gatggcgaca tttccgtgaa | 720 |
| ggaactcggg gacaatccgg atcggctggc cttgctgttc ggcagcgaaa agggtgggcc | 780 |
| ttccgacctg ttcgaggagg cgtcttccgc ctcggtttcc atcccatga tgagccagac | 840 |
| cgagtctctc aacgtttccg tttccctcgg aatcgcgctg cacgagagga tcgacaggaa | 900 |
| tctcgcggcc aaccgataag cgcctctgtt cctcggacgc tcggttcctc gacctcgatt | 960 |
| cgtcagtgat gatcacctca cacggcagcg atcaccactg acatatcgag gtcaacggtc | 1020 |
| gtggtccggg cgggcactcc tcgaaggcgc ggccgacgcc cttgaacgac tcgatgactc | 1080 |
| tagagtaacg ggctactccg tttaacggac ccgttctca cgctttaggc ttgaccccgg | 1140 |
| agcctgcatg gggcattccg ccgtgaaccc ggtggaatgc cccggcaccc gggctttcc | 1200 |
| agcaaagatc acctggcgcc gatgagtaag gcgtacagaa ccactccaca ggaggaccgt | 1260 |
| cgagatgaaa tctaacaatg cgctcatcgt catcctcggc accgtcaccc tggatgctgt | 1320 |
| aggcataggc ttggttatgc cggtactgcc gggcctcttg cggatatcg tccattccga | 1380 |
| cagcatcgcc agtcactatg gcgtgctgct agcgctatat gcgttgatgc aatttctatg | 1440 |
| cgcaccgt tcggagcac tgtccgaccg ctttggccgc cgcccagtcc tgctcgcttc | 1500 |
| gctacttgga gccactatcg actacgcgat catggcgacc acacccgtcc tgtggattct | 1560 |

-continued

```
ctacgccgga cgcatcgtgg ccggcatcac cggcgccaca ggtgcggttg ctggcgccta    1620
tatcgccgac atcaccgatg gggaagatcg ggctcgccac ttcgggctca tgagcgcttg    1680
tttcggcgtg ggtatggtgg caggccccgt ggccggggga ctgttgggcg ccatctcctt    1740
gcatgcacca ttccttgcgg cggcggtgct caacggcctc aacctactac tgggctgctt    1800
cctaatgcag gagtcgcata agggagagcg tcgtccgatg cccttgagag ccttcaaccc    1860
agtcagctcc ttccggtggg cgcggggcat gactatcgtc gccgcactta tgactgtctt    1920
ctttatcatg caactcgtag gacaggtgcc ggcagcgctc tgggtcattt tcggcgagga    1980
ccgctttcgc tggagcgcga cgatgatcgg cctgtcgctt gcggtattcg gaatcttgca    2040
cgccctcgct caagccttcg tcactggtcc cgccaccaaa cgtttcggcg agaagcaggc    2100
cattatcgcc ggcatggcgg ccgacgcgct gggctacgtc ttgctggcgt tcgcgacgcg    2160
aggctggatg gccttcccca ttatgattct tctcgcttcc ggcggcatcg ggatgcccgc    2220
gttgcaggcc atgctgtcca ggcaggtaga tgacgaccat cagggacagc ttcaaggatc    2280
gctcgcggct cttaccagcc taacttcgat cattggaccg ctgatcgtca ggcgatttta    2340
tgccgcctcg gcgagcacat ggaacgggtt ggcatggatt gtaggcgccg ccctatacct    2400
tgtctgcctc cccgcgttgc gtcgcggtgc atggagccgg ccacctcga cctgaatgga    2460
agccggcggc acctcgctaa cggattcacc actccaagaa ttggagccaa tcaattcttg    2520
cggagaactg tgaatgcgca aaccaaccct tggcagaaca tatccatcgc gtccgccatc    2580
tccagcagcg cacgcggcg catctcgggc agcgttgggt cctggccacg ggtgcgcatg     2640
atcgtgctcc tgtcgttgag gactagaatt gatctcctcg accgccaatt gggcatctga    2700
gaatcatctg cgtttctcgc acgcaacgta cttgcaacgt tgcaactcct agtgttgtga    2760
atcacacccc accggggggt gggattgcag tcaccgattt ggtgggtgcg cccaggaaga    2820
tcacgtttac ataggagctt gcaatgagct actccgtggg acaggtggcc ggcttcgccg    2880
gagtgacggt gcgcacgctg caccactacg acgacatcgg cctgctcgta ccgagcgagc    2940
gcagccacgc gggccaccgg cgctacagcg acgccgacct cgaccggctg cagcagatcc    3000
tgttctaccg ggagctgggc ttcccgctcg acgaggtcgc cgccctgctc gacgacccgg    3060
ccgcggaccc cgcgcgcgcac ctgcgccgcc agcacgagct gctgtccgcc cggatcggga    3120
aactgcagaa gatggcggcg gccgtggagc aggcgatgga ggcacgcagc atgggaatca    3180
acctcacccc ggaggagaag ttcgaggtct tcggcgactt cgaccccgac cagtacgagg    3240
aggaggtccg ggaacgctgg gggaacaccg acgcctaccg ccagtccaag gagaagaccg    3300
cctcgtacac caaggaggac tggcagcgca tccaggacga ggccgacgag ctcacccggc    3360
gcttcgtcgc cctgatggac gcgggtgagc ccgccgactc cgaggggcg atggacgccg    3420
ccgaggacca ccggcagggc atcgcccgca accactacga ctgcgggtac gagatgcaca    3480
cctgcctggg cgagatgtac gtgtccgacg aacgtttcac gcgaaacatc gacgccgcca    3540
agccgggcct cgccgcctac atgcgcgacg cgatcctcgc caacgccgtc cggcacaccc    3600
cctgagcggt ggtcgtggcc cgggtctccc gccggtctc accccacggc tcactcccgg    3660
gccacgacca ccgccgtccc gtacgcgcac acctcggtgc ccacgtccgc cgcctccgtc    3720
acgtcgaaac ggaagatccc cgggtaccga gctcgtcagg tggcactttt cggggaaatg    3780
tgcgcggaac ccctatttgt ttatttttct aaatacattc aaatatgtat ccgctcatga    3840
gacaataacc ctgataaatg cttcaataat attgaaaaag gaagagtatg agtattcaac    3900
```

```
atttccgtgt cgcccttatt ccctttttg cggcattttg ccttcctgtt tttgctcacc      3960
cagaaacgct ggtgaaagta aaagatgctg aagatcagtt gggtgcacga gtgggttaca      4020
tcgaactgga tctcaacagc ggtaagatcc ttgagagttt tcgccccgaa gaacgttttc      4080
caatgatgag cacttttaaa gttctgctat gtggcgcggt attatcccgt attgacgccg      4140
ggcaagagca actcggtcgc cgcatacact attctcagaa tgacttggtt gagtactcac      4200
cagtcacaga aaagcatctt acggatggca tgacagtaag agaattatgc agtgctgcca      4260
taaccatgag tgataacact gcggccaact tacttctgac aacgatcgga ggaccgaagg      4320
agctaaccgc ttttttgcac aacatggggg atcatgtaac tcgccttgat cgttgggaac      4380
cggagctgaa tgaagccata ccaaacgacg agcgtgacac cacgatgcct gtagcaatgg      4440
caacaacgtt gcgcaaacta ttaactggcg aactacttac tctagcttcc cggcaacaat      4500
taatagactg gatggaggcg gataaagttg caggaccact tctgcgctcg gcccttccgg      4560
ctggctggtt tattgctgat aaatctggag ccggtgagcg tgggtctcgc ggtatcattg      4620
cagcactggg gccagatggt aagccctccc gtatcgtagt tatctacacg acggggagtc      4680
aggcaactat ggatgaacga atagacaga tcgctgagat aggtgcctca ctgattaagc        4740
attggtaact gtcagaccaa gtttactcat atatacttta gattgattta aaacttcatt      4800
tttaatttaa aaggatctag gtgaagatcc tttttgataa tctcatgacc aaaatccctt      4860
aacgtgagtt ttcgttccac tgagcgtcag accccgtaga aaagatcaaa ggatcttctt      4920
gagatccttt ttttctgcgc gtaatctgct gcttgcaaac aaaaaaacca ccgctaccag      4980
cggtggtttg tttgccggat caagagctac caactctttt tccgaaggta actggcttca      5040
gcagagcgca gataccaaat actgttcttc tagtgtagcc gtagttaggc caccacttca      5100
agaactctgt agcaccgcct acatacctcg ctctgctaat cctgttacca gtggctgctg      5160
ccagtggcga taagtcgtgt cttaccgggt tggactcaag acgatagtta ccggataagg      5220
cgcagcggtc gggctgaacg gggggttcgt gcacacagcc cagcttggag cgaacgacct      5280
acaccgaact gagataccta cagcgtgagc tatgagaaag cgccacgctt cccgaaggga      5340
gaaaggcgga caggtatccg gtaagcggca gggtcggaac aggagagcgc acgagggagc      5400
ttccaggggg aaacgcctgg tatctttata gtcctgtcgg gtttcgccac ctctgacttg      5460
agcgtcgatt tttgtgatgc tcgtcagggg ggcggagcct atggaaaaac gccagcaacg      5520
cggccttttt acggttcctg gccttttgct ggccttttgc tcacatgttc tttcctgcgt      5580
tatcccctga ttctgtggat aaccgtatta ccgcctttga gtgagctgat accgctcgcc      5640
gcagccgaac gaccgagcgc agcgagtcag tgagcgagga agcggaagag cgcccaatac      5700
gcaaaccgcc tctccccgcg cgttggccga ttcattaatg cagctggcac gactagagtc      5760
ccgctgaggc ggcgtagcag gtcagccgcc ccagcggtgg tcaccaaccg gggtggaacg      5820
gcgccggtat cgggtgtgtc cgtggcgctc attccaacct ccgtgtgttt gtgcaggttt      5880
cgcgtgttgc agtccctcgc accggcaccc gcagcgaggg gctcacgggt gccggtgggt      5940
cgactagttc agtgatggtg atggtgatgt cctcgagatc taagcttgga tccgcggccg      6000
ctacgtagaa ttcccatggt atatctcctt cttaaagtta aacaaaatta tttctagacg      6060
ccgtccacgt gcctcctca cgtgacgtga ggtgcaagcc cggacgttcc gcgtgccacg      6120
ccgtgagccg ccgcgtgccg tcggctccct cagcccgggc ggcgtgggga gcccgcctcg      6180
atatgtacac ccgagaagct cccagcgtcc tcctgggccg cgatactcga ccaccacgca      6240
cgcacaccgc actaacgatt cggccggcgc tcgattcggc cggcgctcga ttcggccggc      6300
```

```
gctcgattcg gccggcgctc gattcggccg gcgctcgatt cggccgagca gaagagtgaa    6360
caaccaccga ccacgcttcc gctctgcgcg ccgtacccga cctacctccc gcagctcgaa    6420
gcagctcccg ggagtaccgc cgtactcacc cgcctgtgct caccatccac cgacgcaaag    6480
cccaacccga gcacacctct tgcaccaagg tgccgaccgt ggctttccgc tcgcagggtt    6540
ccagaagaaa tcgaacgatc cagcgcggca aggttcaaaa agcaggggtt ggtgggggag    6600
aggttttggg gggtgtcgcc gggataccgt atatggcttt gttttgcgta gtcgaataat    6660
tttccatata gcctcggcgc gtcggactcg aatagttgat gtgggcgggc acagttgccc    6720
catgaaatcc gcaacggggg gcgtgctgag cgatcggcaa tgggcggatg cggtgttgct    6780
tccgcaccgg ccgttcgcga cgaacaacct ccaacgaggg cagtaccgga tgagccgcga    6840
cgacgcattg gcaatgcggt acgtcgagca ttcaccgcac gcgttgctcg gatctatcgt    6900
catcgactgc gatcacgttg acgccgcgat gcgcgcattc gagcaaccat ccgaccatcc    6960
ggcgccgaac tgggtcgcac aatcgccgtc cggccgcgca cacatcggat ggtggctcgg    7020
ccccaaccac gtgtgccgca ccgacagcgc ccgactgacg ccactgcgct acgcccaccg    7080
catcgaaacc ggcctcaaga tcagcgtcgg cggcgatttc gcgtatggcg ggcaactgac    7140
caaaaacccg attcaccccg attgggagac gatctacggc ccggccaccc cgtacacatt    7200
gcggcagctg gccaccatcc acacaccccg gcagatgccg cgtcggcccg atcgggccgt    7260
gggcctgggc cgcaacgtca ccatgttcga cgccacccgg cgatgggcat acccgcagtg    7320
gtggcaacac cgaaacggaa ccggccgcga ctgggaccat ctcgtcctgc agcactgcca    7380
cgccgtcaac accgagttca cgacaccact gccgttcacc gaagtacgcg ccaccgcgca    7440
atccatctcc aaatggatct ggcgcaattt caccgaagaa cagtaccgag cccgacaagc    7500
gcatctcggt caaaaaggcg gcaaggcaac gacactcgcc aaacaagaag ccgtccgaaa    7560
caatgcaaga aagtacgacg aacatacgat gcgagaggcg attatctgat gggcggagcc    7620
aaaaatccgg tgcgccgaaa gatgacggca gcagcagcag ccgaaaaatt cggtgcctcc    7680
actcgcacaa tccaacgctt gtttgctgag ccgcgtgacg attacctcgg ccgtgcgaaa    7740
gctcgccgtg acaaagctgt cgagctgcgg aagcaggggt tgaagtaccg ggaaatcgcc    7800
gaagcgatgg aactctcgac cgggatcgtc ggccgattac tgcacgacgc ccgcaggcac    7860
ggcgagattt cagcggagga tctgtcggcg taaccaagtc agcgggttgt cgggttccgg    7920
ccggcgctcg gcactcggac cggccggcgg atggtgttct gcctctggcg cagcgtcagc    7980
taccgccgaa ggcctgtcat cgaccggctt cgactgaagt atgagcaacg tcacagcctg    8040
tgattggatg atccgctcac gctcgaccgc tacctgttca gctgccgccc gctgggcatg    8100
agcaacggcc aactctcgtt caa                                           8123
```

<210> SEQ ID NO 56
<211> LENGTH: 8184
<212> TYPE: DNA
<213> ORGANISM: Artificial Sequence
<220> FEATURE:
<223> OTHER INFORMATION: Description of Artificial Sequence: Synthetic
      vector pTip-LCH2 sequence

<400> SEQUENCE: 56

```
gagctcgacc gcgcgggtcc cggacgggga agagcgggga gctttgccag agagcgacga      60
cttcccgttg cgttggtgat tgccggtcag ggcagccatc cgccatcgtc gcgtagggtg     120
tcacacccca ggaatcgcgt cactgaacac agcagccggt aggacgacca tgactgagtt     180
```

-continued

| | | | | | |
|---|---|---|---|---|---|
| ggacaccatc | gcaaatccgt | ccgatcccgc | ggtgcagcgg | atcatcgatg | tcaccaagcc | 240 |
| gtcacgatcc | aacataaaga | caacgttgat | cgaggacgtc | gagcccctca | tgcacagcat | 300 |
| cgcggccggg | gtggagttca | tcgaggtcta | cggcagcgac | agcagtcctt | ttccatctga | 360 |
| gttgctggat | ctgtgcgggc | ggcagaacat | accggtccgc | ctcatcgact | cctcgatcgt | 420 |
| caaccagttg | ttcaaggggg | agcggaaggc | caagacattc | ggcatcgccc | gcgtccctcg | 480 |
| cccggccagg | ttcggcgata | tcgcgagccg | gcgtgnggac | gtcgtcgttc | tcgacggggt | 540 |
| gaagatcgtc | gggaacatcg | gcgcgatagt | acgcacgtcg | ctcgcgctcg | gagcgtcggg | 600 |
| gatcatcctg | gtggacagtg | acatcaccag | catcgcggac | cggcgtctcc | aaagggccag | 660 |
| ccgaggttac | gtcttctccc | ttcccgtcgt | tctctccggt | cgcgaggagg | ccatcgcctt | 720 |
| cattcgggac | agcggtatgc | agctgatgac | gctcaaggcg | gatggcgaca | tttccgtgaa | 780 |
| ggaactcggg | gacaatccgg | atcggctggc | cttgctgttc | ggcagcgaaa | agggtgggcc | 840 |
| ttccgacctg | ttcgaggagg | cgtcttccgc | ctcggtttcc | atccccatga | tgagccagac | 900 |
| cgagtctctc | aacgttttcg | tttccctcgg | aatcgcgctg | cacgagagga | tcgacaggaa | 960 |
| tctcgcggcc | aaccgataag | cgcctctgtt | cctcggacgc | tcggttcctc | gacctcgatt | 1020 |
| cgtcagtgat | gatcacctca | cacggcagcg | atcaccactg | acatatcgag | gtcaacggtc | 1080 |
| gtggtccggg | cgggcactcc | tcgaaggcgc | ggccgacgcc | cttgaacgac | tcgatgactc | 1140 |
| tagagtaacg | ggctactccg | tttaacggac | cccgttctca | cgctttaggc | ttgaccccgg | 1200 |
| agcctgcatg | gggcattccg | ccgtgaaccc | ggtggaatgc | cccggcaccc | ggcttttcc | 1260 |
| agcaaagatc | acctggcgcc | gatgagtaag | gcgtacagaa | ccactccaca | ggaggaccgt | 1320 |
| cgagatgaaa | tctaacaatg | cgctcatcgt | catcctcggc | accgtcaccc | tggatgctgt | 1380 |
| aggcataggc | ttggttatgc | cggtactgcc | gggcctcttg | cgggatatcg | tccattccga | 1440 |
| cagcatcgcc | agtcactatg | gcgtgctgct | agcgctatat | gcgttgatgc | aatttctatg | 1500 |
| cgcacccgtt | ctcggagcac | tgtccgaccg | ctttggccgc | cgcccagtcc | tgctcgcttc | 1560 |
| gctacttgga | gccactatcg | actacgcgat | catggcgacc | acaccgtcc | tgtggattct | 1620 |
| ctacgccgga | cgcatcgtgg | ccggcatcac | cggcgccaca | ggtgcggttg | ctggcgccta | 1680 |
| tatcgccgac | atcaccgatg | gggaagatcg | ggctcgccac | ttcgggctca | tgagcgcttg | 1740 |
| tttcggcgtg | ggtatggtgg | caggcccccgt | ggccggggga | ctgttgggcg | ccatctcctt | 1800 |
| gcatgccacca | ttccttgcgg | cggcggtgct | caacggcctc | aacctactac | tgggctgctt | 1860 |
| cctaatgcag | gagtcgcata | agggagagcg | tcgtccgatg | cccttgagag | ccttcaaccc | 1920 |
| agtcagctcc | ttccggtggg | cgcggggcat | gactatcgtc | gccgcactta | tgactgtctt | 1980 |
| ctttatcatg | caactcgtag | acaggtgcc | ggcagcgctc | tgggtcattt | tcggcgagga | 2040 |
| ccgctttcgc | tggagcgcga | cgatgatcgg | cctgtcgctt | gcggtattcg | gaatcttgca | 2100 |
| cgccctcgct | caagccttcg | tcactggtcc | cgccaccaaa | cgtttcggcg | agaagcaggc | 2160 |
| cattatcgcc | ggcatggcgg | ccgacgcgct | gggctacgtc | ttgctggcgt | tcgcgacgcg | 2220 |
| aggctggatg | gccttcccca | ttatgattct | tctcgcttcc | ggcggcatcg | ggatgccgc | 2280 |
| gttgcaggcc | atgctgtcca | ggcaggtaga | tgacgaccat | cagggacagc | ttcaaggatc | 2340 |
| gctcgcggct | cttaccagcc | taacttcgat | cattggaccg | ctgatcgtca | cggcgattta | 2400 |
| tgccgcctcg | gcgagcacat | ggaacgggtt | ggcatggatt | gtaggcgccg | ccctataccct | 2460 |
| tgtctgcctc | ccgcgttgc | gtcgcggtgc | atggagccgg | gccacctcga | cctgaatgga | 2520 |

```
agccggcggc acctcgctaa cggattcacc actccaagaa ttggagccaa tcaattcttg    2580
cggagaactg tgaatgcgca aaccaaccct tggcagaaca tatccatcgc gtccgccatc    2640
tccagcagcc gcacgcggcg catctcgggc agcgttgggt cctggccacg ggtgcgcatg    2700
atcgtgctcc tgtcgttgag gactagaatt gatctcctcg accgccaatt gggcatctga    2760
gaatcatctg cgtttctcgc acgcaacgta cttgcaacgt tgcaactcct agtgttgtga    2820
atcacacccc accgggggt gggattgcag tcaccgattt ggtgggtgcg cccaggaaga    2880
tcacgtttac ataggagctt gcaatgagct actccgtggg acaggtggcc ggcttcgccg    2940
gagtgacggt gcgcacgctg caccactacg acgacatcgg cctgctcgta ccgagcgagc    3000
gcagccacgc gggccaccgg cgctacagcg acgccgacct cgaccggctg cagcagatcc    3060
tgttctaccg ggagctgggc ttcccgctcg acgaggtcgc cgccctgctc gacgacccgg    3120
ccgcggaccc gcgcgcgcac ctgcgccgcc agcacgagct gctgtccgcc cggatcggga    3180
aactgcagaa gatggcggcg gccgtggagc aggcgatgga ggcacgcagc atgggaatca    3240
acctcacccc ggaggagaag ttcgaggtct tcggcgactt cgaccccgac cagtacgagg    3300
aggaggtccg ggaacgctgg gggaacaccg acgcctaccg ccagtccaag gagaagaccg    3360
cctcgtacac caaggaggac tggcagcgca tccaggacga ggccgacgag ctcacccggc    3420
gcttcgtcgc cctgatggac gcgggtgagc ccgccgactc cgaggggcg atggacgccg    3480
ccgaggacca ccggcagggc atcgcccgca accactacga ctgcgggtac gagatgcaca    3540
cctgcctggg cgagatgtac gtgtccgacg aacgtttcac gcgaaacatc gacgccgcca    3600
agccgggcct cgccgcctac atgcgcgacg cgatcctcgc caacgccgtc cggcacaccc    3660
cctgagcggt ggtcgtggcc cgggtctccc gcccggtctc accccacggc tcactcccgg    3720
gccacgacca ccgccgtccc gtacgcgcac acctcggtgc ccacgtccgc cgcctccgtc    3780
acgtcgaaac ggaagatccc cgggtaccga gctcgtcagg tggcactttt cggggaaatg    3840
tgcgcggaac ccctatttgt ttattttct aaatacattc aaatatgtat ccgctcatga    3900
gacaataacc ctgataaatg cttcaataat attgaaaaag gaagagtatg agtattcaac    3960
atttccgtgt cgcccttatt cccttttttg cggcattttg ccttcctgtt tttgctcacc    4020
cagaaacgct ggtgaaagta aaagatgctg aagatcagtt gggtgcacga gtgggttaca    4080
tcgaactgga tctcaacagc ggtaagatcc ttgagagttt cgccccgaa gaacgttttc    4140
caatgatgag cacttttaaa gttctgctat gtggcgcggt attatcccgt attgacgccg    4200
ggcaagagca actcggtcgc cgcatacact attctcagaa tgacttggtt gagtactcac    4260
cagtcacaga aaagcatctt acggatggca tgacagtaag agaattatgc agtgctgcca    4320
taaccatgag tgataacact gcggccaact tacttctgac aacgatcgga ggaccgaagg    4380
agctaaccgc ttttttgcac aacatggggg atcatgtaac tcgccttgat cgttgggaac    4440
cggagctgaa tgaagccata ccaaacgacg agcgtgacac cacgatgcct gtagcaatgg    4500
caacaacgtt gcgcaaacta ttaactggcg aactacttac tctagcttcc cggcaacaat    4560
taatagactg gatggaggcg gataaagttg caggaccact tctgcgctcg gcccttccgg    4620
ctggctggtt tattgctgat aaatctggag ccggtgagcg tgggtctcgc ggtatcattg    4680
cagcactggg gccagatggt aagccctccc gtatcgtagt tatctacacg acggggagtc    4740
aggcaactat ggatgaacga aatagacaga tcgctgagat aggtgcctca ctgattaagc    4800
attggtaact gtcagaccaa gtttactcat atatacttta gattgattta aaacttcatt    4860
tttaatttaa aaggatctag gtgaagatcc tttttgataa tctcatgacc aaaatccctt    4920
```

```
aacgtgagtt ttcgttccac tgagcgtcag accccgtaga aaagatcaaa ggatcttctt    4980
gagatccttt ttttctgcgc gtaatctgct gcttgcaaac aaaaaaacca ccgctaccag    5040
cggtggtttg tttgccggat caagagctac caactctttt tccgaaggta actggcttca    5100
gcagagcgca gataccaaat actgttcttc tagtgtagcc gtagttaggc caccacttca    5160
agaactctgt agcaccgcct acatacctcg ctctgctaat cctgttacca gtggctgctg    5220
ccagtggcga taagtcgtgt cttaccgggt tggactcaag acgatagtta ccggataagg    5280
cgcagcggtc gggctgaacg gggggttcgt gcacacagcc cagcttggag cgaacgacct    5340
acaccgaact gagataccta cagcgtgagc tatgagaaag cgccacgctt cccgaaggga    5400
gaaaggcgga caggtatccg gtaagcggca gggtcggaac aggagagcgc acgagggagc    5460 ttccagggg  aaacgcctgg tatctttata gtcctgtcgg gtttcgccac ctctgacttg    5520
agcgtcgatt tttgtgatgc tcgtcagggg gcggagcct  atggaaaaac gccagcaacg    5580 cggcctttt  acggttcctg gccttttgct ggccttttgc tcacatgttc tttcctgcgt    5640
tatcccctga ttctgtggat aaccgtatta ccgcctttga gtgagctgat accgctcgcc    5700
gcagccgaac gaccgagcgc agcgagtcag tgagcgagga agcggaagag cgcccaatac    5760
gcaaaccgcc tctccccgcg cgttggccga ttcattaatg cagctggcac gactagagtc    5820
ccgctgaggc ggcgtagcag gtcagccgcc ccagcggtgg tcaccaaccg gggtggaacg    5880
gcgccggtat cgggtgtgtc cgtggcgctc attccaacct ccgtgtgttt gtgcaggttt    5940
cgcgtgttgc agtccctcgc accggcaccc gcagcgaggg gctcacgggt gccggtgggt    6000
cgactagttc agtgatggtg atggtgatgt cctcgagatc taagcttgga tccgcggccg    6060
ctacgtagaa ttcccatatg tatatctcct tcttaaagtt aaacaaaatt atttctagac    6120
gccgtccacg ctgcctcctc acgtgacgtg aggtgcaagc ccggacgttc cgcgtgccac    6180
gccgtgagcc gccgcgtgcc gtcggctccc tcagcccggg cggccgtggg agcccgcctc    6240
gatatgtaca cccgagaagc tcccagcgtc ctcctgggcc gcgatactcg accaccacgc    6300
acgcacaccg cactaacgat tcggccggcg ctcgattcgg ccggcgctcg attcggccgg    6360
cgctcgattc ggccggcgct cgattcggcc ggcgctcgat tcggccgagc agaagagtga    6420
acaaccaccg accacgcttc cgctctgcgc gccgtacccg acctacctcc cgcagctcga    6480
agcagctccc gggagtaccg ccgtactcac ccgcctgtgc tcaccatcca ccgacgcaaa    6540
gcccaacccg agcacacctc ttgcaccaag gtgccgaccg tggctttccg ctcgcagggt    6600
tccagaagaa atcgaacgat ccagcgcggc aaggttcaaa aagcaggggt tggtggggag    6660
gaggttttgg ggggtgtcgc cgggatacct gatatggctt tgttttgcgt agtcgaataa    6720
ttttccatat agcctcggcg cgtcggactc gaatagttga tgtgggcggg cacagttgcc    6780
ccatgaaatc cgcaacgggg ggcgtgctga gcgatcggca atgggcggat gcggtgttgc    6840
ttccgcaccg gccgttcgcg acgaacaacc tccaacgagg tcagtaccgg atgagccgcg    6900
acgacgcatt ggcaatgcgg tacgtcgagc attcaccgca cgcgttgctc ggatctatcg    6960
tcatcgactg cgatcacgtt gacgccgcga tgcgcgcatt cgagcaacca tccgaccatc    7020
cggcgccgaa ctgggtcgca caatcgccgt ccggccgcgc acatcggga  tggtggctcg    7080 gccccaacca cgtgtgccgc accgacagcg cccgactgac gccactgcgc tacgcccacc    7140
gcatcgaaac cggcctcaag atcagcgtcg cggcgatttc gcgtatggc  gggcaactga    7200 ccaaaaaccc gattcacccc gattgggaga cgatctacgg cccggccacc ccgtacacat    7260
```

```
tgcggcagct ggccaccatc cacacacccc ggcagatgcc gcgtcggccc gatcgggccg    7320
tgggcctggg ccgcaacgtc accatgttcg acgccacccg gcgatgggca tacccgcagt    7380
ggtggcaaca ccgaaacgga accggccgcg actgggacca tctcgtcctg cagcactgcc    7440
acgccgtcaa caccgagttc acgacaccac tgccgttcac cgaagtacgc gccaccgcgc    7500
aatccatctc caaatggatc tggcgcaatt tcaccgaaga acagtaccga gcccgacaag    7560
cgcatctcgg tcaaaaaggc ggcaaggcaa cgacactcgc caaacaagaa gccgtccgaa    7620
acaatgcaag aaagtacgac gaacatacga tgcgagaggc gattatctga tgggcggagc    7680
caaaaatccg gtgcgccgaa agatgacggc agcagcagca gccgaaaaat tcggtgcctc    7740
cactcgcaca atccaacgct tgtttgctga gccgcgtgac gattacctcg gccgtgcgaa    7800
agctcgccgt gacaaagctg tcgagctgcg gaagcagggg ttgaagtacc gggaaatcgc    7860
cgaagcgatg gaactctcga ccgggatcgt cggccgatta ctgcacgacg cccgcaggca    7920
cggcgagatt tcagcggagg atctgtcggc gtaaccaagt cagcggggttg tcgggttccg    7980 gccggcgctc ggcactcgga ccggccggcg gatggtgttc tgcctctggc gcagcgtcag    8040
ctaccgccga aggcctgtca tcgaccggct tcgactgaag tatgagcaac gtcacagcct    8100
gtgattggat gatccgctca cgctcgaccg ctacctgttc agctgccgcc cgctgggcat    8160
gagcaacggc caactctcgt tcaa                                           8184

<210> SEQ ID NO 57
<211> LENGTH: 26
<212> TYPE: DNA
<213> ORGANISM: Artificial Sequence
<220> FEATURE:
<223> OTHER INFORMATION: Description of Artificial Sequence: Synthetic
      primer sHN389

<400> SEQUENCE: 57
gttgtacaag catggggact cgccgc                                          26

<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: Synthetic
      primer sHN390

<400> SEQUENCE: 58
gtagatctcc tccgactgca tcaacggcg                                       29

<210> SEQ ID NO 59
<211> LENGTH: 29
<212> TYPE: DNA
<213> ORGANISM: Artificial Sequence
<220> FEATURE:
<223> OTHER INFORMATION: Description of Artificial Sequence: Synthetic
      primer sHN391

<400> SEQUENCE: 59
accgttaacc atcagtactt ggcgtggtg                                       29

<210> SEQ ID NO 60
<211> LENGTH: 18
<212> TYPE: DNA
<213> ORGANISM: Artificial Sequence
<220> FEATURE:
<223> OTHER INFORMATION: Description of Artificial Sequence: Synthetic
      primer sHN321
```

<400> SEQUENCE: 60
gaagctgacc aagttctc                                                 18

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer sHN335

<400> SEQUENCE: 61
gcccagggca catcggaatt catg                                          24

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      primer sHN336

<400> SEQUENCE: 62
accgacactg acgccgatga acga                                          24

<210> SEQ ID NO 63
<211> LENGTH: 30
<212> TYPE: DNA
<213> ORGANISM: Artificial Sequence
<220> FEATURE:
<223> OTHER INFORMATION: Description of Artificial Sequence: Synthetic
      primer sHN349

<400> SEQUENCE: 63
cagcatgaac gtgatgagga atgtcagaag                                    30

<210> SEQ ID NO 64
<211> LENGTH: 30
<212> TYPE: DNA
<213> ORGANISM: Artificial Sequence
<220> FEATURE:
<223> OTHER INFORMATION: Description of Artificial Sequence: Synthetic
      primer sHN351

<400> SEQUENCE: 64
ttcgaggtct tgctggtcac acgcatcgtg                                    30

<210> SEQ ID NO 65
<211> LENGTH: 34
<212> TYPE: DNA
<213> ORGANISM: Artificial Sequence
<220> FEATURE:
<223> OTHER INFORMATION: Description of Artificial Sequence: Synthetic
      primer sHN361

<400> SEQUENCE: 65
aagagctctc tagacgcatc cgaaacctcc accc                               34

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      primer sHN362

```
<400> SEQUENCE: 66
acaacatgaa ctcggatgtg c                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      primer sHN363

<400> SEQUENCE: 67
ccggactcat accggacatg g                                              21

<210> SEQ ID NO 68
<211> LENGTH: 32
<212> TYPE: DNA
<213> ORGANISM: Artificial Sequence
<220> FEATURE:
<223> OTHER INFORMATION: Description of Artificial Sequence: Synthetic
      primer sHN364

<400> SEQUENCE: 68
aaactagtca tggtcgctgt agtggaactc ac                                  32

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic
      primer sHN368

<400> SEQUENCE: 69
aacgttgtct ttatgttgga tc                                             22

<210> SEQ ID NO 70
<211> LENGTH: 35
<212> TYPE: DNA
<213> ORGANISM: Artificial Sequence
<220> FEATURE:
<223> OTHER INFORMATION: Description of Artificial Sequence: Synthetic
      primer sHN373

<400> SEQUENCE: 70
aatgtacaag ttaacgaccg cgcgggtccc ggacg                               35

<210> SEQ ID NO 71
<211> LENGTH: 95
<212> TYPE: DNA
<213> ORGANISM: Artificial Sequence
<220> FEATURE:
<223> OTHER INFORMATION: Description of Artificial Sequence: Synthetic
      primer MCS-1a

<400> SEQUENCE: 71
catgggccac catcaccatc accatatggg aattctacgt agcggccgcg gatccaagct    60
tagatctctc gagcatcacc atcaccatca ctgaa                               95

<210> SEQ ID NO 72
<211> LENGTH: 95
<212> TYPE: DNA
<213> ORGANISM: Artificial Sequence
<220> FEATURE:
<223> OTHER INFORMATION: Description of Artificial Sequence: Synthetic
      primer MCS-1b
```

-continued

<400> SEQUENCE: 72
ctagttcagt gatggtgatg gtgatgctcg agagatctaa gcttggatcc gcggccgcta    60
cgtagaattc ccatatggtg atggtgatgg tggcc    95

<210> SEQ ID NO 73
<211> LENGTH: 98
<212> TYPE: DNA
<213> ORGANISM: Artificial Sequence
<220> FEATURE:
<223> OTHER INFORMATION: Description of Artificial Sequence: Synthetic
      primer MCS-2a

<400> SEQUENCE: 73
tatgggccat caccatcacc atcacgccat gggaattcta cgtagcggcc gcggatccaa    60
gcttagatct ctcgagcatc accatcacca tcactgaa    98

<210> SEQ ID NO 74
<211> LENGTH: 100
<212> TYPE: DNA
<213> ORGANISM: Artificial Sequence
<220> FEATURE:
<223> OTHER INFORMATION: Description of Artificial Sequence: Synthetic
      primer MCS-2b

<400> SEQUENCE: 74
ctagttcagt gatggtgatg gtgatgctcg agagatctaa gcttggatcc gcggccgcta    60
cgtagaattc ccatggcgtg atggtgatgg tgatggccca    100

<210> SEQ ID NO 75
<211> LENGTH: 29
<212> TYPE: DNA
<213> ORGANISM: Artificial Sequence
<220> FEATURE:
<223> OTHER INFORMATION: Description of Artificial Sequence: Synthetic
      primer sHN217

<400> SEQUENCE: 75
tgacgccgtc cattatacct cctcacgtg    29

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer sHN218

<400> SEQUENCE: 76
gagaagggag cggccatggc    20

<210> SEQ ID NO 77
<211> LENGTH: 29
<212> TYPE: DNA
<213> ORGANISM: Artificial Sequence
<220> FEATURE:
<223> OTHER INFORMATION: Description of Artificial Sequence: Synthetic
      primer sHN395

<400> SEQUENCE: 77
tttgttaact agagtaacgg gctactccg    29

<210> SEQ ID NO 78
<211> LENGTH: 28

```
<212> TYPE: DNA
<213> ORGANISM: Artificial Sequence
<220> FEATURE:
<223> OTHER INFORMATION: Description of Artificial Sequence: Synthetic
      primer sHN396

<400> SEQUENCE: 78
aaggtacctc aacgacagga gcacgatc                                            28

<210> SEQ ID NO 79
<211> LENGTH: 33
<212> TYPE: DNA
<213> ORGANISM: Artificial Sequence
<220> FEATURE:
<223> OTHER INFORMATION: Description of Artificial Sequence: Synthetic
      primer sHN397

<400> SEQUENCE: 79
actgttaacg catccgaaac ctccacccca ctc                                      33

<210> SEQ ID NO 80
<211> LENGTH: 34
<212> TYPE: DNA
<213> ORGANISM: Artificial Sequence
<220> FEATURE:
<223> OTHER INFORMATION: Description of Artificial Sequence: Synthetic
      primer sHN398

<400> SEQUENCE: 80
ttggtacctc gctgtagtgg aactcaccga gcac                                     34

<210> SEQ ID NO 81
<211> LENGTH: 26
<212> TYPE: DNA
<213> ORGANISM: Artificial Sequence
<220> FEATURE:
<223> OTHER INFORMATION: Description of Artificial Sequence: Synthetic
      primer sHN147

<400> SEQUENCE: 81
cgtgtacata tcgaggcggg ctccca                                              26

<210> SEQ ID NO 82
<211> LENGTH: 34
<212> TYPE: DNA
<213> ORGANISM: Artificial Sequence
<220> FEATURE:
<223> OTHER INFORMATION: Description of Artificial Sequence: Synthetic
      primer sHN376

<400> SEQUENCE: 82
tttctagacg ccgtccatta tacctcctca cgtg                                     34

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic
      primer sHN388

<400> SEQUENCE: 83
aaagttaacg agagttggcc gttgctc                                             27

<210> SEQ ID NO 84
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      primer sHN120

<400> SEQUENCE: 84
gctgtacacc cgagaagctc ccagcg                                          26

<210> SEQ ID NO 85
<211> LENGTH: 32
<212> TYPE: DNA
<213> ORGANISM: Artificial Sequence
<220> FEATURE:
<223> OTHER INFORMATION: Description of Artificial Sequence: Synthetic
      primer sHN160

<400> SEQUENCE: 85
aacatatgta tatctccttc ttaaagttaa ac                                   32

<210> SEQ ID NO 86
<211> LENGTH: 27
<212> TYPE: DNA
<213> ORGANISM: Artificial Sequence
<220> FEATURE:
<223> OTHER INFORMATION: Description of Artificial Sequence: Synthetic
      primer sHN337

<400> SEQUENCE: 86
aaccatggct agcaaaggag aagaact                                         27

<210> SEQ ID NO 87
<211> LENGTH: 24
<212> TYPE: DNA
<213> ORGANISM: Artificial Sequence
<220> FEATURE:
<223> OTHER INFORMATION: Description of Artificial Sequence: Synthetic
      primer sHN338

<400> SEQUENCE: 87
aagtgttggc caaggaacag gtag                                            24

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      primer sHN339

<400> SEQUENCE: 88
gtcactactt tctcttatgg                                                 20

<210> SEQ ID NO 89
<211> LENGTH: 55
<212> TYPE: DNA
<213> ORGANISM: Artificial Sequence
<220> FEATURE:
<223> OTHER INFORMATION: Description of Artificial Sequence: Synthetic
      primer sHN340

<400> SEQUENCE: 89
ttagatcttt agtgatggtg atggtgatgt ttgtagagct catccatgcc atgtg          55

<210> SEQ ID NO 90
<211> LENGTH: 5987
<212> TYPE: DNA
<213> ORGANISM: Rhodococcus erythropolis
```

<220> FEATURE:
<223> OTHER INFORMATION: endogenous plasmid pRE8424

<400> SEQUENCE: 90

```
gaattcgcgt tgaagcccgg cctctcgtag ctccattgcg acagtcgtgg agtcgtgcgc      60
gttttgaatg gtctgccagg agtgcgacag atccacagat gcctgcttga tgacctgcat     120
ctttcgttcg gtttctttgc gttgaatcat cgcgcgaacc tctttctcgt ccatacggac     180
agcttattga gtgatcaacc acaaaaagtg tgcagtcggt gacggtttgt gcagcaactg     240
gacactacgc gatattatgt gtacggtttg aagtgtagat gaacaggtgt tgctgaatat     300
ggacacttaa gtcataagct gtatcggact cgatcgaagg aactcgcatg aatgttcagc     360
tcggaacgtc cctccccgtc gcaactaccg ctgatcagtt cccggtgttc gtggccggta     420
tggacgaccc gatcaagccg gtgcaggaca agctcactcc cgatgggcgt gtgaagtatt     480
cgactggtgc actgctccga gttgcacgca aagatggaac tgttgcgacg ataagacag      540
catccgtgca cgtcatcaac ccgccgaatg agccgttcag cttcggcacg atctaccgag     600
cagaaggcct tgtctgggtg cagccctaca tgacgggaat ggatcgtctc gcactgtcca     660
tcacggtcga gaacctggtt ccaatgcctg cggcggccgt ctccgcacct gctcgtaaga     720
gcgcggacgc atgacaaagc tggttttcacg aatcgcgata ccggttgttg ccttgctagt    780
cggactgatt gttggtctga atattgttgg cacacaagag attaagcttt ccagcggaat     840
gcaagagcgt cgggactcat gggctgaacg aacggtgacc tggtgcagat ctcctcttcc     900
gacaggttct gttccatctg tcagtgcatg cagagagata ccgggatatg tccgagtgag     960
tccggaattg agcgccgatg ggatccagtg gactaacccc gatggacagg tcatcacgtc    1020
gccgtactcg aagaccagta cctgcggtga tgttccagtt cccgaaggtt ggcgcgcagt    1080
ctatttgacc gtaaacagcc ctgtcccggt ctacaacgga acggaggctg agactgtccc    1140
agaaacattg acgagcgagc gagtgcaaac caatctccag cttggaacct ccggatgcgc    1200
tcttgtgcca gtcgagtcgt ggttgtggaa cgtggatgag caggtcgagg tagatagtcc    1260
gaatgtcgtt gtggagtggc cccgatgagc aattacgaag ccgttcggcg cggtgaccag    1320
gtacgaaggc gtacaacctg gcaaatcatg cgaggaaagc tcaaggcaaa aattgccgat    1380
tacccgattc tgtcctcgac gtttctgttg cttctcgtgc tgtacatctt cgacgctgag    1440
atgtggctct tggccagtgt gctgctggtg tgcgttgtgg caatggtcta cctgagagac    1500
cgaacgaagg ctcggcggcg caaacgtcgt acagctcgat ggtggcgagg aactccggaa    1560
gttgcaggtg ctgcggccaa tctcggtctg atcaattcct ctggacagcc tcctctcatt    1620
cggagttata aattttcgga cgacggattg actcgatcag tcgctttcga ccttccgaca    1680
ggcatcactg gggaagacat gacatcgaaa acggtcaaaa tagctgatgc tttcggtgct    1740
ctacgtgcca gtttcaccaa agtagagccg cgcagggtgg agctacttct gatcgacgca    1800
gacactattt ctcaagcacg agatgcagca tggctcagtg acgtcgagga ctcatcggcc    1860
ggcacattga aggaagaggc cggcggcata cttgggggaca atcggccttg gtgggagcaa    1920
gaaaaggatc ttccgttcga caaaagcacg gacgcctgat ggatcaaaca gacacgatcc    1980
cgattgcgat tggatggaac gaactagccc aacctgtcct ggtcgatata gccaaagatg    2040
ctgctcactg gctcattcaa ggcaaaaccc gttccggaaa atctcaatgc acctacaacc    2100
tgctcgcaca ggctggatcg aatcccgctg tgcgtgtcgt cggagtcgat cccacttccg    2160
tcttactagc cccattcgtc caccgaagac ccgctgaacc gaacatcgag ctcggactga    2220
```

```
acgattttga caaagtcctc cgagtcctcc agttcgtcaa agcagaatcc gaccgacgaa    2280
ttgagtgttt ctgggatcga cgcatagaca aaatttcttt gttctcgcca gcactacctc    2340
tcatcctgct tgtactggaa gaatttcccg gaatcatcga gggcgcacag gatttcgatg    2400
caaccaacgg tctgaaacca gcagatagat acgcaccccg catcacatcg cttgttcgac    2460
agattgctgc tcagtcggcc aaagcaggca tcagaatgtt gctcttggct caacgtgcgg    2520
aagcttccat cgtgggcgga aacgctcgct cgaatttcgc ggtgaaaatg actctccgcg    2580
tagacgaacc tgaatctgtc aaaatgctgc accccaacgc aacacctgaa gagtgcgcac    2640
tggtcgaagg attcgttcct ggacaaggct tcttcgacca acccggacta cggcgccaaa    2700
tgatccgaac ggttcgcgta ggtgagtact cgacctacgc gagttacgtc gaaaacgcag    2760
acctcgcgta tgaagccgca ctgaacatcg accgagcaca acgaatgaca atcgcctcgg    2820
aatacccaca tcttggcgac ataggctgac aaccgaacac acaggaggac ataccttgat    2880
cggctacccg acagacgcaa tcccggtaaa cacctatatt cgacagcaat ttgagaaggt    2940
tgcacatgag gcaggagaaa aacttgcttc acgccgaaac ctgcccacgg aacgagtcgt    3000
aacgactgca ctccggatca aatcaggctg gccgaatgat catctcgtaa taactgaaat    3060
actcagggcc agagtaggtt tggaaggtca agctgtcgtt gacgaacttc gcggcatgca    3120
gatcaccgat gacgaccttg gtgcactagt cggtccacga tgggtcagtt cgatgaccgt    3180
gttcgcaatg tctgagctgc ttctaggcga tgaactcgga aagctcaacg atttacgcgg    3240
tgacgattgg aaacgtgcta gtgactcagc tgctgaagtt ggacgatcac tgggccttaa    3300
atacgacatt tcggacagcg agggagccga acgagattgg tgcgctgctc gaggggcggc    3360
atgggctgtc gcaatgcatg aacacctcga gggacgcgat ttcgaaactc tgactgcacc    3420
gtggatcagt cttgtccgac cgaagttcgt tcaactcttc atggacaatg ctgatcgacc    3480
gtcatttgtt gcccaggtct acgacgagct atgcagccat tctggaggtc atgcaattct    3540
gagtgcagca gatcagaggg ttgatgcgtg aagcacgaag ctacggtatt catccttcgt    3600
ctagctgtcg gcatttacga tcatcgcggg cctgatctgt ggggtggaca tgatgtctac    3660
ggttggattt acgctggtga acgcgctgaa tcgtctgaaa ttcttgctgc gatgtgctgc    3720
tattacaccc ccgactacgc ccgtgaagcc ggattcgaca ttgaagcact gggtgaatac    3780
cggggtctgt tcgatgcact ggtgaagaca agcagaaccc cggaagagaa ggctggcgtt    3840
gtcgaagcat ggggactcgc cgcggactag cggcttcccg acacgccgta ctgaccagca    3900
gatcagcgat aaacgctgtt tctgctggtt aagtggataa aaaccaaata atcgatgaac    3960
ctcgaagtgg agtatccgag ctgaactagc tggatttact ccgaaaatac gagcggcgac    4020
gaagggtgtt ggaccaccct gccgccgcct tcgaggctcc tacttgacta ggaccccgct    4080
cgttatgacc agcgtaagtg ctgaacacct ttccggcaaa gaccggcccc ctgtcctcgt    4140
gtcgtccgat aagcgcggca tccggcacga acttcgaccc aaacttcaac aaatcaccac    4200
gtcagaaact tttaatgcgt gcggccggcc gatttccggc gtgaacggtg tgaccatcgt    4260
caacggtccc aaaggttccg gatttggagg ccttcgctcc tgcggaaagg gctggatctg    4320
cccctgctgt gcgggaaaag tcggcgcaca tcgagcagac gaaatttctc aagttgttgc    4380
tcatcaactc gggactggat ctgttgcgat ggtgaccatg accatgcgcc ataccgctgg    4440
gcagcgtttg catgatttgt ggactggact ttcggcagcc tggaaagctg cgaccaatgg    4500
ccgccgatgg cgtaccgaac gtgaaatgta cggctgcgac ggatacgtac gagctgttga    4560
aatcactcac ggaaaaaacg gttggcacgt tcacgtccac gctctactca tgttcagcgg    4620
```

```
tgacgtgagt gagaacatcc tcgaatcctt ctcggatgcg atgttcgatc ggtggacctc    4680
caaactcgtg tctctgggat tgctgcgcc actacgtaat tcaggtggac tcgacgtaag    4740
aaagattggt ggagaagctg accaagttct cgctgcatac ctgacgaaaa ttgcatccgg    4800
ggtcggcatg gaagtcggca gtggcgacgg aaaaagtggt cggcacggca accgtgcacc    4860
ttgggaaatc gccgttgatg cagtcggagg ggatccacaa gcgttggaac tctgcgcga    4920 gtttgagttc ggttcgatgg gacgccgagc aatcgcatgg tctcgtggac tgcgcgcccg    4980
agctggtctt ggcgtagaac tcacggatgc tcagattgtc gaacaggaag aatctgcccc    5040
ggtcatggtt gcgatcattc cggctcggtc ctggatgatg attcggaact gtgcgcctta    5100
cgttttcgga gagatccttg gactcgtgga agcgggcgcg acctgggaaa accttcgtga    5160
ccacttgcat tatcgattgc ctgcagcgga tgtgcggcct ccgataatat cgattcgtaa    5220
gtgaaatgtc ttggtgtgca acaactttca ctcgtatgaa ccacacttga gggcatcccc    5280
ccgatacttg ccgctttgaa gctgggtgtc tctctgtcag ggctgcgata gcaccgcgta    5340
gcggcttggc cttgacagag agacggcctg tttcatggtt ggtctcgggg ggctgaccgg    5400
gcagatagaa aaaggccggc cgatttggct gccgactatt tttgcaggta aacccatctc    5460
atgagcatca atgaacgtcc cgttggtatc gcagcgaatg cagcttcggt agacgtcgat    5520
ggcgttgtga tgggtgtgta tctctcgctt tatgggcaag aaatcacgct agatcgagat    5580
gatgcgttcc tactcctcga tcgacttcag gacgcgttgc gacctcaagc caactaagaa    5640
ccctccagat ggtctaaacg aggcgcaaac tcgctcctgg gcctgcgggc ggagcaccga    5700
agcgcgagcg aagcggagcg cgtaggtggg ggagcctgcg ggcagcggcg gcggagccgc    5760
cgccttggta ataggtgatc atcggggcca tagcaggtca gaggatgttt ttacgatgac    5820
tcatgctcac cacgccaagt actgatggtc gacggtgaaa catctgcaac ggtggcaacg    5880
gttcggctgc tgacgtcaag ctcgtcaacg agaaaacgag aaatggattt gcgcagctca    5940
gaggcagttc ccactactga tgtgatgtct gccagagcct gtagcca              5987
```

<210> SEQ ID NO 91
<211> LENGTH: 8207
<212> TYPE: DNA
<213> ORGANISM: Artificial Sequence
<220> FEATURE:
<223> OTHER INFORMATION: Description of Artificial Sequence: Synthetic
    vector pTip-QT1 sequence

<400> SEQUENCE: 91

```
gagctcgacc gcgcgggtcc cggacgggga agagcgggga gctttgccag agagcgacga     60
cttccccttg cgttggtgat tgccggtcag ggcagccatc cgccatcgtc gcgtagggtg    120
tcacacccca ggaatcgcgt cactgaacac agcagccggt aggacgacca tgactgagtt    180
ggacaccatc gcaaatccgt ccgatcccgc ggtgcagcgg atcatcgatg tcaccaagcc    240
gtcacgatcc aacataaaga caacgttgat cgaggacgtc gagcccctca tgcacagcat    300
cgcggccggg gtggagttca tcgaggtcta cggcagcgac agcagtcctt ttccatctga    360
gttgctggat ctgtgcgggc ggcagaacat accgtccgc ctcatcgact cctcgatcgt    420
caaccagttg ttcaagggg agcggaaggc caagacattc ggcatcgccc gcgtccctcg    480
cccggccagg ttcggcgata tcgcgagccg gcgtgggac gtcgtcgttc tcgacggggt    540
gaagatcgtc gggaacatcg gcgcgatagt acgcacgtcg ctcgcgctcg gagcgtcggg    600
gatcatcctg gtggacagtg acatcaccag catcgcggac cggcgtctcc aaagggccag    660
```

-continued

```
ccgaggttac gtcttctccc ttcccgtcgt tctctccggt cgcgaggagg ccatcgcctt    720
cattcgggac agcggtatgc agctgatgac gctcaaggcg gatggcgaca tttccgtgaa    780
ggaactcggg gacaatccgg atcggctggc cttgctgttc ggcagcgaaa agggtgggcc    840
ttccgacctg ttcgaggagg cgtcttccgc ctcggtttcc atccccatga tgagccagac    900
cgagtctctc aacgtttccg tttccctcgg aatcgcgctg cacgagagga tcgacaggaa    960
tctcgcggcc aaccgataag cgcctctgtt cctcggacgc tcggttcctc gacctcgatt   1020
cgtcagtgat gatcacctca cacgcagcg atcaccactg acatatcgag gtcaacggtc    1080
gtggtccggg cgggcactcc tcgaaggcgc ggccgacgcc cttgaacgac tcgatgactc    1140
tagagtaacg ggctactccg tttaacggac cccgttctca cgctttaggc ttgaccccgg    1200
agcctgcatg gggcattccg ccgtgaaccc ggtggaatgc ccccggcacc cgggctttcc    1260
agcaaagatc acctggcgcc gatgagtaag gcgtacagaa ccactccaca ggaggaccgt    1320
cgagatgaaa tctaacaatg cgctcatcgt catcctcggc accgtcaccc tggatgctgt    1380
aggcataggc ttggttatgc cggtactgcc gggcctcttg cgggatatcg tccattccga    1440
cagcatcgcc agtcactatg gcgtgctgct agcgctatat gcgttgatgc aatttctatg    1500
cgcacccgtt ctcggagcac tgtccgaccg ctttggccgc cgcccagtcc tgctcgcttc    1560
gctacttgga gccactatcg actacgcgat catggcgacc acaccgtcc tgtggattct    1620
ctacgccgga cgcatcgtgg ccggcatcac cggcgccaca ggtgcggttg ctggcgccta   1680
tatcgccgac atcaccgatg gggaagatcg ggctcgccac ttcgggctca tgagcgcttg   1740
tttcggcgtg gtatggtgg caggccccgt ggccggggga ctgttgggcg ccatctcctt    1800
gcatgcacca ttccttgcgg cggcggtgct caacggcctc aacctactac tgggctgctt   1860
cctaatgcag gagtcgcata agggagagcg tcgtccgatg cccttgagag ccttcaaccc   1920
agtcagctcc ttccggtggg cgcggggcat gactatcgtc gccgcactta tgactgtctt   1980
ctttatcatg caactcgtag acaggtgcc ggcagcgctc tgggtcattt tcggcgagga    2040
ccgctttcgc tggagcgcga cgatgatcgg cctgtcgctt gcggtattcg gaatcttgca   2100
cgccctcgct caagccttcg tcactggtcc cgccaccaaa cgtttcggcg agaagcaggc   2160
cattatcgcc ggcatggcgg ccgacgcgct gggctacgtc ttgctggcgt tcgcgacgcg   2220
aggctggatg gccttcccca ttatgattct tctcgcttcc ggcggcatcg ggatgcccgc   2280
gttgcaggcc atgctgtcca ggcaggtaga tgacgaccat cagggacagc ttcaaggatc   2340
gctcgcggct cttaccagcc taacttcgat cattggaccg ctgatcgtca cggcgattta   2400
tgccgcctcg gcgagcacat ggaacgggtt ggcatggatt gtaggcgccg ccctatacct   2460
tgtctgcctc cccgcgttgc gtcgcggtgc atggagccgg gccacctcga cctgaatgga   2520
agccggcggc acctcgctaa cggattcacc actccaagaa ttggagccaa tcaattcttg   2580
cggagaactg tgaatgcgca aaccaaccct tggcagaaca tatccatcgc gtccgccatc   2640
tccagcagcc gcacgcggcg catctcgggc agcgttgggt cctggccacg ggtgcgcatg   2700
atcgtgctcc tgtcgttgag gactagaatt gatctcctcg accgccaatt gggcatctga   2760
gaatcatctg cgtttctcgc acgcaacgta cttgcaacgt tgcaactcct agtgttgtga   2820
atcacacccc accgggggt gggattgcag tcaccgattt ggtgggtgcg cccaggaaga   2880
tcacgtttac ataggagctt gcaatgagct actccgtggg acaggtggcc ggcttcgccg   2940
gagtgacggt gcgcacgctg caccactacg acgacatcgg cctgctcgta ccgagcgagc   3000
```

```
gcagccacgc gggccaccgg cgctacagcg acgccgacct cgaccggctg cagcagatcc   3060
tgttctaccg ggagctgggc ttcccgctcg acgaggtcgc cgccctgctc gacgacccgg   3120
ccgcggaccc gcgcgcgcac ctgcgccgcc agcacgagct gctgtccgcc cggatcggga   3180
aactgcagaa gatggcggcg gccgtggagc aggcgatgga ggcacgcagc atgggaatca   3240
acctcacccc ggaggagaag ttcgaggtct tcggcgactt cgaccccgac cagtacgagg   3300
aggaggtccg ggaacgctgg gggaacaccg acgcctaccg ccagtccaag gagaagaccg   3360
cctcgtacac caaggaggac tggcagcgca tccaggacga ggccgacgag ctcacccggc   3420
gcttcgtcgc cctgatggac gcgggtgagc ccgccgactc cgaggggcg atggacgccg   3480 ccgaggacca ccggcagggc atcgcccgca accactacga ctgcgggtac gagatgcaca   3540
cctgcctggg cgagatgtac gtgtccgacg aacgtttcac gcgaaacatc gacgccgcca   3600
agccgggcct cgccgcctac atgcgcgacg cgatcctcgc caacgccgtc cggcacaccc   3660
cctgagcggt ggtcgtggcc cgggtctccc gcccggtctc accccacggc tcactcccgg   3720
gccacgacca ccgccgtccc gtacgcgcac acctcggtgc ccacgtccgc cgcctccgtc   3780
acgtcgaaac ggaagatccc cgggtaccga gctcgtcagg tggcactttt cggggaaatg   3840
tgcgcggaac ccctatttgt ttatttttct aaatacattc aaatatgtat ccgctcatga   3900
gacaataacc ctgataaatg cttcaataat attgaaaaag gaagagtatg agtattcaac   3960
atttccgtgt cgcccttatt cccttttttg cggcattttg ccttcctgtt tttgctcacc   4020
cagaaacgct ggtgaaagta aaagatgctg aagatcagtt gggtgcacga gtgggttaca   4080
tcgaactgga tctcaacagc ggtaagatcc ttgagagttt tcgccccgaa gaacgttttc   4140
caatgatgag cacttttaaa gttctgctat gtggcgcggt attatcccgt attgacgccg   4200
ggcaagagca actcggtcgc cgcatacact attctcagaa tgacttggtt gagtactcac   4260
cagtcacaga aaagcatctt acggatggca tgacagtaag agaattatgc agtgctgcca   4320
taaccatgag tgataacact gcggccaact tacttctgac aacgatcgga ggaccgaagg   4380
agctaaccgc ttttttgcac aacatggggg atcatgtaac tcgccttgat cgttgggaac   4440
cggagctgaa tgaagccata ccaaacgacg agcgtgacac cacgatgcct gtagcaatgg   4500
caacaacgtt gcgcaaacta ttaactggcg aactacttac tctagcttcc cggcaacaat   4560
taatagactg gatggaggcg gataaagttg caggaccact tctgcgctcg gcccttccgg   4620
ctggctggtt tattgctgat aaatctggag ccggtgagcg tgggtctcgc ggtatcattg   4680
cagcactggg gccagatggt aagccctccc gtatcgtagt tatctacacg acggggagtc   4740
aggcaactat ggatgaacga atagacaga tcgctgagat aggtgcctca ctgattaagc   4800
attggtaact gtcagaccaa gtttactcat atatacttta gattgattta aaacttcatt   4860
tttaatttaa aaggatctag gtgaagatcc ttttttgataa tctcatgacc aaaatccctt   4920
aacgtgagtt ttcgttccac tgagcgtcag accccgtaga aaagatcaaa ggatcttctt   4980
gagatccttt ttttctgcgc gtaatctgct gcttgcaaac aaaaaaacca ccgctaccag   5040
cggtggtttg tttgccggat caagagctac caactctttt tccgaaggta actggcttca   5100
gcagagcgca gataccaaat actgttcttc tagtgtagcc gtagttaggc caccacttca   5160
agaactctgt agcaccgcct acatacctcg ctctgctaat cctgttacca gtggctgctg   5220
ccagtggcga taagtcgtgt cttaccgggt tggactcaag acgatagtta ccggataagg   5280
cgcagcggtc gggctgaacg ggggttcgt gcacacagcc cagcttggag cgaacgacct   5340
acaccgaact gagataccta cagcgtgagc tatgagaaag cgccacgctt cccgaaggga   5400
```

```
gaaaggcgga caggtatccg gtaagcggca gggtcggaac aggagagcgc acgagggagc   5460 ttccagggg  aaacgcctgg tatctttata gtcctgtcgg gtttcgccac ctctgacttg   5520
agcgtcgatt tttgtgatgc tcgtcagggg ggcggagcct atggaaaaac gccagcaacg   5580 cggcctttt  acggttcctg gccttttgct ggccttttgc tcacatgttc tttcctgcgt   5640
tatcccctga ttctgtggat aaccgtatta ccgcctttga gtgagctgat accgctcgcc   5700
gcagccgaac gaccgagcgc agcgagtcag tgagcgagga agcggaagag cgcccaatac   5760
gcaaaccgcc tctccccgcg cgttggccga ttcattaatg cagctggcac gactagagtc   5820
ccgctgaggc ggcgtagcag gtcagccgcc ccagcggtgg tcaccaaccg gggtggaacg   5880
gcgccggtat cgggtgtgtc cgtggcgctc attccaacct ccgtgtgttt gtgcaggttt   5940
cgcgtgttgc agtccctcgc accggcaccc gcagcgaggg gctcacgggt gccggtgggt   6000
cgactagttc agtgatggtg atggtgatgc tcgagagatc taagcttgga tccgcggccg   6060
ctacgtagaa ttcccatatg gtgatggtga tggtggccca tggtatatct ccttcttaaa   6120
gttaaacaaa attatttcta gacgccgtcc acgctgcctc ctcacgtgac gtgaggtgca   6180
agcccggacg ttccgcgtgc cacgccgtga gccgccgcgt gccgtcggct ccctcagccc   6240
gggcggccgt gggagcccgc ctcgatatgt cacccgaga  agctcccagc gtcctcctgg   6300
gccgcgatac tcgaccacca cgcacgcaca ccgcactaac gattcggccg gcgctcgatt   6360
cggccggcgc tcgattcggc cggcgctcga ttcggccggc gctcgattcg gccggcgctc   6420
gattcggccg agcagaagag tgaacaacca ccgaccacg  ttccgctctg cgcgccgtac   6480
ccgacctacc tcccgcagct cgaagcagct cccgggagta ccgccgtact caccgcctg   6540 tgctcaccat ccaccgacgc aaagcccaac ccgagcacac ctcttgcacc aaggtgccga   6600
ccgtggcttt ccgctcgcag ggttccagaa gaaatcgaac gatccagcgc ggcaaggttc   6660
aaaaagcagg ggttggtggg gaggaggtt  tggggggtgt cgccgggata cctgatatgg   6720
ctttgttttg cgtagtcgaa taattttcca tatagcctcg gcgcgtcgga ctcgaatagt   6780
tgatgtgggc gggcacagtt gccccatgaa atccgcaacg gggggcgtgc tgagcgatcg   6840
gcaatgggcg gatgcggtgt tgcttccgca ccggccgttc gcgacgaaca acctccaacg   6900
aggtcagtac cggatgagcc gcgacgacgc attggcaatg cggtacgtcg agcattcacc   6960
gcacgcgttg ctcggatcta tcgtcatcga ctgcgatcac gttgacgccg cgatgcgcgc   7020
attcgagcaa ccatccgacc atccggcgcc gaactgggtc gcacaatcgc cgtccggccg   7080
cgcacacatc ggatggtggc tcggccccaa ccacgtgtgc cgcaccgaca gcgcccgact   7140
gacgccactg cgctacgccc accgcatcga aaccggcctc aagatcagcg tcggcggcga   7200
tttcgcgtat ggcgggcaac tgaccaaaaa cccgattcac cccgattggg agacgatcta   7260
cggcccggcc accccgtaca cattgcggca gctggccacc atccacacac ccggcagat   7320 gccgcgtcgg cccgatcggg ccgtgggcct gggccgcaac gtcaccatgt cgacgccac   7380 ccggcgatgg gcatacccgc agtggtggca acaccgaaac ggaaccggcc gcgactggga   7440
ccatctcgtc ctgcagcact gccacgccgt caacaccgag ttcacgacac cactgccgtt   7500
caccgaagta cgcgccaccg cgcaatccat ctccaaatgg atctggcgca atttcaccga   7560
agaacagtac cgagcccgac aagcgcatct cggtcaaaaa ggcggcaagg caacgacact   7620
cgccaaacaa gaagccgtcc gaaacaatgc aagaaagtac gacgaacata cgatgcgaga   7680
ggcgattatc tgatgggcgg agccaaaaat ccggtgcgcc gaaagatgac ggcagcagca   7740
```

| | |
|---|---|
| gcagccgaaa aattcggtgc ctccactcgc acaatccaac gcttgtttgc tgagccgcgt | 7800 |
| gacgattacc tcggccgtgc gaaagctcgc cgtgacaaag ctgtcgagct gcggaagcag | 7860 |
| gggttgaagt accgggaaat cgccgaagcg atggaactct cgaccgggat cgtcggccga | 7920 |
| ttactgcacg acgcccgcag gcacggcgag atttcagcgg aggatctgtc ggcgtaacca | 7980 |
| agtcagcggg ttgtcgggtt ccggccggcg ctcggcactc ggaccggccg gcggatggtg | 8040 |
| ttctgcctct ggcgcagcgt cagctaccgc cgaaggcctg tcatcgaccg gcttcgactg | 8100 |
| aagtatgagc aacgtcacag cctgtgattg gatgatccgc tcacgctcga ccgctacctg | 8160 |
| ttcagctgcc gcccgctggg catgagcaac ggccaactct cgttcaa | 8207 |

<210> SEQ ID NO 92
<211> LENGTH: 8211
<212> TYPE: DNA
<213> ORGANISM: Artificial Sequence
<220> FEATURE:
<223> OTHER INFORMATION: Description of Artificial Sequence: Synthetic
      vector pTip-QT2 sequence

<400> SEQUENCE: 92

| | |
|---|---|
| gagctcgacc gcgcgggtcc cggacgggga agagcgggga gctttgccag agagcgacga | 60 |
| cttccccttg cgttggtgat tgccggtcag ggcagccatc cgccatcgtc gcgtagggtg | 120 |
| tcacacccca ggaatcgcgt cactgaacac agcagccgga aggacgacca tgactgagtt | 180 |
| ggacaccatc gcaaatccgt ccgatcccgc ggtgcagcgg atcatcgatg tcaccaagcc | 240 |
| gtcacgatcc aacataaaga caacgttgat cgaggacgtc gagcccctca tgcacagcat | 300 |
| cgcggccggg gtggagttca tcgaggtcta cggcagcgac agcagtcctt ttccatctga | 360 |
| gttgctggat ctgtgcgggc ggcagaacat accggtccgc ctcatcgact cctcgatcgt | 420 |
| caaccagttg ttcaaggggg agcggaaggc caagacattc ggcatcgccc gcgtccctcg | 480 |
| cccggccagg ttcggcgata tcgcgagccg gcgtggggac gtcgtcgttc tcgacggggt | 540 |
| gaagatcgtc gggaacatcg gcgcgatagt acgcacgtcg ctcgcgctcg gagcgtcggg | 600 |
| gatcatcctg gtggacagtg acatcaccag catcgcggac cggcgtctcc aaagggccag | 660 |
| ccgaggttac gtcttctccc ttcccgtcgt tctctccggt cgcgaggagg ccatcgcctt | 720 |
| cattcgggac agcggtatgc agctgatgac gctcaaggcg gatggcgaca tttccgtgaa | 780 |
| ggaactcggg gacaatccgg atcggctggc cttgctgttc ggcagcgaaa agggtgggcc | 840 |
| ttccgacctg ttcgaggagg cgtcttccgc ctcggtttcc atcccatga tgagccagac | 900 |
| cgagtctctc aacgtttccg tttccctcgg aatcgcgctg cacgagagga tcgacaggaa | 960 |
| tctcgcggcc aaccgataag cgcctctgtt cctcggacgc tcggttcctc gacctcgatt | 1020 |
| cgtcagtgat gatcacctca cacggcagcg atcaccactg acatatcgag gtcaacggtc | 1080 |
| gtggtccggg cggcactcc tcgaaggcgc ggccgacgcc cttgaacgac tcgatgactc | 1140 |
| tagagtaacg ggctactccg tttaacggac cccgttctca cgctttaggc ttgaccccgg | 1200 |
| agcctgcatg gggcattccg ccgtgaaccc ggtggaatgc cccggcacc cgggctttcc | 1260 |
| agcaaagatc acctggcgcc gatgagtaag gcgtacagaa ccactccaca ggaggaccgt | 1320 |
| cgagatgaaa tctaacaatg cgctcatcgt catcctcggc accgtcaccc tggatgctgt | 1380 |
| aggcataggc ttggttatgc cggtactgcc gggcctcttg cgggatatcg tccattccga | 1440 |
| cagcatcgcc agtcactatg gcgtgctgct agcgctatat gcgttgatgc aatttctatg | 1500 |
| cgcacccgtt ctcggagcac tgtccgaccg ctttggccgc cgcccagtcc tgctcgcttc | 1560 |

```
gctacttgga gccactatcg actacgcgat catggcgacc acaccgtcc tgtggattct    1620 ctacgccgga cgcatcgtgg ccggcatcac cggcgccaca ggtgcggttg ctggcgccta    1680
tatcgccgac atcaccgatg gggaagatcg ggctcgccac ttcgggctca tgagcgcttg    1740
tttcggcgtg ggtatggtgg caggccccgt ggccggggga ctgttgggcg ccatctcctt    1800
gcatgcacca ttccttgcgg cggcggtgct caacggcctc aacctactac tgggctgctt    1860
cctaatgcag gagtcgcata agggagagcg tcgtccgatg cccttgagag ccttcaaccc    1920
agtcagctcc ttccggtggg cgcggggcat gactatcgtc gccgcactta tgactgtctt    1980
ctttatcatg caactcgtag acaggtgcc ggcagcgctc tgggtcattt tcggcgagga    2040
ccgctttcgc tggagcgcga cgatgatcgg cctgtcgctt gcggtattcg gaatcttgca    2100
cgccctcgct caagccttcg tcactggtcc cgccaccaaa cgtttcggcg agaagcaggc    2160
cattatcgcc ggcatggcgg ccgacgcgct gggctacgtc ttgctggcgt cgcgacgcg    2220 aggctggatg gccttcccca ttatgattct tctcgcttcc ggcggcatcg ggatgcccgc    2280
gttgcaggcc atgctgtcca ggcaggtaga tgacgaccat cagggacagc ttcaaggatc    2340
gctcgcggct cttaccagcc taacttcgat cattggaccg ctgatcgtca cggcgattta    2400
tgccgcctcg gcgagcacat ggaacgggtt ggcatggatt gtaggcgccg ccctatacct    2460
tgtctgcctc cccgcgttgc gtcgcggtgc atggagccgg ccacctcga cctgaatgga    2520 agccggcggc acctcgctaa cggattcacc actccaagaa ttggagccaa tcaattcttg    2580
cggagaactg tgaatgcgca aaccaaccct tggcagaaca tatccatcgc gtccgccatc    2640
tccagcagcc gcacgcggcg catctcgggc agcgttgggt cctggccacg ggtgcgcatg    2700
atcgtgctcc tgtcgttgag gactagaatt gatctcctcg accgccaatt gggcatctga    2760
gaatcatctg cgtttctcgc acgcaacgta cttgcaacgt tgcaactcct agtgttgtga    2820
atcacacccc accgggggt gggattgcag tcaccgattt ggtgggtgcg cccaggaaga    2880
tcacgtttac ataggagctt gcaatgagct actccgtggg acaggtggcc ggcttcgccg    2940
gagtgacggt gcgcacgctg caccactacg acgacatcgg cctgctcgta ccagagcgagc    3000 gcagccacgc gggccaccgg cgctacagcg acgccgacct cgaccggctg cagcagatcc    3060
tgttctaccg ggagctgggc ttcccgctcg acgaggtcgc cgccctgctc gacgacccgg    3120
ccgcggaccc gcgcgcgcac ctgcgccgcc agcacgagct gctgtccgcc cggatcggga    3180
aactgcagaa gatggcggcg gccgtggagc aggcgatgga ggcacgcagc atgggaatca    3240
acctcacccc ggaggagaag ttcgaggtct tcggcgactt cgaccccgac cagtacgagg    3300
aggaggtccg ggaacgctgg gggaacaccg acgcctaccg ccagtccaag gagaagaccg    3360
cctcgtacac caaggaggac tggcagcgca tccaggacga ggccgacgag ctcacccggc    3420
gcttcgtcgc cctgatggac gcgggtgagc ccgccgactc cgagggggcg atggacgccg    3480
ccgaggacca ccggcagggc atcgcccgca accactacga ctgcgggtac agagatgcaca    3540 cctgcctggg cgagatgtac gtgtccgacg aacgtttcac gcgaaacatc gacgccgcca    3600
agccgggcct cgccgcctac atgcgcgacg cgatcctcgc caacgccgtc cggcacaccc    3660
cctgagcggt ggtcgtggcc cgggtctccc gcccggtctc accccacggc tcactcccgg    3720
gccacgacca ccgccgtccc gtacgcgcac acctcggtgc ccacgtccgc cgcctccgtc    3780
acgtcgaaac ggaagatccc cgggtaccga gctcgtcagg tggcactttt cggggaaatg    3840
tgcgcggaac ccctatttgt ttatttttct aaatacattc aaatatgtat ccgctcatga    3900
gacaataacc ctgataaatg cttcaataat attgaaaaag gaagagtatg agtattcaac    3960
```

```
atttccgtgt cgcccttatt cccttttttg cggcattttg ccttcctgtt tttgctcacc   4020
cagaaacgct ggtgaaagta aaagatgctg aagatcagtt gggtgcacga gtgggttaca   4080
tcgaactgga tctcaacagc ggtaagatcc ttgagagttt tcgccccgaa gaacgttttc   4140
caatgatgag cacttttaaa gttctgctat gtggcgcggt attatcccgt attgacgccg   4200
ggcaagagca actcggtcgc cgcatacact attctcagaa tgacttggtt gagtactcac   4260
cagtcacaga aaagcatctt acggatggca tgacagtaag agaattatgc agtgctgcca   4320
taaccatgag tgataacact gcggccaact tacttctgac aacgatcgga ggaccgaagg   4380
agctaaccgc ttttttgcac aacatggggg atcatgtaac tcgccttgat cgttgggaac   4440
cggagctgaa tgaagccata ccaaacgacg agcgtgacac cacgatgcct gtagcaatgg   4500
caacaacgtt gcgcaaacta ttaactggcg aactacttac tctagcttcc cggcaacaat   4560
taatagactg gatggaggcg gataaagttg caggaccact tctgcgctcg gcccttccgg   4620
ctggctggtt tattgctgat aaatctggag ccggtgagcg tgggtctcgc ggtatcattg   4680
cagcactggg gccagatggt aagccctccc gtatcgtagt tatctacacg acggggagtc   4740
aggcaactat ggatgaacga atagacaga tcgctgagat aggtgcctca ctgattaagc   4800
attggtaact gtcagaccaa gtttactcat atatacttta gattgattta aaacttcatt   4860
tttaatttaa aaggatctag gtgaagatcc tttttgataa tctcatgacc aaaatccctt   4920
aacgtgagtt ttcgttccac tgagcgtcag accccgtaga aaagatcaaa ggatcttctt   4980
gagatccttt ttttctgcgc gtaatctgct gcttgcaaac aaaaaaacca ccgctaccag   5040
cggtggtttg tttgccggat caagagctac caactctttt tccgaaggta actggcttca   5100
gcagagcgca gataccaaat actgttcttc tagtgtagcc gtagttaggc caccacttca   5160
agaactctgt agcaccgcct acatacctcg ctctgctaat cctgttacca gtggctgctg   5220
ccagtggcga taagtcgtgt cttaccgggt tggactcaag acgatagtta ccggataagg   5280
cgcagcggtc gggctgaacg gggggttcgt gcacacagcc cagcttggag cgaacgacct   5340
acaccgaact gagatacctc agcgtgagc tatgagaaag cgccacgctt cccgaaggga   5400
gaaaggcgga caggtatccg gtaagcggca gggtcggaac aggagagcgc acgagggagc   5460
ttccagggga aaacgcctgg tatctttata gtcctgtcgg gtttcgccac ctctgacttg   5520
agcgtcgatt tttgtgatgc tcgtcagggg gcggagcct atggaaaaac gccagcaacg   5580 cggcctttt acgttcctg gcttttgct ggccttttgc tcacatgttc tttcctgcgt   5640
tatcccctga ttctgtggat aaccgtatta ccgcctttga gtgagctgat accgctcgcc   5700
gcagccgaac gaccgagcgc agcgagtcag tgagcgagga agcggaagag cgcccaatac   5760
gcaaaccgcc tctccccgcg cgttggccga ttcattaatg cagctggcac gactagagtc   5820
ccgctgaggc ggcgtagcag gtcagccgcc ccagcgtgg tcaccaaccg gggtggaacg   5880
gcgccggtat cgggtgtgtc cgtggcgctc attccaacct ccgtgtgttt gtgcaggttt   5940
cgcgtgttgc agtccctcgc accggcaccg cagcgaggg gctcacgggt gccggtgggt   6000
cgactagttc agtgatggtg atggtgatgc tcgagagatc taagcttgga tccgcggccg   6060
ctacgtagaa ttcccatggc gtgatggtga tggtgatggc ccatatgtat atctccttct   6120
taaagttaaa caaaattatt tctagacgcc gtccacgctg cctcctcacg tgacgtgagg   6180
tgcaagcccg gacgttccgc gtgccacgcc gtgagccgcc gcgtgccgtc ggctccctca   6240
gcccgggcgg ccgtgggagc ccgcctcgat atgtacaccc gagaagctcc cagcgtcctc   6300
```

```
ctgggccgcg atactcgacc accacgcacg cacaccgcac taacgattcg gccggcgctc      6360
gattcggccg gcgctcgatt cggccggcgc tcgattcggc cggcgctcga ttcggccggc      6420
gctcgattcg gccgagcaga agagtgaaca accaccgacc acgcttccgc tctgcgcgcc      6480
gtacccgacc tacctcccgc agctcgaagc agctcccggg agtaccgccg tactcacccg      6540
cctgtgctca ccatccaccg acgcaaagcc caacccgagc acacctcttg caccaaggtg      6600
ccgaccgtgg ctttccgctc gcagggttcc agaagaaatc gaacgatcca gcgcggcaag      6660
gttcaaaaag caggggttgg tggggaggag gttttggggg gtgtcgccgg gatacctgat      6720
atggctttgt tttgcgtagt cgaataattt tccatatagc ctcggcgcgt cggactcgaa      6780
tagttgatgt gggcgggcac agttgcccca tgaaatccgc aacgggggc gtgctgagcg      6840 atcggcaatg gcggatgcg gtgttgcttc cgcaccggcc gttcgcgacg aacaacctcc      6900
aacgaggtca gtaccggatg agccgcgacg acgcattggc aatgcggtac gtcgagcatt      6960
caccgcacgc gttgctcgga tctatcgtca tcgactgcga tcacgttgac gccgcgatgc      7020
gcgcattcga gcaaccatcc gaccatccgg cgccgaactg ggtcgcacaa tcgccgtccg      7080
gccgcgcaca catcggatgg tggctcggcc caaccacgt gtgccgcacc gacagcgccc      7140
gactgacgcc actgcgctac gcccaccgca tcgaaaccgg cctcaagatc agcgtcggcg      7200
gcgatttcgc gtatggcggg caactgacca aaaacccgat tcaccccgat gggagacga      7260 tctacggccc ggccaccccg tacacattgc ggcagctggc caccatccac acacccggc      7320 agatgccgcg tcggcccgat cgggccgtgg gcctgggccg caacgtcacc atgttcgacg      7380
ccacccggcg atgggcatac ccgcagtggt ggcaacaccg aaacggaacc ggccgcgact      7440
gggaccatct cgtcctgcag cactgccacg ccgtcaacac cgagttcacg acaccactgc      7500
cgttcaccga agtacgcgcc accgcgcaat ccatctccaa atggatctgg cgcaatttca      7560
ccgaagaaca gtaccgagcc cgacaagcgc atctcggtca aaaaggcggc aaggcaacga      7620
cactcgccaa acaagaagcc gtccgaaaca atgcaagaaa gtacgacgaa catacgatgc      7680
gagaggcgat tatctgatgg gcggagccaa aaatccggtg cgccgaaaga tgacggcagc      7740
agcagcagcc gaaaaattcg gtgcctccac tcgcacaatc caacgcttgt ttgctgagcc      7800
gcgtgacgat tacctcggcc gtgcgaaagc tcgccgtgac aaagctgtcg agctgcggaa      7860
gcaggggttg aagtaccggg aaatcgccga agcgatggaa ctctcgaccg ggatcgtcgg      7920
ccgattactg cacgacgccc gcaggcacg cgagatttca gcggaggatc tgtcggcgta      7980
accaagtcag cgggttgtcg ggttccggcc ggcgctcggc actcggaccg gccggcggat      8040
ggtgttctgc ctctggcgca gcgtcagcta ccgccgaagg cctgtcatcg accggcttcg      8100
actgaagtat gagcaacgtc acagcctgtg attggatgat ccgctcacgc tcgaccgcta      8160
cctgttcagc tgccgcccgc tgggcatgag caacggccaa ctctcgttca a             8211
```

<210> SEQ ID NO 93
<211> LENGTH: 8275
<212> TYPE: DNA
<213> ORGANISM: Artificial Sequence
<220> FEATURE:
<223> OTHER INFORMATION: Description of Artificial Sequence: Synthetic
      vector pTip-RT1 sequence

<400> SEQUENCE: 93

```
gttaacgacc gcgcgggtcc cggacgggga agagcgggga gctttgccag agagcgacga       60
cttccccttg cgttggtgat tgccggtcag ggcagccatc cgccatcgtc gcgtagggtg      120
```

```
tcacacccca ggaatcgcgt cactgaacac agcagccggt aggacgacca tgactgagtt    180
ggacaccatc gcaaatccgt ccgatcccgc ggtgcagcgg atcatcgatg tcaccaagcc    240
gtcacgatcc aacataaaga caacgttgat cgaggacgtc gagcccctca tgcacagcat    300
cgcggccggg gtggagttca tcgaggtcta cggcagcgac agcagtcctt ttccatctga    360
gttgctggat ctgtgcgggc ggcagaacat accggtccgc ctcatcgact cctcgatcgt    420
caaccagttg ttcaagggggg agcggaaggc caagacattc ggcatcgccc gcgtccctcg    480
cccggccagg ttcggcgata tcgcgagccg gcgtggggac gtcgtcgttc tcgacggggt    540
gaagatcgtc gggaacatcg gcgcgatagt acgcacgtcg ctcgcgctcg gagcgtcggg    600
gatcatcctg gtggacagtg acatcaccag catcgcggac cggcgtctcc aaagggccag    660
ccgaggttac gtcttctccc ttcccgtcgt tctctccggt cgcgaggagg ccatcgcctt    720
cattcgggac agcggtatgc agctgatgac gctcaaggcg gatggcgaca tttccgtgaa    780
ggaactcggg gacaatccgg atcggctggc cttgctgttc ggcagcgaaa agggtgggcc    840
ttccgacctg ttcgaggagg cgtcttccgc ctcggtttcc atccccatga tgagccagac    900
cgagtctctc aacgttttcg tttccctcgg aatcgcgctg cacgagagga tcgacaggaa    960
tctcgcggcc aaccgataag cgcctctgtt cctcggacgc tcggttcctc gacctcgatt   1020
cgtcagtgat gatcacctca cacggcagcg atcaccactg acatatcgag gtcaacggtc   1080
gtggtccggg cggcactcc tcgaaggcgc ggccgacgcc cttgaacgac tcgatgactc   1140
tagagtaacg ggctactccg tttaacggac cccgttctca cgctttaggc ttgaccccgg   1200
agcctgcatg gggcattccg ccgtgaaccc ggtggaatgc ccccggcacc cgggctttcc   1260
agcaaagatc acctggcgcc gatgagtaag gcgtacagaa ccactccaca ggaggaccgt   1320
cgagatgaaa tctaacaatg cgctcatcgt catcctcggc accgtcaccc tggatgctgt   1380
aggcataggc ttggttatgc cggtactgcc gggcctcttg cgggatatcg tccattccga   1440
cagcatcgcc agtcactatg gcgtgctgct agcgctatat gcgttgatgc aatttctatg   1500
cgcacccgtt ctcggagcac tgtccgaccg ctttggccgc cgcccagtcc tgctcgcttc   1560
gctacttgga gccactatcg actacgcgat catggcgacc acaccgtcc tgtggattct   1620
ctacgccgga cgcatcgtgg ccggcatcac cggcgccaca ggtgcggttg ctggcgccta   1680
tatcgccgac atcaccgatg gggaagatcg ggctcgccac ttcgggctca tgagcgcttg   1740
tttcggcgtg ggtatggtgg caggcccccgt ggccggggga ctgttgggcg ccatctcctt   1800
gcatgcacca ttccttgcgg cggcggtgct caacggcctc aacctactac tgggctgctt   1860
cctaatgcag gagtcgcata agggagagcg tcgtccgatg cccttgagag ccttcaaccc   1920
agtcagctcc ttccggtggg cgcggggcat gactatcgtc gccgcactta tgactgtctt   1980
ctttatcatg caactcgtag acaggtgcc ggcagcgctc tgggtcattt tcggcgagga   2040
ccgctttcgc tggagcgcga cgatgatcgg cctgtcgctt gcggtattcg gaatcttgca   2100
cgccctcgct caagccttcg tcactggtcc cgccaccaaa cgtttcggcg agaagcaggc   2160
cattatcgcc ggcatggcgg ccgacgcgct gggctacgtc ttgctggcgt tcgcgacgcg   2220
aggctggatg gccttccccca ttatgattct tctcgcttcc ggcggcatcg ggatgcccgc   2280
gttgcaggcc atgctgtcca ggcaggtaga tgacgaccat cagggacagc ttcaaggatc   2340
gctcgcggct cttaccagcc taacttcgat cattggaccg ctgatcgtca cggcgattta   2400
tgccgcctcg gcgagcacat ggaacggggtt ggcatggatt gtaggcgccg ccctatacct   2460
tgtctgcctc cccgcgttgc gtcgcggtgc atggagccgg gccacctcga cctgaatgga   2520
```

```
agccggcggc acctcgctaa cggattcacc actccaagaa ttggagccaa tcaattcttg   2580
cggagaactg tgaatgcgca accaacccct tggcagaaca tatccatcgc gtccgccatc   2640
tccagcagcc gcacgcggcg catctcgggc agcgttgggt cctggccacg ggtgcgcatg   2700
atcgtgctcc tgtcgttgag gactagaatt gatctcctcg accgccaatt gggcatctga   2760
gaatcatctg cgtttctcgc acgcaacgta cttgcaacgt tgcaactcct agtgttgtga   2820
atcacacccc accgggggt gggattgcag tcaccgattt ggtgggtgcg cccaggaaga   2880
tcacgtttac ataggagctt gcaatgagct actccgtggg acaggtggcc ggcttcgccg   2940
gagtgacggt gcgcacgctg caccactacg acgacatcgg cctgctcgta ccgagcgagc   3000
gcagccacgc gggccaccgg cgctacagcg acgccgacct cgaccggctg cagcagatcc   3060
tgttctaccg ggagctgggc ttcccgctcg acgaggtcgc cgccctgctc gacgacccgg   3120
ccgcggaccc cgcgcgcgcac ctgcgccgcc agcacgagct gctgtccgcc cggatcggga   3180
aactgcagaa gatggcggcg gccgtggagc aggcgatgga ggcacgcagc atgggaatca   3240
acctcacccc ggaggagaag ttcgaggtct tcggcgactt cgaccccgac cagtacgagg   3300
aggaggtccg ggaacgctgg gggaacaccg acgcctaccg ccagtccaag gagaagaccg   3360
cctcgtacac caaggaggac tggcagcgca tccaggacga ggccgacgag ctcacccggc   3420
gcttcgtcgc cctgatggac gcgggtgagc ccgccgactc cgagggggcg atggacgccg   3480
ccgaggacca ccggcagggc atcgcccgca accactacga ctgcgggtac gagatgcaca   3540
cctgcctggg cgagatgtac gtgtccgacg aacgtttcac gcgaaacatc gacgccgcca   3600
agccgggcct cgccgcctac atgcgcgacg cgatcctcgc caacgccgtc cggcacaccc   3660
cctgagcggt ggtcgtggcc cgggtctccc gcccggtctc accccacggc tcactcccgg   3720
gccacgacca ccgccgtccc gtacgcgcac acctcggtgc ccacgtccgc cgcctccgtc   3780
acgtcgaaac ggaagatccc cgggtaccga gctcgtcagg tggcactttt cggggaaatg   3840
tgcgcggaac ccctatttgt ttattttttct aaatacattc aaatatgtat ccgctcatga   3900
gacaataacc ctgataaatg cttcaataat attgaaaaag gaagagtatg agtattcaac   3960
atttccgtgt cgcccttatt cccttttttg cggcattttg ccttcctgtt tttgctcacc   4020
cagaaacgct ggtgaaagta aaagatgctg aagatcagtt gggtgcacga gtgggttaca   4080
tcgaactgga tctcaacagc ggtaagatcc ttgagagttt tcgccccgaa gaacgttttc   4140
caatgatgag cacttttaaa gttctgctat gtggcgcggt attatcccgt attgacgccg   4200
ggcaagagca actcggtcgc cgcatacact attctcagaa tgacttggtt gagtactcac   4260
cagtcacaga aaagcatctt acggatggca tgacagtaag agaattatgc agtgctgcca   4320
taaccatgag tgataacact gcggccaact tacttctgac aacgatcgga ggaccgaagg   4380
agctaaccgc ttttttgcac aacatggggg atcatgtaac tcgccttgat cgttgggaac   4440
cggagctgaa tgaagccata ccaaacgacg agcgtgacac cacgatgcct gtagcaatgg   4500
caacaacgtt gcgcaaacta ttaactggcg aactacttac tctagcttcc cggcaacaat   4560
taatagactg gatggaggcg gataaagttg caggaccact tctgcgctcg gcccttccgg   4620
ctggctggtt tattgctgat aaatctggag ccggtgagcg tgggtctcgc ggtatcattg   4680
cagcactggg gccagatggt aagccctccc gtatcgtagt tatctacacg acggggagtc   4740
aggcaactat ggatgaacga aatagacaga tcgctgagat aggtgcctca ctgattaagc   4800
attggtaact gtcagaccaa gtttactcat atatacttta gattgattta aaacttcatt   4860
```

```
tttaatttaa aaggatctag gtgaagatcc tttttgataa tctcatgacc aaaatccctt    4920
aacgtgagtt ttcgttccac tgagcgtcag accccgtaga aagatcaaa ggatcttctt     4980 gagatccttt ttttctgcgc gtaatctgct gcttgcaaac aaaaaaacca ccgctaccag    5040
cggtggtttg tttgccggat caagagctac caactctttt tccgaaggta actggcttca    5100
gcagagcgca gataccaaat actgttcttc tagtgtagcc gtagttaggc caccacttca    5160
agaactctgt agcaccgcct catacctcg ctctgctaat cctgttacca gtggctgctg     5220
ccagtggcga taagtcgtgt cttaccgggt tggactcaag acgatagtta ccggataagg    5280
cgcagcggtc gggctgaacg gggggttcgt gcacacagcc cagcttggag cgaacgacct    5340
acaccgaact gagataccta cagcgtgagc tatgagaaag cgccacgctt cccgaaggga    5400
gaaaggcgga caggtatccg gtaagcggca gggtcggaac aggagagcgc acgagggagc    5460
ttccaggggg aaacgcctgg tatctttata gtcctgtcgg gtttcgccac ctctgacttg    5520
agcgtcgatt tttgtgatgc tcgtcagggg gcggagcct atggaaaaac gccagcaacg      5580 cggcctttt acgttcctg gccttttgct ggccttttgc tcacatgttc tttcctgcgt      5640
tatcccctga ttctgtggat aaccgtatta ccgcctttga gtgagctgat accgctcgcc    5700
gcagccgaac gaccgagcgc agcgagtcag tgagcgagga agcggaagag cgcccaatac    5760
gcaaaccgcc tctccccgcg cgttggccga ttcattaatg cagctggcac gactagagtc    5820
ccgctgaggc ggcgtagcag gtcagccgcc ccagcggtgg tcaccaaccg ggtggaacg     5880 gcgccggtat cgggtgtgtc cgtggcgctc attccaacct ccgtgtgttt gtgcaggttt    5940
cgcgtgttgc agtccctcgc accggcaccc gcagcgaggg gctcacgggt gccggtgggt    6000
cgactagttc agtgatggtg atggtgatgc tcgagagatc taagcttgga tccgcggccg    6060
ctacgtagaa ttcccatatg gtgatggtga tggtggccca tggtatatct ccttcttaaa    6120
gttaaacaaa attatttcta gacgccgtcc acgctgcctc ctcacgtgac gtgaggtgca    6180
agcccggacg ttccgcgtgc cacgccgtga gccgccgcgt gccgtcggct ccctcagccc    6240
gggcggccgt gggagcccgc ctcgatatgt acaagcatgg ggactcgccg cggactagcg    6300
gcttcccgac acgccgtact gaccagcaga tcagcgataa acgctgtttc tgctggttaa    6360
gtggataaaa accaaataat cgatgaacct cgaagtggag tatccgagct gaactagctg    6420
gatttactcc gaaaatacga gcggcgacga agggtgttgg accaccctgc cgccgccttc    6480
gaggctccta cttgactagg accccgctcg ttatgaccag cgtaagtgct gaacaccttt    6540
ccggcaaaga ccggccccct gtcctcgtgt cgtccgataa gcgcggcatc cggcacgaac    6600
ttcgacccaa acttcaacaa atcaccacgt cagaaacttt taatgcgtgc ggccggccga    6660
tttccggcgt gaacggtgtg accatcgtca acggtcccaa aggttccgga tttggaggcc    6720
ttcgctcctg cggaaagggc tggatctgcc cctgctgtgc gggaaaagtc ggcgcacatc    6780
gagcagacga aatttctcaa gttgttgctc atcaactcgg gactggatct gttgcgatgg    6840
tgaccatgac catgcgccat accgctgggc agcgtttgca tgatttgtgg actggacttt    6900
cggcagcctg gaaagctgcg accaatggcc gccgatggcg taccgaacgt gaaatgtacg    6960
gctgcgacgg atacgtacga gctgttgaaa tcactcacgg aaaaaacggt tggcacgttc    7020
acgtccacgc tctactcatg ttcagcgtg acgtgagtga aacatcctc gaatccttct      7080 cggatgcgat gttcgatcgg tggacctcca aactcgtgtc tctgggattt gctgcgccac    7140
tacgtaattc aggtggactc gacgtaagaa agattggtgg agaagctgac caagttctcg    7200
ctgcatacct gacgaaaatt gcatccgggg tcggcatgga agtcggcagt ggcgacggaa    7260
```

```
aaagtggtcg gcacggcaac cgtgcacctt gggaaatcgc cgttgatgca gtcggaggag   7320
atccacaagc gttggaactc tggcgcgagt ttgagttcgg ttcgatggga cgccgagcaa   7380
tcgcatggtc tcgtggactg cgcgcccgag ctggtcttgg cgtagaactc acggatgctc   7440
agattgtcga acaggaagaa tctgccccgg tcatggttgc gatcattccg gctcggtcct   7500
ggatgatgat tcggaactgt gcgccttacg ttttcggaga gatccttgga ctcgtggaag   7560
cgggcgcgac ctgggaaaac cttcgtgacc acttgcatta tcgattgcct gcagcggatg   7620
tgcggcctcc gataatatcg attcgtaagt gaaatgtctt ggtgtgcaac aactttcact   7680
cgtatgaacc acacttgagg gcatcccccc gatacttgcc gctttgaagc tgggtgtctc   7740
tctgtcaggg ctgcgatagc accgcgtagc ggcttggcct tgacagagag acggcctgtt   7800
tcatggttgg tctcggggggg ctgaccgggc agatagaaaa aggccggccg atttggctgc   7860
cgactatttt tgcaggtaaa cccatctcat gagcatcaat gaacgtcccg ttggtatcgc   7920
agcgaatgca gcttcggtag acgtcgatgg cgttgtgatg ggtgtgtatc tctcgcttta   7980
tgggcaagaa atcacgctag atcgagatga tgcgttccta ctcctcgatc gacttcagga   8040
cgcgttgcga cctcaagcca actaagaacc ctccagatgg tctaaacgag gcgcaaactc   8100
gctcctgggc ctgcgggcgg agcaccgaag cgcgagcgaa gcggagcgcg taggtggggg   8160
agcctgcggg cagcggcggc ggagccgccg ccttggtaat aggtgatcat cggggccata   8220
gcaggtcaga ggatgttttt acgatgactc atgctcacca cgccaagtac tgatg         8275
```

<210> SEQ ID NO 94
<211> LENGTH: 8279
<212> TYPE: DNA
<213> ORGANISM: Artificial Sequence
<220> FEATURE:
<223> OTHER INFORMATION: Description of Artificial Sequence: Synthetic vector pTip-RT2 sequence

<400> SEQUENCE: 94

```
gttaacgacc gcgcgggtcc cggacgggga agagcgggga gctttgccag agagcgacga    60 cttcccccttg cgttggtgat tgccggtcag ggcagccatc cgccatcgtc gcgtagggtg   120
tcacacccca ggaatcgcgt cactgaacac agcagccggt aggacgacca tgactgagtt   180
ggacaccatc gcaaatccgt ccgatcccgc ggtgcagcgg atcatcgatg tcaccaagcc   240
gtcacgatcc aacataaaga caacgttgat cgaggacgtc gagcccctca tgcacagcat   300
cgcggccggg gtggagttca tcgaggtcta cggcagcgac agcagtcctt ttccatctga   360
gttgctggat ctgtgcgggc ggcagaacat accggtccgc ctcatcgact cctcgatcgt   420
caaccagttg ttcaagggggg agcggaaggc caagacattc ggcatcgccc gcgtccctcg   480
cccggccagg ttcggcgata tcgcgagccg gcgtggggac gtcgtcgttc tcgacggggt   540
gaagatcgtc gggaacatcg gcgcgatagt acgcacgtcg ctcgcgctcg gagcgtcggg   600
gatcatcctg gtggacagtg acatcaccag catcgcggac cggcgtctcc aaagggccag   660
ccgaggttac gtcttctccc ttcccgtcgt tctctccggt cgcgaggagg ccatcgcctt   720
cattcgggac agcggtatgc agctgatgac gctcaaggcg gatggcgaca tttccgtgaa   780
ggaactcggg gacaatccgg atcggctggc cttgctgttc ggcagcgaaa agggtgggcc   840
ttccgacctg ttcgaggagg cgtcttccgc ctcggtttcc atccccatga tgagccagac   900
cgagtctctc aacgtttccg tttccctcgg aatcgcgctg cacagagagga tcgacaggaa   960 tctcgcggcc aaccgataag cgcctctgtt cctcggacgc tcggttcctc gacctcgatt  1020
```

```
cgtcagtgat gatcacctca cacggcagcg atcaccactg acatatcgag gtcaacggtc   1080
gtggtccggg cgggcactcc tcgaaggcgc ggccgacgcc cttgaacgac tcgatgactc   1140
tagagtaacg ggctactccg tttaacggac cccgttctca cgctttaggc ttgaccccgg   1200
agcctgcatg gggcattccg ccgtgaaccc ggtggaatgc ccccggcacc cgggctttcc   1260
agcaaagatc acctggcgcc gatgagtaag gcgtacagaa ccactccaca ggaggaccgt   1320
cgagatgaaa tctaacaatg cgctcatcgt catcctcggc accgtcaccc tggatgctgt   1380
aggcataggc ttggttatgc cggtactgcc gggcctcttg cgggatatcg tccattccga   1440
cagcatcgcc agtcactatg gcgtgctgct agcgctatat gcgttgatgc aatttctatg   1500
cgcacccgtt ctcggagcac tgtccgaccg ctttggccgc cgcccagtcc tgctcgcttc   1560
gctacttgga gccactatcg actacgcgat catggcgacc acaccgtcc tgtggattct    1620 ctacgccgga cgcatcgtgg ccggcatcac cggcgccaca ggtgcggttg ctggcgccta   1680
tatcgccgac atcaccgatg gggaagatcg ggctcgccac ttcgggctca tgagcgcttg   1740
tttcggcgtg gtatggtgg caggcccgt ggccggggga ctgttgggcg ccatctcctt    1800
gcatgcacca ttccttgcgg cggcggtgct caacggcctc aacctactac tgggctgctt   1860
cctaatgcag gagtcgcata agggagagcg tcgtccgatg cccttgagag ccttcaaccc   1920
agtcagctcc ttccggtggg cgcggggcat gactatcgtc gccgcactta tgactgtctt   1980
ctttatcatg caactcgtag gacaggtgcc ggcagcgctc tgggtcattt tcggcgagga   2040
ccgctttcgc tggagcgcga cgatgatcgg cctgtcgctt gcggtattcg gaatcttgca   2100
cgccctcgct caagccttcg tcactggtcc cgccaccaaa cgtttcggcg agaagcaggc   2160
cattatcgcc ggcatggcgg ccgacgcgct gggctacgtc ttgctggcgt tcgcgacgcg   2220
aggctggatg gccttcccca ttatgattct tctcgcttcc ggcggcatcg ggatgcccgc   2280
gttgcaggcc atgctgtcca ggcaggtaga tgacgaccat cagggacagc ttcaaggatc   2340
gctcgcggct cttaccagcc taacttcgat cattggaccg ctgatcgtca cggcgattta   2400
tgccgcctcg gcgagcacat ggaacgggtt ggcatggatt gtaggcgccg ccctatacct   2460
tgtctgcctc cccgcgttgc gtcgcggtgc atggagccgg gccacctcga cctgaatgga   2520
agccggcggc acctcgctaa cggattcacc actccaagaa ttggagccaa tcaattcttg   2580
cggagaactg tgaatgcgca aaccaaccct tggcagaaca tatccatcgc gtccgccatc   2640
tccagcagcc gcacgcggcg catctcgggc agcgttgggt cctggccacg ggtgcgcatg   2700
atcgtgctcc tgtcgttgag gactagaatt gatctcctcg accgccaatt gggcatctga   2760
gaatcatctg cgtttctcgc acgcaacgta cttgcaacgt tgcaactcct agtgttgtga   2820
atcacacccc accgggggt gggattgcag tcaccgattt ggtgggtgcg cccaggaaga   2880
tcacgtttac ataggagctt gcaatgagct actccgtggg acaggtggcc ggcttcgccg   2940
gagtgacggt gcgcacgctg caccactacg acgacatcgg cctgctcgta ccgagcgagc   3000
gcagccacgc gggccaccgg cgctacagcg acgccgacct cgaccggctg cagcagatcc   3060
tgttctaccg ggagctgggc ttcccgctcg acgaggtcgc cgccctgctc gacgacccgg   3120
ccgcggaccc gcgcgcgcac ctgcgccgcc agcacgagct gctgtccgcc cggatcggga   3180
aactgcagaa gatggcggcg gccgtggagc aggcgatgga ggcacgcagc atgggaatca   3240
acctcacccc ggaggagaag ttcgaggtct tcggcgactt cgaccccgac cagtacgagg   3300
aggaggtccg ggaacgctgg gggaacaccg acgcctaccc ccagtccaag gagaagaccg   3360
```

```
cctcgtacac caaggaggac tggcagcgca tccaggacga ggccgacgag ctcacccggc   3420
gcttcgtcgc cctgatggac gcgggtgagc ccgccgactc cgaggggggcg atggacgccg   3480 ccgaggacca ccggcagggc atcgcccgca accactacga ctgcgggtac gagatgcaca   3540
cctgcctggg cgagatgtac gtgtccgacg aacgtttcac gcgaaacatc gacgccgcca   3600
agccgggcct cgccgcctac atgcgcgacg cgatcctcgc caacgccgtc cggcacaccc   3660
cctgagcggt ggtcgtggcc cgggtctccc gcccggtctc accccacggc tcactcccgg   3720
gccacgacca ccgccgtccc gtacgcgcac acctcggtgc ccacgtccgc cgcctccgtc   3780
acgtcgaaac ggaagatccc cgggtaccga gctcgtcagg tggcactttt cggggaaatg   3840
tgcgcggaac ccctatttgt ttatttttct aaatacattc aaatatgtat ccgctcatga   3900
gacaataacc ctgataaatg cttcaataat attgaaaaag gaagagtatg agtattcaac   3960
atttccgtgt cgcccttatt cccttttttg cggcattttg ccttcctgtt tttgctcacc   4020
cagaaacgct ggtgaaagta aaagatgctg aagatcagtt gggtgcacga gtgggttaca   4080
tcgaactgga tctcaacagc ggtaagatcc ttgagagttt cgccccgaa gaacgttttc   4140 caatgatgag cacttttaaa gttctgctat gtggcgcggt attatcccgt attgacgccg   4200
ggcaagagca actcggtcgc cgcatacact attctcagaa tgacttggtt gagtactcac   4260
cagtcacaga aaagcatctt acggatggca tgacagtaag agaattatgc agtgctgcca   4320
taaccatgag tgataacact gcggccaact tacttctgac aacgatcgga ggaccgaagg   4380
agctaaccgc ttttttgcac aacatggggg atcatgtaac tcgccttgat cgttgggaac   4440
cggagctgaa tgaagccata ccaaacgacg agcgtgacac cacgatgcct gtagcaatgg   4500
caacaacgtt gcgcaaacta ttaactggcg aactacttac tctagcttcc cggcaacaat   4560
taatagactg gatggaggcg gataaagttg caggaccact tctgcgctcg gcccttccgg   4620
ctggctggtt tattgctgat aaatctggag ccggtgagcg tgggtctcgc ggtatcattg   4680
cagcactggg gccagatggt aagccctccc gtatcgtagt tatctacacg acggggagtc   4740
aggcaactat ggatgaacga atagacaga tcgctgagat aggtgcctca ctgattaagc   4800
attggtaact gtcagaccaa gtttactcat atatacttta gattgattta aaacttcatt   4860
tttaatttaa aaggatctag gtgaagatcc ttttttgataa tctcatgacc aaaatccctt   4920
aacgtgagtt ttcgttccac tgagcgtcag accccgtaga aagatcaaa ggatcttctt   4980 gagatccttt ttttctgcgc gtaatctgct gcttgcaaac aaaaaaacca ccgctaccag   5040
cggtggtttg tttgccggat caagagctac caactctttt tccgaaggta actggcttca   5100
gcagagcgca gataccaaat actgttcttc tagtgtagcc gtagttaggc caccacttca   5160
agaactctgt agcaccgcct acatacctcg ctctgctaat cctgttacca gtggctgctg   5220
ccagtggcga taagtcgtgt cttaccgggt tggactcaag acgatagtta ccggataagg   5280
cgcagcggtc gggctgaacg gggggttcgt gcacacagcc cagcttggag cgaacgacct   5340
acaccgaact gagataccta cagcgtgagc tatgagaaag cgccacgctt cccgaaggga   5400
gaaaggcgga caggtatccg gtaagcgcca gggtcggaac aggagagcgc acgagggagc   5460 ttccagggg aaacgcctgg tatctttata gtcctgtcgg gtttcgccac ctctgacttg   5520
agcgtcgatt tttgtgatgc tcgtcagggg gcggagcct atggaaaaac gccagcaacg   5580
cggccttttt acggttcctg gccttttgct ggccttttgc tcacatgttc tttcctgcgt   5640 tatccccctga ttctgtggat aaccgtatta ccgcctttga gtgagctgat accgctcgcc   5700
gcagccgaac gaccgagcgc agcgagtcag tgagcgagga agcggaagag cgcccaatac   5760
```

```
gcaaaccgcc tctccccgcg cgttggccga ttcattaatg cagctggcac gactagagtc   5820
ccgctgaggc ggcgtagcag gtcagccgcc ccagcggtgg tcaccaaccg gggtggaacg   5880
gcgccggtat cgggtgtgtc cgtggcgctc attccaacct ccgtgtgttt gtgcaggttt   5940
cgcgtgttgc agtccctcgc accggcaccc gcagcgaggg gctcacgggt gccggtgggt   6000
cgactagttc agtgatggtg atggtgatgc tcgagagatc taagcttgga tccgcggccg   6060
ctacgtagaa ttcccatggc gtgatggtga tggtgatggc ccatatgtat atctccttct   6120
taaagttaaa caaaattatt tctagacgcc gtccacgctg cctcctcacg tgacgtgagg   6180
tgcaagcccg gacgttccgc gtgccacgcc gtgagccgcc gcgtgccgtc ggctccctca   6240
gcccgggcgg ccgtgggagc ccgcctcgat atgtacaagc atggggactc gccgcggact   6300
agcggcttcc cgacacgccg tactgaccag cagatcagcg ataaacgctg tttctgctgg   6360
ttaagtggat aaaaaccaaa taatcgatga acctcgaagt ggagtatccg agctgaacta   6420
gctggattta ctccgaaaat acgagcggcg acgaagggtg ttggaccacc ctgccgccgc   6480
cttcgaggct cctacttgac taggaccccg ctcgttatga ccagcgtaag tgctgaacac   6540 cttttccggca aagaccggcc ccctgtcctc gtgtcgtccg ataagcgcgg catccggcac   6600
gaacttcgac ccaaacttca acaaatcacc acgtcagaaa cttttaatgc gtgcggccgg   6660
ccgatttccg gcgtgaacgg tgtgaccatc gtcaacggtc ccaaaggttc cggatttgga   6720
ggccttcgct cctgcggaaa gggctggatc tgcccctgct gtgcgggaaa agtcggcgca   6780
catcgagcag acgaaatttc tcaagttgtt gctcatcaac tcgggactgg atctgttgcg   6840
atggtgacca tgaccatgcg ccataccgct gggcagcgtt tgcatgattt gtggactgga   6900
ctttcggcag cctggaaagc tgcgaccaat ggccgccgat ggcgtaccga acgtgaaatg   6960
tacggctgcg acggatacgt acgagctgtt gaaatcactc acggaaaaaa cggttggcac   7020
gttcacgtcc acgctctact catgttcagc ggtgacgtga gtgagaacat cctcgaatcc   7080
ttctcggatg cgatgttcga tcggtggacc tccaaactcg tgtctctggg atttgctgcg   7140
ccactacgta attcaggtgg actcgacgta agaaagattg gtggagaagc tgaccaagtt   7200
ctcgctgcat acctgacgaa aattgcatcc ggggtcggca tggaagtcgg cagtggcgac   7260
ggaaaaagtg gtcggcacgg caaccgtgca ccttgggaaa tcgccgttga tgcagtcgga   7320
ggagatccac aagcgttgga actctggcgc gagtttgagt tcggttcgat gggacgccga   7380
gcaatcgcat ggtctcgtgg actgcgcgcc cgagctggtc ttggcgtaga actcacggat   7440
gctcagattg tcgaacagga agaatctgcc ccggtcatgg ttgcgatcat tccggctcgg   7500
tcctggatga tgattcggaa ctgtgcgcct tacgttttcg gagagatcct tggactcgtg   7560
gaagcgggcg cgacctggga aaaccttcgt gaccacttgc attatcgatt gcctgcagcg   7620
gatgtgcggc ctccgataat atcgattcgt aagtgaaatg tcttggtgtg caacaacttt   7680
cactcgtatg aaccacactt gagggcatcc ccccgatact tgccgctttg aagctgggtg   7740
tctctctgtc agggctgcga tagcaccgcg tagcggcttg gccttgacag agagacggcc   7800
tgtttcatgg ttggtctcgg ggggctgacc gggcagatag aaaaaggccg gccgatttgg   7860
ctgccgacta ttttttgcagg taaacccatc tcatgagcat caatgaacgt cccgttggta   7920
tcgcagcgaa tgcagcttcg gtagacgtcg atggcgttgt gatgggtgtg tatctctcgc   7980
tttatgggca agaaatcacg ctagatcgag atgatgcgtt cctactcctc gatcgacttc   8040
aggacgcgtt gcgacctcaa gccaactaag aaccctccag atggtctaaa cgaggcgcaa   8100
```

-continued

```
actcgctcct gggcctgcgg gcggagcacc gaagcgcgag cgaagcgcag cgcgtaggtg      8160
ggggagcctg cgggcagcgg cggcggagcc gccgccttgg taataggtga tcatcggggc      8220
catagcaggt cagaggatgt ttttacgatg actcatgctc accacgccaa gtactgatg       8279
```

<210> SEQ ID NO 95
<211> LENGTH: 8384
<212> TYPE: DNA
<213> ORGANISM: Artificial Sequence
<220> FEATURE:
<223> OTHER INFORMATION: Description of Artificial Sequence: Synthetic vector pTip-QC1 sequence

<400> SEQUENCE: 95

```
gagctcgacc gcgcgggtcc cggacgggga agagcgggga gctttgccag agagcgacga        60 cttcccctg cgttggtgat tgccggtcag ggcagccatc cgccatcgtc gcgtagggtg       120
tcacacccca ggaatcgcgt cactgaacac agcagccggt aggacgacca tgactgagtt       180
ggacaccatc gcaaatccgt ccgatcccgc ggtgcagcgg atcatcgatg tcaccaagcc       240
gtcacgatcc aacataaaga caacgttgat cgaggacgtc gagcccctca tgcacagcat       300
cgcggccggg gtggagttca tcgaggtcta cggcagcgac agcagtcctt ttccatctga       360
gttgctggat ctgtgcgggc ggcagaacat accggtccgc ctcatcgact cctcgatcgt       420
caaccagttg ttcaaggggg agcggaaggc caagacattc ggcatcgccc gcgtccctcg       480
cccggccagg ttcggcgata tcgcgagccg gcgtggggac gtcgtcgttc tcgacggggt       540
gaagatcgtc gggaacatcg gcgcgatagt acgcacgtcg ctcgcgctcg gagcgtcggg       600
gatcatcctg gtggacagtg acatcaccag catcgcggac cggcgtctcc aaagggccag       660
ccgaggttac gtcttctccc ttcccgtcgt tctctccggt cgcgaggagg ccatcgcctt       720
cattcgggac agcggtatgc agctgatgac gctcaaggcg gatggcgaca tttccgtgaa       780
ggaactcggg gacaatccgg atcggctggc cttgctgttc ggcagcgaaa agggtggggcc      840 ttccgacctg ttcgaggagg cgtcttccgc ctcggtttcc atccccatga tgagccagac       900
cgagtctctc aacgtttccg tttccctcgg aatcgcgctg cacgagagga tcgacaggaa       960
tctcgcggcc aaccgataag cgcctctgtt cctcggacgc tcggttcctc gacctcgatt      1020
cgtcagtgat gatcacctca cacggcagcg atcaccactg acatatcgag gtcaacggtc      1080
gtggtccggg cgggcactcc tcgaaggcgc ggccgacgcc cttgaacgac tcgatgactc      1140
tagacgcatc cgaaacctcc accccactca cctagtccga catccgtacc ttggaaaccg      1200
acctgtattg gcatttcagt tggacatcga ccagtggcgt tgctaggttc aagaccatgt      1260
ccagcccgaa ggcgtccaga ctctagccac cggaggtagt ccggtggcca catcccgtcg      1320
cgcccgaacg tcacgctctt gtgtggcctt cccttgttgt ttgcgatcag tggcacacct      1380
ctaccgtctg aatttcgagt ctggcctcgg ctgcgcacat ctcgcactgt gacgctgtca      1440
ggtcacccgc ttcgcggcta ccagttcctt tcatcgaatc gagcttccgg tgccgccgcg      1500
cagcctccct gaccatcctc agattttatg gagtctcgca gtgcctttcg ctatctacgt      1560
cctcgggctt gctgtcttcg cccagggcac atccgagttc atgttgtccg gactcatacc      1620
ggacatggcc cgtgacctcg ggtttcggt ccccgccgcc ggactcctca cctccgcctt       1680
cgcggtcggg atgatcatcg gcgctccgtt gatggctatc gccagcatgc ggtggccccg      1740
gcgacgcgcc cttctgacat tcctcatcac gttcatgctg gtccacgtca tcggcgcgct      1800
caccagcagc ttcgaggtct tgctggtcac acgcatcgtg ggagccctcg ccaatgccgg      1860
```

```
attcttggca gtggccctgg gggcggcgat ggcgatggtg cccgccgaca tgaaagggcg    1920
cgccacgtcc gtcctcctcg gcggtgtcac gatcgcatgt gtagccggtg ttcccggggg    1980
cgccttcctg ggtgaaatgt ggggctggcg tgcagcgttc tgggctgtcg tcgtcatctc    2040
cgcccctgca gtggtggcga ttatgttcgc caccccggcc gagccgcttg cagagtccac    2100
accgaatgcc aagcgtgaac tgtcctcact gcgctcacgc aagctccagc tcatgcttgt    2160
cctcggggcg ctgatcaacg gcgcaacgtt ctgttcgttc acgtacatgg cgcccacgct    2220
caccgacatc tccggtttcg actcccgttg gattccgttg ctgctggggc tgttcgggct    2280
cggatcgttc atcggtgtca gcgtcggagg caggctcgcc gacacccggc cgttccaact    2340
gctcgctgtc gggtccgcag cactgttgac gggatggatc gtcttcgctc tcacggcatc    2400
ccaccccgcg gtgacattgg tgatgctgtt cgtgcagggc gctttgtcct cgcggtcgg    2460
ctcgactttg atctcccagg tgctctacgc cgccgacgcg caccgacct tgggtggatc    2520
gttcgcgacg gccgcgttca acgtcggtgc tgcactggga ccggcgctcg gcgggttggc    2580
gatcggcatg ggtctgagct accgcgcccc gctctggacg agcgccgcgc tggtgacact    2640
cgcgatcgtc atcggcgcag ccaccttgtc tctgtggcgg cgaccagcgt ctgtccacga    2700
atctgtcccc gcctgaccag aaaccaggat ctgtgagtgt ggtgactgat ctgtgcacgc    2760
tcagcagtca ccgcgcgctc gcgtcgtacc gagggccagc gccaacaggt gtgtggagct    2820
ctgcccctgc ctcttcacg cgaactcact gttcagtgcg gcgatacgtg ctcggtgagt    2880
tccactacag cgaccatgac tagaattgat ctcctcgacc gccaattggg catctgagaa    2940
tcatctgcgt ttctcgcacg caacgtactt gcaacgttgc aactcctagt gttgtgaatc    3000
acccccacc gggggtggg attgcagtca ccgatttggt gggtgcgccc aggaagatca    3060
cgtttacata ggagcttgca atgagctact ccgtgggaca ggtggccggc ttcgccggag    3120
tgacggtgcg cacgctgcac cactacgacg acatcggcct gctcgtaccg agcgagcgca    3180
gccacgcggg ccaccggcgc tacagcgacg ccgacctcga ccggctgcag cagatcctgt    3240
tctaccggga gctgggcttc ccgctcgacg aggtcgccgc cctgctcgac gacccggccg    3300
cggacccgcg cgcgcacctg cgccgccagc acgagctgct gtccgcccgg atcgggaaac    3360
tgcagaagat ggcggcggcc gtggagcagg cgatggaggc acgcagcatg gaatcaacc    3420
tcaccccgga ggagaagttc gaggtcttcg gcgacttcga ccccgaccag tacgaggagg    3480
aggtccggga acgctggggg aacaccgacg cctaccgcca gtccaaggag aagaccgcct    3540
cgtacaccaa ggaggactgg cagcgcatcc aggacgagc cgacgagctc acccggcgct    3600
tcgtcgccct gatggacgcg ggtgagcccc ccgactccga gggggcgatg gacgccgccg    3660
aggaccaccg gcagggcatc gcccgcaacc actacgactg cgggtacgag atgcacacct    3720
gcctgggcga gatgtacgtg tccgacgaac gtttcacgcg aaacatcgac gccgccaagc    3780
cgggcctcgc cgcctacatg cgcgacgcga tcctcgccaa cgccgtccgg cacacccct    3840
gagcggtggt cgtggcccgg gtctcccgcc cggtctcacc ccacggctca ctcccgggcc    3900
acgaccaccg ccgtcccgta cgcgcacacc tcggtgccca cgtccgccgc ctccgtcacg    3960
tcgaaacgga agatccccgg gtaccgagct cgtcaggtgg cacttttcgg ggaaatgtgc    4020
gcggaacccc tatttgttta ttttttctaaa tacattcaaa tatgtatccg ctcatgagac    4080
aataaccctg ataaatgctt caataatatt gaaaaaggaa gagtatgagt attcaacatt    4140
tccgtgtcgc ccttattccc ttttttgcgg cattttgcct tcctgttttt gctcacccag    4200
aaacgctggt gaaagtaaaa gatgctgaag atcagttggg tgcacgagtg ggttacatcg    4260
```

```
aactggatct caacagcggt aagatccttg agagttttcg ccccgaagaa cgttttccaa    4320
tgatgagcac ttttaaagtt ctgctatgtg gcgcggtatt atcccgtatt gacgccgggc    4380
aagagcaact cggtcgccgc atacactatt ctcagaatga cttggttgag tactcaccag    4440
tcacagaaaa gcatcttacg gatggcatga cagtaagaga attatgcagt gctgccataa    4500
ccatgagtga taacactgcg gccaacttac ttctgacaac gatcggagga ccgaaggagc    4560
taaccgcttt tttgcacaac atggggatc atgtaactcg ccttgatcgt tgggaaccgg    4620
agctgaatga agccatacca aacgacgagc gtgacaccac gatgcctgta gcaatggcaa    4680
caacgttgcg caaactatta actggcgaac tacttactct agcttcccgg caacaattaa    4740
tagactggat ggaggcggat aaagttgcag gaccacttct gcgctcggcc cttccggctg    4800
gctggtttat tgctgataaa tctggagccg gtgagcgtgg gtctcgcggt atcattgcag    4860
cactggggcc agatggtaag ccctcccgta tcgtagttat ctacacgacg gggagtcagg    4920
caactatgga tgaacgaaat agacagatcg ctgagatagg tgcctcactg attaagcatt    4980
ggtaactgtc agaccaagtt tactcatata ctttagat tgatttaaaa cttcattttt    5040
aatttaaaag gatctaggtg aagatccttt ttgataatct catgaccaaa atcccttaac    5100
gtgagttttc gttccactga gcgtcagacc ccgtagaaaa gatcaaagga tcttcttgag    5160
atcctttttt tctgcgcgta atctgctgct tgcaaacaaa aaaaccaccg ctaccagcgg    5220
tggtttgttt gccggatcaa gagctaccaa ctcttttttcc gaaggtaact ggcttcagca    5280
gagcgcagat accaaatact gttcttctag tgtagccgta gttaggccac cacttcaaga    5340
actctgtagc accgcctaca tacctcgctc tgctaatcct gttaccagtg gctgctgcca    5400
gtggcgataa gtcgtgtctt accgggttgg actcaagacg atagttaccg gataaggcgc    5460
agcggtcggg ctgaacgggg ggttcgtgca cacagcccag cttggagcga acgacctaca    5520
ccgaactgag atacctacag cgtgagctat gagaaagcgc cacgcttccc gaagggagaa    5580
aggcggacag gtatccggta agcggcaggg tcggaacagg agagcgcacg agggagcttc    5640 caggggggaaa cgcctggtat ctttatagtc ctgtcgggtt tcgccacctc tgacttgagc    5700
gtcgattttt gtgatgctcg tcagggggc ggagcctatg gaaaaacgcc agcaacgcgg    5760
cctttttacg gttcctggcc ttttgctggc cttttgctca catgttcttt cctgcgttat    5820
cccctgattc tgtggataac cgtattaccg cctttgagtg agctgatacc gctcgccgca    5880
gccgaacgac cgagcgcagc gagtcagtga gcgaggaagc ggaagagcgc ccaatacgca    5940
aaccgcctct ccccgcgcgt tggccgattc attaatgcag ctggcacgac tagtcccg    6000 ctgaggcggc gtagcaggtc agccgcccca gcggtggtca ccaaccgggg tggaacggcg    6060
ccggtatcgg gtgtgtccgt ggcgctcatt ccaacctccg tgtgtttgtg caggtttcgc    6120
gtgttgcagt ccctcgcacc ggcacccgca gcgaggggct cacgggtgcc ggtgggtcga    6180
ctagttcagt gatggtgatg gtgatgctcg agagatctaa gcttggatcc gcggccgcta    6240
cgtagaattc ccatatggtg atggtgatgg tggcccatgg tatatctcct tcttaaagtt    6300
aaacaaaatt atttctagac gccgtccacg ctgcctcctc acgtgacgtg aggtgcaagc    6360
ccggacgttc cgcgtgccac gccgtgagcc gccgcgtgcc gtcggctccc tcagcccggg    6420
cggccgtggg agcccgcctc gatatgtaca cccgagaagc tcccagcgtc ctcctgggcc    6480
gcgatactcg accaccacgc acgcacaccg cactaacgat tcggccgcg ctcgattcgg    6540 ccggcgctcg attcggccgg cgctcgattc ggccggcgct cgattcggcc ggcgctcgat    6600
```

-continued

```
tcggccgagc agaagagtga acaaccaccg accacgcttc cgctctgcgc gccgtacccg      6660
acctacctcc cgcagctcga agcagctccc gggagtaccg ccgtactcac ccgcctgtgc      6720
tcaccatcca ccgacgcaaa gcccaacccg agcacacctc ttgcaccaag gtgccgaccg      6780
tggctttccg ctcgcagggt tccagaagaa atcgaacgat ccagcgcggc aaggttcaaa      6840
aagcaggggt tggtggggag gaggttttgg ggggtgtcgc cgggatacct gatatggctt      6900
tgttttgcgt agtcgaataa ttttccatat agcctcggcg cgtcggactc gaatagttga      6960
tgtgggcggg cacagttgcc ccatgaaatc cgcaacgggg ggcgtgctga gcgatcggca      7020
atgggcggat gcgtgttgc ttccgcaccg gccgttcgcg acgaacaacc tccaacgagg       7080
tcagtaccgg atgagccgcg acgacgcatt ggcaatgcgg tacgtcgagc attcaccgca      7140
cgcgttgctc ggatctatcg tcatcgactg cgatcacgtt gacgccgcga tgcgcgcatt      7200
cgagcaacca tccgaccatc cggcgccgaa ctgggtcgca caatcgccgt ccggccgcgc      7260
acacatcgga tggtggctcg gccccaacca cgtgtgccgc accgacagcg cccgactgac      7320
gccactgcgc tacgcccacc gcatcgaaac cggcctcaag atcagcgtcg cggcgatttt     7380
cgcgtatggc gggcaactga ccaaaaaccc gattcacccc gattgggaga cgatctacgg      7440
cccggccacc ccgtacacat gcggcagct ggccaccatc cacacacccc ggcagatgcc       7500
gcgtcggccc gatcgggccg tgggcctggg ccgcaacgtc accatgttcg acgccacccg      7560
gcgatgggca tacccgcagt ggtggcaaca ccgaaacgga accggccgcg actgggacca      7620
tctcgtcctg cagcactgcc acgccgtcaa caccgagttc acgacaccac tgccgttcac      7680
cgaagtacgc gccaccgcgc aatccatctc caaatggatc tggcgcaatt tcaccgaaga      7740
acagtaccga gcccgacaag cgcatctcgg tcaaaaaggc ggcaaggcaa cgacactcgc      7800
caaacaagaa gccgtccgaa acaatgcaag aaagtacgac gaacatacga tgcgagaggc      7860
gattatctga tgggcggagc caaaaatccg gtgcgccgaa agatgacggc agcagcagca      7920
gccgaaaaat tcggtgcctc cactcgcaca atccaacgct tgtttgctga gccgcgtgac      7980
gattacctcg gccgtgcgaa agctcgccgt gacaaagctg tcgagctgcg gaagcagggg      8040
ttgaagtacc gggaaatcgc cgaagcgatg gaactctcga ccgggatcgt cggccgatta      8100
ctgcacgacg cccgcaggca cggcgagatt tcagcggagg atctgtcggc gtaaccaagt      8160 cagcggggttg tcgggttccg gccggcgctc ggcactcgga ccggccggcg gatggtgttc      8220
tgcctctggc gcagcgtcag ctaccgccga aggcctgtca tcgaccggct tcgactgaag      8280
tatgagcaac gtcacagcct gtgattggat gatccgctca cgctcgaccg ctacctgttc      8340
agctgccgcc cgctgggcat gagcaacggc caactctcgt tcaa                      8384
```

<210> SEQ ID NO 96
<211> LENGTH: 8388
<212> TYPE: DNA
<213> ORGANISM: Artificial Sequence
<220> FEATURE:
<223> OTHER INFORMATION: Description of Artificial Sequence: Synthetic
      vector pTip-QC2 sequence

<400> SEQUENCE: 96

```
gagctcgacc gcgcgggtcc cggacgggga agagcgggga gctttgccag agagcgacga        60
cttccccttg cgttggtgat tgccggtcag ggcagccatc cgccatcgtc gcgtagggtg       120
tcacacccca ggaatcgcgt cactgaacac agcagccgt aggacgacca tgactgagtt        180
ggacaccatc gcaaatccgt ccgatcccgc ggtgcagcgg atcatcgatg tcaccaagcc       240
```

-continued

```
gtcacgatcc aacataaaga caacgttgat cgaggacgtc gagccctca tgcacagcat    300
cgcggccggg gtggagttca tcgaggtcta cggcagcgac agcagtcctt ttccatctga    360
gttgctggat ctgtgcgggc ggcagaacat accggtccgc ctcatcgact cctcgatcgt    420
caaccagttg ttcaaggggg agcggaaggc caagacattc ggcatcgccc gcgtccctcg    480
cccggccagg ttcggcgata tcgcgagccg cgtggggac gtcgtcgttc tcgacggggt    540
gaagatcgtc gggaacatcg gcgcgatagt acgcacgtcg ctcgcgctcg gagcgtcggg    600
gatcatcctg gtggacagtg acatcaccag catcgcggac cggcgtctcc aaagggccag    660
ccgaggttac gtcttctccc ttcccgtcgt tctctccggt cgcgaggagg ccatcgcctt    720
cattcgggac agcggtatgc agctgatgac gctcaaggcg gatggcgaca tttccgtgaa    780
ggaactcggg gacaatccgg atcggctggc cttgctgttc ggcagcgaaa agggtgggcc    840
ttccgacctg ttcgaggagg cgtcttccgc ctcggtttcc atccccatga tgagccagac    900
cgagtctctc aacgtttccg tttccctcgg aatcgcgctg cacgagagga tcgacaggaa    960
tctcgcggcc aaccgataag cgcctctgtt cctcggacgc tcggttcctc gacctcgatt   1020
cgtcagtgat gatcacctca cacggcagcg atcaccactg acatatcgag gtcaacggtc   1080
gtggtccggg cggcactcc tcgaaggcgc ggccgacgcc cttgaacgac tcgatgactc   1140
tagacgcatc cgaaacctcc accccactca cctagtccga catccgtacc ttggaaaccg   1200
acctgtattg gcatttcagt tggacatcga ccagtggcgt tgctaggttc aagaccatgt   1260
ccagcccgaa ggcgtccaga ctctagccac cggaggtagt ccggtggcca catcccgtcg   1320
cgcccgaacg tcacgctctt gtgtggcctt cccttgttgt ttgcgatcag tggcacacct   1380
ctaccgtctg aatttcgagt ctggcctcgg ctgcgcacat ctcgcactgt gacgctgtca   1440
ggtcacccgc ttcgcggcta ccagttcctt tcatcgaatc gagcttccgg tgccgccgcg   1500
cagcctccct gaccatcctc agattttatg gagtctcgca gtgcctttcg ctatctacgt   1560
cctcgggctt gctgtcttcg cccagggcac atccgagttc atgttgtccg gactcatacc   1620
ggacatggcc cgtgacctcg gggtttcggt ccccgccgcc ggactcctca cctccgcctt   1680
cgcggtcggg atgatcatcg gcgctccgtt gatggctatc gccagcatgc ggtggccccg   1740
gcgacgcgcc cttctgacat tcctcatcac gttcatgctg gtccacgtca tcggcgcgct   1800
caccagcagc ttcgaggtct tgctggtcac acgcatcgtg ggagccctcg ccaatgccgg   1860
attcttggca gtggccctgg gggcggcgat ggcgatggtg cccgccgaca tgaaagggcg   1920
cgccacgtcc gtcctcctcg gcggtgtcac gatcgcatgt gtagccggtg ttcccggggg   1980
cgccttcctg ggtgaaatgt ggggctggcg tgcagcgttc tgggctgtcg tcgtcatctc   2040
cgcccctgca gtggtggcga ttatgttcgc caccccggcc gagccgcttg cagagtccac   2100
accgaatgcc aagcgtgaac tgtcctcact gcgctcacgc aagctccagc tcatgcttgt   2160
cctcggggcg ctgatcaacg gcgcaacgtt ctgttcgttc acgtacatgg cgcccacgct   2220
caccgacatc tccggtttcg actcccgttg gattccgttg ctgctggggc tgttcgggct   2280
cggatcgttc atcggtgtca gcgtcggagg caggctcgcc gacacccggc cgttccaact   2340
gctcgctgtc gggtccgcag cactgttgac gggatggatc gtcttcgctc tcacggcatc   2400
ccaccccgcg gtgacattgg tgatgctgtt cgtgcagggc gctttgtcct tcgcggtcgg   2460
ctcgactttg atctcccagg tgctctacgc cgccgacgcg caccgacct tgggtggatc   2520
gttcgcgacg gccgcgttca acgtcggtgc tgcactggga ccggcgctcg gcggttggc   2580
gatcggcatg ggtctgagct accgcgcccc gctctggacg agcgccgcgc tggtgacact   2640
```

```
cgcgatcgtc atcggcgcag ccaccttgtc tctgtggcgg cgaccagcgt ctgtccacga   2700
atctgtcccc gcctgaccag aaaccaggat ctgtgagtgt ggtgactgat ctgtgcacgc   2760
tcagcagtca ccgcgcgctc gcgtcgtacc gagggccagc gccaacaggt gtgtggagct   2820
ctgcccctgc ctcttttcacg cgaactcact gttcagtgcg gcgatacgtg ctcggtgagt   2880
tccactacag cgaccatgac tagaattgat ctcctcgacc gccaattggg catctgagaa   2940
tcatctgcgt ttctcgcacg caacgtactt gcaacgttgc aactcctagt gttgtgaatc   3000
acaccccacc gggggtggg attgcagtca ccgatttggt gggtgcgccc aggaagatca    3060
cgtttacata ggagcttgca atgagctact ccgtgggaca ggtggccggc ttcgccggag   3120
tgacggtgcg cacgctgcac cactacgacg acatcggcct gctcgtaccg agcgagcgca   3180
gccacgcggg ccaccggcgc tacagcgacg ccgacctcga ccggctgcag cagatcctgt   3240
tctaccggga gctgggcttc ccgctcgacg aggtcgccgc cctgctcgac gacccggccg   3300
cggacccgcg cgcgcacctg cgccgccagc acgagctgct gtccgcccgg atcgggaaac   3360
tgcagaagat ggcggcggcc gtggagcagg cgatggaggc acgcagcatg ggaatcaacc   3420
tcaccccgga ggagaagttc gaggtcttcg gcgacttcga ccccgaccag tacgaggagg   3480
aggtccggga acgctggggg aacaccgacg cctaccgcca gtccaaggag aagaccgcct   3540
cgtacaccaa ggaggactgg cagcgcatcc aggacgagcg cgacgagctc acccggcgct   3600
tcgtcgccct gatggacgcg ggtgagcccc ccgactccga gggggcgatg gacgccgccg   3660
aggaccaccg gcagggcatc gcccgcaacc actacgactg cgggtacgag atgcacacct   3720
gcctgggcga gatgtacgtg tccgacgaac gtttcacgcg aaacatcgac gccgccaagc   3780
cgggcctcgc cgcctacatg cgcgacgcga tcctcgccaa cgccgtccgg cacacccct   3840 gagcggtggt cgtggcccgg gtctcccgcc cggtctcacc ccacggctca ctcccgggcc   3900
acgaccaccg ccgtcccgta cgcgcacacc tcggtgccca cgtccgccgc ctccgtcacg   3960
tcgaaacgga agatccccgg gtaccgagct cgtcaggtgg cacttttcgg ggaaatgtgc   4020
gcggaacccc tatttgttta ttttttctaaa tacattcaaa tatgtatccg ctcatgagac   4080
aataaccctg ataaatgctt caataatatt gaaaaaggaa gagtatgagt attcaacatt   4140
tccgtgtcgc ccttattccc ttttttgcgg cattttgcct tcctgttttt gctcacccag   4200
aaacgctggt gaaagtaaaa gatgctgaag atcagttggg tgcacgagtg ggttacatcg   4260
aactggatct caacagcggt aagatccttg agagttttcg ccccgaagaa cgttttccaa   4320
tgatgagcac ttttaaagtt ctgctatgtg gcgcggtatt atcccgtatt gacgccgggc   4380
aagagcaact cggtcgccgc atacactatt ctcagaatga cttggttgag tactcaccag   4440
tcacagaaaa gcatcttacg gatggcatga cagtaagaga attatgcagt gctgccataa   4500
ccatgagtga taacactgcg gccaacttac ttctgacaac gatcggagga ccgaaggagc   4560
taaccgcttt tttgcacaac atgggggatc atgtaactcg ccttgatcgt tgggaaccgg   4620
agctgaatga agccatacca aacgacgagc gtgacaccac gatgcctgta gcaatggcaa   4680
caacgttgcg caaactatta actggcgaac tacttactct agcttcccgg caacaattaa   4740
tagactggat ggaggcggat aaagttgcag gaccacttct gcgctcggcc cttccggctg   4800
gctggtttat tgctgataaa tctggagccg gtgagcgtgg gtctcgcggt atcattgcag   4860
cactggggcc agatggtaag ccctcccgta tcgtagttat ctacacgacg gggagtcagg   4920
caactatgga tgaacgaaat agacagatcg ctgagatagg tgcctcactg attaagcatt   4980
```

-continued

```
ggtaactgtc agaccaagtt tactcatata tactttagat tgatttaaaa cttcattttt    5040
aatttaaaag gatctaggtg aagatccttt ttgataatct catgaccaaa atcccttaac    5100
gtgagttttc gttccactga gcgtcagacc ccgtagaaaa gatcaaagga tcttcttgag    5160
atcctttttt tctgcgcgta atctgctgct tgcaaacaaa aaaaccaccg ctaccagcgg    5220
tggtttgttt gccggatcaa gagctaccaa ctcttttcc gaaggtaact ggcttcagca    5280
gagcgcagat accaaatact gttcttctag tgtagccgta gttaggccac cacttcaaga    5340
actctgtagc accgcctaca tacctcgctc tgctaatcct gttaccagtg gctgctgcca    5400
gtggcgataa gtcgtgtctt accgggttgg actcaagacg atagttaccg gataaggcgc    5460
agcggtcggg ctgaacgggg ggttcgtgca cacagcccag cttggagcga acgacctaca    5520
ccgaactgag atacctacag cgtgagctat gagaaagcgc cacgcttccc gaagggagaa    5580
aggcggacag gtatccggta agcggcaggg tcggaacagg agagcgcacg agggagcttc    5640
cagggggaaa cgcctggtat ctttatagtc ctgtcgggtt tcgccacctc tgacttgagc    5700
gtcgattttt gtgatgctcg tcagggggc ggagcctatg gaaaaacgcc agcaacgcgg    5760 ccttttacg gttcctggcc ttttgctggc cttttgctca catgttcttt cctgcgttat    5820
cccctgattc tgtggataac cgtattaccg cctttgagtg agctgatacc gctcgccgca    5880
gccgaacgac cgagcgcagc gagtcagtga gcgaggaagc ggaagagcgc ccaatacgca    5940
aaccgcctct ccccgcgcgt tggccgattc attaatgcag ctggcacgac tagagtcccg    6000
ctgaggcggc gtagcaggtc agccgcccca gcggtggtca ccaaccgggg tggaacggcg    6060
ccggtatcgg gtgtgtccgt ggcgctcatt ccaacctccg tgtgtttgtg caggtttcgc    6120
gtgttgcagt ccctcgcacc ggcacccgca gcgaggggct cacgggtgcc ggtgggtcga    6180
ctagttcagt gatggtgatg gtgatgctcg agagatctaa gcttggatcc gcggccgcta    6240
cgtagaattc ccatggcgtg atggtgatgg tgatggccca tatgtatatc tccttcttaa    6300
agttaaacaa aattatttct agacgccgtc cacgctgcct cctcacgtga cgtgaggtgc    6360
aagcccggac gttccgcgtg ccacgccgtg agccgccgcg tgccgtcggc tccctcagcc    6420
cgggcggccg tgggagcccg cctcgatatg tacacccgag aagctcccag cgtcctcctg    6480
ggccgcgata ctcgaccacc acgcacgcac accgcactaa cgattcggcc ggcgctcgat    6540
tcggccggcg ctcgattcgg ccggcgctcg attcggccgg cgctcgattc ggccggcgct    6600
cgattcggcc gagcagaaga gtgaacaacc accgaccacg cttccgctct gcgcgccgta    6660
cccgacctac ctcccgcagc tcgaagcagc tcccgggagt accgccgtac tcacccgcct    6720
gtgctcacca tccaccgacg caaagcccaa cccgagcaca cctcttgcac caaggtgccg    6780
accgtggctt tccgctcgca gggttccaga agaaatcgaa cgatccagcg cggcaaggtt    6840
caaaaagcag gggttggtgg ggaggaggtt ttgggggggtg tcgccgggat acctgatatg    6900
gctttgtttt gcgtagtcga ataatttttcc atatagcctc ggcgcgtcgg actcgaatag    6960
ttgatgtggg cggcacagt tgccccatga atccgcaac gggggcgtg ctgagcgatc    7020 ggcaatgggg ggatgcggtg ttgcttccgc accggccgtt cgcgacgaac aacctccaac    7080
gaggtcagta ccggatgagc cgcgacgacg cattggcaat gcggtacgtc gagcattcac    7140
cgcacgcgtt gctcggatct atcgtcatcg actgcgatca cgttgacgcc gcgatgcgcg    7200
cattcgagca accatccgac catccggcgc cgaactgggt cgcacaatcg ccgtccggcc    7260
gcgcacacat cggatggtgg ctcggcccca accacgtgtg ccgcaccgac agcgcccgac    7320
tgacgccact gcgctacgcc caccgcatcg aaaccggcct caagatcagc gtcggcggcg    7380
```

| | |
|---|---|
| atttcgcgta tggcgggcaa ctgaccaaaa acccgattca ccccgattgg gagacgatct | 7440 |
| acggcccggc cacccgtac acattgcggc agctggccac catccacaca ccccggcaga | 7500 |
| tgccgcgtcg gcccgatcgg gccgtgggcc tgggccgcaa cgtcaccatg ttcgacgcca | 7560 |
| cccggcgatg ggcatacccg cagtggtggc aacaccgaaa cggaaccggc cgcgactggg | 7620 |
| accatctcgt cctgcagcac tgccacgccg tcaacaccga gttcacgaca ccactgccgt | 7680 |
| tcaccgaagt acgcgccacc gcgcaatcca tctccaaatg gatctggcgc aatttcaccg | 7740 |
| aagaacagta ccgagcccga caagcgcatc tcggtcaaaa aggcggcaag caacgacac | 7800 |
| tcgccaaaca agaagccgtc cgaaacaatg caagaaagta cgacgaacat acgatgcgag | 7860 |
| aggcgattat ctgatgggcg gagccaaaaa tccggtgcgc cgaaagatga cggcagcagc | 7920 |
| agcagccgaa aaattcggtg cctccactcg cacaatccaa cgcttgtttg ctgagccgcg | 7980 |
| tgacgattac ctcggccgtg cgaaagctcg ccgtgacaaa gctgtcgagc tgcggaagca | 8040 |
| ggggttgaag taccgggaaa tcgccgaagc gatggaactc tcgaccggga tcgtcggccg | 8100 |
| attactgcac gacgcccgca ggcacggcga gatttcagcg gaggatctgt cggcgtaacc | 8160 |
| aagtcagcgg gttgtcgggt tccggccggc gctcggcact cggaccggcc ggcggatggt | 8220 |
| gttctgcctc tggcgcagcg tcagctaccg ccgaaggcct gtcatcgacc ggcttcgact | 8280 |
| gaagtatgag caacgtcaca gcctgtgatt ggatgatccg ctcacgctcg accgctacct | 8340 |
| gttcagctgc cgcccgctgg gcatgagcaa cggccaactc tcgttcaa | 8388 |

<210> SEQ ID NO 97
<211> LENGTH: 8452
<212> TYPE: DNA
<213> ORGANISM: Artificial Sequence
<220> FEATURE:
<223> OTHER INFORMATION: Description of Artificial Sequence: Synthetic vector pTip-RC1 sequence

<400> SEQUENCE: 97

| | |
|---|---|
| gttaacgacc gcgcgggtcc cggacgggga agagcgggga gctttgccag agagcgacga | 60 |
| cttcccttg cgttggtgat tgccggtcag ggcagccatc cgccatcgtc gcgtagggtg | 120 |
| tcacacccca ggaatcgcgt cactgaacac agcagccgt aggacgacca tgactgagtt | 180 |
| ggacaccatc gcaaatccgt ccgatcccgc ggtgcagcgg atcatcgatg tcaccaagcc | 240 |
| gtcacgatcc aacataaaga caacgttgat cgaggacgtc gagcccctca tgcacagcat | 300 |
| cgcggccggg gtggagttca tcgaggtcta cggcagcgac agcagtcctt ttccatctga | 360 |
| gttgctggat ctgtgcgggc ggcagaacat accggtccgc ctcatcgact cctcgatcgt | 420 |
| caaccagttg ttcaagggg agcggaaggc caagacattc ggcatcgccc gcgtccctcg | 480 |
| cccggccagg ttcggcgata tcgcgagccg gcgtgggac gtcgtcgttc tcgacggggt | 540 |
| gaagatcgtc gggaacatcg gcgcgatagt acgcacgtcg ctcgcgctcg gagcgtcggg | 600 |
| gatcatcctg gtggacagtg acatcaccag catcgcggac cggcgtctcc aaagggccag | 660 |
| ccgaggttac gtcttctccc ttcccgtcgt tctctccggt cgcgaggagg ccatcgcctt | 720 |
| cattcgggac agcggtatgc agctgatgac gctcaaggcg gatggcgaca tttccgtgaa | 780 |
| ggaactcggg gacaatccgg atcggctggc cttgctgttc ggcagcgaaa agggtgggcc | 840 |
| ttccgacctg ttcgaggagg cgtcttccgc ctcggtttcc atccccatga tgagccagac | 900 |
| cgagtctctc aacgtttccg tttccctcgg aatcgcgctg cacagagagga tcgacaggaa | 960 |
| tctcgcggcc aaccgataag cgcctctgtt cctcggacgc tcggttcctc gacctcgatt | 1020 |

```
cgtcagtgat gatcacctca cacggcagcg atcaccactg acatatcgag gtcaacggtc    1080
gtggtccggg cgggcactcc tcgaaggcgc ggccgacgcc cttgaacgac tcgatgactc    1140
tagacgcatc cgaaacctcc accccactca cctagtccga catccgtacc ttggaaaccg    1200
acctgtattg gcatttcagt tggacatcga ccagtggcgt tgctaggttc aagaccatgt    1260
ccagcccgaa ggcgtccaga ctctagccac cggaggtagt ccggtggcca catcccgtcg    1320
cgcccgaacg tcacgctctt gtgtggcctt cccttgttgt ttgcgatcag tggcacacct    1380
ctaccgtctg aatttcgagt ctggcctcgg ctgcgcacat ctcgcactgt gacgctgtca    1440
ggtcacccgc ttcgcggcta ccagttcctt tcatcgaatc gagcttccgg tgccgccgcg    1500
cagcctccct gaccatcctc agattttatg gagtctcgca gtgcctttcg ctatctacgt    1560
cctcgggctt gctgtcttcg cccagggcac atccgagttc atgttgtccg gactcatacc    1620
ggacatggcc cgtgacctcg gggtttcggt ccccgccgcc ggactcctca cctccgcctt    1680
cgcggtcggg atgatcatcg cgctccgtt gatggctatc gccagcatgc ggtggccccg     1740
gcgacgcgcc cttctgacat tcctcatcac gttcatgctg gtccacgtca tcggcgcgct    1800
caccagcagc ttcgaggtct tgctggtcac acgcatcgtg ggagccctcg ccaatgccgg    1860
attcttggca gtggccctgg gggcggcgat ggcgatggtg cccgccgaca tgaaagggcg    1920
cgccacgtcc gtcctcctcg gcggtgtcac gatcgcatgt gtagccggtg ttcccggggg    1980
cgccttcctg ggtgaaatgt ggggctggcg tgcagcgttc tgggctgtcg tcgtcatctc    2040
cgcccctgca gtggtggcga ttatgttcgc caccccggcc gagccgcttg cagagtccac    2100
accgaatgcc aagcgtgaac tgtcctcact gcgctcacgc aagctccagc tcatgcttgt    2160
cctcggggcg ctgatcaacg gcgcaacgtt ctgttcgttc acgtacatgg cgcccacgct    2220
caccgacatc tccggtttcg actcccgttg gattccgttg ctgctggggc tgttcgggct    2280
cggatcgttc atcggtgtca gcgtcggagg caggctcgcc gacacccggc cgttccaact    2340
gctcgctgtc gggtccgcag cactgttgac gggatggatc gtcttcgctc tcacggcatc    2400
ccaccccgcg gtgacattgg tgatgctgtt cgtgcagggc gctttgtcct tcgcggtcgg    2460
ctcgactttg atctcccagg tgctctacgc cgccgacgcg gcaccgacct tgggtggatc    2520
gttcgcgacg gccgcgttca acgtcggtgc tgcactggga ccggcgctcg gcggttggc     2580
gatcggcatg ggtctgagct accgcgcccc gctctggacg agcgccgcgc tggtgacact    2640
cgcgatcgtc atcggcgcag ccaccttgtc tctgtggcgg cgaccagcgt ctgtccacga    2700
atctgtcccc gcctgaccag aaaccaggat ctgtgagtgt ggtgactgat ctgtgcacgc    2760
tcagcagtca ccgcgcgctc gcgtcgtacc gagggccagc gccaacaggt gtgtggagct    2820
ctgcccctgc ctcttccacg cgaactcact gttcagtgcg gcgatacgtg ctcggtgagt    2880
tccactacag cgaccatgac tagaattgat ctcctcgacc gccaattggg catctgagaa    2940
tcatctgcgt ttctcgcacg caacgtactt gcaacgttgc aactcctagt gttgtgaatc    3000
acaccccacc gggggtgggg attgcagtca ccgatttggt gggtgcgccc aggaagatca    3060
cgtttacata ggagcttgca atgagctact ccgtgggaca ggtggccggc ttcgccggag    3120
tgacggtgcg cacgctgcac cactacgacg acatcggcct gctcgtaccg agcgagcgca    3180
gccacgcggg ccaccggcgc tacagcgacg ccgacctcga ccggctgcag cagatcctgt    3240
tctaccggga gctgggcttc ccgctcgacg aggtcgccgc cctgctcgac gacccggccg    3300
cggacccgcg cgcgcacctg cgccgccagc acagctgct gtccgccggg atcgggaaac     3360
```

```
tgcagaagat ggcggcggcc gtggagcagg cgatggaggc acgcagcatg ggaatcaacc    3420
tcaccccgga ggagaagttc gaggtcttcg gcgacttcga ccccgaccag tacgaggagg    3480
aggtccggga acgctggggg aacaccgacg cctaccgcca gtccaaggag aagaccgcct    3540
cgtacaccaa ggaggactgg cagcgcatcc aggacgaggc cgacgagctc acccggcgct    3600
tcgtcgccct gatggacgcg ggtgagcccg ccgactccga gggggcgatg gacgccgccg    3660
aggaccaccg gcagggcatc gcccgcaacc actacgactg cgggtacgag atgcacacct    3720
gcctgggcga gatgtacgtg tccgacgaac gtttcacgcg aaacatcgac gccgccaagc    3780
cgggcctcgc cgcctacatg cgcgacgcga tcctcgccaa cgccgtccgg cacaccccct    3840
gagcggtggt cgtggcccgg gtctcccgcc cggtctcacc ccacggctca ctcccgggcc    3900
acgaccaccc ccgtcccgta cgcgcacacc tcggtgccca cgtccgccgc ctccgtcacg    3960
tcgaaacgga agatccccgg gtaccgagct cgtcaggtgg cacttttcgg ggaaatgtgc    4020
gcggaacccc tatttgttta tttttctaaa tacattcaaa tatgtatccg ctcatgagac    4080
aataaccctg ataaatgctt caataatatt gaaaaggaa gagtatgagt attcaacatt     4140
tccgtgtcgc ccttattccc ttttttgcgg catttttgcct tcctgttttt gctcacccag    4200
aaacgctggt gaaagtaaaa gatgctgaag atcagttggg tgcacgagtg ggttacatcg    4260
aactggatct caacagcggt aagatccttg agagttttcg ccccgaagaa cgttttccaa    4320
tgatgagcac ttttaaagtt ctgctatgtg gcgcggtatt atcccgtatt gacgccgggc    4380
aagagcaact cggtcgccgc atacactatt ctcagaatga cttggttgag tactcaccag    4440
tcacagaaaa gcatcttacg gatggcatga cagtaagaga attatgcagt gctgccataa    4500
ccatgagtga taacactgcg gccaacttac ttctgacaac gatcgaggga ccgaaggagc    4560
taaccgcttt tttgcacaac atggggatc atgtaactcg ccttgatcgt tgggaaccgg    4620
agctgaatga agccatacca aacgacgagc gtgacaccac gatgcctgta gcaatggcaa    4680
caacgttgcg caaactatta actggcgaac tacttactct agcttcccgg caacaattaa    4740
tagactggat ggaggcggat aaagttgcag gaccacttct gcgctcggcc cttccggctg    4800
gctggtttat tgctgataaa tctggagccg gtgagcgtgg gtctcgcggt atcattgcag    4860
cactggggcc agatggtaag ccctcccgta tcgtagttat ctacacgacg gggagtcagg    4920
caactatgga tgaacgaaat agacagatcg ctgagatagg tgcctcactg attaagcatt    4980
ggtaactgtc agaccaagtt tactcatata ctttagat tgatttaaaa cttcattttt       5040
aatttaaaag gatctaggtg aagatccttt ttgataatct catgaccaaa atcccttaac    5100
gtgagttttc gttccactga gcgtcagacc ccgtagaaaa gatcaaagga tcttcttgag    5160
atcctttttt tctgcgcgta atctgctgct tgcaaacaaa aaaaccaccg ctaccagcgg    5220
tggtttgttt gccggatcaa gagctaccaa ctcttttttcc gaaggtaact ggcttcagca    5280
gagcgcagat accaaatact gttcttctag tgtagccgta gttaggccac cacttcaaga    5340
actctgtagc accgcctaca tacctcgctc tgctaatcct gttaccagtg gctgctgcca    5400
gtggcgataa gtcgtgtctt accgggttgg actcaagacg atagttaccg gataaggcgc    5460
agcggtcggg ctgaacgggg ggttcgtgca cacagcccag cttggagcga acgacctaca    5520
ccgaactgag atacctacag cgtgagctat gagaaagcgc cacgcttccc gaagggagaa    5580
aggcggacag gtatccggta agcggcaggg tcggaacagg agagcgcacg agggagcttc    5640 caggggggaaa cgcctggtat ctttatagtc ctgtcgggtt tcgccacctc tgacttgagc    5700
gtcgattttt gtgatgctcg tcaggggggc ggagcctatg gaaaaacgcc agcaacgcgg    5760
```

```
ccttttacg gttcctggcc ttttgctggc cttttgctca catgttcttt cctgcgttat    5820
cccctgattc tgtggataac cgtattaccg cctttgagtg agctgatacc gctcgccgca    5880
gccgaacgac cgagcgcagc gagtcagtga gcgaggaagc ggaagagcgc ccaatacgca    5940
aaccgcctct ccccgcgcgt tggccgattc attaatgcag ctggcacgac tagagtcccg    6000
ctgaggcggc gtagcaggtc agccgcccca cggtggtca ccaaccgggg tggaacggcg    6060
ccggtatcgg gtgtgtccgt ggcgctcatt ccaacctccg tgtgtttgtg caggtttcgc    6120
gtgttgcagt ccctcgcacc ggcacccgca gcgaggggct cacgggtgcc ggtgggtcga    6180
ctagttcagt gatggtgatg gtgatgctcg agagatctaa gcttggatcc gcggccgcta    6240
cgtagaattc ccatatggtg atggtgatgg tggcccatgg tatatctcct tcttaaagtt    6300
aaacaaaatt atttctagac gccgtccacg ctgcctcctc acgtgacgtg aggtgcaagc    6360
ccggacgttc cgcgtgccac gccgtgagcc gccgcgtgcc gtcggctccc tcagcccggg    6420
cggccgtggg agcccgcctc gatatgtaca agcatgggga ctcgccgcgg actagcggct    6480
tcccgacacg ccgtactgac cagcagatca gcgataaacg ctgtttctgc tggttaagtg    6540
gataaaaacc aaataatcga tgaacctcga agtggagtat ccgagctgaa ctagctggat    6600
ttactccgaa aatacgagcg gcgacgaagg gtgttggacc accctgccgc gccttcgag    6660
gctcctactt gactaggacc ccgctcgtta tgaccagcgt aagtgctgaa cacctttccg    6720
gcaaagaccg gccccctgtc ctcgtgtcgt ccgataagcg cggcatccgg cacgaacttc    6780
gacccaaact tcaacaaatc accacgtcag aaacttttaa tgcgtgcggc cggccgattt    6840
ccggcgtgaa cggtgtgacc atcgtcaacg gtcccaaagg ttccggattt ggaggccttc    6900
gctcctgcgg aaagggctgg atctgcccct gctgtgcggg aaaagtcggc gcacatcgag    6960
cagacgaaat ttctcaagtt gttgctcatc aactcgggac tggatctgtt gcgatggtga    7020
ccatgaccat gcgccatacc gctgggcagc gtttgcatga tttgtggact ggactttcgg    7080
cagcctggaa agctgcgacc aatggccgcc gatggcgtac cgaacgtgaa atgtacggct    7140
gcgacggata cgtacgagct gttgaaatca ctcacgaaaa aaacggttgg cacgttcacg    7200
tccacgctct actcatgttc agcggtgacg tgagtgagaa catcctcgaa tccttctcgg    7260
atgcgatgtt cgatcggtgg acctccaaac tcgtgtctct gggatttgct gcgccactac    7320
gtaattcagg tggactcgac gtaagaaaga ttggtggaga agctgaccaa gttctcgctg    7380
catacctgac gaaaattgca tccggggtcg gcatggaagt cggcagtggc gacggaaaaa    7440
gtggtcggca cggcaaccgt gcaccttggg aaatcgccgt tgatgcagtc ggaggagatc    7500
cacaagcgtt ggaactctgg cgcgagtttg agttcggttc gatgggacgc cgagcaatcg    7560
catggtctcg tggactgcgc gcccgagctg gtcttggcgt agaactcacg gatgctcaga    7620
ttgtcgaaca ggaagaatct gccccggtca tggttgcgat cattccggct cggtcctgga    7680
tgatgattcg gaactgtgcg ccttacgttt tcggagagat ccttggactc gtggaagcgg    7740
gcgcgacctg ggaaaacctt cgtgaccact tgcattatcg attgcctgca gcggatgtgc    7800
ggcctccgat aatatcgatt cgtaagtgaa atgtcttggt gtgcaacaac tttcactcgt    7860
atgaaccaca cttgagggca tcccccgat acttgccgct ttgaagctgg gtgtctctct    7920
gtcagggctg cgatagcacc gcgtagcggc ttggccttga cagagacg gcctgtttca    7980
tggttggtct cggggggctg accgggcaga tagaaaaagg ccggccgatt tggctgccga    8040
ctattttgc aggtaaaccc atctcatgag catcaatgaa cgtcccgttg gtatcgcagc    8100
```

```
gaatgcagct tcggtagacg tcgatggcgt tgtgatgggt gtgtatctct cgctttatgg    8160
gcaagaaatc acgctagatc gagatgatgc gttcctactc ctcgatcgac ttcaggacgc    8220
gttgcgacct caagccaact aagaaccctc cagatggtct aaacgaggcg caaactcgct    8280
cctgggcctg cgggcggagc accgaagcgc gagcgaagcg gagcgcgtag gtggggagc    8340 ctgcgggcag cggcggcgga gccgccgcct tggtaatagg tgatcatcgg ggccatagca    8400
ggtcagagga tgttttacg atgactcatg ctcaccacgc caagtactga tg             8452
```

<210> SEQ ID NO 98
<211> LENGTH: 8456
<212> TYPE: DNA
<213> ORGANISM: Artificial Sequence
<220> FEATURE:
<223> OTHER INFORMATION: Description of Artificial Sequence: Synthetic
      vector pTip-RC2 sequence

<400> SEQUENCE: 98

```
gttaacgacc gcgcgggtcc cggacgggga agagcgggga gctttgccag agagcgacga      60
cttccccttg cgttggtgat tgccggtcag ggcagccatc cgccatcgtc gcgtagggtg     120
tcacacccca ggaatcgcgt cactgaacac agcagccggt aggacgacca tgactgagtt     180
ggacaccatc gcaaatccgt ccgatcccgc ggtgcagcgg atcatcgatg tcaccaagcc     240
gtcacgatcc aacataaaga caacgttgat cgaggacgtc gagcccctca tgcacagcat     300
cgcggccggg gtggagttca tcgaggtcta cggcagcgac agcagtcctt ttccatctga     360
gttgctggat ctgtgcgggc ggcagaacat accggtccgc ctcatcgact cctcgatcgt     420
caaccagttg ttcaaggggg agcggaaggc caagacattc ggcatcgccc gcgtccctcg     480
cccggccagg ttcggcgata tcgcgagccg gcgtggggac gtcgtcgttc tcgacggggt     540
gaagatcgtc gggaacatcg gcgcgatagt acgcacgtcg ctcgcgctcg gagcgtcggg     600
gatcatcctg tgtgacagtg acatcaccag catcgcggac cggcgtctcc aaagggccag     660
ccgaggttac gtcttctccc ttcccgtcgt tctctccggt cgcgaggagg ccatcgcctt     720
cattcgggac agcggtatgc agctgatgac gctcaaggcg gatggcgaca tttccgtgaa     780
ggaactcggg gacaatccgg atcggctggc cttgctgttc ggcagcgaaa agggtgggcc     840
ttccgacctg ttcgaggagg cgtcttccgc ctcggtttcc atcccatga tgagccagac     900 cgagtctctc aacgtttccg tttccctcgg aatcgcgctg cacgagagga tcgacaggaa     960
tctcgcggcc aaccgataag cgcctctgtt cctcggacgc tcggttcctc gacctcgatt    1020
cgtcagtgat gatcacctca cacggcagcg atcaccactg acatatcgag gtcaacggtc    1080
gtggtccggg cgggcactcc tcgaaggcgc ggccgacgcc cttgaacgac tcgatgactc    1140
tagacgcatc cgaaacctcc accccactca cctagtccga catccgtacc ttggaaaccg    1200
acctgtattg gcatttcagt tggacatcga ccagtggcgt tgctaggttc aagaccatgt    1260
ccagcccgaa ggcgtccaga ctctagccac cggaggtagt ccggtggcca catcccgtcg    1320
cgcccgaacg tcacgctctt gtgtggcctt cccttgttgt ttgcgatcag tggcacacct    1380
ctaccgtctg aatttcgagt ctggcctcgg ctgcgcacat ctcgcactgt gacgctgtca    1440
ggtcacccgc ttcgcggcta ccagttcctt tcatcgaatc gagcttccgg tgccgccgcg    1500
cagcctccct gaccatcctc agattttatg gagtctcgca gtgcctttcg ctatctacgt    1560
cctcgggctt gctgtcttcg cccagggcac atccgagttc atgttgtccg gactcatacc    1620
ggacatggcc cgtgacctcg gggtttcggt ccccgccgcc ggactcctca cctccgcctt    1680
```

-continued

```
cgcggtcggg atgatcatcg gcgctccgtt gatggctatc gccagcatgc ggtggccccg    1740
gcgacgcgcc cttctgacat tcctcatcac gttcatgctg gtccacgtca tcggcgcgct    1800
caccagcagc ttcgaggtct tgctggtcac acgcatcgtg ggagccctcg ccaatgccgg    1860
attcttggca gtggccctgg gggcggcgat ggcgatggtg cccgccgaca tgaaagggcg    1920
cgccacgtcc gtcctcctcg gcggtgtcac gatcgcatgt gtagccggtg ttcccggggg    1980
cgccttcctg ggtgaaatgt ggggctggcg tgcagcgttc tgggctgtcg tcgtcatctc    2040
cgcccctgca gtggtggcga ttatgttcgc cacccccggcc gagccgcttg cagagtccac    2100
accgaatgcc aagcgtgaac tgtcctcact gcgctcacgc aagctccagc tcatgcttgt    2160
cctcggggcg ctgatcaacg cgcaacgtt ctgttcgttc acgtacatgg cgcccacgct    2220
caccgacatc tccggtttcg actcccgttg gattccgttg ctgctggggc tgttcgggct    2280
cggatcgttc atcggtgtca gcgtcggagg caggctcgcc gacacccggc cgttccaact    2340
gctcgctgtc gggtccgcag cactgttgac gggatggatc gtcttcgctc tcacggcatc    2400
ccaccccgcg gtgacattgg tgatgctgtt cgtgcagggc gctttgtcct cgcggtcgg    2460 ctcgactttg atctcccagg tgctctacgc cgccgacgcg caccgacct tgggtggatc    2520 gttcgcgacg gccgcgttca acgtcggtgc tgcactggga ccggcgctcg gcggttggc    2580 gatcggcatg ggtctgagct accgcgcccc gctctggacg agcgccgcgc tggtgacact    2640
cgcgatcgtc atcggcgcag ccaccttgtc tctgtggcgg cgaccagcgt ctgtccacga    2700
atctgtcccc gcctgaccag aaaccaggat ctgtgagtgt ggtgactgat ctgtgcacgc    2760
tcagcagtca ccgcgcgctc gcgtcgtacc gagggccagc gccaacaggt gtgtggagct    2820
ctgcccctgc ctctttcacg cgaactcact gttcagtgcg gcgatacgtg ctcggtgagt    2880
tccactacag cgaccatgac tagaattgat ctcctcgacc gccaattggg catctgagaa    2940
tcatctgcgt ttctcgcacg caacgtactt gcaacgttgc aactcctagt gttgtgaatc    3000 acacccccacc gggggggtggg attgcagtca ccgatttggt gggtgcgccc aggaagatca    3060
cgtttacata ggagcttgca atgagctact ccgtgggaca ggtggccggc ttcgccggag    3120
tgacggtgcg cacgctgcac cactacgacg acatcggcct gctcgtaccg agcgagcgca    3180
gccacgcggg ccaccggcgc tacagcgacg ccgacctcga ccggctgcag cagatcctgt    3240
tctaccggga gctgggcttc ccgctcgacg aggtcgccgc cctgctcgac gacccggccg    3300 cggaccccgcg cgcgcacctg cgccgccagc acgagctgct gtccgcccgg atcgggaaac    3360
tgcagaagat ggcggcggcc gtggagcagg cgatggagga cgcagcatg ggaatcaacc    3420 tcaccccgga ggagaagttc gaggtcttcg gcgacttcga ccccgaccag tacgaggagg    3480
aggtccggga acgctggggg aacaccgacg cctaccgcca gtccaaggag aagaccgcct    3540
cgtacaccaa ggaggactgg cagcgcatcc aggacgaggc cgacgagctc acccggcgct    3600
tcgtcgccct gatggacgcg ggtgagcccg ccgactccga gggggcgatg gacgccgccg    3660
aggaccaccg gcagggcatc gcccgcaacc actacgactg cgggtacgag atgcacacct    3720
gcctgggcga gatgtacgtg tccgacgaac gtttcacgcg aaacatcgac gccgccaagc    3780
cgggcctcgc cgcctacatg cgcgacgcga tcctcgccaa cgccgtccgg cacaccccct    3840
gagcggtggt cgtggcccgg gtctcccgcc cggtctcacc ccacggctca ctcccgggcc    3900
acgaccaccg ccgtcccgta cgcgcacacc tcggtgccca cgtccgccgc ctccgtcacg    3960
tcgaaacgga agatccccgg gtaccgagct cgtcaggtgg cacttttcgg ggaaatgtgc    4020
gcggaacccc tatttgttta ttttctaaa tacattcaaa tatgtatccg ctcatgagac    4080
```

```
aataaccctg ataaatgctt caataatatt gaaaaaggaa gagtatgagt attcaacatt    4140
tccgtgtcgc ccttattccc ttttttgcgg cattttgcct tcctgttttt gctcacccag    4200
aaacgctggt gaaagtaaaa gatgctgaag atcagttggg tgcacgagtg ggttacatcg    4260
aactggatct caacagcggt aagatccttg agagttttcg ccccgaagaa cgttttccaa    4320
tgatgagcac ttttaaagtt ctgctatgtg gcgcggtatt atcccgtatt gacgccgggc    4380
aagagcaact cggtcgccgc atacactatt ctcagaatga cttggttgag tactcaccag    4440
tcacagaaaa gcatcttacg gatggcatga cagtaagaga attatgcagt gctgccataa    4500
ccatgagtga taacactgcg gccaacttac ttctgacaac gatcggagga ccgaaggagc    4560
taaccgcttt tttgcacaac atgggggatc atgtaactcg ccttgatcgt tgggaaccgg    4620
agctgaatga agccatacca aacgacgagc gtgacaccac gatgcctgta gcaatggcaa    4680
caacgttgcg caaactatta actggcgaac tacttactct agcttcccgg caacaattaa    4740
tagactggat ggaggcggat aaagttgcag gaccacttct gcgctcggcc cttccggctg    4800
gctggtttat tgctgataaa tctggagccg gtgagcgtgg gtctcgcggt atcattgcag    4860
cactggggcc agatggtaag ccctcccgta tcgtagttat ctacacgacg gggagtcagg    4920
caactatgga tgaacgaaat agacagatcg ctgagatagg tgcctcactg attaagcatt    4980
ggtaactgtc agaccaagtt tactcatata ctttagat tgatttaaaa cttcattttt    5040
aatttaaaag gatctaggtg aagatccttt ttgataatct catgaccaaa atcccttaac    5100
gtgagttttc gttccactga gcgtcagacc ccgtagaaaa gatcaaagga tcttcttgag    5160
atcctttttt tctgcgcgta atctgctgct tgcaaacaaa aaaaccaccg ctaccagcgg    5220
tggtttgttt gccggatcaa gagctaccaa ctctttttcc gaaggtaact ggcttcagca    5280
gagcgcagat accaaatact gttcttctag tgtagccgta gttaggccac cacttcaaga    5340
actctgtagc accgcctaca tacctcgctc tgctaatcct gttaccagtg gctgctgcca    5400
gtggcgataa gtcgtgtctt accgggttgg actcaagacg atagttaccg gataaggcgc    5460
agcggtcggg ctgaacgggg ggttcgtgca cacagcccag cttggagcga acgacctaca    5520
ccgaactgag atacctacag cgtgagctat gagaaagcgc cacgcttccc gaagggagaa    5580
aggcggacag gtatccggta agcggcaggg tcggaacagg agagcgcacg agggagcttc    5640 caggggggaaa cgcctggtat ctttatagtc ctgtcgggtt tcgccacctc tgacttgagc    5700
gtcgattttt gtgatgctcg tcagggggc ggagcctatg gaaaaacgcc agcaacgcgg    5760 ccttttttacg gttcctggcc ttttgctggc cttttgctca catgttcttt cctgcgttat    5820
cccctgattc tgtggataac cgtattaccg cctttgagtg agctgatacc gctcgccgca    5880
gccgaacgac cgagcgcagc gagtcagtga gcgaggaagc ggaagagcgc ccaatacgca    5940
aaccgcctct ccccgcgcgt tggccgattc attaatgcag ctggcacgac tagagtcccg    6000
ctgaggcggc gtagcaggtc agccgcccca gcggtggtca ccaaccgggg tggaacggcg    6060
ccggtatcgg gtgtgtccgt ggcgctcatt ccaacctccg tgtgtttgtg caggtttcgc    6120
gtgttgcagt ccctcgcacc ggcacccgca gcgagggggct cacgggtgcc ggtgggtcga    6180
ctagttcagt gatggtgatg gtgatgctcg agagatctaa gcttggatcc gcggccgcta    6240
cgtagaattc ccatggcgtg atggtgatgg tgatggccca tatgtatatc tccttcttaa    6300
agttaaacaa aattatttct agacgccgtc cacgctgcct cctcacgtga cgtgaggtgc    6360
aagcccggac gttccgcgtg ccacgccgtg agccgccgcg tgccgtcggc tccctcagcc    6420
```

```
cgggcggccg tgggagcccg cctcgatatg tacaagcatg gggactcgcc gcggactagc    6480
ggcttcccga cacgccgtac tgaccagcag atcagcgata aacgctgttt ctgctggtta    6540
agtggataaa aaccaaataa tcgatgaacc tcgaagtgga gtatccgagc tgaactagct    6600
ggatttactc cgaaaatacg agcggcgacg aagggtgttg gaccaccctg ccgccgcctt    6660
cgaggctcct acttgactag gaccccgctc gttatgacca gcgtaagtgc tgaacacctt    6720
tccggcaaag accggccccc tgtcctcgtg tcgtccgata agcgcggcat ccggcacgaa    6780
cttcgaccca aacttcaaca aatcaccacg tcagaaactt ttaatgcgtg cggccggccg    6840
atttccggcg tgaacggtgt gaccatcgtc aacggtccca aaggttccgg atttggaggc    6900
cttcgctcct gcggaaaggg ctggatctgc ccctgctgtg cgggaaaagt cggcgcacat    6960
cgagcagacg aaatttctca agttgttgct catcaactcg ggactggatc tgttgcgatg    7020
gtgaccatga ccatgcgcca taccgctggg cagcgtttgc atgatttgtg gactggactt    7080
tcggcagcct ggaaagctgc gaccaatggc cgccgatggc gtaccgaacg tgaaatgtac    7140
ggctgcgacg gatacgtacg agctgttgaa atcactcacg gaaaaaacgg ttggcacgtt    7200
cacgtccacg ctctactcat gttcagcggt gacgtgagtg agaacatcct cgaatccttc    7260
tcggatgcga tgttcgatcg gtggacctcc aaactcgtgt ctctgggatt tgctgcgcca    7320
ctacgtaatt caggtggact cgacgtaaga aagattggtg gagaagctga ccaagttctc    7380
gctgcatacc tgacgaaaat tgcatccggg gtcggcatgg aagtcggcag tggcgacgga    7440
aaaagtggtc ggcacggcaa ccgtgcacct tgggaaatcg ccgttgatgc agtcggagga    7500
gatccacaag cgttggaact ctggcgcgag tttgagttcg gttcgatggg acgccgagca    7560
atcgcatggt ctcgtggact gcgcgcccga gctggtcttg gctagaaact cacggatgct    7620
cagattgtcg aacaggaaga atctgccccg gtcatggttg cgatcattcc ggctcggtcc    7680
tggatgatga ttcggaactg tgcgccttac gttttcggag agatccttgg actcgtggaa    7740
gcgggcgcga cctgggaaaa ccttcgtgac cacttgcatt atcgattgcc tgcagcggat    7800
gtgcggcctc cgataatatc gattcgtaag tgaaatgtct tggtgtgcaa caactttcac    7860
tcgtatgaac cacacttgag ggcatccccc cgatacttgc cgctttgaag ctgggtgtct    7920
ctctgtcagg gctgcgatag caccgcgtag cggcttggcc ttgacagaga gacggcctgt    7980
ttcatggttg gtctcggggg gctgaccggg cagatagaaa aaggccggcc gatttggctg    8040
ccgactattt ttgcaggtaa acccatctca tgagcatcaa tgaacgtccc gttggtatcg    8100
cagcgaatgc agcttcggta gacgtcgatg gcgttgtgat gggtgtgtat ctctcgcttt    8160
atgggcaaga aatcacgcta gatcgagatg atgcgttcct actcctcgat cgacttcagg    8220
acgcgttgcg acctcaagcc aactaagaac cctccagatg gtctaaacga ggcgcaaact    8280
cgctcctggg cctgcgggcg gagcaccgaa gcgcgagcga agcggagcgc gtaggtgggg    8340
gagcctgcgg gcagcggcgg cggagccgcc gccttggtaa taggtgatca tcggggccat    8400
agcaggtcag aggatgtttt tacgatgact catgctcacc acgccaagta ctgatg        8456
```

<210> SEQ ID NO 99  
<211> LENGTH: 5984  
<212> TYPE: DNA  
<213> ORGANISM: Artificial Sequence  
<220> FEATURE:  
<223> OTHER INFORMATION: Description of Artificial Sequence: Synthetic vector pNit-QT1 sequence

<400> SEQUENCE: 99

```
gttaactaga gtaacgggct actccgttta acggaccccg ttctcacgct ttaggcttga    60
ccccggagcc tgcatggggc attccgccgt gaacccggtg gaatgccccc ggcacccggg   120
ctttccagca agatcacct ggcgccgatg agtaaggcgt acagaaccac tccacaggag    180
gaccgtcgag atgaaatcta acaatgcgct catcgtcatc ctcggcaccg tcaccctgga   240
tgctgtaggc ataggcttgg ttatgccggt actgccgggc ctcttgcggg atatcgtcca   300
ttccgacagc atcgccagtc actatggcgt gctgctagcg ctatatgcgt tgatgcaatt   360
tctatgcgca cccgttctcg gagcactgtc cgaccgcttt ggccgccgcc cagtcctgct   420
cgcttcgcta cttggagcca ctatcgacta cgcgatcatg cgaccacac ccgtcctgtg    480 gattctctac gccggacgca tcgtggccgg catcaccggc gccacaggtg cggttgctgg   540
cgcctatatc gccgacatca ccgatgggga agatcgggct cgccacttcg ggctcatgag   600
cgcttgtttc ggcgtgggta tggtggcagg ccccgtggcc gggggactgt tgggcgccat   660
ctccttgcat gcaccattcc ttgcggcggc ggtgctcaac ggcctcaacc tactactggg   720
ctgcttccta atgcaggagt cgcataaggg agagcgtcgt ccgatgccct tgagagcctt   780
caacccagtc agctccttcc ggtgggcgcg ggcatgact atcgtcgccg cacttatgac    840
tgtcttcttt atcatgcaac tcgtaggaca ggtgccggca gcgctctggg tcattttcgg   900
cgaggaccgc tttcgctgga gcgcgacgat gatcggcctg tcgcttgcgg tattcggaat   960
cttgcacgcc ctcgctcaag ccttcgtcac tggtcccgcc accaaacgtt tcggcgagaa  1020
gcaggccatt atcgccggca tggcggccga cgcgctgggc tacgtcttgc tggcgttcgc  1080
gacgcgaggc tggatggcct tccccattat gattcttctc gcttccggcg gcatcgggat  1140
gcccgcgttg caggccatgc tgtccaggca ggtagatgac gaccatcagg acagcttca   1200 aggatcgctc gcggctctta ccagcctaac ttcgatcatt ggaccgctga tcgtcacggc  1260
gatttatgcc gcctcggcga gcacatggaa cgggttggca tggattgtag cgccgccct   1320 ataccttgtc tgcctccccg cgttgcgtcg cggtgcatgg agccgggcca cctcgacctg  1380
aatggaagcc ggcggcacct cgctaacgga ttcaccactc caagaattgg agccaatcaa  1440
ttcttgcgga gaactgtgaa tgcgcaaacc aaccctggc agaacatatc catcgcgtcc   1500
gccatctcca gcagccgcac gcggcgcatc tcgggcagcg ttgggtcctg ccacgggtg   1560 cgcatgatcg tgctcctgtc gttgaggtac cgagctcgtc aggtggcact tttcggggaa  1620
atgtgcgcgg aaccctatt tgtttatttt tctaaataca ttcaaatatg tatccgctca   1680
tgagacaata accctgataa atgcttcaat aatattgaaa aaggaagagt atgagtattc   1740
aacatttccg tgtcgccctt attccttttt tgcggcatt ttgccttcct gtttttgctc    1800
acccagaaac gctggtgaaa gtaaaagatg ctgaagatca gttgggtgca cgagtgggtt  1860
acatcgaact ggatctcaac agcggtaaga tccttgagag ttttcgcccc gaagaacgtt  1920
ttccaatgat gagcactttt aaagttctgc tatgtggcgc ggtattatcc cgtattgacg  1980
ccgggcaaga gcaactcggt cgccgcatac actattctca gaatgacttg gttgagtact  2040
caccagtcac agaaaagcat cttacggatg gcatgacagt aagagaatta tgcagtgctg  2100
ccataaccat gagtgataac actgcggcca acttacttct gacaacgatc ggaggaccga  2160
aggagctaac cgcttttttg cacaacatgg ggatcatgt aactcgcctt gatcgttggg   2220
aaccggagct gaatgaagcc ataccaaacg acgagcgtga ccacgatg cctgtagcaa    2280 tggcaacaac gttgcgcaaa ctattaactg gcgaactact tactctagct tcccggcaac  2340
aattaataga ctggatggag gcggataaag ttgcaggacc acttctgcgc tcggcccttc  2400
```

-continued

```
cggctggctg gtttattgct gataaatctg gagccggtga gcgtgggtct cgcggtatca    2460
ttgcagcact ggggccagat ggtaagccct cccgtatcgt agttatctac acgacgggga    2520
gtcaggcaac tatggatgaa cgaaatagac agatcgctga gataggtgcc tcactgatta    2580
agcattggta actgtcagac caagtttact catatatact ttagattgat ttaaaacttc    2640
atttttaatt taaaaggatc taggtgaaga tccttttga taatctcatg accaaaatcc     2700
cttaacgtga gttttcgttc cactgagcgt cagaccccgt agaaaagatc aaaggatctt    2760
cttgagatcc ttttttctg cgcgtaatct gctgcttgca acaaaaaaa ccaccgctac      2820 cagcggtggt ttgtttgccg gatcaagagc taccaactct ttttccgaag gtaactggct    2880
tcagcagagc gcagatacca aatactgttc ttctagtgta gccgtagtta ggccaccact    2940
tcaagaactc tgtagcaccg cctacatacc tcgctctgct aatcctgtta ccagtggctg    3000
ctgccagtgg cgataagtcg tgtcttaccg ggttggactc aagacgatag ttaccggata    3060
aggcgcagcg gtcgggctga acggggggtt cgtgcacaca gcccagcttg gagcgaacga    3120
cctacaccga actgagatac ctacagcgtg agctatgaga aagcgccacg cttcccgaag    3180
ggagaaaggc ggacaggtat ccggtaagcg gcagggtcgg aacaggagag cgcacgaggg    3240
agcttccagg gggaaacgcc tggtatcttt atagtcctgt cgggtttcgc cacctctgac    3300
ttgagcgtcg attttgtga tgctcgtcag ggggcggag cctatggaaa aacgccagca     3360
acgcggcctt tttacggttc ctggcctttt gctggccttt tgctcacatg ttctttcctg    3420
cgttatcccc tgattctgtg gataaccgta ttaccgcctt tgagtgagct gataccgctc    3480
gccgcagccg aacgaccgag cgcagcgagt cagtgagcga ggaagcggaa gagcgcccaa    3540
tacgcaaacc gcctctcccc gcgcgttggc cgattcatta atgcagctgg cacgactaga    3600
gtcccgctga ggcggcgtag caggtcagcc gccccagcgg tggtcaccaa ccggggtgga    3660
acggcgccgg tatcgggtgt gtccgtggcg ctcattccaa cctccgtgtg tttgtgcagg    3720
tttcgcgtgt tgcagtccct cgcaccggca cccgcagcga ggggctcacg ggtgccggtg    3780
ggtcgactag ttcagtgatg gtgatggtga tgctcgagag atctaagctt ggatccgcgg    3840
ccgctacgta gaattcccat atggtgatgg tgatggtggc ccatggtata tctccttctt    3900
aaagttaaac aaaattattt ctagacgccg tccattatac ctcctcacgt gacgtgaggt    3960
gcaagcccgg acgttccgcg tgccacgccg tgagccgccg cgtgccgtcg gctccctcag    4020
cccgggcggc cgtgggagcc cgcctcgata tgtacacccg agaagctccc agcgtcctcc    4080
tgggccgcga tactcgacca ccacgcacgc acccgcact aacgattcgg ccggcgctcg     4140
attcggccgg cgctcgattc ggccggcgct cgattcggcc ggcgtcgat tcggccggcg     4200 ctcgattcgg ccgagcagaa gagtgaacaa ccaccgacca cgcttccgct ctgcgcgccg    4260
tacccgacct acctcccgca gctcgaagca gctcccggga gtaccgccgt actcacccgc    4320
ctgtgctcac catccaccga cgcaaagccc aacccgagca cacctcttgc accaaggtgc    4380
cgaccgtggc tttccgctcg cagggttcca gaagaaatcg aacgatccag cgcggcaagg    4440
ttcaaaaagc aggggttggt ggggaggagg ttttgggggg tgtcgccggg atacctgata    4500
tggctttgtt ttgcgtagtc gaataatttt ccatatagcc tcggcgcgtc ggactcgaat    4560
agttgatgtg ggcgggcaca gttgccccat gaaatccgca acgggggcg tgctgagcga    4620 tcggcaatgg gcggatgcgg tgttgcttcc gcaccggccg ttcgcgacga acaacctcca    4680
acgaggtcag taccggatga gccgcgacga cgcattggca atgcggtacg tcgagcattc    4740
```

```
accgcacgcg ttgctcggat ctatcgtcat cgactgcgat cacgttgacg ccgcgatgcg    4800
cgcattcgag caaccatccg accatccggc gccgaactgg gtcgcacaat cgccgtccgg    4860
ccgcgcacac atcggatggt ggctcggccc caaccacgtg tgccgcaccg acagcgcccg    4920
actgacgcca ctgcgctacg cccaccgcat cgaaaccggc ctcaagatca gcgtcggcgg    4980
cgatttcgcg tatggcgggc aactgaccaa aaacccgatt caccccgatt gggagacgat    5040
ctacggcccg gccaccccgt acacattgcg gcagctggcc accatccaca caccccggca    5100
gatgccgcgt cggcccgatc gggccgtggg cctggccgc aacgtcacca tgttcgacgc    5160
cacccggcga tgggcatacc cgcagtggtg gcaacaccga aacggaaccg gccgcgactg    5220
ggaccatctc gtcctgcagc actgccacgc cgtcaacacc gagttcacga caccactgcc    5280
gttcaccgaa gtacgcgcca ccgcgcaatc catctccaaa tggatctggc gcaatttcac    5340
cgaagaacag taccgagccc gacaagcgca tctcggtcaa aaaggcggca aggcaacgac    5400
actcgccaaa caagaagccg tccgaaacaa tgcaagaaag tacgacgaac atacgatgcg    5460
agaggcgatt atctgatggg cggagccaaa atccggtgc gccgaaagat gacggcagca    5520
gcagcagccg aaaaattcgg tgcctccact cgcacaatcc aacgcttgtt tgctgagccg    5580
cgtgacgatt acctcggccg tgcgaaagct cgccgtgaca agctgtcga gctgcggaag    5640 caggggttga agtaccggga aatcgccgaa gcgatgaac tctcgaccgg gatcgtcggc    5700
cgattactgc acgacgcccg caggcacggc gagatttcag cggaggatct gtcggcgtaa    5760
ccaagtcagc gggttgtcgg gttccggccg gcgctcggca ctcggaccgg ccggcggatg    5820
gtgttctgcc tctggcgcag cgtcagctac cgccgaaggc ctgtcatcga ccggcttcga    5880
ctgaagtatg agcaacgtca cagcctgtga ttggatgatc cgctcacgct cgaccgctac    5940
ctgttcagct gccgcccgct gggcatgagc aacggccaac tctc                     5984
```

<210> SEQ ID NO 100
<211> LENGTH: 5988
<212> TYPE: DNA
<213> ORGANISM: Artificial Sequence
<220> FEATURE:
<223> OTHER INFORMATION: Description of Artificial Sequence: Synthetic vector pNit-QT2 sequence

<400> SEQUENCE: 100

```
gttaactaga gtaacgggct actccgttta acggaccccg ttctcacgct ttaggcttga      60 cccccggagcc tgcatggggc attccgccgt gaacccggtg gaatgccccc ggcacccggg    120
ctttccagca aagatcacct ggcgccgatg agtaaggcgt acagaaccac tccacaggag    180
gaccgtcgag atgaaatcta acaatgcgct catcgtcatc ctcggcaccg tcaccctgga    240
tgctgtaggc ataggcttgg ttatgccggt actgccgggc ctcttgcggg atatcgtcca    300
ttccgacagc atcgccagtc actatggcgt gctgctagcg ctatatgcgt tgatgcaatt    360
tctatgcgca cccgttctcg gagcactgtc cgaccgcttt ggccgccgcc cagtcctgct    420
cgcttcgcta cttggagcca ctatcgacta cgcgatcatg gcgaccacac ccgtcctgtg    480
gattctctac gccggacgca tcgtggccgg catcaccggc gccacaggtg cggttgctgg    540
cgcctatatc gccgacatca ccgatgggga agatcgggct cgccacttcg ggctcatgag    600
cgcttgtttc ggcgtgggta tggtggcagg ccccgtggcc gggggactgt tgggcgccat    660
ctccttgcat gcaccattcc ttgcggcggc ggtgctcaac ggcctcaacc tactactggg    720
ctgcttccta atgcaggagt cgcataaggg agagcgtcgt ccgatgccct tgagagcctt    780
```

```
caacccagtc agctccttcc ggtgggcgcg gggcatgact atcgtcgccg cacttatgac    840
tgtcttcttt atcatgcaac tcgtaggaca ggtgccggca gcgctctggg tcattttcgg    900
cgaggaccgc tttcgctgga gcgcgacgat gatcggcctg tcgcttgcgg tattcggaat    960
cttgcacgcc ctcgctcaag ccttcgtcac tggtcccgcc accaaacgtt tcggcgagaa   1020
gcaggccatt atcgccggca tggcggccga cgcgctgggc tacgtcttgc tggcgttcgc   1080
gacgcgaggc tggatggcct tccccattat gattcttctc gcttccggcg catcgggat    1140
gcccgcgttg caggccatgc tgtccaggca ggtagatgac gaccatcagg gacagcttca   1200
aggatcgctc gcggctctta ccagcctaac ttcgatcatt ggaccgctga tcgtcacggc   1260
gatttatgcc gcctcggcga gcacatggaa cgggttggca tggattgtag gcgccgccct   1320
ataccttgtc tgcctccccg cgttgcgtcg cggtgcatgg agccgggcca cctcgacctg   1380
aatggaagcc ggcggcacct cgctaacgga ttcaccactc aagaattgg  agccaatcaa   1440
ttcttgcgga gaactgtgaa tgcgcaaacc aaccccttggc agaacatatc catcgcgtcc   1500
gccatctcca gcagccgcac gcggcgcatc tcgggcagcg ttgggtcctg ccacgggtg    1560
cgcatgatcg tgctcctgtc gttgaggtac cgagctcgtc aggtggcact tttcggggaa   1620
atgtgcgcgg aacccctatt tgtttatttt tctaaataca ttcaaatatg tatccgctca   1680
tgagacaata accctgataa atgcttcaat aatattgaaa aaggaagagt atgagtattc   1740
aacatttccg tgtcgccctt attccttttt ttgcggcatt ttgccttcct gttttttgctc   1800
acccagaaac gctggtgaaa gtaaaagatg ctgaagatca gttgggtgca cgagtgggtt   1860
acatcgaact ggatctcaac agcggtaaga tccttgagag ttttcgcccc gaagaacgtt   1920
ttccaatgat gagcactttt aaagttctgc tatgtggcgc ggtattatcc cgtattgacg   1980
ccgggcaaga gcaactcggt cgccgcatac actattctca gaatgacttg gttgagtact   2040
caccagtcac agaaaagcat cttacggatg gcatgacagt aagagaatta tgcagtgctg   2100
ccataaccat gagtgataac actgcggcca acttacttct gacaacgatc ggaggaccga   2160
aggagctaac cgcttttttg cacaacatgg gggatcatgt aactcgcctt gatcgttggg   2220
aaccggagct gaatgaagcc ataccaaacg acgagcgtga ccacgatgt  cctgtagcaa   2280
tggcaacaac gttgcgcaaa ctattaactg gcgaactact tactctagct tcccggcaac   2340
aattaataga ctggatggag gcggataaag ttgcaggacc acttctgcgc tcggcccttc   2400
cggctggctg gtttattgct gataaatctg gagccggtga gcgtgggtct cgcggtatca   2460
ttgcagcact ggggccagat ggtaagccct cccgtatcgt agttatctac acgacgggga   2520
gtcaggcaac tatggatgaa cgaaatagac agatcgctga gataggtgcc tcactgatta   2580
agcattggta actgtcagac caagtttact catatatact ttagattgat ttaaaacttc   2640
atttttaatt taaaaggatc taggtgaaga tccttttttga taatctcatg accaaaatcc   2700
cttaacgtga gttttcgttc cactgagcgt cagaccccgt agaaaagatc aaaggatctt   2760
cttgagatcc ttttttttctg cgcgtaatct gctgcttgca acaaaaaaa  ccaccgctac   2820
cagcggtggt ttgtttgccg gatcaagagc taccaactct ttttccgaag gtaactggct   2880
tcagcagagc gcagatacca aatactgttc ttctagtgta gccgtagtta ggccaccact   2940
tcaagaactc tgtagcaccg cctacatacc tcgctctgct aatcctgtta ccagtggctg   3000
ctgccagtgg cgataagtcg tgtcttaccg ggttggactc aagacgatag ttaccggata   3060
aggcgcagcg gtcgggctga acggggggtt cgtgcacaca gcccagcttg gagcgaacga   3120
cctacaccga actgagatac ctacagcgtg agctatgaga aagcgccacg cttcccgaag   3180
```

```
ggagaaaggc ggacaggtat ccggtaagcg gcagggtcgg aacaggagag cgcacgaggg      3240
agcttccagg gggaaacgcc tggtatcttt atagtcctgt cgggtttcgc cacctctgac      3300
ttgagcgtcg atttttgtga tgctcgtcag ggggcggag cctatggaaa acgccagca       3360 acgcggcctt tttacggttc ctggcctttt gctggccttt tgctcacatg ttctttcctg     3420
cgttatcccc tgattctgtg gataaccgta ttaccgcctt tgagtgagct gataccgctc     3480
gccgcagccg aacgaccgag cgcagcgagt cagtgagcga ggaagcggaa gagcgcccaa     3540
tacgcaaacc gcctctcccc gcgcgttggc cgattcatta atgcagctgg cacgactaga     3600
gtcccgctga ggcggcgtag caggtcagcc gccccagcgg tggtcaccaa ccggggtgga     3660
acggcgccgg tatcggtgt gtccgtggcg ctcattccaa cctccgtgtg tttgtgcagg      3720
tttcgcgtgt tgcagtccct cgcaccggca cccgcagcga ggggctcacg ggtgccggtg     3780
ggtcgactag ttcagtgatg gtgatggtga tgctcgagag atctaagctt ggatccgcgg     3840
ccgctacgta gaattcccat ggcgtgatgg tgatggtgat ggcccatatg tatatctcct     3900
tcttaaagtt aaacaaaatt atttctagac gccgtccatt atacctcctc acgtgacgtg     3960
aggtgcaagc ccgacgttc cgcgtgccac gccgtgagcc gccgcgtgcc gtcggctccc      4020
tcagcccggg cggccgtggg agcccgcctc gatatgtaca cccgagaagc tcccagcgtc     4080
ctcctgggcc gcgatactcg accaccacgc acgcacaccg cactaacgat tcggccggcg     4140
ctcgattcgg ccggcgctcg attcggccgg cgctcgattc ggccggcgct cgattcggcc     4200
ggcgctcgat tcgccgagc agaagagtga acaaccaccg accacgcttc cgctctgcgc     4260
gccgtacccg acctacctcc cgcagctcga agcagctccc gggagtaccg ccgtactcac     4320
ccgcctgtgc tcaccatcca ccgacgcaaa gcccaacccg agcacacctc ttgcaccaag     4380
gtgccgaccg tggctttccg ctcgcagggt tccagaagaa atcgaacgat ccagcgcggc     4440
aaggttcaaa aagcagggt tggtggggag gaggttttgg ggggtgtcgc cgggatacct     4500
gatatggctt tgttttgcgt agtcgaataa ttttccatat agcctcggcg cgtcggactc     4560
gaatagttga tgtgggcggg cacagttgcc ccatgaaatc cgcaacgggg ggcgtgctga     4620
gcgatcggca atgggcggat gcggtgttgc ttccgcaccg gccgttcgcg acgaacaacc     4680
tccaacgagg tcagtaccgg atgagccgcg acgacgcatt ggcaatgcgg tacgtcgagc     4740
attcaccgca cgcgttgctc ggatctatcg tcatcgactg cgatcacgtt gacgccgcga     4800
tgcgcgcatt cgagcaacca tccgaccatc cggcgccgaa ctgggtcgca caatcgccgt     4860
ccggccgcgc acacatcgga tggtggctcg gccccaacca cgtgtgccgc accgacagcg     4920
cccgactgac gccactgcgc tacgcccacc gcatcgaaac cggcctcaag atcagcgtcg     4980
gcggcgattt cgcgtatggc gggcaactga ccaaaaaccc gattcacccc gattgggaga     5040
cgatctacgg cccggccacc ccgtacacat tgccggcagct ggccaccatc cacacacccc    5100
ggcagatgcc gcgtcggccc gatcgggccg tgggcctggg ccgcaacgtc accatgttcg     5160
acgccacccg gcgatgggca tacccgcagt ggtggcaaca ccgaaacgga accggccgcg     5220
actgggacca tctcgtcctg cagcactgcc acgccgtcaa caccgagttc acgacaccac     5280
tgccgttcac cgaagtacgc gccaccgcgc aatccatctc caaatggatc tggcgcaatt     5340
tcaccgaaga acagtaccga gcccgacaag cgcatctcgg tcaaaaggc ggcaaggcaa      5400 cgacactcgc caaacaagaa gccgtccgaa acaatgcaag aaagtacgac gaacatacga     5460
tgcgagaggc gattatctga tgggcggagc caaaaatccg gtgcgccgaa agatgacggc     5520
```

```
agcagcagca gccgaaaaat tcggtgcctc cactcgcaca atccaacgct tgtttgctga    5580
gccgcgtgac gattacctcg gccgtgcgaa agctcgccgt gacaaagctg tcgagctgcg    5640
gaagcagggg ttgaagtacc gggaaatcgc cgaagcgatg gaactctcga ccgggatcgt    5700
cggccgatta ctgcacgacg cccgcaggca cggcgagatt tcagcggagg atctgtcggc    5760
gtaaccaagt cagcgggttg tcgggttccg gccggcgctc ggcactcgga ccggccggcg    5820
gatggtgttc tgcctctggc gcagcgtcag ctaccgccga aggcctgtca tcgaccggct    5880
tcgactgaag tatgagcaac gtcacagcct gtgattggat gatccgctca cgctcgaccg    5940
ctacctgttc agctgccgcc cgctgggcat gagcaacggc caactctc                 5988
```

<210> SEQ ID NO 101
<211> LENGTH: 6058
<212> TYPE: DNA
<213> ORGANISM: Artificial Sequence
<220> FEATURE:
<223> OTHER INFORMATION: Description of Artificial Sequence: Synthetic
      vector pNit-RT1 sequence

<400> SEQUENCE: 101

```
gttaactaga gtaacgggct actccgttta acggaccccg ttctcacgct ttaggcttga      60
ccccggagcc tgcatggggc attccgccgt gaacccggtg gaatgccccc ggcacccggg     120
ctttccagca aagatcacct ggcgccgatg agtaaggcgt acagaaccac tccacaggag     180
gaccgtcgag atgaaatcta acaatgcgct catcgtcatc ctcggcaccg tcaccctgga     240
tgctgtaggc ataggcttgg ttatgccggt actgccgggc tcttgcgggg atatcgtcca     300
ttccgacagc atcgccagtc actatggcgt gctgctagcg ctatatgcgt tgatgcaatt     360
tctatgcgca cccgttctcg gagcactgtc cgaccgcttt ggccgccgcc cagtcctgct     420
cgcttcgcta cttggagcca ctatcgacta cgcgatcatg gcgaccacac ccgtcctgtg     480
gattctctac gccggacgca tcgtggccgg catcaccggc gccacaggtg cggttgctgg     540
cgcctatatc gccgacatca ccgatgggga agatcgggct cgccacttcg gctcatgag      600 cgcttgtttc ggcgtgggta tggtggcagg ccccgtggcc gggggactgt gggcgccat      660 ctccttgcat gcaccattcc ttgcggcggc ggtgctcaac ggcctcaacc tactactggg    720
ctgcttccta atgcaggagt cgcataaggg agagcgtcgt ccgatgccct tgagagcctt    780
caacccagtc agctccttcc ggtgggcgcg gggcatgact atcgtcgccg cacttatgac    840
tgtcttcttt atcatgcaac tcgtaggaca ggtgccggca gcgctctggg tcattttcgg    900
cgaggaccgc tttcgctgga gcgcgacgat gatcggcctg tcgcttgcgg tattcggaat    960
cttgcacgcc ctcgctcaag ccttcgtcac tggtcccgcc accaaacgtt tcggcgagaa   1020
gcaggccatt atcgccggca tggcggccga cgcgctgggc tacgtcttgc tggcgttcgc   1080
gacgcgaggc tggatggcct tccccattat gattcttctc gcttccggcg gcatcgggat   1140
gcccgcgttg caggccatgc tgtccaggca ggtagatgac gaccatcagg gacagcttca   1200
aggatcgctc gcggctctta ccagcctaac ttcgatcatt ggaccgctga tcgtcacggc   1260
gatttatgcc gcctcggcga gcacatggaa cgggttggca tggattgtag gcgccgccct   1320
ataccttgtc tgcctccccg cgttgcgtcg cggtgcatgg agccgggcca cctcgacctg   1380
aatggaagcc ggcggcacct cgctaacgga ttcaccactc caagaattgg agccaatcaa   1440
ttcttgcgga gaactgtgaa tgcgcaaacc aaccccttgc agaacatatc catcgcgtcc   1500
gccatctcca gcagccgcac gcggcgcatc tcgggcagcg ttgggtcctg gccacggggtg   1560
```

```
cgcatgatcg tgctcctgtc gttgaggtac cgagctcgtc aggtggcact tttcggggaa    1620
atgtgcgcgg aacccctatt tgtttatttt tctaaataca ttcaaatatg tatccgctca    1680
tgagacaata accctgataa atgcttcaat aatattgaaa aaggaagagt atgagtattc    1740
aacatttccg tgtcgccctt attccctttt ttgcggcatt ttgccttcct gttttttgctc   1800 acccagaaac gctggtgaaa gtaaaagatg ctgaagatca gttgggtgca cgagtgggtt    1860
acatcgaact ggatctcaac agcggtaaga tccttgagag ttttcgcccc gaagaacgtt    1920
ttccaatgat gagcactttt aaagttctgc tatgtggcgc ggtattatcc cgtattgacg    1980
ccgggcaaga gcaactcggt cgccgcatac actattctca gaatgacttg gttgagtact    2040
caccagtcac agaaaagcat cttacggatg gcatgacagt aagagaatta tgcagtgctg    2100
ccataaccat gagtgataac actgcggcca acttacttct gacaacgatc ggaggaccga    2160
aggagctaac cgcttttttg cacaacatgg gggatcatgt aactcgcctt gatcgttggg    2220
aaccggagct gaatgaagcc ataccaaacg acgagcgtga caccacgatg cctgtagcaa    2280
tggcaacaac gttgcgcaaa ctattaactg gcgaactact tactctagct tcccggcaac    2340
aattaataga ctggatggag gcggataaag ttgcaggacc acttctgcgc tcggcccttc    2400
cggctggctg gtttattgct gataaatctg gagccggtga gcgtgggtct cgcggtatca    2460
ttgcagcact ggggccagat ggtaagccct cccgtatcgt agttatctac acgacgggga    2520
gtcaggcaac tatggatgaa cgaaatagac agatcgctga gataggtgcc tcactgatta    2580
agcattggta actgtcagac caagtttact catatatact ttagattgat ttaaaacttc    2640
atttttaatt taaaaggatc taggtgaaga tcctttttga taatctcatg accaaaatcc    2700
cttaacgtga gttttcgttc cactgagcgt cagaccccgt agaaaagatc aaaggatctt    2760
cttgagatcc ttttttttctg cgcgtaatct gctgcttgca acaaaaaaaa ccaccgctac    2820
cagcggtggt ttgtttgccg gatcaagagc taccaactct ttttccgaag gtaactggct    2880
tcagcagagc gcagatacca aatactgttc ttctagtgta gccgtagtta ggccaccact    2940
tcaagaactc tgtagcaccg cctacatacc tcgctctgct aatcctgtta ccagtggctg    3000
ctgccagtgg cgataagtcg tgtcttaccg ggttggactc aagacgatag ttaccggata    3060
aggcgcagcg gtcgggctga acggggggtt cgtgcacaca gcccagcttg gagcgaacga    3120
cctacaccga actgagatac ctacagcgtg agctatgaga aagcgccacg cttcccgaag    3180
ggagaaaggc ggacaggtat ccggtaagcg gcagggtcgg aacaggagag cgcacgaggg    3240
agcttccagg gggaaacgcc tggtatcttt atagtcctgt cgggtttcgc cacctctgac    3300
ttgagcgtcg atttttgtga tgctcgtcag ggggcggag cctatggaaa aacgccagca    3360
acgcggcctt tttacggttc ctggcctttt gctggccttt tgctcacatg ttctttcctg    3420
cgttatcccc tgattctgtg ataaccgta ttaccgcctt tgagtgagct gataccgctc     3480
gccgcagccg aacgaccgag cgcagcgagt cagtgagcga ggaagcggaa gagcgcccaa    3540
tacgcaaacc gcctctcccc gcgcgttggc cgattcatta atgcagctgg cacgactaga    3600
gtcccgctga gcggcgtag caggtcagcc gccccagcgg tggtcaccaa ccggggtgga     3660
acggcgccgg tatcgggtgt gtccgtggcg ctcattccaa cctccgtgtg tttgtgcagg    3720
tttcgcgtgt tgcagtccct cgcaccggca cccgcagcga ggggctcacg ggtgccggtg    3780
ggtcgactag ttcagtgatg gtgatggtga tgctcgagag atctaagctt ggatccgcgg    3840
ccgctacgta gaattcccat atggtgatgg tgatggtggc ccatggtata tctccttctt    3900
aaagttaaac aaaattattt ctagacgccg tccattatac ctcctcacgt gacgtgaggt    3960
```

```
gcaagcccgg acgttccgcg tgccacgccg tgagccgccg cgtgccgtcg gctccctcag    4020
cccgggcggc cgtgggagcc cgcctcgata tgtacaagca tggggactcg ccgcggacta    4080
gcggcttccc gacacgccgt actgaccagc agatcagcga taaacgctgt ttctgctggt    4140
taagtggata aaaaccaaat aatcgatgaa cctcgaagtg gagtatccga gctgaactag    4200
ctggatttac tccgaaaata cgagcggcga cgaagggtgt tggaccaccc tgccgccgcc    4260
ttcgaggctc ctacttgact aggaccccgc tcgttatgac cagcgtaagt gctgaacacc    4320
tttccggcaa agaccggccc cctgtcctcg tgtcgtccga taagcgcggc atccggcacg    4380
aacttcgacc caaacttcaa caaatcacca cgtcagaaac ttttaatgcg tgcggccggc    4440
cgatttccgg cgtgaacggt gtgaccatcg tcaacggtcc caaaggttcc ggatttggag    4500
gccttcgctc ctgcggaaag gctggatct gccctgctg tgcgggaaaa gtcggcgcac    4560
atcgagcaga cgaaatttct caagttgttg ctcatcaact cgggactgga tctgttgcga    4620
tggtgaccat gaccatgcgc ataccgctg gcagcgttt gcatgatttg tggactggac    4680
tttcggcagc ctggaaagct gcgaccaatg gccgccgatg gcgtaccgaa cgtgaaatgt    4740
acggctgcga cggatacgta cgagctgttg aaatcactca cggaaaaaac ggttggcacg    4800
ttcacgtcca cgctctactc atgttcagcg gtgacgtgag tgagaacatc ctcgaatcct    4860
tctcggatgc gatgttcgat cggtggacct ccaaactcgt gtctctggga tttgctgcgc    4920
cactacgtaa ttcaggtgga ctcgacgtaa gaaagattgg tggagaagct gaccaagttc    4980
tcgctgcata cctgacgaaa attgcatccg gggtcggcat ggaagtcggc agtggcgacg    5040
gaaaaagtgg tcggcacggc aaccgtgcac cttgggaaat cgccgttgat gcagtcggag    5100
gagatccaca agcgttggaa ctctggcgcg agtttgagtt cggttcgatg ggacgccgag    5160
caatcgcatg gtctcgtgga ctgcgcgccc gagctggtct tggcgtagaa ctcacggatg    5220
ctcagattgt cgaacaggaa gaatctgccc cggtcatggt tgcgatcatt ccggctcggt    5280
cctggatgat gattcggaac tgtgcgcctt acgttttcgg agagatcctt ggactcgtgg    5340
aagcgggcgc gacctgggaa aaccttcgtg accacttgca ttatcgattg cctgcagcgg    5400
atgtgcggcc tccgataata tcgattcgta agtgaaatgt cttggtgtgc aacaactttc    5460
actcgtatga accacacttg agggcatccc ccgatactt gccgctttga agctgggtgt    5520
ctctctgtca gggctgcgat agcaccgcgt agcggcttgg ccttgacaga gagacggcct    5580
gtttcatggt tggtctcggg gggctgaccg ggcagataga aaaaggccgg ccgatttggc    5640
tgccgactat ttttgcaggt aaacccatct catgagcatc aatgaacgtc ccgttggtat    5700
cgcagcgaat gcagcttcgg tagacgtcga tggcgttgtg atgggtgtgt atctctcgct    5760
ttatgggcaa gaaatcacgc tagatcgaga tgatgcgttc ctactcctcg atcgacttca    5820
ggacgcgttg cgacctcaag ccaactaaga accctccaga tggtctaaac gaggcgcaaa    5880
ctcgctcctg ggcctgcggg cggagcaccg aagcgcgagc gaagcggagc gcgtaggtgg    5940
gggagcctgc gggcagcggc ggcggagccg ccgccttggt aataggtgat catcggggcc    6000
atagcaggtc agaggatgtt tttacgatga ctcatgctca ccacgccaag tactgatg    6058
```

<210> SEQ ID NO 102
<211> LENGTH: 6062
<212> TYPE: DNA
<213> ORGANISM: Artificial Sequence
<220> FEATURE:
<223> OTHER INFORMATION: Description of Artificial Sequence: Synthetic vector pNit-RT2 sequence

<400> SEQUENCE: 102

```
gttaactaga gtaacgggct actccgttta acggaccccg ttctcacgct ttaggcttga        60
ccccggagcc tgcatggggc attccgccgt gaacccggtg gaatgccccc ggcacccggg       120
ctttccagca aagatcacct ggcgccgatg agtaaggcgt acagaaccac tccacaggag       180
gaccgtcgag atgaaatcta acaatgcgct catcgtcatc ctcggcaccg tcaccctgga       240
tgctgtaggc ataggcttgg ttatgccggt actgccgggc ctcttgcggg atatcgtcca       300
ttccgacagc atcgccagtc actatggcgt gctgctagcg ctatatgcgt tgatgcaatt       360
tctatgcgca cccgttctcg gagcactgtc cgaccgcttt ggccgccgcc cagtcctgct       420
cgcttcgcta cttggagcca ctatcgacta cgcgatcatg gcgaccacac ccgtcctgtg       480
gattctctac gccggacgca tcgtggccgg catcaccggc gccacaggtg cggttgctgg       540
cgcctatatc gccgacatca ccgatgggga agatcgggct cgccacttcg ggctcatgag       600
cgcttgtttc ggcgtgggta tggtggcagg ccccgtggcc gggggactgt gggcgccat        660
ctccttgcat gcaccattcc ttgcggcggc ggtgctcaac ggcctcaacc tactactggg       720
ctgcttccta atgcaggagt cgcataaggg agagcgtcgt ccgatgccct tgagagcctt       780
caacccagtc agctccttcc ggtgggcgcg gggcatgact atcgtcgccg cacttatgac       840
tgtcttcttt atcatgcaac tcgtaggaca ggtgccggca gcgctctggg tcattttcgg       900
cgaggaccgc tttcgctgga gcgcgacgat gatcggcctg tcgcttgcgg tattcggaat       960
cttgcacgcc ctcgctcaag ccttcgtcac tggtcccgcc accaaacgtt tcggcgagaa      1020
gcaggccatt atcgccggca tggcggccga cgcgctgggc tacgtcttgc tggcgttcgc      1080
gacgcgaggc tggatggcct tccccattat gattcttctc gcttccggcg gcatcgggat      1140
gcccgcgttg caggccatgc tgtccaggca ggtagatgac gaccatcagg acagcttca       1200
aggatcgctc gcggctctta ccagcctaac ttcgatcatt ggaccgctga tcgtcacggc      1260
gatttatgcc gcctcggcga gcacatggaa cgggttggca tggattgtag gcgccgccct      1320
ataccttgtc tgcctccccg cgttgcgtcg cggtgcatgg agccgggcca cctcgacctg      1380
aatggaagcc ggcggcacct cgctaacgga ttcaccactc caagaattgg agccaatcaa      1440
ttcttgcgga gaactgtgaa tgcgcaaacc aaccccttggc agaacatatc catcgcgtcc     1500
gccatctcca gcagccgcac gcggcgcatc tcgggcagcg ttgggtcctg gccacgggtg      1560
cgcatgatcg tgctcctgtc gttgaggtac cgagctcgtc aggtggcact tttcggggaa      1620
atgtgcgcgg aaccctatt  tgtttatttt tctaaataca ttcaaatatg tatccgctca      1680
tgagacaata accctgataa atgcttcaat aatattgaaa aaggaagagt atgagtattc      1740
aacatttccg tgtcgccctt attccctttt ttgcggcatt ttgccttcct gtttttgctc      1800
acccagaaac gctggtgaaa gtaaaagatg ctgaagatca gttgggtgca cgagtgggtt      1860
acatcgaact ggatctcaac agcggtaaga tccttgagag ttttcgcccc gaagaacgtt      1920
ttccaatgat gagcactttt aaagttctgc tatgtggcgc ggtattatcc cgtattgacg      1980
ccgggcaaga gcaactcggt cgccgcatac actattctca gaatgacttg gttgagtact      2040
caccagtcac agaaaagcat cttacggatg gcatgacagt aagagaatta tgcagtgctg      2100
ccataaccat gagtgataac actgcggcca acttacttct gacaacgatc ggaggaccga      2160
aggagctaac cgcttttttg cacaacatgg gggatcatgt aactcgcctt gatcgttggg      2220
aaccggagct gaatgaagcc ataccaaacg acgagcgtga ccaccacgatg cctgtagcaa      2280
```

```
tggcaacaac gttgcgcaaa ctattaactg gcgaactact tactctagct tcccggcaac    2340
aattaataga ctggatggag gcggataaag ttgcaggacc acttctgcgc tcggcccttc    2400
cggctggctg gtttattgct gataaatctg gagccggtga gcgtgggtct cgcggtatca    2460
ttgcagcact ggggccagat ggtaagccct cccgtatcgt agttatctac acgacgggga    2520
gtcaggcaac tatggatgaa cgaaatagac agatcgctga gataggtgcc tcactgatta    2580
agcattggta actgtcagac caagtttact catatatact ttagattgat ttaaaacttc    2640
atttttaatt taaaaggatc taggtgaaga tcctttttga taatctcatg accaaaatcc    2700
cttaacgtga gttttcgttc cactgagcgt cagaccccgt agaaaagatc aaaggatctt    2760
cttgagatcc ttttttttctg cgcgtaatct gctgcttgca acaaaaaaaa ccaccgctac    2820
cagcggtggt ttgtttgccg gatcaagagc taccaactct ttttccgaag gtaactggct    2880
tcagcagagc gcagatacca aatactgttc ttctagtgta gccgtagtta ggccaccact    2940
tcaagaactc tgtagcaccg cctacatacc tcgctctgct aatcctgtta ccagtggctg    3000
ctgccagtgg cgataagtcg tgtcttaccg ggttggactc aagacgatag ttaccggata    3060
aggcgcagcg gtcgggctga acggggggtt cgtgcacaca gcccagcttg gagcgaacga    3120
cctacaccga actgagatac ctacagcgtg agctatgaga aagcgccacg cttcccgaag    3180
ggagaaaggc ggacaggtat ccggtaagcg gcagggtcgg aacaggagag cgcacgaggg    3240
agcttccagg gggaaacgcc tggtatcttt atagtcctgt cgggtttcgc cacctctgac    3300
ttgagcgtcg atttttgtga tgctcgtcag ggggggcggag cctatggaaa aacgccagca    3360
acgcggcctt tttacggttc ctggcctttt gctggccttt tgctcacatg ttctttcctg    3420
cgttatcccc tgattctgtg gataaccgta ttaccgcctt tgagtgagct gataccgctc    3480
gccgcagccg aacgaccgag cgcagcgagt cagtgagcga ggaagcggaa gagcgcccaa    3540
tacgcaaacc gcctctcccc gcgcgttggc cgattcatta atgcagctgg cacgactaga    3600
gtcccgctga ggcggcgtag caggtcagcc gccccagcgg tggtcaccaa ccggggtgga    3660
acggcgccgg tatcggtgt gtccgtggcg ctcattccaa cctccgtgtg tttgtgcagg    3720
tttcgcgtgt tgcagtccct cgcaccggca cccgcagcga ggggctcacg ggtgccggtg    3780
ggtcgactag ttcagtgatg gtgatggtga tgctcgagag atctaagctt ggatccgcgg    3840
ccgctacgta gaattcccat ggcgtgatgg tgatggtgat ggcccatatg tatatctcct    3900
tcttaaagtt aaacaaaatt atttctagac gccgtccatt ataccctcct acgtgacgtg    3960
aggtgcaagc ccggacgttc cgcgtgccac gccgtgagcc gccgcgtgcc gtcggctccc    4020
tcagcccggg cggccgtggg agcccgcctc gatatgtaca agcatgggga ctcgccgcgg    4080
actagcggct tcccgacacg ccgtactgac cagcagatca gcgataaacg ctgtttctgc    4140
tggttaagtg gataaaaacc aaataatcga tgaacctcga agtggagtat ccgagctgaa    4200
ctagctggat ttactccgaa aatacgagcg gcgacgaagg tgttggacc accctgccgc    4260 cgccttcgag gctcctactt gactaggacc ccgctcgtta tgaccagcgt aagtgctgaa    4320
cacctttccg gcaaagaccg gcccctgtc ctcgtgtcgt ccgataagcg cggcatccgg    4380
cacgaacttc gacccaaact tcaacaaatc accacgtcag aaactttttaa tgcgtgcggc    4440 cggccgattt ccggcgtgaa cggtgtgacc atcgtcaacg gtcccaaagg ttccggattt    4500
ggaggccttc gctcctgcgg aaagggctgg atctgcccct gctgtgcggg aaagtcggc    4560 gcacatcgag cagacgaaat ttctcaagtt gttgctcatc aactcgggac tggatctgtt    4620
gcgatggtga ccatgaccat gcgccatacc gctgggcagc gttttgcatga tttgtggact    4680
```

```
ggactttcgg cagcctggaa agctgcgacc aatggccgcc gatggcgtac cgaacgtgaa      4740
atgtacggct gcgacggata cgtacgagct gttgaaatca ctcacggaaa aaacggttgg      4800
cacgttcacg tccacgctct actcatgttc agcggtgacg tgagtgagaa catcctcgaa      4860
tccttctcgg atgcgatgtt cgatcggtgg acctccaaac tcgtgtctct gggatttgct      4920
gcgccactac gtaattcagg tggactcgac gtaagaaaga ttggtggaga agctgaccaa      4980
gttctcgctg catacctgac gaaaattgca tccggggtcg gcatggaagt cggcagtggc      5040
gacggaaaaa gtggtcggca cggcaaccgt gcacctgggg aaatcgccgt tgatgcagtc      5100
ggaggagatc cacaagcgtt ggaactctgg cgcgagtttg agttcggttc gatgggacgc      5160
cgagcaatcg catggtctcg tggactgcgc gcccgagctg gtcttggcgt agaactcacg      5220
gatgctcaga ttgtcgaaca ggaagaatct gccccggtca tggttgcgat cattccggct      5280
cggtcctgga tgatgattcg gaactgtgcg ccttacgttt tcggagagat ccttggactc      5340
gtggaagcgg gcgcgacctg ggaaaacctt cgtgaccact tgcattatcg attgcctgca      5400
gcggatgtgc ggcctccgat aatatcgatt cgtaagtgaa atgtcttggt gtgcaacaac      5460
tttcactcgt atgaaccaca cttgagggca tcccccgat acttgccgct ttgaagctgg       5520
gtgtctctct gtcagggctg cgatagcacc gcgtagcggc ttggccttga cagagagacg      5580
gcctgtttca tggttggtct cgggggggctg accgggcaga tagaaaaagg ccggccgatt     5640
tggctgccga ctatttttgc aggtaaaccc atctcatgag catcaatgaa cgtcccgttg      5700
gtatcgcagc gaatgcagct tcggtagacg tcgatgcgt tgtgatgggt gtgtatctct       5760
cgctttatgg gcaagaaatc acgctagatc gagatgatgc gttcctactc ctcgatcgac      5820
ttcaggacgc gttgcgacct caagccaact aagaaccctc cagatggtct aaacgaggcg      5880
caaactcgct cctgggcctg cgggcggagc accgaagcgc gagcgaagcg gagcgcgtag      5940 gtggggagc ctgcgggcag cggcggcgga ccgccgcct tggtaatagg tgatcatcgg        6000
ggccatagca ggtcagagga tgttttacg atgactcatg ctcaccacgc caagtactga       6060
tg                                                                    6062
```

<210> SEQ ID NO 103
<211> LENGTH: 6153
<212> TYPE: DNA
<213> ORGANISM: Artificial Sequence
<220> FEATURE:
<223> OTHER INFORMATION: Description of Artificial Sequence: Synthetic
      vector pNit-QC1 sequence

<400> SEQUENCE: 103

```
gttaacgcat ccgaaacctc caccccactc acctagtccg acatccgtac cttggaaacc        60
gacctgtatt ggcatttcag ttggacatcg accagtggcg ttgctaggtt caagaccatg       120
tccagcccga aggcgtccag actctagcca ccggaggtag tccggtggcc acatcccgtc       180
gcgcccgaac gtcacgctct tgtgtggcct tcccttgttg tttgcgatca gtggcacacc       240
tctaccgtct gaatttcgag tctggcctcg gctgcgcaca tctcgcactg tgacgctgtc       300
aggtcacccg cttcgcggct accagttcct ttcatcgaat cgagcttccg gtgccgccgc       360
gcagcctccc tgaccatcct cagattttat ggagtctcgc agtgcctttc gctatctacg       420
tcctcgggct tgctgtcttc gcccagggca catccgagtt catgttgtcc ggactcatac       480
cggacatggc ccgtgacctc ggggtttcgg tccccgccgc cggactcctc acctccgcct       540
tcgcggtcgg gatgatcatc ggcgctccgt tgatggctat cgccagcatg cggtggcccc       600
```

```
ggcgacgcgc ccttctgaca ttcctcatca cgttcatgct ggtccacgtc atcggcgcgc    660
tcaccagcag cttcgaggtc ttgctggtca cacgcatcgt gggagccctc gccaatgccg    720
gattcttggc agtggccctg ggggcggcga tggcgatggt gcccgccgac atgaaagggc    780
gcgccacgtc cgtcctcctc ggcggtgtca cgatcgcatg tgtagccggt gttcccgggg    840
gcgccttcct gggtgaaatg tggggctggc gtgcagcgtt ctgggctgtc gtcgtcatct    900
ccgcccctgc agtggtggcg attatgttcg ccaccccggc cgagccgctt gcagagtcca    960
caccgaatgc caagcgtgaa ctgtcctcac tgcgctcacg caagctccag ctcatgcttg   1020
tcctcggggc gctgatcaac ggcgcaacgt tctgttcgtt cacgtacatg cgcccacgc    1080 tcaccgacat ctccggtttc gactcccgtt ggattccgtt gctgctgggg ctgttcgggc   1140
tcggatcgtt catcggtgtc agcgtcggag gcaggctcgc cgacacccgg ccgttccaac   1200
tgctcgctgt cgggtccgca gcactgttga cgggatggat cgtcttcgct ctcacggcat   1260
cccaccccgc ggtgacattg gtgatgctgt tcgtgcaggg cgctttgtcc ttcgcggtcg   1320
gctcgacttt gatctcccag gtgctctacg ccgccgacgc ggcaccgacc ttgggtggat   1380
cgttcgcgac ggccgcgttc aacgtcggtg ctgcactggg accggcgctc ggcgggttgg   1440
cgatcggcat gggtctgagc taccgcgccc cgctctggac gagcgccgcg ctggtgacac   1500
tcgcgatcgt catcggcgca gccaccttgt ctctgtggcg cgaccagcg tctgtccacg    1560 aatctgtccc cgcctgacca gaaaccagga tctgtgagtg tggtgactga tctgtgcacg   1620
ctcagcagtc accgcgcgct cgcgtcgtac cgagggccag cgccaacagg tgtgtggagc   1680 tctgccctg cctcttcac gcgaactcac tgttcagtgc ggcgatacgt gctcggtgag     1740
ttccactaca gcgaggtacc gagctcgtca ggtggcactt ttcggggaaa tgtgcgcgga   1800
acccctattt gtttattttt ctaaatacat tcaaatatgt atccgctcat gagacaataa   1860
ccctgataaa tgcttcaata atattgaaaa aggaagagta tgagtattca acatttccgt   1920
gtcgccctta ttcccttttt tgcggcattt tgccttcctg tttttgctca cccagaaacg   1980
ctggtgaaag taaaagatgc tgaagatcag ttgggtgcac gagtgggtta catcgaactg   2040
gatctcaaca gcggtaagat ccttgagagt tttcgccccg aagaacgttt tccaatgatg   2100 agcacttta aagttctgct atgtggcgcg gtattatccc gtattgacgc cgggcaagag    2160
caactcggtc gccgcataca ctattctcag aatgacttgg ttgagtactc accagtcaca   2220
gaaaagcatc ttacgatgg catgacagta agagaattat gcagtgctgc cataaccatg    2280
agtgataaca ctgcggccaa cttacttctg acaacgatcg aggaccgaa ggagctaacc     2340 gctttttgc acaacatggg ggatcatgta actcgccttg atcgttggga accggagctg    2400
aatgaagcca taccaaacga cgagcgtgac accacgatgc ctgtagcaat ggcaacaacg   2460
ttgcgcaaac tattaactgg cgaactactt actctagctt cccggcaaca attaatagac   2520
tggatggagg cggataaagt tgcaggacca cttctgcgct cggcccttcc ggctggctgg   2580
tttattgctg ataaatctgg agccggtgag cgtgggtctc gcggtatcat tgcagcactg   2640
gggccagatg gtaagccctc ccgtatcgta gttatctaca cgacggggag tcaggcaact   2700
atggatgaac gaaatagaca gatcgctgag ataggtgcct cactgattaa gcattggtaa   2760
ctgtcagacc aagtttactc atatatactt tagattgatt taaaacttca tttttaattt   2820
aaaaggatct aggtgaagat cctttttgat aatctcatga ccaaaatccc ttaacgtgag   2880
ttttcgttcc actgagcgtc agaccccgta gaaaagatca aaggatcttc ttgagatcct   2940
```

```
tttttttctgc gcgtaatctg ctgcttgcaa acaaaaaaac caccgctacc agcggtggtt    3000
tgtttgccgg atcaagagct accaactctt tttccgaagg taactggctt cagcagagcg    3060
cagataccaa atactgttct tctagtgtag ccgtagttag gccaccactt caagaactct    3120
gtagcaccgc ctacatacct cgctctgcta atcctgttac cagtggctgc tgccagtggc    3180
gataagtcgt gtcttaccgg gttggactca agacgatagt taccggataa ggcgcagcgg    3240
tcgggctgaa cggggggttc gtgcacacag cccagcttgg agcgaacgac ctacaccgaa    3300
ctgagatacc tacagcgtga gctatgagaa agcgccacgc ttcccgaagg gagaaaggcg    3360
gacaggtatc cggtaagcgg cagggtcgga acaggagagc gcacgaggga gcttccaggg    3420
ggaaacgcct ggtatcttta tagtcctgtc gggtttcgcc acctctgact gagcgtcga    3480 tttttgtgat gctcgtcagg ggggcggagc ctatggaaaa acgccagcaa cgcggccttt    3540
ttacggttcc tggccttttg ctggcctttt gctcacatgt tctttcctgc gttatcccct    3600
gattctgtgg ataaccgtat taccgccttt gagtgagctg ataccgctcg ccgcagccga    3660
acgaccgagc gcagcgagtc agtgagcgag gaagcggaag agcgcccaat acgcaaaccg    3720
cctctccccg cgcgttggcc gattcattaa tgcagctggc acgactagag tcccgctgag    3780
gcggcgtagc aggtcagccg ccccagcggt ggtcaccaac cggggtggaa cggcgccggt    3840
atcgggtgtg tccgtggcgc tcattccaac ctccgtgtgt ttgtgcaggt ttcgcgtgtt    3900
gcagtccctc gcaccggcac ccgcagcgag gggctcacgg gtgccggtgg gtcgactagt    3960
tcagtgatgg tgatggtgat gctcgagaga tctaagcttg gatccgcggc cgctacgtag    4020
aattcccata tggtgatggt gatggtggcc catggtatat ctccttctta aagttaaaca    4080
aaattatttc tagacgccgt ccattatacc tcctcacgtg acgtgaggtg caagcccgga    4140
cgttccgcgt gccacgccgt gagccgccgc gtgccgtcgg ctccctcagc ccgggcggcc    4200
gtgggagccc gcctcgatat gtacacccga gaagctccca gcgtcctcct gggccgcgat    4260
actcgaccac cacgcacgca caccgcacta acgattcggc cggcgctcga ttcggccggc    4320
gctcgattcg gccggcgctc gattcggccg gcgctcgatt cggccggcgc tcgattcggc    4380
cgagcagaag agtgaacaac caccgaccac gcttccgctc tgcgcgccgt acccgaccta    4440
cctcccgcag ctcgaagcag ctcccgggag taccgccgta ctcacccgcc tgtgctcacc    4500
atccaccgac gcaaagccca acccgagcac acctcttgca ccaaggtgcc gaccgtggct    4560
ttccgctcgc agggttccag aagaaatcga acgatccagc gcggcaaggt tcaaaaagca    4620
ggggttggtg gggaggaggt tttgggggt gtcgccggga tacctgatat ggctttgttt    4680
tgcgtagtcg aataatttc catatagcct cggcgcgtcg gactcgaata gttgatgtgg    4740
gcgggcacag ttgccccatg aaatccgcaa cgggggggcgt gctgagcgat cggcaatggg    4800 cggatgcgt gttgcttccg caccggccgt tcgcgacgaa caacctccaa cgaggtcagt    4860 accgatgag ccgcgacgac gcattggcaa tgcggtacgt cgagcattca ccgcacgcgt    4920
tgctcggatc tatcgtcatc gactgcgatc acgttgacgc cgcgatgcgc gcattcgagc    4980
aaccatccga ccatccggcg ccgaactggg tcgcacaatc gccgtccggc cgcgcacaca    5040
tcggatggtg gctcggcccc aaccacgtgt gccgcaccga cagcgcccga ctgacgccac    5100
tgcgctacgc ccaccgcatc gaaaccggcc tcaagatcag cgtcggcggc gatttcgcgt    5160
atggcgggca actgaccaaa aacccgattc accccgattg ggagacgatc tacggcccgg    5220
ccaccccgta cacattgcgg cagctggcca ccatccacac accccggcag atgccgcgtc    5280
ggcccgatcg ggccgtgggc ctgggccgca acgtcaccat gttcgacgcc acccggcgat    5340
```

-continued

```
gggcataccc gcagtggtgg caacaccgaa acggaaccgg ccgcgactgg gaccatctcg      5400
tcctgcagca ctgccacgcc gtcaacaccg agttcacgac accactgccg ttcaccgaag      5460
tacgcgccac cgcgcaatcc atctccaaat ggatctggcg caatttcacc gaagaacagt      5520
accgagcccg acaagcgcat ctcggtcaaa aaggcggcaa ggcaacgaca ctcgccaaac      5580
aagaagccgt ccgaaacaat gcaagaaagt acgacgaaca tacgatgcga gaggcgatta      5640
tctgatgggc ggagccaaaa atccggtgcg ccgaaagatg acggcagcag cagcagccga      5700
aaaattcggt gcctccactc gcacaatcca acgcttgttt gctgagccgc gtgacgatta      5760
cctcggccgt gcgaaagctc gccgtgacaa agctgtcgag ctgcggaagc aggggttgaa      5820
gtaccgggaa atcgccgaag cgatggaact ctcgaccggg atcgtcggcc gattactgca      5880
cgacgcccgc aggcacggcg agatttcagc ggaggatctg tcggcgtaac caagtcagcg      5940
ggttgtcggg ttccggccgg cgctcggcac tcggaccggc cggcggatgg tgttctgcct      6000
ctggcgcagc gtcagctacc gccgaaggcc tgtcatcgac cggcttcgac tgaagtatga      6060
gcaacgtcac agcctgtgat tggatgatcc gctcacgctc gaccgctacc tgttcagctg      6120
ccgcccgctg ggcatgagca acggccaact ctc                                  6153
```

<210> SEQ ID NO 104
<211> LENGTH: 6157
<212> TYPE: DNA
<213> ORGANISM: Artificial Sequence
<220> FEATURE:
<223> OTHER INFORMATION: Description of Artificial Sequence: Synthetic
      vector pNit-QC2 sequence

<400> SEQUENCE: 104

```
gttaacgcat ccgaaacctc cacccactc acctagtccg acatccgtac cttggaaacc       60
gacctgtatt ggcatttcag ttggacatcg accagtggcg ttgctaggtt caagaccatg     120
tccagcccga aggcgtccag actctagcca ccggaggtag tccggtggcc acatcccgtc     180
gcgcccgaac gtcacgctct tgtgtggcct tcccttgttg tttgcgatca gtggcacacc     240
tctaccgtct gaatttcgag tctggcctcg gctgcgcaca tctcgcactg tgacgctgtc     300
aggtcacccg cttcgcggct accagttcct ttcatcgaat cgagcttccg gtgccgccgc     360
gcagcctccc tgaccatcct cagatttat ggagtctcgc agtgcctttc gctatctacg      420
tcctcgggct tgctgtcttc gcccagggca catccgagtt catgttgtcc ggactcatac     480
cggacatggc ccgtgacctc ggggtttcgg tcccgccgc cggactcctc acctccgcct      540
tcgcggtcgg gatgatcatc ggcgctccgt tgatggctat cgccagcatg cggtggcccc     600
ggcgacgcgc ccttctgaca ttcctcatca cgttcatgct ggtccacgtc atcgcgcgc      660 tcaccagcag cttcgaggtc ttgctggtca cacgcatcgt gggagccctc gccaatgccg     720
gattcttggc agtggccctg ggggcggcga tggcgatggt gcccgccgac atgaaagggc     780
gcgccacgtc cgtcctcctc ggcggtgtca cgatcgcatg tgtagccggt gttcccgggg     840
gcgccttcct gggtgaaatg tggggctggc gtgcagcgtt ctgggctgtc gtcgtcatct     900
ccgcccctgc agtggtggcg attatgttcg ccaccccggc cgagccgctt gcagagtcca     960
caccgaatgc caagcgtgaa ctgtcctcac tgcgctcacg caagctccag ctcatgcttg    1020
tcctcggggc gctgatcaac ggcgcaacgt tctgttcgtt cacgtacatg gcgcccacgc    1080
tcaccgacat ctccggttc gactcccgtt ggattccgtt gctgctgggg ctgttcgggc     1140
tcggatcgtt catcggtgtc agcgtcggag gcaggctcgc cgacacccgg ccgttccaac    1200
```

```
tgctcgctgt cgggtccgca gcactgttga cgggatggat cgtcttcgct ctcacggcat    1260
cccacccgc  ggtgacattg gtgatgctgt tcgtgcaggg cgctttgtcc ttcgcggtcg    1320
gctcgacttt gatctcccag gtgctctacg ccgccgacgc ggcaccgacc ttgggtggat    1380
cgttcgcgac ggccgcgttc aacgtcggtg ctgcactggg accggcgctc ggcgggttgg    1440
cgatcggcat gggtctgagc taccgcgccc cgctctggac gagcgccgcg ctggtgacac    1500
tcgcgatcgt catcggcgca gccaccttgt ctctgtggcg gcgaccagcg tctgtccacg    1560
aatctgtccc cgcctgacca gaaaccagga tctgtgagtg tggtgactga tctgtgcacg    1620
ctcagcagtc accgcgcgct cgcgtcgtac cgagggccag cgccaacagg tgtgtggagc    1680
tctgccctg  cctcttcac  gcgaactcac tgttcagtgc ggcgatacgt gctcggtgag    1740
ttccactaca gcgaggtacc gagctcgtca ggtggcactt tcggggaaa  tgtgcgcgga    1800
accctattt  gtttattttt ctaaatacat tcaaatatgt atccgctcat gagacaataa    1860
ccctgataaa tgcttcaata atattgaaaa aggaagagta tgagtattca acatttccgt    1920
gtcgcccta  ttcccttttt tgcggcattt tgccttcctg ttttttgctca cccagaaacg    1980
ctggtgaaag taaaagatgc tgaagatcag ttgggtgcac gagtgggtta catcgaactg    2040
gatctcaaca gcggtaagat ccttgagagt tttcgccccg aagaacgttt tccaatgatg    2100
agcactttta aagttctgct atgtggcgcg gtattatccc gtattgacgc cgggcaagag    2160
caactcggtc gccgcataca ctattctcag aatgacttgg ttgagtactc accagtcaca    2220
gaaaagcatc ttacggatgg catgacagta agagaattat gcagtgctgc cataaccatg    2280
agtgataaca ctgcggccaa cttacttctg acaacgatcg gaggaccgaa ggagctaacc    2340
gcttttttgc acaacatggg ggatcatgta actcgccttg atcgttggga accggagctg    2400
aatgaagcca taccaaacga cgagcgtgac accacgatgc ctgtagcaat ggcaacaacg    2460
ttgcgcaaac tattaactgg cgaactactt actctagctt cccggcaaca attaatagac    2520
tggatggagg cggataaagt tgcaggacca cttctgcgct cggcccttcc ggctggctgg    2580
tttattgctg ataaatctgg agccggtgag cgtgggtctc gcggtatcat tgcagcactg    2640
gggccagatg gtaagccctc ccgtatcgta gttatctaca cgacggggag tcaggcaact    2700
atggatgaac gaaatagaca gatcgctgag ataggtgcct cactgattaa gcattggtaa    2760
ctgtcagacc aagtttactc atatatactt tagattgatt taaaacttca tttttaattt    2820
aaaaggatct aggtgaagat cctttttgat aatctcatga ccaaaatccc ttaacgtgag    2880
ttttcgttcc actgagcgtc agaccccgta gaaaagatca aaggatcttc ttgagatcct    2940
ttttttctgc gcgtaatctg ctgcttgcaa acaaaaaaac caccgctacc agcggtggtt    3000
tgtttgccgg atcaagagct accaactctt tttccgaagg taactggctt cagcagagcg    3060
cagataccaa atactgttct tctagtgtag ccgtagttag gccaccactt caagaactct    3120
gtagcaccgc ctacatacct cgctctgcta atcctgttac cagtggctgc tgccagtggc    3180
gataagtcgt gtcttaccgg gttggactca agacgatagt taccggataa ggcgcagcgg    3240
tcgggctgaa cggggggttc gtgcacacag cccagcttgg agcgaacgac ctacaccgaa    3300
ctgagatacc tacagcgtga gctatgagaa agcgccacgc ttcccgaagg gagaaaggcg    3360
gacaggtatc cggtaagcgg cagggtcgga acaggagagc gcacgaggga gcttccaggg    3420
ggaaacgcct ggtatcttta tagtcctgtc gggtttcgcc acctctgact tgagcgtcga    3480
tttttgtgat gctcgtcagg gggcggagc  ctatggaaaa acgccagcaa cgcggccttt    3540
```

-continued

```
ttacggttcc tggccttttg ctggccttttt gctcacatgt tctttcctgc gttatcccct    3600
gattctgtgg ataaccgtat taccgccttt gagtgagctg ataccgctcg ccgcagccga    3660
acgaccgagc gcagcgagtc agtgagcgag gaagcggaag agcgcccaat acgcaaaccg    3720
cctctccccg cgcgttggcc gattcattaa tgcagctggc acgactagag tcccgctgag    3780
gcggcgtagc aggtcagccg ccccagcggt ggtcaccaac cggggtggaa cggcgccggt    3840
atcgggtgtg tccgtggcgc tcattccaac ctccgtgtgt tgtgcaggt ttcgcgtgtt     3900
gcagtccctc gcaccggcac ccgcagcgag gggctcacgg gtgccggtgg gtcgactagt    3960
tcagtgatgg tgatggtgat gctcgagaga tctaagcttg gatccgcggc cgctacgtag    4020
aattcccatg gcgtgatggt gatggtgatg gcccatatgt atatctcctt cttaaagtta    4080
aacaaaatta tttctagacg ccgtccatta tacctcctca cgtgacgtga ggtgcaagcc    4140
cggacgttcc gcgtgccacg ccgtgagccg ccgcgtgccg tcggctccct cagcccgggc    4200
ggccgtggga gcccgcctcg atatgtacac ccgagaagct cccagcgtcc tcctgggccg    4260
cgatactcga ccaccacgca cgcacaccgc actaacgatt cggccggcgc tcgattcggc    4320
cggcgctcga ttcggccggc gctcgattcg gccggcgctc gattcggccg cgctcgatt     4380
cggccgagca gaagagtgaa caaccaccga ccacgcttcc gctctgcgcg ccgtacccga    4440
cctacctccc gcagctcgaa gcagctcccg ggagtaccgc cgtactcacc cgcctgtgct    4500
caccatccac cgacgcaaag cccaacccga gcacacctct tgcaccaagg tgccgaccgt    4560
ggcttttccgc tcgcagggtt ccagaagaaa tcgaacgatc cagcgcggca aggttcaaaa    4620
agcaggggtt ggtggggagg aggttttggg gggtgtcgcc gggatacctg atatggcttt    4680
gttttgcgta gtcgaataat tttccatata gcctcggcgc gtcggactcg aatagttgat    4740
gtgggcgggc acagttgccc catgaaatcc gcaacggggg gcgtgctgag cgatcggcaa    4800
tgggcggatg cggtgttgct tccgcaccgg ccgttcgcga cgaacaacct ccaacgaggt    4860
cagtaccgga tgagccgcga cgacgcattg gcaatgcggt acgtcgagca ttcaccgcac    4920
gcgttgctcg gatctatcgt catcgactgc gatcacgttg acgccgcgat gcgcgcattc    4980
gagcaaccat ccgaccatcc ggcgccgaac tgggtcgcac aatcgccgtc cggccgcgca    5040
cacatcggat ggtggctcgg ccccaaccac gtgtgccgca ccgacagcgc ccgactgacg    5100
ccactgcgct acgccaccg catcgaaacc ggcctcaaga tcagcgtcgg cggcgatttc     5160
gcgtatggcg ggcaactgac caaaaacccg attcaccccg attgggagac gatctacggc    5220
ccggccaccc cgtacacatt gcggcagctg gccaccatca acacacccg gcagatgccg      5280
cgtcggcccg atcgggccgt gggcctgggc cgcaacgtca ccatgttcga cgccacccgg    5340
cgatgggcat cccgcagtg gtggcaacac cgaaacggaa ccggccgcga ctgggaccat     5400
ctcgtcctgc agcactgcca cgccgtcaac accgagttca cgacaccact gccgttcacc    5460
gaagtacgcg ccaccgcgca atccatctcc aaatggatct ggcgcaattt caccgaagaa    5520
cagtaccgag cccgacaagc gcatctcggt caaaaaggcg gcaaggcaac gacactcgcc    5580
aaacaagaag ccgtccgaaa caatgcaaga agtacgacg aacatacgat gcgagaggcg     5640
attatctgat gggcggagcc aaaaatccgg tgcgccgaaa gatgacggca gcagcagcag    5700
ccgaaaaatt cggtgcctcc actcgcacaa tccaacgctt gtttgctgag ccgcgtgacg    5760
attacctcgg ccgtgcgaaa gctcgccgtg acaaagctgt cgagctgcgg aagcaggggt    5820
tgaagtaccg ggaaatcgcc gaagcgatgg aactctcgac cggatcgtc ggccgattac      5880
tgcacgacgc ccgcaggcac ggcgagattt cagcggagga tctgtcggcg taaccaagtc    5940
```

-continued

| | |
|---|---|
| agcgggttgt cgggttccgg ccggcgctcg gcactcggac cggccggcgg atggtgttct | 6000 |
| gcctctggcg cagcgtcagc taccgccgaa ggcctgtcat cgaccggctt cgactgaagt | 6060 |
| atgagcaacg tcacagcctg tgattggatg atccgctcac gctcgaccgc tacctgttca | 6120 |
| gctgccgccc gctgggcatg agcaacggcc aactctc | 6157 |

<210> SEQ ID NO 105
<211> LENGTH: 6227
<212> TYPE: DNA
<213> ORGANISM: Artificial Sequence
<220> FEATURE:
<223> OTHER INFORMATION: Description of Artificial Sequence: Synthetic
      vector pNit-RC1 sequence

<400> SEQUENCE: 105

| | |
|---|---|
| gttaacgcat ccgaaacctc caccccactc acctagtccg acatccgtac cttggaaacc | 60 |
| gacctgtatt ggcatttcag ttggacatcg accagtggcg ttgctaggtt caagaccatg | 120 |
| tccagcccga aggcgtccag actctagcca ccggaggtag tccggtggcc acatcccgtc | 180 |
| gcgcccgaac gtcacgctct tgtgtggcct tcccttgttg tttgcgatca gtggcacacc | 240 |
| tctaccgtct gaatttcgag tctggcctcg gctgcgcaca tctcgcactg tgacgctgtc | 300 |
| aggtcacccg cttcgcggct accagttcct ttcatcgaat cgagcttccg gtgccgccgc | 360 |
| gcagcctccc tgaccatcct cagattttat ggagtctcgc agtgcctttc gctatctacg | 420 |
| tcctcgggct tgctgtcttc gcccagggca catccgagtt catgttgtcc ggactcatac | 480 |
| cggacatggc ccgtgacctc ggggtttcgg tccccgccgc cggactcctc acctccgcct | 540 |
| tcgcggtcgg gatgatcatc ggcgctccgt tgatggctat cgccagcatg cggtggcccc | 600 |
| ggcgacgcgc ccttctgaca ttcctcatca cgttcatgct ggtccacgtc atcggcgcgc | 660 |
| tcaccagcag cttcgaggtc ttgctggtca cacgcatcgt gggagccctc gccaatgccg | 720 |
| gattcttggc agtggccctg ggggcggcga tggcgatggt gcccgccgac atgaaagggc | 780 |
| gcgccacgtc cgtcctcctc ggcggtgtca cgatcgcatg tgtagccggt gttcccgggg | 840 |
| gcgccttcct gggtgaaatg tggggctggc gtgcagcgtt ctgggctgtc gtcgtcatct | 900 |
| ccgcccctgc agtggtggcg attatgttcg ccaccccggc cgagccgctt gcagagtcca | 960 |
| caccgaatgc caagcgtgaa ctgtcctcac tgcgctcacg caagctccag ctcatgcttg | 1020 |
| tcctcggggc gctgatcaac ggcgcaacgt tctgttcgtt cacgtacatg gcgcccacgc | 1080 |
| tcaccgacat ctccggtttc gactcccgtt ggattccgtt gctgctgggg ctgttcgggc | 1140 |
| tcggatcgtt catcggtgtc agcgtcggag gcaggctcgc cgacacccgg ccgttccaac | 1200 |
| tgctcgctgt cgggtccgca gcactgttga cgggatggat cgtcttcgct ctcacggcat | 1260 |
| cccaccccgc ggtgacattg gtgatgctgt tcgtgcaggg cgctttgtcc ttcgcggtcg | 1320 |
| gctcgacttt gatctcccag gtgctctacg ccgccgacgc ggcaccgacc ttgggtggat | 1380 |
| cgttcgcgac ggccgcgttc aacgtcggtg ctgcactggg accggcgctc ggcgggttgg | 1440 |
| cgatcggcat gggtctgagc taccgcgccc gctctggac gagcgccgcg ctggtgacac | 1500 |
| tcgcgatcgt catcggcgca gccaccttgt tctgtggcg gcgaccagcg tctgtccacg | 1560 |
| aatctgtccc cgcctgacca gaaaccagga tctgtgagtg tggtgactga tctgtgcacg | 1620 |
| ctcagcagtc accgcgcgct cgcgtcgtac cgagggccag cgccaacagg tgtgtggagc | 1680 |
| tctgcccctg cctctttcac gcgaactcac tgttcagtgc ggcgatacgt gctcggtgag | 1740 |
| ttccactaca gcgaggtacc gagctcgtca ggtggcactt ttcggggaaa tgtgcgcgga | 1800 |

```
accccctattt gtttattttt ctaaatacat tcaaatatgt atccgctcat gagacaataa    1860
ccctgataaa tgcttcaata atattgaaaa aggaagagta tgagtattca acatttccgt    1920
gtcgcccttta ttcccttttt tgcggcattt tgccttcctg tttttgctca cccagaaacg    1980
ctggtgaaag taaaagatgc tgaagatcag ttgggtgcac gagtgggtta catcgaactg    2040
gatctcaaca gcggtaagat ccttgagagt tttcgccccg aagaacgttt tccaatgatg    2100
agcacttttta aagttctgct atgtggcgcg gtattatccc gtattgacgc cgggcaagag    2160
caactcggtc gccgcataca ctattctcag aatgacttgg ttgagtactc accagtcaca    2220
gaaaagcatc ttacggatgg catgacagta agagaattat gcagtgctgc cataaccatg    2280
agtgataaca ctgcggccaa cttacttctg acaacgatcg gaggaccgaa ggagctaacc    2340
gcttttttgc acaacatggg ggatcatgta actcgccttg atcgttggga accggagctg    2400
aatgaagcca taccaaacga cgagcgtgac accacgatgc ctgtagcaat ggcaacaacg    2460
ttgcgcaaac tattaactgg cgaactactt actctagctt cccggcaaca attaatagac    2520
tggatggagg cggataaagt tgcaggacca cttctgcgct cggcccttcc ggctggctgg    2580
tttattgctg ataaatctgg agccggtgag cgtgggtctc gcggtatcat tgcagcactg    2640
gggccagatg gtaagccctc ccgtatcgta gttatctaca cgacggggag tcaggcaact    2700
atggatgaac gaaatagaca gatcgctgag ataggtgcct cactgattaa gcattggtaa    2760
ctgtcagacc aagtttactc atatatactt tagattgatt taaaacttca ttttttaattt    2820
aaaaggatct aggtgaagat cctttttgat aatctcatga ccaaaatccc ttaacgtgag    2880
ttttcgttcc actgagcgtc agaccccgta gaaaagatca aaggatcttc ttgagatcct    2940
ttttttctgc gcgtaatctg ctgcttgcaa acaaaaaaac caccgctacc agcggtggtt    3000
tgtttgccgg atcaagagct accaactctt tttccgaagg taactggctt cagcagagcg    3060
cagataccaa atactgttct tctagtgtag ccgtagttag gccaccactt caagaactct    3120
gtagcaccgc ctacatacct cgctctgcta atcctgttac cagtggctgc tgccagtggc    3180
gataagtcgt gtcttaccgg gttggactca agacgatagt taccggataa ggcgcagcgg    3240
tcgggctgaa cggggggttc gtgcacacag cccagcttgg agcgaacgac ctacaccgaa    3300
ctgagatacc tacagcgtga gctatgagaa agcgccacgc ttcccgaagg gagaaaggcg    3360
gacaggtatc cggtaagcgg cagggtcgga acaggagagc gcacgaggga gcttccaggg    3420
ggaaacgcct ggtatcttta tagtcctgtc gggtttcgcc acctctgact tgagcgtcga    3480
tttttgtgat gctcgtcagg gggcggagc ctatggaaaa acgccagcaa cgcggccttt    3540
ttacggttcc tggccttttg ctggcctttt gctcacatgt tctttcctgc gttatcccct    3600
gattctgtgg ataaccgtat taccgccttt gagtgagctg ataccgctcg ccgcagccga    3660
acgaccgagc gcagcgagtc agtgagcgag gaagcggaag agcgcccaat acgcaaaccg    3720
cctctccccg cgcgttggcc gattcattaa tgcagctggc acgactagag tcccgctgag    3780
gcggcgtagc aggtcagccg ccccagcggt ggtcaccaac cggggtggaa cggcgccggt    3840
atcgggtgtg tccgtggcgc tcattccaac ctccgtgtgt ttgtgcaggt ttcgcgtgtt    3900
gcagtccctc gcaccggcac ccgcagcgag gggctcacgg gtgccggtgg tcgactagt    3960
tcagtgatgg tgatggtgat gctcgagaga tctaagcttg gatccgcggc cgctacgtag    4020
aattcccata tggtgatggt gatggtggcc catggtatat ctccttctta aagttaaaca    4080
aaattatttc tagacgccgt ccattatacc tcctcacgtg acgtgaggtg caagcccgga    4140
```

```
cgttccgcgt gccacgccgt gagccgccgc gtgccgtcgg ctccctcagc ccgggcggcc    4200
gtgggagccc gcctcgatat gtacaagcat ggggactcgc cgcggactag cggcttcccg    4260
acacgccgta ctgaccagca gatcagcgat aaacgctgtt tctgctggtt aagtggataa    4320
aaaccaaata atcgatgaac ctcgaagtgg agtatccgag ctgaactagc tggatttact    4380
ccgaaaatac gagcggcgac gaagggtgtt ggaccaccct gccgccgcct tcgaggctcc    4440
tacttgacta ggaccccgct cgttatgacc agcgtaagtg ctgaacacct ttccggcaaa    4500
gaccggcccc ctgtcctcgt gtcgtccgat aagcgcggca tccggcacga acttcgaccc    4560
aaacttcaac aaatcaccac gtcagaaact tttaatgcgt gcggccggcc gatttccggc    4620
gtgaacggtg tgaccatcgt caacggtccc aaaggttccg gatttggagg ccttcgctcc    4680
tgcggaaagg gctggatctg cccctgctgt gcgggaaaag tcggcgcaca tcgagcagac    4740
gaaatttctc aagttgttgc tcatcaactc gggactggat ctgttgcgat ggtgaccatg    4800
accatgcgcc ataccgctgg gcagcgtttg catgatttgt ggactggact ttcggcagcc    4860
tggaaagctg cgaccaatgg ccgccgatgg cgtaccgaac gtgaaatgta cggctgcgac    4920
ggatacgtac gagctgttga atcactcac ggaaaaaacg gttggcacgt tcacgtccac    4980
gctctactca tgttcagcgg tgacgtgagt gagaacatcc tcgaatcctt ctcggatgcg    5040
atgttcgatc ggtggacctc caaactcgtg tctctgggat ttgctgcgcc actacgtaat    5100
tcaggtggac tcgacgtaag aaagattggt ggagaagctg accaagttct cgctgcatac    5160
ctgacgaaaa ttgcatccgg ggtcggcatg gaagtcggca gtggcgacgg aaaaagtggt    5220
cggcacggca accgtgcacc ttgggaaatc gccgttgatg cagtcggagg agatccacaa    5280
gcgttggaac tctggcgcga gtttgagttc ggttcgatgg gacgccgagc aatcgcatgg    5340
tctcgtggac tgcgcgcccg agctggtctt ggcgtagaac tcacggatgc tcagattgtc    5400
gaacaggaag aatctgcccc ggtcatggtt gcgatcattc cggctcggtc ctggatgatg    5460
attcggaact gtgcgcctta cgttttcgga gagatccttg gactcgtgga agcgggcgcg    5520
acctgggaaa accttcgtga ccacttgcat tatcgattgc ctgcagcgga tgtgcggcct    5580
ccgataatat cgattcgtaa gtgaaatgtc ttggtgtgca acaactttca ctcgtatgaa    5640
ccacacttga gggcatcccc ccgatacttg ccgctttgaa gctgggtgtc tctctgtcag    5700
ggctgcgata gcaccgcgta gcggcttggc cttgacagag agacggcctg tttcatggtt    5760
ggtctcgggg ggctgaccgg gcagatagaa aaaggccggc cgatttggct gccgactatt    5820
tttgcaggta aacccatctc atgagcatca atgaacgtcc cgttggtatc gcagcgaatg    5880
cagcttcggt agacgtcgat ggcgttgtga tgggtgtgta tctctcgctt tatgggcaag    5940
aaatcacgct agatcgagat gatgcgttcc tactcctcga tcgacttcag gacgcgttgc    6000
gacctcaagc caactaagaa ccctccagat ggtctaaacg aggcgcaaac tcgctcctgg    6060
gcctgcgggc ggagcaccga agcgcgagcg aagcggagcg cgtaggtggg ggagcctgcg    6120
ggcagcggcg gcggagccgc cgccttggta ataggtgatc atcggggcca tagcaggtca    6180
gaggatgttt ttacgatgac tcatgctcac cacgccaagt actgatg                 6227
```

<210> SEQ ID NO 106
<211> LENGTH: 6231
<212> TYPE: DNA
<213> ORGANISM: Artificial Sequence
<220> FEATURE:
<223> OTHER INFORMATION: Description of Artificial Sequence: Synthetic
    vector pNit-RC2 sequence

<400> SEQUENCE: 106

```
gttaacgcat ccgaaacctc caccccactc acctagtccg acatccgtac cttggaaacc    60
gacctgtatt ggcatttcag ttggacatcg accagtggcg ttgctaggtt caagaccatg   120
tccagcccga aggcgtccag actctagcca ccggaggtag tccggtggcc acatcccgtc   180
gcgcccgaac gtcacgctct tgtgtggcct tcccttgttg tttgcgatca gtggcacacc   240
tctaccgtct gaatttcgag tctggcctcg gctgcgcaca tctcgcactg tgacgctgtc   300
aggtcacccg cttcgcggct accagttcct ttcatcgaat cgagcttccg gtgccgccgc   360
gcagcctccc tgaccatcct cagatttat ggagtctcgc agtgccttc gctatctacg    420
tcctcgggct tgctgtcttc gcccagggca catccgagtt catgttgtcc ggactcatac   480
cggacatggc ccgtgacctc gggtttcgg tccccgccgc cggactcctc acctccgcct    540
tcgcggtcgg gatgatcatc ggcgctccgt tgatggctat cgccagcatg cggtggcccc   600
ggcgacgcgc ccttctgaca ttcctcatca cgttcatgct ggtccacgtc atcgcgcgc   660
tcaccagcag cttcgaggtc ttgctggtca cacgcatcgt gggagccctc gccaatgccg   720
gattcttggc agtggccctg ggggcggcga tggcgatggt gcccgccgac atgaaagggc   780
gcgccacgtc cgtcctcctc ggcggtgtca cgatcgcatg tgtagccggt gttcccgggg   840
gcgccttcct gggtgaaatg tggggctggc gtgcagcgtt ctgggctgtc gtcgtcatct   900
ccgcccctgc agtggtggcg attatgttcg ccaccccggc cgagccgctt gcagagtcca   960
caccgaatgc caagcgtgaa ctgtcctcac tgcgctcacg caagctccag ctcatgcttg  1020
tcctcgggc gctgatcaac ggcgcaacgt tctgttcgtt cacgtacatg gcgcccacgc  1080
tcaccgacat ctccggtttc gactcccgtt ggattccgtt gctgctgggg ctgttcgggc  1140
tcggatcgtt catcggtgtc agcgtcggag gcaggctcgc cgacacccgg ccgttccaac  1200
tgctcgctgt cgggtccgca gcactgttga cgggatggat cgtcttcgct ctcacggcat  1260
cccaccccgc ggtgacattg gtgatgctgt tcgtgcaggg cgctttgtcc ttcgcggtcg  1320
gctcgacttt tgatctcccag gtgctctacg ccgccgacgc ggcaccgacc ttgggtggat  1380
cgttcgcgac ggccgcgttc aacgtcggtg ctgcactggg accggcgctc ggcgggttgg  1440
cgatcggcat gggtctgagc taccgcgccc cgctctggac gagcgccgcg ctggtgacac  1500
tcgcgatcgt catcggcgca gccaccttgt ctctgtggcg gcgaccagcg tctgtccacg  1560
aatctgtccc cgcctgacca gaaaccagga tctgtgagtg tggtgactga tctgtgcacg  1620
ctcagcagtc accgcgcgct cgcgtcgtac cgagggccag cgccaacagg tgtgtggagc  1680
tctgccctg cctctttcac gcgaactcac tgttcagtgc ggcgatacgt gctcggtgag  1740
ttccactaca gcgaggtacc gagctcgtca ggtggcactt tcggggaaa tgtgcgcgga  1800
acccctattt gtttattttt ctaaatacat tcaaatatgt atccgctcat gagacaataa  1860
ccctgataaa tgcttcaata atattgaaaa aggaagagta tgagtattca acatttccgt  1920
gtcgccctta ttcccttttt tgcggcattt tgccttcctg ttttgctca cccagaaacg  1980
ctggtgaaag taaaagatgc tgaagatcag ttgggtgcac gagtgggtta catcgaactg  2040
gatctcaaca gcggtaagat ccttgagagt tttcgccccg aagaacgttt tccaatgatg  2100
agcactttta aagttctgct atgtggcgcg gtattatccc gtattgacgc cgggcaagag  2160
caactcggtc gccgcataca ctattctcag aatgacttgg ttgagtactc accagtcaca  2220
gaaaagcatc ttacgatgg catgacagta agagaattat gcagtgctgc cataaccatg  2280
agtgataaca ctgcggccaa cttacttctg acaacgatcg gaggaccgaa ggagctaacc  2340
```

```
gcttttttgc acaacatggg ggatcatgta actcgccttg atcgttggga accggagctg      2400
aatgaagcca taccaaacga cgagcgtgac accacgatgc ctgtagcaat ggcaacaacg      2460
ttgcgcaaac tattaactgg cgaactactt actctagctt cccggcaaca attaatagac      2520
tggatggagg cggataaagt tgcaggacca cttctgcgct cggcccttcc ggctggctgg      2580
tttattgctg ataaatctgg agccggtgag cgtgggtctc gcggtatcat tgcagcactg      2640
gggccagatg gtaagccctc ccgtatcgta gttatctaca cgacggggag tcaggcaact      2700
atggatgaac gaaatagaca gatcgctgag ataggtgcct cactgattaa gcattggtaa      2760
ctgtcagacc aagtttactc atatatactt tagattgatt taaaacttca ttttttaattttt   2820 aaaaggatct aggtgaagat cctttttgat aatctcatga ccaaaatccc ttaacgtgag      2880
ttttcgttcc actgagcgtc agaccccgta gaaaagatca aaggatcttc ttgagatcct      2940
ttttttctgc gcgtaatctg ctgcttgcaa acaaaaaaac caccgctacc agcggtggtt      3000
tgtttgccgg atcaagagct accaactctt tttccgaagg taactggctt cagcagagcg      3060
cagataccaa atactgttct tctagtgtag ccgtagttag gccaccactt caagaactct      3120
gtagcaccgc ctacatacct cgctctgcta atcctgttac cagtggctgc tgccagtggc      3180
gataagtcgt gtcttaccgg gttggactca agacgatagt taccggataa ggcgcagcgg      3240
tcgggctgaa cggggggttc gtgcacacag cccagcttgg agcgaacgac ctacaccgaa      3300
ctgagatacc tacagcgtga gctatgagaa agcgccacgc ttcccgaagg gagaaaggcg      3360
gacaggtatc cggtaagcgg cagggtcgga acaggagagc gcacgaggga gcttccaggg      3420
ggaaacgcct ggtatcttta tagtcctgtc gggtttcgcc acctctgact tgagcgtcga      3480
tttttgtgat gctcgtcagg ggggcggagc ctatggaaaa acgccagcaa cgcggccttt      3540
ttacggttcc tggccttttg ctggcctttt gctcacatgt tctttcctgc gttatcccct      3600
gattctgtgg ataaccgtat taccgccttt gagtgagctg ataccgctcg ccgcagccga      3660
acgaccgagc gcagcgagtc agtgagcgag gaagcggaag agcgcccaat acgcaaaccg      3720
cctctccccg cgcgttggcc gattcattaa tgcagctggc acgactagag tcccgctgag      3780
gcggcgtagc aggtcagccg ccccagcggt ggtcaccaac cggggtggaa cggcgccggt      3840
atcgggtgtg tccgtggcgc tcattccaac ctccgtgtgt ttgtgcaggt ttcgcgtgtt      3900
gcagtccctc gcaccggcac ccgcagcgag gggctcacgg gtgccggtgg gtcgactagt      3960
tcagtgatgt tgatggtgat gctcgagaga tctaagcttg gatccgcggc cgctacgtag      4020
aattcccatg gcgtgatggt gatggtgatg gcccatatgt atatctcctt cttaaagtta      4080
aacaaaatta tttctagacg ccgtccatta tacctcctca cgtgacgtga ggtgcaagcc      4140
cggacgttcc gcgtgccacg ccgtgagccg ccgcgtgccg tcggctccct cagcccgggc      4200
ggccgtggga gcccgcctcg atatgtacaa gcatggggac tcgccgcgga ctagcggctt      4260
cccgacacgc cgtactgacc agcagatcag cgataaacgc tgtttctgct ggttaagtgg      4320
ataaaaacca ataatcgat gaacctcgaa gtggagtatc cgagctgaac tagctggatt      4380
tactccgaaa atacgagcgg cgacgaaggg tgttggacca cctgccgcc gccttcgagg      4440 ctcctacttg actaggaccc cgctcgttat gaccagcgta agtgctgaac acctttccgg      4500
caaagaccgg cccctgtcc tcgtgtcgtc cgataagcgc ggcatccggc acgaacttcg      4560
acccaaactt caacaaatca ccacgtcaga aactttaat gcgtgcggcc ggccgatttc      4620
cggcgtgaac ggtgtgacca tcgtcaacgg tcccaaaggt tccggatttg gaggccttcg      4680
```

-continued

```
ctcctgcgga aagggctgga tctgcccctg ctgtgcggga aaagtcggcg cacatcgagc      4740
agacgaaatt tctcaagttg ttgctcatca actcgggact ggatctgttg cgatggtgac      4800
catgaccatg cgccataccg ctgggcagcg tttgcatgat ttgtggactg gactttcggc      4860
agcctggaaa gctgcgacca atggccgccg atggcgtacc gaacgtgaaa tgtacggctg      4920
cgacggatac gtacgagctg ttgaaatcac tcacggaaaa aacggttggc acgttcacgt      4980
ccacgctcta ctcatgttca gcggtgacgt gagtgagaac atcctcgaat ccttctcgga      5040
tgcgatgttc gatcggtgga cctccaaact cgtgtctctg ggatttgctg cgccactacg      5100
taattcaggt ggactcgacg taagaaagat tggtggagaa gctgaccaag ttctcgctgc      5160
atacctgacg aaaattgcat ccggggtcgg catggaagtc ggcagtggcg acggaaaaag      5220
tggtcggcac ggcaaccgtg caccttggga aatcgccgtt gatgcagtcg gaggagatcc      5280
acaagcgttg gaactctggc gcgagtttga gttcggttcg atgggacgcc gagcaatcgc      5340
atggtctcgt ggactgcgcg cccgagctgg tcttggcgta gaactcacgg atgctcagat      5400
tgtcgaacag gaagaatctg ccccggtcat ggttgcgatc attccggctc ggtcctggat      5460
gatgattcgg aactgcgcgc ttacgttttt cggagagatc cttggactcg tggaagcggg      5520
cgcgacctgg gaaaaccttc gtgaccactt gcattatcga ttgcctgcag cggatgtgcg      5580
gcctccgata atatcgattc gtaagtgaaa tgtcttggtg tgcaacaact ttcactcgta      5640
tgaaccacac ttgagggcat cccccgata cttgccgctt tgaagctggg tgtctctctg       5700
tcagggctgc gatagcaccg cgtagcggct tggccttgac agagagacgg cctgtttcat      5760
ggttggtctc gggggggctga ccgggcagat agaaaaaggc cggccgattt ggctgccgac    5820 tattttttgca ggtaaaccca tctcatgagc atcaatgaac gtcccgttgg tatcgcagcg    5880
aatgcagctt cggtagacgt cgatggcgtt gtgatgggtg tgtatctctc gctttatggg    5940
caagaaatca cgctagatcg agatgatgcg ttcctactcc tcgatcgact tcaggacgcg    6000
ttgcgacctc aagccaacta agaaccctcc agatggtcta aacgaggcgc aaactcgctc    6060
ctgggcctgc gggcggagca ccgaagcgcg agcgaagcgg agcgcgtagg tgggggagcc    6120
tgcgggcagc ggcggcggag ccgccgcctt ggtaataggt gatcatcggg gccatagcag    6180
gtcagaggat gttttttacga tgactcatgc tcaccacgcc aagtactgat g              6231
```

<210> SEQ ID NO 107
<211> LENGTH: 124
<212> TYPE: DNA
<213> ORGANISM: Rhodococcus erythropolis
<220> FEATURE:
<223> OTHER INFORMATION: mutated TipA gene promoter

<400> SEQUENCE: 107

```
cgcccgggct gagggagccg acggcacgcg gcggctcacg gcgtggcacg cggaacgtcc       60
gggcttgcac ctcacgtcac gtgaggaggt ataatggacg gcgtcagaga aggggacggc      120
catg                                                                   124
```

<210> SEQ ID NO 108
<211> LENGTH: 422
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (151)..(222)

<400> SEQUENCE: 108

```
gtgtacatat cgaggcgggc tcccacggcc gcccgggctg agggagccga cggcacgcgg      60
cggctcacgg cgtggcacgc ggaacgtccg ggcttgcacc tcacgtcacg tgaggaggca     120
gcgtggacgg cgtcagagaa gggagcggcc atg ggc cac cat cac cat cac cat     174
                                 Met Gly His His His His His His
                                  1               5 atg gga att cta cgt agc ggc cgc gga tcc aag ctt aga tct cga gga     222
Met Gly Ile Leu Arg Ser Gly Arg Gly Ser Lys Leu Arg Ser Arg Gly
         10                  15                  20 tgaactagtc gacccaccgg cacccgtgag cccctcgctg cgggtgccgg tgcgagggac     282
tgcaacacgc gaaacctgca caaacacacg gaggttggaa tgagcgccac ggacacaccc     342
gataccggcg ccgttccacc ccggttggtg accaccgctg gggcggctga cctgctacgc     402
cgcctcagcg ggactctagt                                                 422
```

<210> SEQ ID NO 109
<211> LENGTH: 24
<212> TYPE: PRT
<213> ORGANISM: Artificial Sequence
<220> FEATURE:
<223> OTHER INFORMATION: Description of Artificial Sequence: Synthetic peptide

<400> SEQUENCE: 109

```
Met Gly His His His His His His Met Gly Ile Leu Arg Ser Gly Arg
 1               5                  10                  15

Gly Ser Lys Leu Arg Ser Arg Gly
             20
```

<210> SEQ ID NO 110
<211> LENGTH: 42
<212> TYPE: DNA
<213> ORGANISM: Artificial Sequence
<220> FEATURE:
<223> OTHER INFORMATION: Description of Artificial Sequence: Synthetic nucleotide sequence

<400> SEQUENCE: 110

```
gtctagaaat aattttgttt aactttaaga aggagatata cc                         42
```

<210> SEQ ID NO 111
<211> LENGTH: 416
<212> TYPE: DNA
<213> ORGANISM: Artificial Sequence
<220> FEATURE:
<223> OTHER INFORMATION: Description of Artificial Sequence: Synthetic nucleotide sequence
<220> FEATURE:
<221> NAME/KEY: CDS
<222> LOCATION: (151)..(216)

<400> SEQUENCE: 111

```
gtgtacatat cgaggcgggc tcccacggcc gcccgggctg agggagccga cggcacgcgg      60
cggctcacgg cgtggcacgc ggaacgtccg ggcttgcacc tcacgtcacg tgaggaggca     120
gcgtggacgg cgtcagagaa gggagcggcc atg gga att cta cgt agc ggc cgc     174
                                 Met Gly Ile Leu Arg Ser Gly Arg
                                  1               5 gga tcc aag ctt aga tct cga gga cat cac cat cac cat cac              216
Gly Ser Lys Leu Arg Ser Arg Gly His His His His His His
         10                  15                  20
```

```
tgaactagtc gacccaccgg cacccgtgag cccctcgctg cgggtgccgg tgcgagggac    276
tgcaacacgc gaaacctgca caaacacacg gaggttggaa tgagcgccac ggacacaccc    336
gataccggcg ccgttccacc ccggttggtg accaccgctg gggcggctga cctgctacgc    396
cgcctcagcg ggactctagt                                                416
```

```
<210> SEQ ID NO 112
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Met Gly Ile Leu Arg Ser Gly Arg Gly Ser Lys Leu Arg Ser Arg Gly
 1               5                  10                  15

His His His His His His
            20
```

```
<210> SEQ ID NO 113
<211> LENGTH: 42
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 113
gtctagaaat aattttgttt aactttaaga aggagatata cc                        42
```

```
<210> SEQ ID NO 114
<211> LENGTH: 425
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (151)..(225)

<400> SEQUENCE: 114
gtgtacatat cgaggcgggc tcccacggcc gcccgggctg agggagccga cggcacgcgg     60
cggctcacgg cgtggcacgc ggaacgtccg ggcttgcacc tcacgtcacg tgaggaggca    120
gcgtggacgg cgtcagagaa gggagcgcat atg ggc cat cac cat cac cat cac    174
                                  Met Gly His His His His His His
                                   1               5 gcc atg gga att cta cgt agc ggc cgc gga tcc aag ctt aga tct cga    222
Ala Met Gly Ile Leu Arg Ser Gly Arg Gly Ser Lys Leu Arg Ser Arg
         10                  15                  20 gga tgaactagtc gacccaccgg cacccgtgag cccctcgctg cgggtgccgg          275
Gly
 25 tgcgagggac tgcaacacgc gaaacctgca caaacacacg gaggttggaa tgagcgccac    335 ggacacaccc gataccggcg ccgttccacc ccggttggtg accaccgctg gggcggctga    395 cctgctacgc cgcctcagcg ggactctagt                                    425
```

```
<210> SEQ ID NO 115
<211> LENGTH: 25
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 115

Met Gly His His His His His His Ala Met Gly Ile Leu Arg Ser Gly
  1               5                  10                  15

Arg Gly Ser Lys Leu Arg Ser Arg Gly
            20                  25

<210> SEQ ID NO 116
<211> LENGTH: 43
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 116
gtctagaaat aattttgttt aactttaaga aggagatata cat                      43

<210> SEQ ID NO 117
<211> LENGTH: 416
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (151)..(216)

<400> SEQUENCE: 117
gtgtacatat cgaggcgggc tcccacggcc gcccgggctg agggagccga cggcacgcgg     60
cggctcacgg cgtggcacgc ggaacgtccg ggcttgcacc tcacgtcacg tgaggaggca   120
gcgtggacgg cgtcagagaa gggagcgcat atg gga att cta cgt agc ggc cgc   174
                                 Met Gly Ile Leu Arg Ser Gly Arg
                                   1               5 gga tcc aag ctt aga tct cga gga cat cac cat cac cat cac              216
Gly Ser Lys Leu Arg Ser Arg Gly His His His His His His
         10                  15                  20 tgaactagtc gacccaccgg cacccgtgag cccctcgctg cgggtgccgg tgcgagggac   276
tgcaacacgc gaaacctgca caaacacacg gaggttggaa tgagcgccac ggacacaccc   336
gataccggcg ccgttccacc ccggttggtg accaccgctg gggcggctga cctgctacgc   396
cgcctcagcg ggactctagt                                                416

<210> SEQ ID NO 118
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Met Gly Ile Leu Arg Ser Gly Arg Gly Ser Lys Leu Arg Ser Arg Gly
  1               5                  10                  15

His His His His His His
            20

<210> SEQ ID NO 119
<211> LENGTH: 43
```

```
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 119
gtctagaaat aatttgttt aactttaaga aggagatata cat                    43

<210> SEQ ID NO 120
<211> LENGTH: 81
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (3)..(68)

<400> SEQUENCE: 120 cc atg gga att cta cgt agc ggc cgc gga tcc aag ctt aga tct ctc    47
   Met Gly Ile Leu Arg Ser Gly Arg Gly Ser Lys Leu Arg Ser Leu
   1               5                  10                  15 gag cat cac cat cac cat cac tgaactagtc gac                        81
Glu His His His His His His
                20

<210> SEQ ID NO 121
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Met Gly Ile Leu Arg Ser Gly Arg Gly Ser Lys Leu Arg Ser Leu Glu
1               5                   10                  15

His His His His His His
            20

<210> SEQ ID NO 122
<211> LENGTH: 82
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (4)..(69)

<400> SEQUENCE: 122 cat atg gga att cta cgt agc ggc cgc gga tcc aag ctt aga tct ctc   48
    Met Gly Ile Leu Arg Ser Gly Arg Gly Ser Lys Leu Arg Ser Leu
    1               5                  10                  15 gag cat cac cat cac cat cac tgaactagtc gac                        82
Glu His His His His His His
                20

<210> SEQ ID NO 123
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 123

Met Gly Ile Leu Arg Ser Gly Arg Gly Ser Lys Leu Arg Ser Leu Glu
1               5                   10                  15
His His His His His His
            20

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 124
gtcagagaag ggagcggcca tg                                          22

<210> SEQ ID NO 125
<211> LENGTH: 45
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 125
gtctagaaat aattttgttt aactttaaga aggagatata ccatg                 45

<210> SEQ ID NO 126
<211> LENGTH: 14
<212> TYPE: PRT
<213> ORGANISM: Rhodococcus erythropolis

<400> SEQUENCE: 126

Gly Leu Arg Ser Cys Gly Lys Gly Trp Ile Cys Pro Cys Cys
1               5                   10

<210> SEQ ID NO 127
<211> LENGTH: 8
<212> TYPE: PRT
<213> ORGANISM: Rhodococcus erythropolis

<400> SEQUENCE: 127

Met Val Thr Met Thr Met Arg His
1               5

<210> SEQ ID NO 128
<211> LENGTH: 26
<212> TYPE: PRT
<213> ORGANISM: Rhodococcus erythropolis

<400> SEQUENCE: 128

Gly Cys Asp Gly Tyr Val Arg Ala Val Glu Ile Thr His Gly Lys Asn
1               5                   10                  15
Gly Trp His Val His Val His Ala Leu Leu
            20                  25

<210> SEQ ID NO 129
<211> LENGTH: 10
<212> TYPE: PRT
<213> ORGANISM: Rhodococcus erythropolis

<400> SEQUENCE: 129

```
Leu Ala Ala Tyr Leu Thr Lys Ile Ala Ser
 1               5                  10

<210> SEQ ID NO 130
<211> LENGTH: 21
<212> TYPE: PRT
<213> ORGANISM: Rhodococcus erythropolis

<400> SEQUENCE: 130

Trp Arg Glu Phe Glu Phe Gly Ser Met Gly Arg Arg Ala Ile Ala Trp
 1               5                  10                  15

Ser Arg Gly Leu Arg
            20

<210> SEQ ID NO 131
<211> LENGTH: 14
<212> TYPE: PRT
<213> ORGANISM: Arcanobacterium pyrogens

<400> SEQUENCE: 131

Gly Leu His Thr Cys Gly Ser Val Trp Ala Cys Pro Val Cys
 1               5                  10

<210> SEQ ID NO 132
<211> LENGTH: 8
<212> TYPE: PRT
<213> ORGANISM: Arcanobacterium pyrogens

<400> SEQUENCE: 132

Met Leu Thr Leu Thr Gln Arg His
 1               5

<210> SEQ ID NO 133
<211> LENGTH: 26
<212> TYPE: PRT
<213> ORGANISM: Arcanobacterium pyrogens

<400> SEQUENCE: 133

Gly Leu Val Gly Tyr Val Arg Ala Asn Glu Ile Thr His Gly Lys His
 1               5                  10                  15

Gly Trp His Val His Ser His Val Leu Ile
            20                  25

<210> SEQ ID NO 134
<211> LENGTH: 10
<212> TYPE: PRT
<213> ORGANISM: Arcanobacterium pyrogens

<400> SEQUENCE: 134

Ile Gly Asn Tyr Val Ser Lys Met Gln Thr
 1               5                  10

<210> SEQ ID NO 135
<211> LENGTH: 21
<212> TYPE: PRT
<213> ORGANISM: Arcanobacterium pyrogens

<400> SEQUENCE: 135

Trp Lys Glu Tyr Glu Lys Ala Ser Phe Gly Arg Arg Ala Leu Thr Trp
 1               5                  10                  15

Ser Lys Gly Leu Arg
            20
```

-continued

<210> SEQ ID NO 136
<211> LENGTH: 8
<212> TYPE: PRT
<213> ORGANISM: Brevibacterium lactofermentium

<400> SEQUENCE: 136

Met Phe Val Gly Thr Val Arg His
1               5

<210> SEQ ID NO 137
<211> LENGTH: 26
<212> TYPE: PRT
<213> ORGANISM: Brevibacterium lactofermentium

<400> SEQUENCE: 137

Val Glu His Thr Tyr Ser Asp Tyr Glu Val Thr Asp Ser Trp Ala Asn
1               5                   10                  15

Gly Trp His Leu His Arg Asn Met Leu Leu
            20                  25

<210> SEQ ID NO 138
<211> LENGTH: 10
<212> TYPE: PRT
<213> ORGANISM: Brevibacterium lactofermentium

<400> SEQUENCE: 138

Met Ala Thr Tyr Leu Ala Lys Gly Met Ser
1               5                   10

<210> SEQ ID NO 139
<211> LENGTH: 20
<212> TYPE: PRT
<213> ORGANISM: Brevibacterium lactofermentium

<400> SEQUENCE: 139

Trp Arg Glu Tyr Glu Val Gly Ser Lys Asn Leu Arg Ser Ser Trp Ser
1               5                   10                  15

Arg Gly Ala Lys
            20

<210> SEQ ID NO 140
<211> LENGTH: 14
<212> TYPE: PRT
<213> ORGANISM: Streptomyces phaeochromogenes

<400> SEQUENCE: 140

Gly Leu Val Arg Cys Gly Arg Ile Trp Phe Cys Pro Glu Cys
1               5                   10

<210> SEQ ID NO 141
<211> LENGTH: 8
<212> TYPE: PRT
<213> ORGANISM: Streptomyces phaeochromogenes

<400> SEQUENCE: 141

Leu Val Thr Phe Thr Ala Arg His
1               5

<210> SEQ ID NO 142
<211> LENGTH: 27
<212> TYPE: PRT
<213> ORGANISM: Streptomyces phaeochromogenes

<400> SEQUENCE: 142

```
Gly Tyr Ile Gly Met Val Arg Ala Ala Glu Val Thr Arg Ser Lys Lys
 1               5                  10                  15

Asn Gly Tyr His Pro His Leu Asn Leu Leu Val
            20                  25
```

<210> SEQ ID NO 143
<211> LENGTH: 10
<212> TYPE: PRT
<213> ORGANISM: Streptomyces phaeochromogenes

<400> SEQUENCE: 143

```
Leu Ile Glu Tyr Leu Thr Lys Asn Gln Asp
 1               5                  10
```

<210> SEQ ID NO 144
<211> LENGTH: 21
<212> TYPE: PRT
<213> ORGANISM: Streptomyces phaeochromogenes

<400> SEQUENCE: 144

```
Trp Ala Gln Tyr Glu Glu Ala Leu Ala Gly Arg Arg Ala Ile Glu Trp
 1               5                  10                  15

Thr Arg Gly Leu Arg
            20
```

<210> SEQ ID NO 145
<211> LENGTH: 14
<212> TYPE: PRT
<213> ORGANISM: Streptomyces lividans

<400> SEQUENCE: 145

```
Gly Leu Met Arg Cys Gly Arg Ile Trp Leu Cys Pro Val Cys
 1               5                  10
```

<210> SEQ ID NO 146
<211> LENGTH: 8
<212> TYPE: PRT
<213> ORGANISM: Streptomyces lividans

<400> SEQUENCE: 146

```
Leu Val Thr Phe Thr Ala Arg His
 1               5
```

<210> SEQ ID NO 147
<211> LENGTH: 26
<212> TYPE: PRT
<213> ORGANISM: Streptomyces lividans

<400> SEQUENCE: 147

```
Gly Tyr Val Gly Met Arg Ala Thr Glu Val Thr Val Gly Gln Ile Asn
 1               5                  10                  15

Gly Trp His Pro His Ile His Ala Ile Val
            20                  25
```

<210> SEQ ID NO 148
<211> LENGTH: 10
<212> TYPE: PRT
<213> ORGANISM: Streptomyces lividans

<400> SEQUENCE: 148

```
Leu Ala Glu Tyr Ile Ala Lys Thr Gln Asp
 1               5                  10
```

<210> SEQ ID NO 149
<211> LENGTH: 21
<212> TYPE: PRT
<213> ORGANISM: Streptomyces lividans

<400> SEQUENCE: 149

Trp His Glu Tyr Glu Arg Ala Thr Arg Gly Arg Arg Ala Ile Glu Trp
1               5                   10                  15

Thr Arg Tyr Leu Arg
            20

<210> SEQ ID NO 150
<211> LENGTH: 14
<212> TYPE: PRT
<213> ORGANISM: Streptomyces nigrifaciens

<400> SEQUENCE: 150

Gly Leu Met Arg Cys Gly Arg Ile Trp Leu Cys Pro Val Cys
1               5                   10

<210> SEQ ID NO 151
<211> LENGTH: 8
<212> TYPE: PRT
<213> ORGANISM: Streptomyces nigrifaciens

<400> SEQUENCE: 151

Leu Val Thr Phe Thr Ala Arg His
1               5

<210> SEQ ID NO 152
<211> LENGTH: 26
<212> TYPE: PRT
<213> ORGANISM: Streptomyces nigrifaciens

<400> SEQUENCE: 152

Gly Tyr Val Gly Met Arg Ala Thr Glu Val Thr Val Gly Gln Ile Asn
1               5                   10                  15

Gly Trp His Pro His Ile His Ala Ile Val
            20                  25

<210> SEQ ID NO 153
<211> LENGTH: 10
<212> TYPE: PRT
<213> ORGANISM: Streptomyces nigrifaciens

<400> SEQUENCE: 153

Leu Ala Glu Tyr Ile Ala Lys Thr Gln Asp
1               5                   10

<210> SEQ ID NO 154
<211> LENGTH: 21
<212> TYPE: PRT
<213> ORGANISM: Streptomyces nigrifaciens

<400> SEQUENCE: 154

Trp His Glu Tyr Glu Arg Ala Thr Lys Gly Arg Arg Ala Ile Glu Trp
1               5                   10                  15

Thr Arg Tyr Leu Arg
            20

<210> SEQ ID NO 155
<211> LENGTH: 30
<212> TYPE: DNA
<213> ORGANISM: Rhodococcus erythropolis

<400> SEQUENCE: 155
cgagcgaagc ggagcgcgta ggtgggggag                                    30

<210> SEQ ID NO 156
<211> LENGTH: 27
<212> TYPE: DNA
<213> ORGANISM: Arcanobacterium pyrogens

<400> SEQUENCE: 156
caggtatgcg gaaaacttta ggaacaa                                       27

<210> SEQ ID NO 157
<211> LENGTH: 32
<212> TYPE: DNA
<213> ORGANISM: Brevibacterium lactofermentium

<400> SEQUENCE: 157
gaaatagaag tgaacacctc taaggaaccg ca                                 32

<210> SEQ ID NO 158
<211> LENGTH: 31
<212> TYPE: DNA
<213> ORGANISM: Streptomyces phaeochromogenes

<400> SEQUENCE: 158
ctggcaaaaa gggacgccta ggtaaagggt t                                  31

<210> SEQ ID NO 159
<211> LENGTH: 30
<212> TYPE: DNA
<213> ORGANISM: Streptomyces lividans

<400> SEQUENCE: 159
gaggcaaaag cgaacacctt gggaaagaaa                                    30

<210> SEQ ID NO 160
<211> LENGTH: 32
<212> TYPE: DNA
<213> ORGANISM: Streptomyces nigrifaciens

<400> SEQUENCE: 160
gacccaaaac gtgtcgcgcc ttgggaaaga aa                                 32

<210> SEQ ID NO 161
<211> LENGTH: 270
<212> TYPE: DNA
<213> ORGANISM: Rhodococcus erythropolis

<400> SEQUENCE: 161
tgagggcatc cccccgatac ttgccgcttt gaagctgggt gtctctctgt cagggctgcg   60
atagcaccgc gtagcggctt ggccttgaca gagagacggc ctgtttcatg gttggtctcg  120
gggggctgac cgggcagata gaaaaaggcc ggccgatttg gctgccgact attttttgcag 180 gtaaacccat ctcatgagca tcaatgaacg tcccgttgta tcgcagcgcg tgcagcttcg  240
gtagacgtcg atggcgttgt gatgggtgtg                                   270

<210> SEQ ID NO 162
<211> LENGTH: 170
<212> TYPE: DNA
<213> ORGANISM: Artificial Sequence
<220> FEATURE:

-continued

<223> OTHER INFORMATION: Description of Artificial Sequence: Synthetic
      nucleotide sequence

<400> SEQUENCE: 162
tgtacatatc gaggcgggct cccacggccg cccgggctga gggagccgac ggcacgcggc      60
ggctcacggc gtggcacgcg gaacgtccgg gcttgcacct cacgtcacgt gaggaggcag     120
cgtggacggc gtctagaaat aattttgttt aactttaaga agaagatata               170

<210> SEQ ID NO 163
<211> LENGTH: 95
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (3)..(92)

<400> SEQUENCE: 163 cc atg ggc cac cat cac cat cac cat atg gga att cta cgt agc ggc       47
   Met Gly His His His His His His Met Gly Ile Leu Arg Ser Gly
   1               5                   10                  15 cgc gga tcc aag ctt aga tct ctc gag cat cac cat cac cat cac tga      95
Arg Gly Ser Lys Leu Arg Ser Leu Glu His His His His His His
            20                  25                  30

<210> SEQ ID NO 164
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Met Gly His His His His His His Met Gly Ile Leu Arg Ser Gly Arg
1               5                   10                  15

Gly Ser Lys Leu Arg Ser Leu Glu His His His His His His
            20                  25                  30

<210> SEQ ID NO 165
<211> LENGTH: 99
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (4)..(96)

<400> SEQUENCE: 165 cat atg ggc cat cac cat cac cat cac gcc atg gga att cta cgt agc      48
    Met Gly His His His His His His Ala Met Gly Ile Leu Arg Ser
    1               5                   10                  15 ggc cgc gga tcc aag ctt aga tct ctc gag cat cac cat cac cat cac      96
Gly Arg Gly Ser Lys Leu Arg Ser Leu Glu His His His His His His
            20                  25                  30 tga                                                                  99

<210> SEQ ID NO 166
<211> LENGTH: 31
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 166

Met Gly His His His His His His Ala Met Gly Ile Leu Arg Ser Gly
  1               5                  10                  15

Arg Gly Ser Lys Leu Arg Ser Leu Glu His His His His His His
             20                  25                  30

<210> SEQ ID NO 167
<211> LENGTH: 197
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 167
actagtcgac ccaccggcac ccgtgagccc ctcgctgcgg gtgccggtgc gagggactgc      60
aacacgcgaa acctgcacaa acacacggag gttggaatga gcgccacgga cacacccgat     120
accggcgccg ttccaccccg gttggtgacc accgctgggg cggctgacct gctacgccgc     180
ctcagcggga ctctagt                                                    197

<210> SEQ ID NO 168
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 168

His His His His His His
  1               5

<210> SEQ ID NO 169
<211> LENGTH: 147
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 169
cgcccgggct gagggagccg acggcacgcg gcggctcacg gcgtggcacg cggaacgtcc      60
gggcttgcac ctcacgtcac gtgaggaggt ataatggacg gcgtctagaa ataattttgt     120
ttaactttaa gaaggagata taccatg                                         147

<210> SEQ ID NO 170
<211> LENGTH: 124
<212> TYPE: DNA
<213> ORGANISM: Rhodococcus erythropolis
<220> FEATURE:
<223> OTHER INFORMATION: mutated TipA gene promoter

<400> SEQUENCE: 170
cgcccgggct gagggagccg acggcacgcg gcggctcacg gcgtggcacg cggaacgtcc      60
gggcttgcac ctcacgtcac gtgaggaggt ataatggacg gcgtcagaga agggagcggc     120
catg                                                                  124
```